(12) United States Patent
Ishikawa et al.

(10) Patent No.: US 8,138,206 B2
(45) Date of Patent: Mar. 20, 2012

(54) PIPERIDINE DERIVATIVE

(75) Inventors: Shiho Ishikawa, Ushiku (JP); Tsuyoshi Nagase, Tsukkuba (JP); Nagaaki Sato, Tsukuba (JP); Hidekazu Takahashi, Tsukuba (JP); Shigeru Tokita, Tsukkuba (JP); Toshihiro Wada, Osaka (JP)

(73) Assignee: MSD. K.K., Chiyoda-Ku (JP)

( * ) Notice: Subject to any disclaimer, the term of this patent is extended or adjusted under 35 U.S.C. 154(b) by 1121 days.

(21) Appl. No.: 11/921,435

(22) PCT Filed: May 29, 2006

(86) PCT No.: PCT/JP2006/311155
§ 371 (c)(1),
(2), (4) Date: Nov. 29, 2007

(87) PCT Pub. No.: WO2006/129826
PCT Pub. Date: Dec. 7, 2006

(65) Prior Publication Data
US 2009/0137576 A1 May 28, 2009

(30) Foreign Application Priority Data

May 30, 2005 (JP) .................... 2005-157739
Apr. 19, 2006 (JP) .................... 2006-115778

(51) Int. Cl.
| | |
|---|---|
| A61K 31/445 | (2006.01) |
| A61K 31/44 | (2006.01) |
| A61K 31/535 | (2006.01) |
| C07D 211/10 | (2006.01) |
| C07D 401/00 | (2006.01) |
| C07D 491/00 | (2006.01) |
| C07D 491/10 | (2006.01) |
| C07D 405/00 | (2006.01) |
| C07D 413/00 | (2006.01) |

(52) U.S. Cl. ............ 514/317; 514/230.8; 514/278; 514/318; 514/320; 514/321; 514/323; 514/326; 546/16; 546/17; 546/19; 546/187; 546/192; 546/208; 546/209; 546/212; 546/214

(58) Field of Classification Search ........... 514/230.8, 514/278, 317, 318, 320, 321, 323, 326; 546/16, 546/17, 19, 187, 192, 208, 209, 212, 214
See application file for complete search history.

(56) References Cited

U.S. PATENT DOCUMENTS

| | | | |
|---|---|---|---|
| 7,547,693 B2 * | 6/2009 | Ohtake et al. ............ 514/228.8 |
| 7,595,316 B2 | 9/2009 | Ohtake et al. | |
| 2004/0087573 A1 | 5/2004 | Apodaca et al. | |
| 2006/0019964 A1 | 1/2006 | Ancliff et al. | |
| 2006/0025404 A1 | 2/2006 | Ancliff et al. | |
| 2006/0052597 A1 | 3/2006 | Best et al. | |
| 2006/0178375 A1 | 8/2006 | Ohtake et al. | |
| 2010/0210637 A1 | 8/2010 | Ohtake et al. | |

FOREIGN PATENT DOCUMENTS

| | | |
|---|---|---|
| EP | 1642898 | 6/2004 |
| WO | WO0212214 | 2/2002 |
| WO | WO200403556 | 4/2004 |
| WO | WO2004037800 | 5/2004 |
| WO | WO2005007644 | 1/2005 |
| WO | WO 2005028438 A1 * | 3/2005 |

OTHER PUBLICATIONS

International Preliminary Report on Patentability for WO2006/129826,Dec. 6, 2007.
EPO Supplementary Search Report for EP 06747135.9, Dec. 18, 2009.
Response submitted in EP 06747135.9, Dec. 7, 2010.
EPO Communication in EP 067471359 Feb. 19, 2010.

* cited by examiner

*Primary Examiner* — Sreeni Padmanabhan
*Assistant Examiner* — Jody Karol
(74) *Attorney, Agent, or Firm* — J. Eric Thies; Gerard M. Devlin

(57) ABSTRACT

Disclosed is a substance having an antagonistic effect on the binding of histamine to a histamine H3 receptor or an inhibitory effect on the activity which a histamine H3 receptor constantly exhibits. A compound represented by the formula (I) or a pharmaceutically acceptable salt thereof; (I)

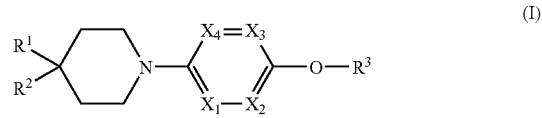

wherein R1 represents a phenyl group which may be substituted or the like and R2 represents a cyano group which may be substituted or the like, or R1 and R2 together form an aliphatic heterocylic ring which may be substituted; R3 represents a group represented by the formula (II-1) below;

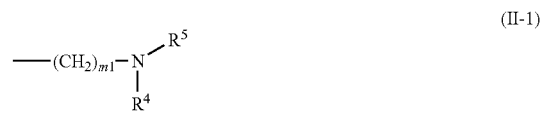

and all of X1 to X4 represent a carbon atom or the like: (II-1) where R4 and R5 represent a lower alkyl group or the like; and m1 represents an integer of 2 to 4.

20 Claims, No Drawings

PIPERIDINE DERIVATIVE

CROSS REFERENCE TO RELATED APPLICATIONS

This application is a U.S. National Phase application under 35 U.S.C. §371 of PCT Application No. PCT/JP2006/311155, filed May 29, 2006, which claims priority under 35 U.S.C. §119 from Japanese Application No. JP2005-157739 filed May 30, 2005, and from Japanese Application No. JP2006-115778 filed Apr. 19, 2006.

TECHNICAL FIELD

The present invention relates to novel piperidine derivatives.

BACKGROUND ART

It has been known that, in organisms such as typically mammals, histamine that is a physiologically-active endogenous factor functions as a neurotransmitter and has extensive pharmacological activities (for example, see Life Science, Vol. 17, p. 503 (1975)).

Immunohistochemical studies have made it clear that a histamine-agonistic (producing) cell body exists in the nodal papillary nucleus in a posterior hypothalamic region and that histamine nerve fibers project in an extremely broad range in a brain, which supports various pharmacological effects of histamine (for example, see Journal of Comparative Neurology, Vol. 273, p. 283). The existence of histamine-agonistic nerves in the nodal papillary nucleus in a posterior hypothalamic region suggests that histamine may have an important role in control of physiological functions relating to brain functions, especially to hypothalamic functions (sleep, vigilance rhythm, incretion, eating and drinking action, sexual action, etc.) (for example, see Progress in Neurobiology, Vol. 63, p. 637 (2001)).

The existence of the projection to the brain region that relates to vigilance sustenance, for example, to cerebral cortex suggests the role in control of vigilance or vigilance-sleep cycle. The existence of the projection to many peripheral structures such as hippocampus and amygdaloid complex suggests the role in control of autonomic nerves, emotion, control of motivated action and learning/memory process.

When released from producing cells, histamine acts with a specific polymer that is referred to as a receptor on the surface of a cell membrane or inside a target cell, therefore exhibiting its pharmacological effects for control of various body functions. Heretofore, four types of histamine receptors have been found. In particular, the presence of a histamine receptor that participates in the central and peripheral nervous functions, a histamine-H3 receptor, has been shown by various pharmacological and physiological studies (for example, see Trends in Pharmacological Science, Vol. 8, p. 24 (1987)). Recently, human and rodent histamine-H3 receptor genes have been identified and their existence has been revealed (for example, see Molecular Pharmacology, Vol. 55, p. 1101 (1999)).

The histamine-H3 receptor exists in the presynaptic membrane of central or peripheral neurocytes and functions as a self-receptor, therefore controlling the release of histamine and controlling even the release of other neurotransmitters. Specifically, it is reported that a histamine-H3 receptor agonist, or its antagonist or inverse-agonist controls the release of histamine, noradrenaline, serotonin, acetylcholine or dopamine from nerve ending. For example, the release of these neurotransmitters is inhibited by an agonist such as (R)-(α)-methylhistamine, and is promoted by an antagonist or inverse-agonist such as thioperamide (for example, see Trends in Pharmacological Science, Vol. 19, p. 177 (1998)).

Known compounds having a histamine-H3 receptor antagonistic effect are described, for example, in WO2004/089373, WO2004/35556. In particular, those in WO2004/089373 have a piperidine skeleton nucleus, but differ from the compounds of the invention in the position of the nitrogen atom in the piperidine skeleton nucleus.

Patent Reference 1: WO2004/089373

DISCLOSURE OF THE INVENTION

An object of the invention is to provide novel substances having a histamine-H3 receptor antagonistic effect (an effect of inhibiting histamine from binding to a histamine-H3 receptor) or inverse-agonistic effect (an effect of inhibiting the homeostatic activity that a histamine-H3 receptor has), or that is, novel substances that acts as a histamine-H3 receptor antagonist or inverse-agonist in living bodies.

To attain the above object, the present inventors provide the following compounds or pharmaceutically-acceptable salts thereof.

(1) Compounds of a formula (I) or pharmaceutically-acceptable salts thereof:

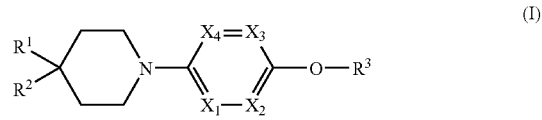

[wherein, $R^1$ represents an aryl group optionally having from 1 to 3 substituents selected from a substituent group α; a 5- or 6-membered heteroaryl group having from 1 to 3 hetero atoms selected from a group consisting of a nitrogen atom, a sulfur atom and an oxygen atom, and optionally having from 1 to 3 substituents selected from the substituent group α; a heteroarylalkyl group optionally having from 1 to 3 substituents selected from the substituent group α; an aralkyl group optionally having from 1 to 3 substituents selected from the substituent group α; or an arylcarbonyl group optionally having from 1 to 3 substituents selected from the substituent group α; and the heteroaryl group may form a condensed ring with a phenyl group or a pyridyl group;

$R^2$ represents an aryl group; a heteroaryl group having from 1 to 3 hetero atoms selected from a group consisting of a nitrogen atom, a sulfur atom and an oxygen atom; a cyano group; a lower alkyl group; a lower alkoxy group; or a hydroxy group; or $R^1$ and $R^2$, taken together, may form a 5- or 6-membered aliphatic heterocyclic group having from 1 to 3 hetero atoms selected from a group consisting of a nitrogen atom, a sulfur atom and an oxygen atom, the aliphatic heterocyclic group may further form a condensed ring with a phenyl group or a pyridyl group, the aliphatic heterocyclic group may have 1 or 2, the same or different substituents selected from a substituent group β, the phenyl group or the pyridyl group that may be condensed with the aliphatic heterocyclic group to form a condensed ring may have 1 or 2, the same or different substituents selected from a substituent group γ;

R³ represents
a) a group of a formula (II-1):

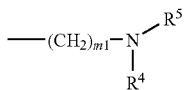
(II-1)

(wherein R⁴ and R⁵ may be the same or different, each representing a lower alkyl group optionally substituted with a halogen atom, or a cycloalkyl group optionally substituted with a halogen atom; or R⁴ and R⁵, taken together with the nitrogen atom, form a 5- to 8-membered monocyclic ring, or 6- to 8-membered bicyclic ring, and the monocyclic ring may have, as a substituent, a lower alkyl group optionally substituted with a halogen atom, or a halogen atom or an oxo group; m1 indicates an integer of from 2 to 4; the hydrogen atom in —(CH₂)m1- may be substituted with a lower alkyl group having from 1 to 3 carbon atoms),
b) a group of a formula (II-2):

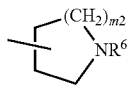
(II-2)

(wherein R⁶ represents a lower alkyl group or a cycloalkyl group; m2 indicates an integer of from 0 to 4), or
c) a group of a formula (II-3):

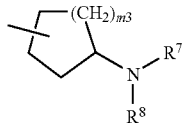
(II-3)

(wherein R⁷ and R⁸ may be the same or different, each representing a lower alkyl group optionally substituted with a halogen atom, or a cycloalkyl group optionally substituted with a halogen atom; or R⁷ and R⁸, taken together with the nitrogen atom, form a 5- to 8-membered monocyclic ring, or 6- to 8-membered bicyclic ring, and the monocyclic ring may have, as a substituent, a lower alkyl group optionally substituted with a halogen atom, or a halogen atom or an oxo group; m3 indicates an integer of from 0 to 4), $X_1$ to $X_4$ are all carbon atoms, or 1 or 2 of $X_1$ to $X_4$ are nitrogen atoms, and the remainder are carbon atoms; and when $X_1$ to $X_4$ are carbon atoms, then $X_1$ to $X_4$ may be substituted with a lower alkyl group optionally substituted with a halogen atom or a lower alkoxy group, a cycloalkyl group optionally substituted with a halogen atom or a lower alkoxy group, a lower alkoxy group optionally substituted with a halogen atom or a lower alkoxy group, or a cyano group or a halogen atom].

Substituent group α: a lower alkyl group optionally substituted with a halogen atom, a lower alkoxy group optionally substituted with a halogen atom, and a halogen atom, Substituent group β: a halogen atom; an oxo group; a lower alkyl group optionally substituted with a halogen atom or a lower alkoxy group; a lower alkoxy group optionally substituted with a halogen atom or a lower alkoxy group;

a 5- or 6-membered, nitrogen-containing aliphatic hetero ring optionally substituted with an oxo group or a lower alkyl group, and optionally having 1 or 2 double bonds in the ring; an aralkyl group; a heteroarylalkyl group; a lower alkylsulfonyl group; a cycloalkylsulfonyl group; an aryl group; and a heteroaryl group (the aralkyl group, the heteroarylalkyl group, the lower alkylsulfonyl group, the cycloalkylsulfonyl group, the aryl group and the heteroaryl group may be substituted with a lower alkyl group optionally substituted with a lower alkoxy group or a halogen atom, a cycloalkyl group optionally substituted with a lower alkoxy group or a halogen atom, a lower alkoxy group optionally substituted with a halogen atom (when the group has two such lower alkoxy groups, they may form, taken together, a 5- or 6-membered ring), a halogen atom, a cyano group, a hydroxyl group, an alkylsulfonyl group, a cycloalkylsulfonyl group, an aryl group, a heteroaryl group, an alkylaminocarbonyl group, an alkanoylamino group, an alkylamino group or a dialkylamino group), Substituent group γ: a lower alkyl group optionally substituted with a lower alkoxy group or a halogen atom, a lower alkoxy group optionally substituted with a halogen atom, and a halogen atom.

The compounds or its salts of above (1) acts as a histamine-H3 receptor antagonist or inverse-agonist in living bodies. Accordingly, the invention provides a histamine-H3 receptor antagonist or inverse-agonist comprising the compounds of above (1) or pharmaceutically-acceptable salts thereof.

Recent studies have shown that a histamine-H3 receptor has extremely high homeostatic activities (activities observed in the absence of an endogenous agonistic factor (e.g., histamine)) in the receptor-expressing cells/tissues or in a membrane fraction derived from the expressing cells/tissues and even in living bodies (for example, see Nature, Vol. 408, p. 860). It is reported that these homeostatic activities are inhibited by an inverse-agonist. For example, thioperamide or syproxyfan inhibits the homeostatic self-receptor activity of a histamine-H3 receptor, and, as a result, promotes the release of neurotransmitters (e.g., histamine) from nerve ending.

Regarding rats, a high-level selective inhibitor of histamine synthase (histidine decarboxylase) inhibits the vigilance of rats, and therefore histamine participates in controlling motive vigilance. Regarding cats, administration of a histamine-H3 receptor agonist, (R)-(α)-methylhistamine to cats increases their deep slow-wave sleep (for example, see Brain Research, Vol. 523, p. 325 (1990)).

Contrary to this, a histamine-H3 receptor antagonist or inverse-agonist, thioperamide dose-dependently increases vigilance, and decreases slow-wave and REM sleep (for example, see Life Science, Vol. 48, p. 2397 (1991)). A histamine-H3 receptor antagonist or inverse-agonist, thioperamide or GT-2331 reduces emotional cataplexy and sleep of narcoleptic dogs (for example, see Brain Research, Vol. 793, p. 279 (1998)).

These informations suggest that the H3 receptor may participate in control of vigilance-sleep and in sleep disorder-associated diseases, further suggesting a possibility that a selective histamine-H3 agonist, antagonist or inverse-agonist may be useful for treatment of sleep disorders or various sleep disorder-associated diseases (for example, idiopathic hypersomnnia, repetitive hypersomnnia, true hypersomnnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia, true insomnia, depression, anxiety, schizophrenia). Accordingly, it may be considered that the compounds of above (1) or its salts acting as a histamine-H3 receptor antagonist or inverse-agonist may be effective for prevention and remedy of sleep disorders and various sleep disorder-associated diseases.

In rats, a histamine-H3 receptor antagonist or inverse-agonist, thioperamide or GT-2331 relieves the condition of learning disorder (LD) and attention deficit hyperactivity disorder (ADHD) (for example, see Life Science, Vol. 69, p. 469 (2001)). Further in rats, a histamine-H3 receptor agonist, (R)-(α)-methylhistamine lowers their object cognitive and learning effects in the object cognition test and the passive turnout test with them.

On the other hand, in a scopolamine-induced amnesia test, a histamine-H3 receptor antagonist or inverse-agonist, thioperamide dose-dependently relieves amnesia induced by the chemical (for example, see Pharmacology, Biochemistry and Behavior, Vol. 68, p. 735 (2001)).

These informations suggest a possibility that a histamine-H3 receptor antagonist or inverse-agonist may be useful for prevention or remedy of memory/learning disorder and various diseases accompanied by it (e.g., Alzheimer's disease, Parkinson's disease, attention deficit/hyperactivity disorder). Accordingly, it may also be considered that the compounds of above (1) or it salts may be effective for prevention or remedy of such memory/learning disorder and various diseases accompanied by it.

Regarding rats, administration of histamine to their ventricle inhibits their eating behavior, therefore suggesting that histamine may participate in control of eating behavior (for example, see Journal of Physiology and Pharmacology, Vol. 49, p. 191 (1998)). In fact, a histamine-H3 receptor antagonist or inverse-agonist, thioperamide dose-dependently inhibits eating behavior and promotes intracerebral histamine release (for example, see Behavioral Brain Research, Vol. 104, p. 147 (1999)).

These informations suggest that a histamine-H3 receptor may participate in eating behavior control, further suggesting that a histamine-H3 antagonist or inverse-agonist may be useful for prevention or remedy of metabolic system diseases (metabolic syndromes) such as eating disorder, obesity, diabetes, emaciation, hyperlipemia. Accordingly, it may be considered that the compounds of above (1) or its salts may be effective also for prevention or remedy of such metabolic system diseases.

In rats, a histamine-H3 receptor agonist, (R)-(α)-methylhistamine dose-dependently lowers their basal diastolic pressure, and this action is antagonized by a histamine-H3 receptor antagonist or inverse-agonist, thioperamide (for example, see European Journal of Pharmacology, Vol. 234, p. 129, (1993)).

These informations suggest that a histamine-H3 receptor may participate in control of blood pressure, heart beat and cardiac output, further suggesting that a histamine-H3 receptor agonist, antagonist or inverse-agonist may be useful for prevention or remedy of circulatory system diseases such as hypertension and various cardiac disorders. Accordingly, it may be considered that the compounds of above (1) or its salts may be effective also for prevention or remedy of such circulatory system diseases.

In mice, a histamine-H3 receptor antagonist or inverse-agonist, thioperamide dose-dependently inhibits the spasm induced by electric shock or the epileptoid seizure induced by pentylene tetrazole (PTZ) (for example, see European Journal of Pharmacology, Vol. 234, p. 129 (1993) and Pharmacology, Biochemistry and Behavior, Vol. 68, p. 735 (2001)).

These informations suggest that a histamine-H3 receptor antagonist or inverse-agonist may be useful for prevention or remedy of epilepsy or central spasm. Accordingly, it may be considered that the compounds of above (1) or its salts may be effective also for prevention or remedy of such epilepsy or central spasm.

Accordingly, the invention further provides a preventive or remedy for metabolic system diseases, circulatory system diseases or nervous system diseases, which contains, as the active ingredient thereof, the compounds of above (1) or pharmaceutically-acceptable salts thereof.

The metabolic system diseases are at least one selected from obesity, diabetes, hormone secretion disorder, hyperlipemia, gout and fatty liver.

The circulatory system diseases are at least one selected from stenocardia, acute/congestive cardiac insufficiency, cardiac infarction, coronary arteriosclerosis, hypertension, nephropathy and electrolyte disorder.

The nervous system diseases are at least one selected from sleep disorder, diseases accompanied by sleep disorder, bulimia, emotional disorder, epilepsy, delirium, dementia, attention deficit/hyperactivity disorder, memory disorder, Alzheimer's disease, Parkinson's disease, cognition disorder, motion disorder, paresthesia, dysosmia, morphine resistance, drug dependency, alcoholism and tremor.

The nervous system diseases are at least one selected from idiopathic hypersomnnia, repetitive hypersomnnia, true hypersomnnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia, true insomnia, depression, anxiety, schizophrenia.

The compounds of above (1) or pharmaceutically-acceptable salts thereof may be used, as combined with co-drugs. Accordingly, the invention further provides a preventive or remedy for metabolic system diseases, circulator system diseases or nervous system diseases, which contains the compounds of above (1) or pharmaceutically-acceptable salts thereof and a co-drug, as the active ingredients thereof. The co-drug includes a remedy for diabetes, a remedy for hyperlipemia, a remedy for hypertension, an anti-obesity drug. Two or more such co-drugs may be used herein, as combined.

The preventive or remedy for metabolic system diseases, circulator system diseases or nervous system diseases, which the invention provides herein, may comprise the following (i), (ii) and (iii):
(i) a compound or pharmaceutically-acceptable salt thereof of any of above (1);
(ii) at least one selected from a group of the following (a) to (g):
(a) a histamine-H3 receptor antagonist or inverse-agonist except (i);
(b) a biguanide,
(c) a PPAR (peroxisome proliferator-activated receptor)-agonist;
(d) insulin,
(e) somatostatin,
(f) an α-glucosidase inhibitor,
(g) an insulin secretion promoter;
(iii) a pharmaceutically-acceptable carrier.

The invention provides a substance having an effect of inhibiting histamine from binding to a histamine-H3 receptor or having an activity of inhibiting the homeostatic activity that a histamine-H3 receptor has, or that is, a substance capable of effectively functioning as an antagonist or an inverse-agonist to a histamine-H3 receptor when taken in living bodies.

BEST MODE FOR CARRYING OUT THE INVENTION

The meanings of the terms used in this description are described first, and then the compounds of the invention are described.

"Aryl group" includes a hydrocarbon-ring aryl group having from 6 to 14 carbon atoms, for example, a phenyl group, a naphthyl group, a biphenyl group, an anthryl group et al.

"Lower alkyl group" means a linear or branched alkyl group having from 1 to 6 carbon atoms, including, for example, a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-2-methylpropyl group et al.

"Cycloalkyl group" means a cycloalkyl group having from 3 to 9 carbon atoms, concretely including, for example, a cyclopropyl group, a cyclobutyl group, a cyclopentyl group, a cyclohexyl group, a cycloheptyl group, a cyclooctyl group, a cyclononyl group et al.

"Lower alkoxy group" means a hydroxyl group of which the hydrogen atom is substituted with the above-mentioned lower alkyl group, including, for example, a methoxy group, an ethoxy group, a propoxy group, an isopropoxy group, a butoxy group, a sec-butoxy group, a tert-butoxy group, a pentyloxy group, an isopentyloxy group, a hexyloxy group, an isohexyloxy group et al.

"Lower alkylsulfonyl group" means a sulfonyl group to which the above-mentioned alkyl group bonds, including a methylsulfonyl group, an ethylsulfonyl group, a propylsulfonyl group, an isopropylsulfonyl group, a butylsulfonyl group et al.

"Cycloalkylsulfonyl group" means a sulfonyl group to which the above-mentioned "cycloalkyl group" bonds, including, for example, a cyclopropylsulfonyl group, a cyclobutylsulfonyl group, a cyclopentylsulfonyl group, a cyclohexylsulfonyl group, a cycloheptylsulfonyl group, a cyclooctylsulfonyl group, a cyclononylsulfonyl group et al.

"Aralkyl group" means the above-mentioned lower alkyl group having the above-mentioned aryl group, including, for example, a benzyl group, a 1-phenylethyl group, a 2-phenylethyl group, a 1-naphthylmethyl group, a 2-naphthylmethyl group et al.

"Heteroaryl group" means a 5- to 7-membered monocyclic ring having from 1 to 3 hetero atoms selected from an oxygen atom, a sulfur atom and a nitrogen atom, or a bicyclic ring of the monocyclic ring condensed with a benzene ring or a pyridine ring, including, for example, a furyl group, a thienyl group, a pyrrolyl group, an imidazolyl group, a triazolyl group, a thiazolyl group, a thiadiazolyl group, an isothiazolyl group, an oxazolyl group, an isoxazolyl group, a pyridyl group, a pyrimidinyl group, a pyridazinyl group, a pyrazolyl group, a pyrazinyl group, a quinolyl group, an isoquinolyl group, a quinazolyl group, a quinolidinyl group, an quinoxalinyl group, a cinnolinyl group, a benzimidazolyl group, a imidazopyridyl group, a benzofuranyl group, a naphthyridinyl group, a 1,2-benzisoxazolyl group, a benzoxazolyl group, a benzothiazolyl group, an oxazolopyridyl group, a pyridothiazolyl group, an isothiazolopyridyl group, a benzothienyl group et al.

"Halogen atom" is, for example, a fluorine atom, a chlorine atom, a bromine atom or an iodine atom.

Next, the symbols used in the formula (I):

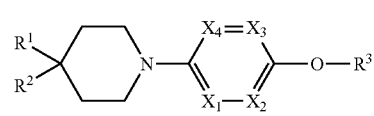

[wherein the symbols have the same meanings as above] in the invention are described.

$R^1$ is an aryl group optionally having from 1 to 3 substituents selected from the substituent group α; a 5- or 6-membered heteroaryl group having from 1 to 3 hetero atoms selected from a group consisting of a nitrogen atom, a sulfur atom and an oxygen atom, and optionally having from 1 to 3 substituents selected from the substituent group α; a heteroarylalkyl group optionally having from 1 to 3 substituents selected from the substituent group α; an aralkyl group optionally having from 1 to 3 substituents selected from the substituent group α; or an arylcarbonyl group optionally having from 1 to 3 substituents selected from the substituent group α; and the heteroaryl group may form a condensed ring with a phenyl group or a pyridyl group.

"Aryl group" for $R^1$ may be the same as those defined in the above; and of those, it includes a phenyl group, a biphenyl group and a naphthyl group et al, preferably a phenyl group.

In case where the "5- or 6-membered heteroaryl group having from 1 to 3 hetero atoms selected from a group consisting of a nitrogen atom, a sulfur atom and an oxygen atom, and optionally having from 1 to 3 substituents selected from the substituent group α" for $R^1$ has 2 or 3 hetero atoms in the ring thereof, they may be the same or different. The 5- or 6-membered heteroaryl group concretely includes, for example, a furyl group, a thienyl group, a pyrrolyl group, an imidazolyl group, a triazolyl group, a thiazolyl group, a thiadiazolyl group, an isothiazolyl group, an oxazolyl group, an isoxazolyl group, a pyridyl group, a pyrimidinyl group, a pyridazinyl group, a pyrazolyl group, a pyrazinyl group et al. The heteroaryl group may form a condensed ring with a phenyl group or a pyridyl group.

The heteroaryl group optionally forming a condensed ring with a phenyl group or a pyridyl group includes a benzoxazolyl group, a benzimidazolyl group, an indolyl group et al.

"Aralkyl group" for $R^1$ includes the same as those of the above-defined aralkyl group, concretely, for example, a benzyl group, a phenylethyl group et al.

"Arylcarbonyl group" for $R^1$ means a carbonyl group to which the above-defined "aryl group" bonds, concretely including, for example, a phenylcarbonyl group et al.

$R^1$ may have from 1 to 3 substituents selected from the substituent group α.

In case where $R^1$ has 2 or 3 substituents selected from the substituent group α, they may be the same or different.

"Lower alkyl group optionally substituted with a halogen atom" for the substituent means the same group as the above-defined lower alkyl group, or means the above-defined lower alkyl group substituted with from 1 to 3 halogen atoms. Concretely, it includes, for example, a methyl group, an ethyl group, a propyl group, an isopropyl group, a trifluoromethyl group, a difluoromethyl group, a fluoromethyl group et al.

"Lower alkoxy group optionally substituted with a halogen atom" for the substituent means the same group as the above-defined lower alkoxy group, or means the above-defined "lower alkoxy group" in which the hydrogen atoms are substituted with from 1 to 3, the same or different halogen atoms. Concretely, it includes, for example, a methoxy group, an ethoxy group, a trifluoromethoxy group et al.

"Halogen atom" for the substituent includes the same as those of the above-defined "halogen atom", concretely including, for example, a fluorine atom, a chlorine atom, a bromine atom.

As in the above, $R^1$ optionally having from 1 to 3 substituents selected from the substituent group α concretely includes, for example, a phenyl group, a 2-fluorophenyl group, a 3-fluorophenyl group, a 4-fluorophenyl group, a 2-chlorophenyl group, a 3-chlorophenyl group, a 4-chlorophenyl group, a 2,4-difluorophenyl group, a 3,4-difluorophenyl group, a 2-methylphenyl group, a 3-methylphenyl group, a 4-methylphenyl group, a 2-methoxyphenyl group, a 3-methoxyphenyl group, a 4-methoxyphenyl group, a 3-methoxy-2-pyridyl group, a 3-fluoro-4-pyridyl group, a 3-fluoro-2-pyridyl group, a 4-fluoro-3-pyridyl group, a 4-trifluoromethyl-3-pyridyl group, a 4-methoxy-3-pyridyl group, a 4-methyl-3-pyridyl group, a 6-chloro-2-pyridyl group, a 5-chloro-2-pyridyl group, a 4-chloro-2-pyridyl group, a 4-chloro-3-pyridyl group, a 5-chloro-3-pyridyl group, a 2-chloro-4-pyridyl group, a 3-chloro-4-pyridyl group, a 2-pyridyl group, a 3-pyridyl group, a 4-pyridyl group, a benzyl group, a 2-pyridylmethyl group, a 3-pyridylmethyl group, a 4-pyridylmethyl group, a phenylcarbonyl group et al.

$R^1$ is preferably an aryl group optionally having from 1 to 3 substituents selected from the substituent group α, or a 5- or 6-membered heteroaryl group having from 1 to 3 hetero atoms selected from a group consisting of a nitrogen atom, a sulfur atom and an oxygen atom and optionally having from 1 to 3 substituents selected from the substituent group α.

$R^2$ represents an aryl group; a heteroaryl group having from 1 to 3 hetero atoms selected from a group consisting of a nitrogen atom, a sulfur atom and an oxygen atom; a cyano group; a lower alkyl group; a lower alkoxy group; or a hydroxy group.

"Aryl group" for $R^2$ includes the same group as those of the above-defined aryl group, and is preferably a phenyl group.

"Heteroaryl group having from 1 to 3 hetero atoms selected from a group consisting of a nitrogen atom, a sulfur atom and an oxygen atom" for $R^2$ means the same group as the "heteroaryl group having from 1 to 3 hetero atoms selected from a group consisting of a nitrogen atom, a sulfur atom and an oxygen atom" for the above-mentioned $R^1$, and concretely includes, for example, a furyl group, a thienyl group, a pyrrolyl group, an imidazolyl group, a triazolyl group, a thiazolyl group, a thiadiazolyl group, an isothiazolyl group, an oxazolyl group, an isoxazolyl group, a pyridyl group, a pyrimidinyl group, a pyridazinyl group, a pyrazolyl group, a pyrazinyl group et al.

"Lower alkyl group" and "lower alkoxy group" for $R^2$ have the same meanings as above.

$R^2$ is preferably an aryl group; a heteroaryl group having from 1 to 3 hetero atoms selected from a group consisting of a nitrogen atom, a sulfur atom and an oxygen atom; a cyano group; a lower alkyl group; or a hydroxy group et al.

$R^1$ and $R^2$, taken together, may form a 5- or 6-membered aliphatic heterocyclic group having from 1 to 3 hetero atoms selected from a group consisting of a nitrogen atom, a sulfur atom and an oxygen atom, the aliphatic heterocyclic group may further form a condensed ring with a phenyl group or a pyridyl group, and the aliphatic heterocyclic group may have 1 or 2, the same or different substituents selected from the substituent group β, the phenyl group or the pyridyl group that may be condensed with the aliphatic heterocyclic group to form a condensed ring may have 1 or 2, the same or different substituents selected from the substituent group γ.

"5- or 6-membered aliphatic heterocyclic group" to be formed by $R^1$ and $R^2$ taken together means a 5- or 6-membered aliphatic heterocyclic group in which from 1 to 3 constitutive atoms are hetero atoms selected from a group consisting of a nitrogen atom, a sulfur atom and an oxygen atom.

In case where the 5- or 6-membered heterocyclic group has 2 or 3 such hetero atoms in the ring thereof, they may be the same or different.

In case where $R^1$ and $R^2$, taken together, form a 5- or 6-membered aliphatic heterocyclic group having from 1 to 3 hetero atoms selected from a group consisting of a nitrogen atom, a sulfur atom and an oxygen atom, it may have 1 or 2, the same or different substituents selected from the above-mentioned substituent group β.

The lower alkyl group for the substituent means the same group as the above-defined lower alkyl group, concretely including, for example, a methyl group, an ethyl group, an isopropyl group et al.

The lower alkoxy group for the substituent means the same group as the above-defined lower alkoxy group, concretely including, for example, a methoxy group, an ethoxy group, an isopropyloxy group et al.

These lower alkyl group and lower alkoxy group may be substituted with a halogen atom or a lower alkoxy group.

The aralkyl group for the substituent means the same group as the above-defined aralkyl group, concretely including, for example, a benzyl group, a phenylethyl group et al.

The heteroarylalkyl group for the substituent means a lower alkyl group to which the above-defined heteroaryl group bonds, concretely including, for example, a pyridylmethyl group et al.

The lower alkylsulfonyl group for the substituent means the same group as the above-defined lower alkylsulfonyl group, concretely including, for example, a methylsulfonyl group, an ethylsulfonyl group, an isopropylsulfonyl group et al.

The cycloalkylsulfonyl group for the substituent means the same group as the above-defined cycloalkylsulfonyl group, concretely including, for example, a cyclopropylsulfonyl group, a cyclobutylsulfonyl group, a cyclopentylsulfonyl group et al.

The aryl group for the substituent means the same group as the above-defined aryl group, concretely including, for example, a phenyl group et al.

The heteroaryl group for the substituent means the same group as the above-defined heteroaryl group, concretely including, for example, a pyridyl group, a pyrimidinyl group, a thienyl group, a thiazolyl group et al.

The aralkyl group, the heteroarylalkyl group, the lower alkylsulfonyl group, the cycloalkylsulfonyl group, the aryl group and the heteroaryl group for the substituent may be substituted with a lower alkyl group, a cycloalkyl group (the lower alkyl group and the cycloalkyl group may be substituted with a lower alkoxy group or a halogen atom, and when the group has two alkoxy groups, then they may form, taken together, a 5- or 6-membered ring), a halogen atom, a cyano group, a hydroxy group, an alkylsulfonyl group, a cycloalkylsulfonyl group, an aryl group, a heteroaryl group, an alkylaminocarbonyl group, an alkanoylamino group, an alkylamino group, a dialkylamino group.

The 5- or 6-membered aliphatic heterocyclic group includes a group of the following formula (III):

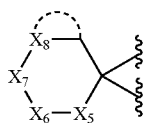

[wherein $X_5$ represents an oxygen atom or a single bond; $X_6$ represents a carbon atom or an oxygen atom; $X_7$ represents a carbon atom or a nitrogen atom; $X_8$ represents a carbon atom or a nitrogen atom; when $X_8$ is a carbon atom, then the group may be condensed with a phenyl group or a pyridyl group to form a condensed ring at the site between $X_8$ and the carbon atom adjacent to $X_8$].

The group of formula (III) concretely includes, for example, groups of a formula (II-1):

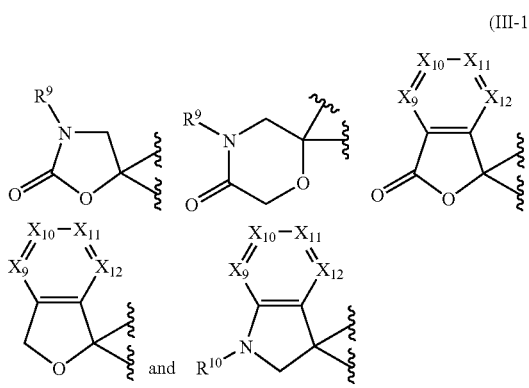

[wherein
$R^9$ represents
1) a lower alkyl group optionally substituted with a halogen atom or a lower alkoxy group,
2) an aryl group,
3) an aralkyl group,
4) a heteroarylalkyl group, or
5) a heteroaryl group, in which the aryl, aralkyl, heteroarylalkyl and heteroaryl groups may be substituted with a halogen atom, a lower alkyl group optionally substituted with a lower alkoxy group or from 1 to 3 halogen atoms, a lower alkoxy group optionally substituted with from 1 to 3 halogen atoms, a cyano group, a hydroxy group, an alkylsulfonyl group, a cycloalkylsulfonyl group, an aryl group, a heteroaryl group, an alkylaminocarbonyl group, an alkanoylamino group, an alkylamino group or a dialkylamino group;
$R^{10}$ represents a lower alkyl group optionally substituted with from 1 to 3 halogen atoms, or a lower alkylsulfonyl group;
$X_9$ to $X_{12}$ represent a carbon atom or a nitrogen atom, in which the carbon atom may be independently substituted with a lower alkyl group optionally substituted with a halogen atom or a lower alkoxy group, a cycloalkyl group optionally substituted with a halogen atom or a lower alkoxy group, a lower alkoxy group optionally substituted with a halogen atom or a lower alkoxy group, or a cyano group or a halogen atom].

The aralkyl group for $R^9$ means the same group as the above-defined group, concretely including, for example, a benzyl group, a phenylethyl group et al.

The heteroarylalkyl group for $R^9$ means a lower alkyl group to which the above-defined heteroaryl group bonds, concretely including, for example, a pyridylmethyl group et al.

In case where $R^9$ is an aryl group, an aralkyl group or a heteroarylalkyl group, then these groups may be substituted with a halogen atom, a lower alkyl group (the lower alkyl group may be substituted with from 1 to 3 halogen atoms), or a lower alkoxy group (the lower alkoxy group may be substituted with from 1 to 3 halogen atoms).

The halogen atom for the substituent means the same group as the above-defined halogen atom, concretely including, for example, a fluorine atom, a chlorine atom, a bromine atom.

The lower alkyl group for the substituent means the same group as the above-defined lower alkyl group, concretely including, for example, a methyl group, an ethyl group, an isopropyl group et al.

The lower alkyl group substituted with a lower alkoxy group for the substituent concretely includes, for example, a methoxymethyl group, an ethoxymethyl group, a methoxyethyl group et al.

The lower alkyl group substituted with from 1 to 3 halogen atoms for the substituent concretely includes, for example, a fluoromethyl group, a difluoromethyl group, a trifluoromethyl group et al.

The lower alkoxy group for the substituent indicates the same group as the above-defined lower alkoxy group, concretely including, for example, a methoxy group, an ethoxy group, an isopropyloxy group et al.

The lower alkoxy group substituted with a halogen atom for $R^{10}$ includes a trifluoromethoxy group, a difluoromethoxy group, a fluoromethoxy group, a 2-fluoroethoxy group, a 2,2-difluoroethoxy group, a 2,2,2-trifluoroethoxy group et al.

The lower alkylsulfonyl group includes a methylsulfonyl group, an ethylsulfonyl group, an n-propylsulfonyl group et al.

$X_9$ to $X_{12}$ represent a carbon atom or a nitrogen atom, in which the carbon atom may be independently substituted with a lower alkyl group optionally substituted with a lower alkoxy group or a halogen atom, a lower alkoxy group optionally substituted with a halogen atom, or a cyano group or a halogen atom.

The lower alkyl group for the substituent for the carbon atom for $X_9$ to $X_{12}$ means the same group as the above-defined group, concretely including, for example, a methyl group, an ethyl group, an isopropyl group et al. The lower alkyl group may be substituted with a lower alkoxy group or a halogen atom.

The lower alkyl group substituted with a lower alkoxy group for the substituent concretely includes, for example, a methoxymethyl group, an ethoxymethyl group, a methoxyethyl group et al.

The lower alkyl group substituted with a halogen atom for the substituent concretely includes, for example, a fluoromethyl group, a difluoromethyl group, a trifluoromethyl group et al.

As in the above, a formula (V):

in the formula (I) in which $R^1$ and $R^2$, taken together, form a 5- or 6-membered aliphatic heterocyclic group having from 1 to 3 hetero atoms selected from a group consisting of a nitrogen atom, a sulfur atom and an oxygen atom (the aliphatic heterocyclic group may have 1 or 2, the same or different substituents selected from the above-mentioned substituent group P) concretely includes, for example, the following:

3-phenyl-1-oxa-3,8-diazaspiro[4,5]decan-2-one,
3-(pyridin-2-yl)-1-oxa-3,8-diazaspiro[4,5]decan-2-one,
3-(pyridin-4-yl)-1-oxa-3,8-diazaspiro[4,5]decan-2-one,
4-(pyridin-4-yl)-1-oxa-4,9-diazaspiro[5,5]undecan-3-one,
4-(pyridin-2-yl)-1-oxa-4,9-diazaspiro[5,5]undecan-3-one,
3-(4-fluorophenyl)-1-oxa-3,8-diazaspiro[4,5]decan-2-one,
3-(6-fluoropyridin-3-yl)-1-oxa-3,8-diazaspiro[4,5]decan-2-one,
3-(6-trifluoromethyl-pyridin-3-yl)-1-oxa-3,8-diazaspiro[4,5]decan-2-one,
3-(2-fluorophenyl)-1-oxa-3,8-diazaspiro[4,5]decan-2-one,
3-(2-fluoropyridin-4-yl)-1-oxa-3,8-diazaspiro[4,5]decan-2-one,
3-(6-difluoromethyl-pyridin-3-yl)-1-oxa-3,8-diazaspiro[4,5]decan-2-one,
3-(5-fluoropyridin-2-yl)-1-oxa-3,8-diazaspiro[4,5]decan-2-one,
3-(6-fluoropyridin-2-yl)-1-oxa-3,8-diazaspiro[4,5]decan-2-one,
3-(3-fluorophenyl)-1-oxa-3,8-diazaspiro[4,5]decan-2-one,
3-(4-methoxyphenyl)-1-oxa-3,8-diazaspiro[4,5]decan-2-one,
3-(3-methoxyphenyl)-1-oxa-3,8-diazaspiro[4,5]decan-2-one,
3-(2-methoxyphenyl)-1-oxa-3,8-diazaspiro[4,5]decan-2-one,
3-(6-methoxypyridin-3-yl)-1-oxa-3,8-diazaspiro[4,5]decan-2-one,
3-(6-methylpyridin-3-yl)-1-oxa-3,8-diazaspiro[4,5]decan-2-one,
3-(4-trifluoromethoxyphenyl)-1-oxa-3,8-diazaspiro[4,5]decan-2-one,
4-(4-fluorophenyl)-1-oxa-4,9-diazaspiro[5,5]undecan-3-one,
4-(3-fluorophenyl)-1-oxa-4,9-diazaspiro[5,5]undecan-3-one,
4-(2-fluorophenyl)-1-oxa-4,9-diazaspiro[5,5]undecan-3-one,
4-(2-fluoropyridin-4-yl)-1-oxa-4,9-diazaspiro[5,5]undecan-3-one,
4-ethyl-1-oxa-4,9-diazaspiro[5,5]undecan-3-one,
4-phenyl-1-oxa-4,9-diazaspiro[5,5]undecan-3-one,
4-methyl-1-oxa-4,9-diazaspiro[5,5]undecan-3-one,
4-(6-fluoropyridin-3-yl)-1-oxa-4,9-diazaspiro[5,5]undecan-3-one,
4-(4-methoxyphenyl)-1-oxa-4,9-diazaspiro[5,5]undecan-3-one,
4-(3-methoxyphenyl)-1-oxa-4,9-diazaspiro[5,5]undecan-3-one,
3-(4-hydroxyphenyl)-1-oxa-3,8-diazaspiro[4,5]decan-2-one,
4-(6-methoxypyridin-3-yl)-1-oxa-4,9-diazaspiro[5,5]undecan-3-one,
4-(6-methoxypyridin-2-yl)-1-oxa-4,9-diazaspiro[5,5]undecan-3-one,
4-(4-methylphenyl)-1-oxa-4,9-diazaspiro[5,5]undecan-3-one,
4-(6-methylpyridin-3-yl)-1-oxa-4,9-diazaspiro[5,5]undecan-3-one,
4-(3,4-difluorophenyl)-1-oxa-4,9-diazaspiro[5,5]undecan-3-one,
4-(2,4-difluorophenyl)-1-oxa-4,9-diazaspiro[5,5]undecan-3-one,
4-pyrazin-2-yl-1-oxa-4,9-diazaspiro[5,5]undecan-3-one,
4-(3-methoxypyridin-2-yl)-1-oxa-4,9-diazaspiro[5,5]undecan-3-one,
4-(5-methoxypyridin-2-yl)-1-oxa-4,9-diazaspiro[5,5]undecan-3-one,
4-(1-ethyl-3-methyl-2-oxo-1,2-dihydropyridin-4-yl)-1-oxa-4,9-diazaspiro[5,5]undecan-3-one,
4-(1-ethyl-3-methoxy-2-oxo-1,2-dihydropyridin-4-yl)-1-oxa-4,9-diazaspiro[5,5]undecan-3-one,
4-(5-fluoropyridin-2-yl)-1-oxa-4,9-diazaspiro[5,5]undecan-3-one,
5-(3-oxo-1-oxa-4,9-diazaspiro[5,5]undecan-4-yl)nicotinonitrile,
4-(3-methylpyridin-2-yl)-1-oxa-4,9-diazaspiro[5,5]undecan-3-one,
4-[1-(difluoromethyl)-6-oxo-1,6-dihydropyridin-3-yl]-1-oxa-4,9-diazaspiro[5,5]undecan-3-one,
4-(1-isopropyl-6-oxo-1,6-dihydropyridin-3-yl)-1-oxa-4,9-diazaspiro[5,5]undecan-3-one,
4-(1-ethyl-6-oxo-1,6-dihydropyridin-3-yl)-1-oxa-4,9-diazaspiro[5,5]undecan-3-one,
4-benzyl-1-oxa-4,9-diazaspiro[5,5]undecan-3-one,
4-[6-(trifluoromethyl)pyridin-3-yl]-1-oxa-4,9-diazaspiro[5,5]undecan-3-one,
4-(6-isopropylpyridin-3-yl)-1-oxa-4,9-diazaspiro[5,5]undecan-3-one,
4-(2-ethoxypyrimidin-5-yl)-1-oxa-4,9-diazaspiro[5,5]undecan-3-one,
4-(2-methoxypyrimidin-5-yl)-1-oxa-4,9-diazaspiro[5,5]undecan-3-one,
4-(5-methoxypyrazin-2-yl)-1-oxa-4,9-diazaspiro[5,5]undecan-3-one,
4-[4-(trifluoro)phenyl]-1-oxa-4,9-diazaspiro[5,5]undecan-3-one,
4-(3-oxo-1-oxa-4,9-diazaspiro[5,5]undecan-4-yl)benzonitrile,
4-[4-(methylsulfonyl)phenyl]-1-oxa-4,9-diazaspiro[5,5]undecan-3-one,
4-pyridin-3-yl-1-oxa-4,9-diazaspiro[5,5]undecan-3-one,
4-[5-(trifluoromethyl)pyridin-3-yl]-1-oxa-4,9-diazaspiro[5,5]undecan-3-one,
4-(5-methoxypyridin-3-yl)-1-oxa-4,9-diazaspiro[5,5]undecan-3-one,
4-(1-methyl-1H-pyrazol-3-yl)-1-oxa-4,9-diazaspiro[5,5]undecan-3-one,
4-(1-methyl-1H-pyrazol-4-yl)-1-oxa-4,9-diazaspiro[5,5]undecan-3-one,
4-[6-difluoromethoxy)pyridin-3-yl]-1-oxa-4,9-diazaspiro[5,5]undecan-3-one,
4-(2-isopropoxypyrimidin-5-yl)-1-oxa-4,9-diazaspiro[5,5]undecan-3-one,
4-[3-trifluoromethyl)pyridin-2-yl]-1-oxa-4,9-diazaspiro[5,5]undecan-3-one,
4-isopropyl-1-oxa-4,9-diazaspiro[5,5]undecan-3-one,
4-(2,2,2-trifluoromethyl)-1-oxa-4,9-diazaspiro[5,5]undecan-3-one,
4-propyl-1-oxa-4,9-diazaspiro[5,5]undecan-3-one,
4-(1-ethylpropyl)-1-oxa-4,9-diazaspiro[5,5]undecan-3-one,
4-cyclopropyl-1-oxa-4,9-diazaspiro[5,5]undecan-3-one,
4-cyclobutyl-1-oxa-4,9-diazaspiro[5,5]undecan-3-one,
4-cyclopentyl-1-oxa-4,9-diazaspiro[5,5]undecan-3-one,
4-cyclohexyl-1-oxa-4,9-diazaspiro[5,5]undecan-3-one,
3-ethyl-1-oxa-3,8-diazaspiro[4,5]decan-2-one,
3-[4-(methylsulfonyl)phenyl]-1-oxa-3,8-diazaspiro[4,5]decan-2-one, 3-(2-ethoxypyrimidin-5-yl)-1-oxa-3,8-diazaspiro[4,5]decan-2-one,
3-(1-methyl-1H-pyrazol-3-yl)-1-oxa-3,8-diazaspiro[4,5]decan-2-one,
3-(1-methyl-1H-pyrazol-4-yl)-1-oxa-3,8-diazaspiro[4,5]decan-2-one,
5-(2-oxo-1-oxa-3,8-diazaspiro[4,5]decan-2-yl)nicotinonitrile,
3-pyrazin-2-yl-1-oxa-3,8-diazaspiro[4,5]decan-2-one,
3-(2-methoxypyrimidin-5-yl)-1-oxa-3,8-diazaspiro[4,5]decan-2-one et al.

The group of formula (III), a type of the condensed ring group which is formed by $R^1$ and $R^2$, taken together, to give a 5- or 6-membered aliphatic hetero ring having from 1 to 3 hetero atoms selected from a group consisting of a nitrogen atom, a sulfur atom and an oxygen atom, as condensed with a phenyl group or a pyridyl group (the condensed ring group may have 1 or 2, the same or different substituents selected from the above-mentioned substituent group γ) concretely includes, for example, a tetrahydrofuranyl group, an oxazolidinyl group, a morpholinyl group, a 1,3-dihydro-4-isobenzofuranyl group, a 1,3-dihydro-furo[3,4-c]pyridinyl group, a 5,7-dihydro-furo[3,4-b]pyridinyl group, a 2,3-dihydro-1H-indolyl group, a 2,3-dihydro-1H-pyrrolo[2,3-c]pyridinyl group, a 2,3-dihydro-[2,3-b]pyridinyl group, a 2,3-dihydro-1H-pyrrolo[3,2-c]pyridinyl group et al.

The aliphatic heterocyclic group may have 1 or 2 substituents selected from the above-mentioned substituent group β.

"Lower alkyl group" for the substituent means the same group as the above-defined "lower alkyl group", or means the above-defined "lower alkyl group" substituted with a halogen atom.

"5- or 6-membered heteroaryl group having, in the ring thereof, from 1 to 3 hetero atoms selected from a nitrogen atom, a sulfur atom and an oxygen atom" for the substituent concretely includes, for example, a furyl group, a thienyl group, a pyrrolyl group, an imidazolyl group, a triazolyl group, a thiazolyl group, a thiadiazolyl group, an isothiazolyl group, an oxazolyl group, an isoxazolyl group, a pyridyl group, a pyrimidinyl group, a pyridazinyl group, a pyrazolyl group, a pyrazinyl group et al.

"Lower alkyl group" for the substituent means the same group as the above-defined "lower alkyl group", or means the above-defined "lower alkyl group" substituted with 1 to 3 halogen atoms. Concretely, for example, it includes a methyl group, an ethyl group, an isopropyl group, a propyl group, a trifluoromethyl group, a difluoromethyl group, a fluoromethyl group et al.

"Lower alkylsulfonyl group" for the substituent means the same group as the above-defined "lower alkylsulfonyl group", and concretely includes, for example, a methylsulfonyl group, an ethylsulfonyl group, an isopropylsulfonyl group, a propylsulfonyl group et al.

The condensed ring group of the aliphatic heterocyclic group condensed with a phenyl group or a pyridyl group may have 1 or 2 substituents selected from the above-mentioned substituent group γ.

"Lower alkyl group" for the substituent means the same group as the above-defined "lower alkyl group", or means the above-defined "lower alkyl group" substituted with from 1 to 3 halogen atoms. Concretely, for example, it includes a methyl group, an ethyl group, an isopropyl group, a propyl group, a trifluoromethyl group, a difluoromethyl group, a fluoromethyl group et al.

"Lower alkoxy group" for the substituent means the same group as the above-defined lower alkoxy group, or means the above-defined "lower alkoxy group" in which the hydrogen atoms are substituted with from 1 to 3, the same or different halogen atoms. Concretely, it includes, for example, a methoxy group, an ethoxy group, a trifluoromethoxy group et al.

"Halogen atom" for the substituent means the same group as the above-defined halogen atom, and concretely includes, for example, a fluorine atom, a chlorine atom, a bromine atom, an iodine atom.

$R^3$ represents
a) a group of a formula (II-1):

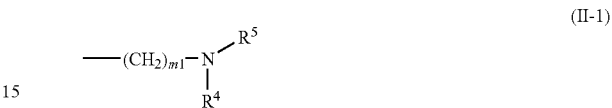

[wherein the symbols have the same meanings as above],
b) a group of a formula (II-2):

[wherein the symbols have the same meanings as above], or
c) a group of a formula (II-3):

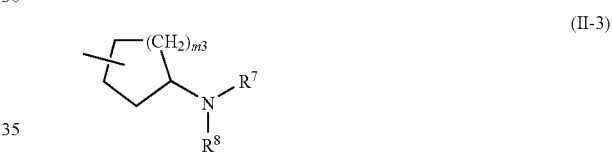

[wherein the symbols have the same meanings as above].

a) In case where $R^3$ is a group of formula (II-1),
m1 is an integer of from 2 to 4, preferably 3 or 4, more preferably 3.

$R^4$ and $R^5$ may be the same or different, each representing a lower alkyl group optionally substituted with a halogen atom, or a cycloalkyl group optionally substituted with a halogen atom; or $R^4$ and $R^5$, taken together with the nitrogen atom, form a 5- to 8-membered monocyclic ring, or 6- to 8-membered bicyclic ring, and the monocyclic ring may have, as a substituent, a lower alkyl group optionally substituted with a halogen atom, or a halogen atom or an oxo group; m1 indicates an integer of from 2 to 4; the hydrogen atom in —(CH$_2$)m1- may be substituted with a lower alkyl group having from 1 to 3 carbon atoms.

"Lower alkyl group" for $R^4$ and $R^5$ may be the same group as the above-mentioned lower alkyl group, including a methyl group, an ethyl group, a propyl group, an isopropyl group et al. The lower alkyl groups may be the same or different.

"Cycloalkyl group" for $R^4$ and $R^5$ may have the same meaning as the above-mentioned cycloalkyl group, including a cyclopropyl group, a cyclobutyl group et al.

The monocyclic ring to be formed by $R^4$ and $R^5$ taken together with the nitrogen atom includes a pyrrolidine ring, a piperidine ring, a homopiperidine ring, a heptamethylenimine ring, a piperazine ring, a morpholine ring, a homomorpholine ring.

The bicyclic ring to be formed by $R^4$ and $R^5$ taken together with the nitrogen atom is an aza-bicyclic ring, and this is a non-aromatic ring containing, as only one hetero atom to constitute the ring, the nitrogen atom adjacent to both $R^4$ and $R^5$ in the above formula (II-1). The bicyclic ring preferably has from 6 to 10 ring-constituting atoms, more preferably has from 7 to 9 ring-constituting atoms.

The bicyclic ring includes, for example, groups of a formula (VI):

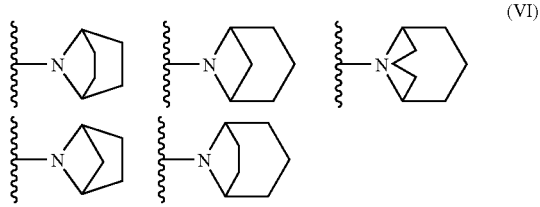

(VI)

The hydrogen atom in —(CH$_2$)m1- in the above formula (II-1) may be substituted with a lower alkyl group having from 1 to 3 carbon atoms. The lower alkyl group includes a methyl group, an ethyl group, an n-propyl group, an isopropyl group et al.

In case where $R^3$ is a group of formula (II-1), it is desirable that m 1 is 3 or 4 and $R^4$ and $R^5$, taken together with the nitrogen atom, form a 5- to 8-membered monocyclic ring (the monocyclic ring may have, as a substituent, a lower alkyl group optionally substituted with a halogen atom, or a halogen atom), or a 6- to 10-membered bicyclic ring; more preferably, m1 is 3 and $R^4$ and $R^5$, taken together with the nitrogen atom, form a 5- to 8-membered monocyclic ring (the monocyclic ring may have, as a substituent, a lower alkyl group optionally substituted with a halogen atom, or a halogen atom), or a 6- to 10-membered bicyclic ring.

b) In case where $R^3$ is a group of formula (II-2), m2 indicates an integer of from 0 to 4, but preferably 2 or 3.

$R^6$ represents a lower alkyl group or a cycloalkyl group.

"Lower alkyl group" for $R^6$ has the same meaning as that of the above-mentioned lower alkyl group, including, for example, a methyl group, an ethyl group, a propyl group, a butyl group, a pentyl group et al.

"Cycloalkyl group" for $R^6$ has the same meaning as that of the above-mentioned cycloalkyl group, including, for example, a cyclopropyl group, a cyclobutyl group, a cyclopentyl group, a cyclohexyl group et al.

In case where $R^3$ is a group of formula (II-2), two different carbon atoms of the carbon atoms constituting $R^3$ may bond to each other via —(CH$_2$)$_{m11}$— (where m11 indicates an integer of from 1 to 3) to form a bicyclic ring. The bicyclic ring includes, for example, groups of a formula (VII):

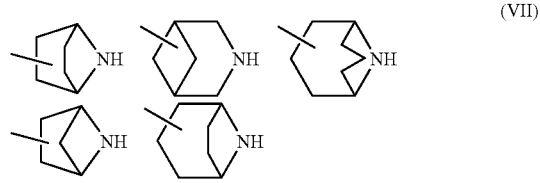

(VII)

c) In case where $R^3$ is a group of formula (II-3), m3 indicates an integer of from 0 to 4, but preferably 2 or 3.

$R^1$ and $R^8$ may be the same or different, each representing a lower alkyl group optionally substituted with a halogen atom, or a cycloalkyl group optionally substituted with a halogen atom; or $R^7$ and $R^8$, taken together with the nitrogen atom, form a 5- to 8-membered monocyclic ring, or 6- to 8-membered bicyclic ring, and the monocyclic ring may have, as a substituent, a lower alkyl group optionally substituted with a halogen atom, or a halogen atom or an oxo group.

Preferred embodiments and more preferred embodiments of $R^7$ and $R^8$ may be the same as those of $R^4$ and $R^5$.

In case where $R^3$ is a group of formula (II-3), two different carbon atoms of the carbon atoms constituting $R^3$ (but excepting the carbon atoms in $R^7$ and $R^8$) may bond to each other via a single bond or —(CH$_2$)$_{m11}$— (where m11 indicates an integer of from 1 to 3) to form a bicyclic ring. The bicyclic ring includes, for example, groups of a formula (VIII):

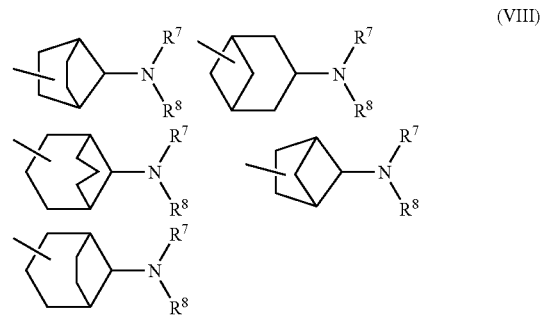

(VIII)

[wherein the symbols have the same meanings as above].

In case where $R^3$ is a bicyclic ring of the above formula (VI), preferred embodiments of $R^7$ and $R^8$ may be the same as those of $R^4$ and $R^5$.

As in the above, $R^3$ includes, for example, a 2-dimethylamino-ethyl group, a 2-diethylamino-ethyl group, a 2-di-n-propylamino-ethyl group, a 2-diisopropylamino-ethyl group, a 3-dimethylamino-propyl group, a 3-diethylamino-propyl group, a 3-di-n-propylamino-propyl group, a 3-diisopropylamino-propyl group, a 4-dimethylamino-butyl group, a 4-diethylamino-butyl group, a 4-di-n-propylamino-butyl group, a 4-diisopropylamino-butyl group, a 2-(ethylmethylamino) ethyl group, a 2-(ethylpropylamino)ethyl group, a 2-(ethylisopropylamino)ethyl group, a 2-(methylisopropylamino) ethyl group, a 2-(ethyl-n-propyl-amino)ethyl group, a 3-(ethylmethylamino)propyl group, a 3-(ethylpropylamino) propyl group, a 3-(ethylisopropylamino)propyl group, a 3-(methylisopropylamino)propyl group, a 2-(ethyl-n-propyl-amino)propyl group, a 4-(ethylmethylamino)butyl group, a 4-(ethylpropylamino)butyl group, a 4-(ethylisopropylamino) butyl group, a 2-(ethyl-n-propyl-amino)butyl group, a 2-dicyclopropylamino-ethyl group, a 2-dicyclobutylamino-ethyl group, a 2-dicyclopentylamino-ethyl group, a 2-dicyclohexylamino-ethyl group, a 3-dicyclopropylamino-propyl group, a 3-dicyclobutylamino-propyl group, a 3-dicyclopentylamino-propyl group, a 3-dicyclohexylamino-propyl group, a 4-dicyclopropylamino-butyl group, a 4-dicyclobutylamino-butyl group, a 4-dicyclopentylamino-butyl group, a 4-dicyclohexylamino-butyl group, a 2-(cyclobutyl-cyclopropylamino)ethyl group, a 2-(cyclobutyl-cyclopentyl-amino)ethyl group, a 2-(cyclohexyl-cyclopentyl)ethyl group, a 3-(cyclobutyl-cyclopropyl-amino)propyl group, a 3-(cyclobutyl-cyclopentyl-amino)propyl group, a 3-(cyclohexyl-cyclopentyl-amino) propyl group, a 4-(cyclobutyl-cyclopropyl-amino)butyl group, a 4-(cyclobutyl-cyclopentyl-amino)butyl group, a 4-cyclohexyl-cyclopentyl-amino)butyl group, a 2-cyclopropyl-methyl-amino)ethyl group, a 2-cyclopropyl-ethyl-amino)ethyl group, a 2-(cyclopropyl-n-propyl-amino)ethyl group, a 2-(cyclopropyl-isopropyl-amino)ethyl group, a 2-cyclobutyl-methyl-amino)ethyl group, a 2-(cyclobutyl-ethyl-amino)ethyl group, a 2-(cyclobutyl-n-propyl-amino) ethyl group, a 2-(cyclobutyl-isopropyl-amino)ethyl group, a 2-(cyclopentyl-methyl-amino)ethyl group, a 2-(cyclopentyl-ethyl-amino)ethyl group, a 2-(cyclopentyl-n-propyl-amino) ethyl group, a 2-(cyclopentyl-isopropyl-amino)ethyl group, a 2-(cyclohexyl-methyl-amino)ethyl group, a 2-(cyclohexyl-ethyl-amino)ethyl group, a 2-(cyclohexyl-n-propyl-amino) ethyl group, a 2-(cyclohexyl-isopropyl-amino)ethyl group, a 3-(cyclopropyl-methyl-amino)propyl group, a 3-(cyclopropyl-ethyl-amino)propyl group, a 3-(cyclopropyl-n-propyl-amino)propyl group, a 3-(cyclopropyl-isopropyl-amino)propyl group, a 3-(cyclobutyl-methyl-amino)propyl group, a 3-(cyclobutyl-ethyl-amino)propyl group, a 3-(cyclobutyl-n-propyl-amino)propyl group, a 3-(cyclobutyl-isopropyl-amino)propyl group, a 3-(cyclopentyl-methyl-amino)propyl group, a 3-(cyclopentyl-ethyl-amino)propyl group, a 3-(cyclopentyl-n-propyl-amino)propyl group, a 3-(cyclopentyl-isopropyl-amino)propyl group, a 3-(cyclohexyl-methyl-amino)propyl group, a 3-(cyclohexyl-ethyl-amino)propyl group, a 3-(cyclohexyl-n-propyl-amino)propyl group, a 3-(cyclohexyl-isopropyl-amino)propyl group, a 4-(cyclopropyl-methyl-amino)butyl group, a 4-(cyclopropyl-ethyl-amino)butyl group, a 4-(cyclopropyl-n-propyl-amino)butyl group, a 4-(cyclopropyl-isopropyl-amino)butyl group, a 4-(cyclobutyl-methyl-amino)butyl group, a 4-(cyclobutyl-ethyl-amino)butyl group, a 4-cyclobutyl-n-propyl-amino)butyl group, a 4-(cyclobutyl-isopropyl-amino)butyl group, a 4-(cyclopentyl-methyl-amino)butyl group, a 4-(cyclopentyl-ethyl-amino)butyl group, a 4-(cyclopentyl-n-propyl-amino) butyl group, a 4-(cyclopentyl-isopropyl-amino)butyl group, a 4-(cyclohexyl-methyl-amino)butyl group, a 4-(cyclohexyl-ethyl-amino)butyl group, a 4-(cyclohexyl-n-propyl-amino) butyl group, a 4-(cyclohexyl-isopropyl-amino)butyl group, a 2-pyrrolidin-1-ylethyl group, a 2-piperidin-1-ylethyl group, a 2-homopiperidin-1-ylethyl group, a 2-heptamethylenimin-1-ylethyl group, a 2-morpholin-4-ylethyl group, a 2-homomorpholin-4-ylethyl group, a 3-pyrrolidin-1-ylpropyl group, a 3-piperidin-1-ylpropyl group, a 3-homopiperidin-1-ylpropyl group, a 3-heptamethylenimin-1-ylpropyl group, a 3-morpholin-4-ylpropyl group, a 3-homomorpholin-4-ylpropyl group, a 4-pyrrolidin-1-ylbutyl group, a 4-piperidin-1-ylbutyl group, a 4-homopyrrolidin-1-ylbutyl group, a 4-heptamethylenimin-1-ylbutyl group, a 4-morpholin-4-ylbutyl group, a 4-homomorpholin-4-ylbutyl group, a 2-(5-aza-bicyclo[2.1.1]hexan-5-yl)ethyl group, a 2-(6-aza-bicyclo[3.1.1]heptan-6-yl)ethyl group, a 2-(7-aza-bicyclo[2.1.1]heptan-7-yl) ethyl group, a 2-(8-aza-bicyclo[3.2.1]octan-8-yl)ethyl group, a 2-(9-aza-bicyclo[3.3.1]nonan-9-yl)ethyl group, a 3-(5-aza-bicyclo[2.1.1]hexan-5-yl)propyl group, a 3-(6-aza-bicyclo[3.1.1]heptan-6-yl)propyl group, a 3-(7-aza-bicyclo[2.1.1] heptan-7-yl)propyl group, a 3-(8-aza-bicyclo[3.2.1]octan-8-yl)propyl group, a 3-(9-aza-bicyclo[3.3.1]nonan-9-yl)propyl group, a 4-(5-aza-bicyclo[2.1.1]hexan-5-yl)butyl group, a 4-(6-aza-bicyclo[3.1.1]heptan-6-yl)butyl group, a 4-(7-aza-bicyclo[2.1.1]heptan-7-yl)butyl group, a 4-(8-aza-bicyclo[3.2.1]octan-8-yl)butyl group, a 4-(9-aza-bicyclo[3.3.1]nonan-9-yl)butyl group, a 1-methylazetidin-3-yl group, a 1-methylazetidin-2-yl group, a 1-ethylazetidin-3-yl group, a 1-ethylazetidin-2-yl group, a 1-isopropylazetidin-3-yl group, a 1-isopropylazetitin-2-yl group, a 1-cyclopropylazetidin-3-yl group, a 1-cyclobutylazetidin-2-yl group, a 1-cyclobutylazetidin-3-yl group, a 1-cyclobutylazetidin-2-yl group, a 1-cyclopentylazetidin-3-yl group, a 1-cyclopentylazetidin-2-yl group, a 1-cyclohexylazetidin-3-yl group, a 1-cyclohexylazetidin-2-yl group, a 1-methylpyrrolidin-3-yl group, a 1-methylpyrrolidin-2-yl group, a 1-ethylpyrrolidin-3-yl group, a 1-ethylpyrrolidin-3-yl group, a 1-isopropylpyrrolidin-3-yl group, a 1-isopropyl-pyrrolidin-2-yl group, a 1-cyclopropylpyrrolidin-3-yl group, a 1-cyclopropylpyrrolidin-2-yl group, a 1-cyclopropylpyrrolidin-3-yl group, a 1-cyclobutylpyrrolidin-2-yl group, a 1-cyclopentylpyrrolidin-3-yl group, a 1-cyclopentylpyrrolidin-2-yl group, a 1-cyclopentylpyrrolidin-3-yl group, a 1-cyclohexylpyrrolidin-3-yl group, a 1-cyclohexylpyrrolidin-2-yl group, a 1-methylpiperidin-4-yl group, a 1-methylpiperidin-3-yl group, a 1-methylpiperidin-2-yl group, a 1-ethylpiperidin-4-yl group, a 1-ethylpiperidin-3-yl group, a 1-ethylpiperidin-2-yl group, a 1-isopropylpiperidin-4-yl group, a 1-isopropylpiperidin-3-yl group, a 1-isopropylpiperidin-2-yl group, a 1-cyclopropylpiperidin-4-yl group, a 1-cyclopropylpiperidin-3-yl group, a 1-cyclopropylpiperidin-2-yl group, a 1-cyclobutylpiperidin-4-yl group, a 1-cyclobutylpiperidin-3-yl group, a 1-cyclobutylpiperidin-2-yl group, a 1-cyclopentylpiperidin-4-yl group, a 1-cyclopentylpiperidin-3-yl group, a 1-cyclopentylpiperidin-2-yl group, a 1-cyclohexylpiperidin-4-yl group, a 1-cyclohexylpiperidin-3-yl group, a 1-cyclohexylpiperidin-2-yl group, a 3-dimethylaminocyclobutyl group, a 3-dimethylaminocyclobutyl group, a 3-diisopropylaminocyclobutyl group, 3-dicyclopropylaminobutyl group, a 3-dicyclobutylaminobutyl group, a 3-dicyclopentylaminobutyl group, a 3-dicyclohexylaminobutyl group, a 3-dimethylaminocyclobutyl group, a 2-diethylaminocyclobutyl group, a 2-diisopropylaminocyclobutyl group, a 2-dicyclopropylaminobutyl group, a 2-dicyclobutylaminobutyl group, a 2-dicyclopentylaminobutyl group, a 2-dicyclohexylaminobutyl group, a 3-(cyclopropyl-methylamino)cyclobutyl group, a 3-(cyclopropyl-ethyl-amino)cyclobutyl group, a 3-(cyclobutyl-methyl-amino)cyclobutyl group, a 3-(cyclobutyl-ethyl-amino)cyclobutyl group, a 3-(cyclopentyl-methyl-amino)cyclobutyl group, a 3-(cyclopentyl-ethyl-amino)cyclobutyl group, a 3-(cyclohexyl-methyl-amino)cyclobutyl group, a 2-(cyclopropyl-methyl-amino)cyclobutyl group, a 2-(cyclopropyl-ethyl-amino)cyclobutyl group, a 2-(cyclobutyl-methyl-amino)cyclobutyl group, a 2-(cyclobutyl-ethyl-amino)cyclobutyl group, a 2-(cyclopentyl-methyl-amino)cyclobutyl group, a 2-(cyclopentyl-ethyl-amino)cyclobutyl group, a 2-(cyclohexyl-methyl-amino)cyclobutyl group, a 3-pyrrolidin-1-yl-cyclobutyl group, a 2-pyrrolidin-1-yl-cyclobutyl group, a 3-pyrrolidin-1-yl-cyclopentyl group, a 2-pyrrolidin-1-yl-cyclopentyl group, a 4-pyrrolidin-1-yl-cyclohexyl group, a 3-pyrrolidin-1-yl-cyclohexyl group, a 2-pyrrolidin-1-yl-cyclohexyl group, a 3-piperidin-1-yl-cyclobutyl group, a 2-piperidin-1-yl-cyclobutyl group, a 3-piperidin-1-yl-cyclopentyl group, a 2-piperidin-1-yl-cyclopentyl group, a 4-piperidin-1-yl-cyclohexyl group, a 3-piperidin-1-yl-cyclohexyl group, a 2-piperidin-1-yl-cyclohexyl group, a 3-homopiperidin-1-yl-cyclobutyl group, a 2-homopiperidin-1-yl-cyclobutyl group, a 3-homopiperidin-1-yl-cyclopentyl group, a 2-homopiperidin-1-yl-cyclopentyl group, a 4-homopiperidin-1-yl-cyclohexyl group, a 3-homopiperidin-1-yl-cyclohexyl group, a 2-homopiperidin-1-yl-cyclohexyl group, a 3-heptamethylenimin-1-yl-cyclobutyl group, a 2-heptamethylenimin-1-yl-cyclobutyl group, a 3-heptamethylenimin-1-yl-cyclopentyl group, a 2-heptamethylenimin-1-yl-cyclopentyl group, a 4-heptamethylenimin-1-yl-cyclohexyl group, a 3-heptamethylenimin-1-yl-cyclohexyl group, a 2-heptamethylenimin-1-yl-cyclohexyl group, a 2-morpholin-4-yl-cyclobutyl group, a 3-morpholin-4-yl-cyclobutyl group, a 2-morpholin-4-yl-cyclopentyl group, a 3-morpholin-4-yl-cyclopentyl group, a 2-morpholin-4-yl-cyclohexyl group, a 3-morpholin-4-yl-cyclohexyl group, a 4-morpholin-4-yl-cyclohexyl group, 2-homomorpholin-4-yl-cyclobutyl group, a 3-homomorpholin-4-yl-cyclobutyl group, a 4-homomorpholin-4-yl-cyclobutyl group, a 2-homomorpholin-4-yl-cyclopentyl group, a 3-homomorpholin-4-yl-cyclopentyl group, a 4-homomorpholin-4-yl-cyclopentyl group, a 2-homomorpholin-4-yl-cyclohexyl group, a 3-homomorpholin-4-yl-cyclohexyl group, a 4-homomorpholin-4-yl-cyclohexyl group, a 2-(5-aza-bicyclo[2.1.1]hexan-5-yl)cyclobutyl group, a 2-(6-aza-bicyclo[3.1.1]heptan-6-yl)cyclobutyl group, a 2-(7-aza-bicyclo[2.1.1]heptan-7-yl)cyclobutyl group, a 2-(8-aza-bicyclo[3.2.1]octan-8-yl)cyclobutyl group, a 2-(9-aza-bicyclo[3.3.1-]nonan-9-yl)cyclobutyl group, a 3-(5-aza-bicyclo[2.1.1]hexan-5-yl)cyclobutyl group, a 3-(6-aza-bicyclo[3.1.1]heptan-6-yl)cyclobutyl group, a 3-(7-aza-bicyclo[2.1.1]heptan-7-yl)cyclobutyl group, a 3-(8-aza-bicyclo[3.2.1]octan-8-yl)cyclobutyl group, a 3-(9-aza-bicyclo[3.3.1]nonan-9-yl)cyclobutyl group, a 2-(5-aza-bicyclo[2.1.1]hexan-5-yl)cyclopentyl group, a 2-(6-aza-bicyclo[3.1.1]heptan-6-yl)cyclopentyl group, a 2-(7-aza-bicyclo[2.1.1]heptan-7-yl)cyclopentyl group, a 2-(8-aza-bicyclo[3.2.1]octan-8-yl)cyclopentyl group, a 2-(9-aza-bicyclo[3.3.1]nonan-9-yl)cyclopentyl group, a 3-(5-aza-bicyclo[2.1.1]hexan-5-yl)cyclopentyl group, a 3-(6-aza-bicyclo[3.1.1]heptan-6-yl)cyclopentyl group, a 3-(7-aza-bicyclo[2.1.1]heptan-7-yl)cyclopentyl group, a 3-(8-aza-bicyclo[3.2.1]octan-8-yl)cyclopentyl group, a 3-(9-aza-bicyclo[3.3.1]nonan-9-yl)cyclopentyl group, a 2-(5-aza-bicyclo[2.1.1]hexan-5-yl)cyclohexyl group, a 2-(6-aza-bicyclo[3.1.1]heptan-6-yl)cyclohexyl group, a 2-(7-aza-bicyclo[2.1.1]heptan-7-yl)cyclohexyl group, a 2-(8-aza-bicyclo[3.2.1]octan-8-yl)cyclohexyl group, a 2-(9-aza-bicyclo[3.3.1]nonan-9-yl)cyclohexyl group, a 3-(5-aza-bicyclo[2.1.1]hexan-5-yl)cyclohexyl group, a 3-(6-aza-bicyclo[3.1.1]heptan-6-yl)cyclohexyl group, a 3-(7-aza-bicyclo[2.1.1]heptan-7-yl)cyclohexyl group, a 3-(8-aza-bicyclo[3.2.1]octan-8-yl)cyclohexyl group, a 3-(9-aza-bicyclo[3.3.1]nonan-9-yl)cyclohexyl group, a 3-(7-aza-bicyclo[2.2.1]hept-7-yl)propyl group, a 3-(8-aza-bicyclo[3.2.1]oct-8-yl)propyl group, a 3-(3,3-difluoropyrrolidin-1-yl)propyl group, a 3-(3-fluoropiperidin-1-yl)propyl group, a 3-[(3R)-3-fluoropyrrolidin-1-yl]propyl group, a 3-(4,4-difluoropiperidin-1-yl)propyl group, a 3-(4-fluoropiperidin-1-yl)propyl group, a 3-(3,3-difluoropiperidin-1-yl)propyl group, a 3-[(3R)-3-methylpiperidin-1-yl]propyl group, a 3-[(2R,5R)-2,5-dimethylpyrrolidin-1-yl]propyl group, a 3-[3-methylpyrrolidin-1-yl]propyl group, a 3-[(2S)-2-methylpyrrolidin-1-yl]propyl group, a 3-[(2R)-2-methylpyrrolidin-1-yl]propyl group, a 3-[(3S)-3-methylpiperidin-1-yl]propyl group, a 3-(azepan-1-yl)propyl group, a 3-[(2-oxopyrrolidin-1-yl)]propyl group et al. Of those, preferred are a 3-piperidin-1-ylpropyl group, a 1-cyclobutylpiperidin-4-yl group, a 1-cyclopentylpiperidin-4-yl group, a 3-[(3S)-3-methylpiperidin-1-yl]propyl group, a 3-[(2R)-2-methylpyrrolidin-1-yl]propyl group, a 3-[(2S)-2-methylpyrrolidin-1-yl]propyl group, a 1-cyclopentylpiperidin-4-yl group, a 3-(pyrrolidin-1-yl)propyl group, a 3-(piperidin-1-yl)propyl group et al.

$X_1$ to $X_4$ are all carbon atoms, or 1 or 2 of $X_1$ to $X_4$ are nitrogen atoms, and the remainder are carbon atoms.

As preferable $X_1$ to $X_4$, one of $X_1$ to $X_4$ is a nitrogen atom and the remainder are carbon atoms, or they are all carbon atoms.

From the above, preferred and recommended embodiments of the compounds of the invention are the following:

1) Compounds of formula (I) where $R^1$ is an aryl group optionally having from 1 to 3 substituents selected from the substituent group α, or a 5- or 6-membered heteroaryl group having from 1 to 3 hetero atoms selected from a group consisting of a nitrogen atom, a sulfur atom and an oxygen atom and optionally having from 1 to 3 substituents selected from the substituent group α;

2) Compounds of formula (I) where $R^2$ is an aryl group, a heteroaryl group having from 1 to 3 hetero atoms selected from a group consisting of a nitrogen atom, a sulfur atom and an oxygen atom, or a cyano group, a lower alkyl group or a hydroxy group;

3) Compounds of formula (I) where $R^1$ and $R^2$, taken together, form a 5- or 6-membered aliphatic heterocyclic group having from 1 to 3 hetero atoms selected from a group consisting of a nitrogen atom, a sulfur atom and an oxygen atom;

4) Compounds of the above 3) where the 5- or 6-membered aliphatic heterocyclic group is the following:

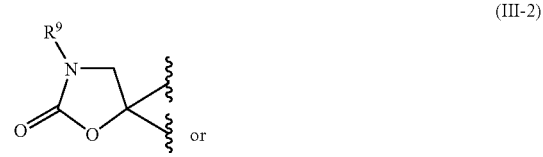

(III-2)

or

(III-3)

5) Compounds of formula (I) where $R^1$ and $R^2$, taken together, form a 5- or 6-membered aliphatic heterocyclic group having from 1 to 3 hetero atoms selected from a group consisting of a nitrogen atom, a sulfur atom and an oxygen atom, and the aliphatic heterocyclic group is further condensed with a phenyl group or a pyridyl group to form a condensed ring (the aliphatic heterocyclic group may have 1 or 2, the same or different substituents selected from the substituent group β, and the condensed ring of the aliphatic heterocyclic group with a phenyl group or a pyridyl group may have 1 or 2, the same or different substituents selected from the substituent group γ);

6) Compounds of the above 5) where the 5- or 6-membered aliphatic heterocyclic group is the following:

(III-4)

(III-5)

or

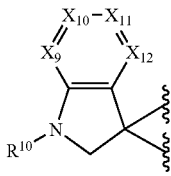

(III-6)

7) Compounds of formula (I) where $R^3$ is formula (II-1) and m1 is 3;

8) Compounds of formula (I) where $R^3$ is selected from a group consisting of a 3-piperidin-1-ylpropyl group, a 1-cyclobutylpiperidin-4-yl group, a 1-cyclopentylpiperidin-4-yl group, a 3-[(3S)-3-methylpiperidin-1-yl]propyl group, a 3-[(2R)-2-methylpyrrolidin-1-yl]propyl group, a 3-[(2S)-2-methylpyrrolidin-1-yl]propyl group, a 1-cyclopentylpiperidin-4-yl group, a 3-(pyrrolidin-1-yl)propyl group and a 3-(piperidin-1-yl)propyl group.

Concrete examples of the compounds of the invention are, for example, the following:

1'-[4-(3-piperidin-1-ylpropoxy)phenyl]-3H-spiro[2-benzofuran-1,4'-piperidine],
4-phenyl-1-[4-(3-piperidin-1-ylpropoxy)phenyl]piperidin-4-ol,
3-phenyl-8-[4-(3-piperidin-1-ylpropoxy)phenyl]-1-oxa-3,8-diazabispiro[4,5]decan-2-one,
1'-[4-(3-piperidin-1-ylpropoxy)phenyl]-3H-spiro[2-benzofuran-1,4'-piperidine]-3-one,
4-phenyl-9-[4-(3-pyrrolidin-1-ylpropoxy)phenyl]-1-oxa-4,9-diazaspiro[5,5]undecan-3-one,
9-[4-(3-((2S)-2-methylpyrrolidin-1-yl)propoxy)phenyl]-4-phenyl-1-oxa-4,9-diazaspiro[5,5]undecan-3-one,
9-[4-(3-((3S)-3-methylpiperidin-1-yl)propoxy)phenyl]-4-phenyl-1-oxa-4,9-diazaspiro[5,5]undecan-3-one,
4-(4-fluorophenyl)-1-[4-(3-piperidin-1-ylpropoxy)phenyl]piperidin-4-ol trifluoroacetate,
1-[4-(3-piperidin-1-ylpropoxy)phenyl]-4-pyridin-3-ylpiperidin-4-ol trifluoroacetate,
4-(4-methoxyphenyl)-1-[4-(3-piperidin-1-ylpropoxy)phenyl]piperidin-4-ol trifluoroacetate,
5-fluoro-1'-[4-(3-piperidin-1-ylpropoxy)phenyl]-3H-spiro[2-benzofuran-1,4'-piperidine]trifluoroacetate,
5-fluoro-1'-[4-(3-piperidin-1-ylpropoxy)phenyl]-3H-spiro[2-benzofuran-1,4'-piperidin]-3-one trifluoroacetate,
7-fluoro-1'-[4-(3-piperidin-1-ylpropoxy)phenyl]-3H-spiro[2-benzofuran-1,4'-piperidin]-3-one trifluoroacetate,
5-methoxy-1'-[4-(3-piperidin-1-ylpropoxy)phenyl]-3H-spiro[2-benzofuran-1,4'-piperidine]-3-one trifluoroacetate,
6-methoxy-1'-[4-(3-piperidin-1-ylpropoxy)phenyl]-3H-spiro[2-benzofuran-1,4'-piperidine]-3-one trifluoroacetate,
7-methoxy-1'-[4-(3-piperidin-1-ylpropoxy)phenyl]-3H-spiro[2-benzofuran-1,4'-piperidine]-3-one trifluoroacetate,
1'-[4-(3-piperidin-1-ylpropoxy)phenyl]-1H-spiro[furo[3,4-c]pyridine-3,4'-piperidin]-1-one trifluoroacetate,
1-(methylsulfonyl)-1'-[4-(3-piperidin-1-ylpropoxy)phenyl]-1,2-dihydrospiro[indole-3,4'-piperidine]trifluoroacetate,
1-(ethylsulfonyl)-7-fluoro-1'-[4-(3-piperidin-1-ylpropoxy)phenyl]-1,2-dihydrospiro[indole-3,4'-piperidine]trifluoroacetate,
1-(ethylsulfonyl)-5-fluoro-1'-[4-(3-piperidin-1-ylpropoxy)phenyl]-1,2-dihydrospiro[indole-3,4'-piperidine]trifluoroacetate,
4-tert-butoxy-1'-[4-(3-piperidin-1-ylpropoxy)phenyl]-3H-spiro[2-benzofuran-1,4'-piperidin]-3-one trifluoroacetate,
1-(ethylsulfonyl)-1'-[4-(3-piperidin-1-ylpropoxy)phenyl]-1,2-dihydrospiro[indole-3,4'-piperidine]trifluoroacetate,
3,3-dimethyl-1'-[4-(3-piperidin-1-ylpropoxy)phenyl]-3H-spiro[2-benzofuran-1,4'-piperidine]trifluoroacetate,
3-methyl-1'-[4-(3-piperidin-1-ylpropoxy)phenyl]-3H-spiro[2-benzofuran-1,4'-piperidine]trifluoroacetate,
1'-[4-(3-piperidin-1-ylpropoxy)phenyl]-3,4-dihydrospiro[chromene-2,4'-piperidine]trifluoroacetate, phenyl {1-[4-(3-piperidin-1-ylpropoxy)phenyl]piperidin-4-yl}methanone trifluoroacetate,
4-phenyl-1-[4-(3-piperidin-1-ylpropoxy)phenyl]piperidine-4-carbonitrile trifluoroacetate,
4-benzyl-1-[4-(3-piperidin-1-ylpropoxy)phenyl]piperidine-4-carbonitrile trifluoroacetate,
4-methyl-4-phenyl-1-[4-(3-piperidin-1-ylpropoxy)phenyl]piperidine trifluoroacetate,
4,4-diphenyl-1-[4-(3-piperidin-1-ylpropoxy)phenyl]piperidine trifluoroacetate,
4-(3-methoxyphenyl)-1-[4-(3-piperidin-1-ylpropoxy)phenyl]piperidin-4-ol trifluoroacetate,
4-(4-fluorophenyl)-9-[4-(3-[(3S)-3-methylpiperidin-1-yl]propoxy)phenyl]-1-oxa-4,9-diazaspiro[5,5]undecan-3-one,
4-(6-fluoropyridin-3-yl)-9-[4-{3-[(3S)-3-methylpiperidin-1-yl]propoxy}phenyl]-1-oxa-4,9-diazaspiro[5,5]undecan-3-one,
4-(methoxyphenyl)-9-[4-{3-[(3S)-3-methylpiperidin-1-yl]propoxy}phenyl]-1-oxa-4,9-diazaspiro[5,5]undecan-3-one,
4-(4-methylphenyl)-9-[4-{3-[(3S)-3-methylpiperidin-1-yl]propoxy}phenyl]-1-oxa-4,9-diazaspiro[5,5]undecan-3-one,
4-(6-methoxypyridin-3-yl)-9-[4-{3-[(3S)-3-methylpiperidin-1-yl]propoxy}phenyl]-1-oxa-4,9-diazaspiro[5,5]undecan-3-one,
9-[4-{3-[(3S)-3-methylpiperidin-1-yl]propoxy}phenyl]-4-(2-methylpyridin-5-yl)-1-oxa-4,9-diazaspiro[5,5]undecan-3-one,
4-(3,4-difluorophenyl)-9-[4-{3-[(3S)-3-methylpiperidin-1-yl]propoxy}phenyl]-1-oxa-4,9-diazaspiro[5,5]undecan-3-one,
4-(2,4-difluorophenyl)-9-[4-{3-[(3S)-3-piperidin-1-yl]propoxy}phenyl]-1-oxa-4,9-diazaspiro[5,5]undecan-3-one,
4-phenyl-9-[4-(3-piperidin-1-ylpropoxy)phenyl]-1-oxa-4,9-diazaspiro[5,5]undecan-3-one,
9-[4-(3-piperidin-1-ylpropoxy)phenyl]-4-pyridin-4-yl-1-oxa-4,9-diazaspiro[5,5]undecan-3-one,
9-[4-(3-piperidin-1-ylpropoxy)phenyl]-4-pyridin-2-yl-1-oxa-4,9-diazaspiro[5,5]undecan-3-one,
4-[6-(difluoromethoxy)pyridin-3-yl]-9-(4-{3-[(3S)-3-methylpiperidin-1-yl]propoxy}phenyl)-1-oxa-4,9-diazaspiro[5,5]undecan-3-one,
4-(6-isopropoxypyridin-3-yl)-9-(4-{3-[(3S)-3-methylpiperidin-1-yl]propoxy}phenyl)-1-oxa-4,9-diazaspiro[5,5]undecan-3-one,
4-(6-isopropoxypyridin-3-yl)-9-[4-(3-piperidin-1-ylpropoxy)phenyl]-1-oxa-4,9-diazaspiro[5,5]undecan-3-one,
4-[6-difluoromethoxy)pyridin-3-yl]-9-[4-(3-piperidin-1-ylpropoxy)phenyl]-1-oxa-4,9-diazaspiro[5,5]undecan-3-one,
4-(2-methoxypyrimidin-5-yl)-9-[4-(3-piperidin-1-ylpropoxy)phenyl]-1-oxa-4,9-diazaspiro[5,5]undecan-3-one,
4-(2-methoxypyrimidin-5-yl)-9-[4-{3-[(3S)-3-methylpiperidin-1-yl]propoxy}phenyl]-1-oxa-4,9-diazaspiro[5,5]undecan-3-one, 4-(6-methoxypyridin-3-yl)-9-[4-(3-pyrrolidin-1-ylpropoxy)phenyl]-1-oxa-4,9-diazaspiro[5,5]undecan-3-one, 4-(2-methoxypyridin-5-yl)-9-[4-{3-[(2S)-2-methylpyrrolidin-1-yl]propoxy}phenyl]-1-oxa-4,9-diazaspiro[5,5]undecan-3-one, 4-(6-methoxypyridin-3-yl)-9-(4-{3-[(2R)-2-methylpyrrolidin-1-yl]propoxy}phenyl)-1-oxa-4,9-diazaspiro[5,5]undecan-3-one, 4-(4-fluorophenyl)-9-(4-{3-[(2R)-2-methylpyrrolidin-1-yl]propoxy}phenyl)-1-oxa-4,9-diazaspiro[5,5]undecan-3-one, 4-(4-methoxyphenyl)-9-(4-{3-[(2R)-2-methylpyrrolidin-1-yl]propoxy}phenyl)-1-oxa-4,9-diazaspiro[5,5]undecan-3-one, 4-(1,3-benzodioxol-5-yl)-9-(4-{3-[(2R)-2-methylpyrrolidin-1-yl]propoxy}phenyl)-1-oxa-4,9-diazaspiro[5,5]undecan-3-one, 4-(2-methoxypyridin-4-yl)-9-(4-{3-[(3S)-3-methylpiperidin-1-yl]propoxy}phenyl)-1-oxa-4,9-diazaspiro[5,5]undecan-3-one, 4-(1-methyl-6-oxo-1,6-dihydropyridin-3-yl)-9-(4-{3-[(3S)-3-methylpiperidin-1-yl]propoxy}phenyl)-1-oxa-4,9-diazaspiro[5,5]undecan-3-one, 4-(2-methoxypyridin-4-yl)-9-[4-(3-piperidin-1-ylpropoxy)phenyl]-1-oxa-4,9-diazaspiro[5,5]undecan-3-one, 4-(1-methyl-6-oxo-1,6-dihydropyridin-3-yl)-9-[4-(3-piperidin-1-ylpropoxy)phenyl]-1-oxa-4,9-diazaspiro[5,5]undecan-3-one, 9-(4-{3-[(2R)-2-methylpyrrolidin-1-yl]propoxy}phenyl)-4-pyridin-2-yl-1-oxa-4,9-diazaspiro[5,5]undecan-3-one, 4-(5-methylpyridin-2-yl)-9-(4-{3-[(2R)-2-methylpyrrolidin-1-yl]propoxy}phenyl)-1-oxa-4,9-diazaspiro[5,5]undecan-3-one, 4-(4-methylpyridin-2-yl)-9-(4-{3-[(2R)-2-methylpyrrolidin-1-yl]propoxy}phenyl)-1-oxa-4,9-diazaspiro[5,5]undecan-3-one, 4-(3-methylpyridin-2-yl)-9-(4-{3-[(2R)-2-methylpyrrolidin-1-yl]propoxy}phenyl)-1-oxa-4,9-diazaspiro[5,5]undecan-3-one, 4-(5-methoxypyridin-2-yl)-9-(4-{3-[(2R)-2-methylpyrrolidin-1-yl]propoxy}phenyl)-1-oxa-4,9-diazaspiro[5,5]undecan-3-one, 4-(6-methoxypyridin-2-yl)-9-(4-{3-[(2R)-2-methylpyrrolidin-1-yl]propoxy}phenyl)-1-oxa-4,9-diazaspiro[5,5]undecan-3-one, 9-(4-{3-[(2R)-2-methylpyrrolidin-1-yl]propoxy}phenyl)-4-(3-thienyl)-1-oxa-4,9-diazaspiro[5,5]undecan-3-one, 9-(4-{3-[(2R)-2-methylpyrrolidin-1-yl]propoxy}phenyl)-4-(2-thienyl)-1-oxa-4,9-diazaspiro[5,5]undecan-3-one, 4-(4-methoxyphenyl)-9-[4-(3-pyrrolidin-1-ylpropoxy)phenyl]-1-oxa-4,9-diazaspiro[5,5]undecan-3-one, 4-(6-fluoropyridin-3-yl)-9-[4-(3-pyrrolidin-1-ylpropoxy)phenyl]-1-oxa-4,9-diazaspiro[5,5]undecan-3-one, 4-[6-(difluoromethoxy)pyridin-3-yl]-9-[4-(3-pyrrolidin-1-ylpropoxy)phenyl]-1-oxa-4,9-diazaspiro[5,5]undecan-3-one, 5-[9-(4-{3-[(2R)-2-methylpyrrolidin-1-yl]propoxy}phenyl)-3-oxo-1-oxa-4,9-diazaspiro[5,5]undecan-4-yl]nicotinonitrile, 9-(4-{3-[(2R)-2-methylpyrrolidin-1-yl]propoxy}phenyl)-4-(1,3-thiazol-2-yl)-1-oxa-4,9-diazaspiro[5,5]undecan-3-one, 3-(4-fluorophenyl)-8-[4-(3-piperidin-1-ylpropoxy)phenyl]-1-oxa-3,8-diazaspiro[4,5]decan-2-one, 8-[4-(3-piperidin-1-ylpropoxy)phenyl]-3-(pyridin-2-yl)-1-oxa-3,8-diazaspiro[4,5]decan-2-one, 8-[4-(3-piperidin-1-ylpropoxy)phenyl]-3-(pyridin-4-yl)-1-oxa-3,8-diazaspiro[4,5]decan-2-one, 3-(6-fluoropyridin-3-yl)-8-[4-(3-piperidin-1-ylpropoxy)phenyl]-1-oxa-3,8-diazaspiro[4,5]decan-2-one, 8-[4-(3-piperidin-1-ylpropoxy)phenyl]-3-[6-(trifluoromethyl)pyridin-3-yl]-1-oxa-3,8-diazaspiro[4,5]decan-2-one, 3-(2-fluorophenyl)-8-[4-(3-piperidin-1-ylpropoxy)phenyl]-1-oxa-3,8-diazaspiro[4,5]decan-2-one, 3-(2-fluoropyridin-4-yl)-8-[4-(3-piperidin-1-ylpropoxy)phenyl]-1-oxa-3,8-diazaspiro[4,5]decan-2-one, 3-[6-(difluoromethyl)pyridin-3-yl]-8-[4-(3-piperidin-1-ylpropoxy)phenyl]-1-oxa-3,8-diazaspiro[4,5]decan-2-one, 3-(5-fluoropyridin-2-yl)-8-[4-(3-piperidin-1-ylpropoxy)phenyl]-1-oxa-3,8-diazaspiro[4,5]decan-2-one, 3-(6-fluoropyridin-2-yl)-8-[4-(3-piperidin-1-ylpropoxy)phenyl]-1-oxa-3,8-diazaspiro[4,5]decan-2-one, 3-(3-fluorophenyl)-8-[4-(3-piperidin-1-ylpropoxy)phenyl]-1-oxa-3,8-diazaspiro[4,5]decan-2-one, 3-(4-methoxyphenyl)-8-[4-(3-piperidin-1-ylpropoxy)phenyl]-1-oxa-3,8-diazaspiro[4,5]decan-2-one, 3-(3-methoxyphenyl)-8-[4-(3-piperidin-1-ylpropoxy)phenyl]-1-oxa-3,8-diazaspiro[4,5]decan-2-one, 3-(6-methoxypyridin-3-yl)-8-[4-(3-piperidin-1-ylpropoxy)phenyl]-1-oxa-3,8-diazaspiro[4,5]decan-2-one, 3-(6-methylpyridin-3-yl)-8-[4-(3-piperidin-1-ylpropoxy)phenyl]-1-oxa-3,8-diazaspiro[4,5]decan-2-one, 3-(2-methoxyphenyl)-8-[4-(3-piperidin-1-ylpropoxy)phenyl]-1-oxa-3,8-diazaspiro[4,5]decan-2-one, 8-[4-(3-piperidin-1-ylpropoxy)phenyl]-3-[4-(trifluoromethoxy)phenyl]-1-oxa-3,8-diazaspiro[4,5]decan-2-one, 4-(1-ethyl-6-oxo-1,6-dihydropyridin-3-yl)-9-(4-{3-[(3S)-3-methylpiperidin-1-yl]propoxy}phenyl)-1-oxa-4,9-diazaspiro[5,5]undecan-3-one, 9-(4-{3-[(3S)-3-methylpiperidin-1-yl]propoxy}phenyl)-4-pyrazin-2-yl-1-oxa-4,9-diazaspiro[5,5]undecan-3-one, 9-(4-{3-[(3S)-3-methylpiperidin-1-yl]propoxy}phenyl)-4-pyridin-2-yl-1-oxa-4,9-diazaspiro[5,5]undecan-3-one, 4-(3-methoxypyridin-2-yl)-9-(4-{3-[(3S)-3-methylpiperidin-1-yl]propoxy}phenyl)-1-oxa-4,9-diazaspiro[5,5]undecan-3-one, 4-(1-ethyl-5-methyl-6-oxo-1,6-dihydropyridin-3-yl)-9-(4-{3-[(3S)-3-methylpiperidin-1-yl]propoxy}phenyl)-1-oxa-4,9-diazaspiro[5,5]undecan-3-one, 4-(1-ethyl-5-methoxy-6-oxo-1,6-dihydropyridin-3-yl)-9-(4-{3-[(3S)-3-methylpiperidin-1-yl]propoxy}phenyl)-1-oxa-4,9-diazaspiro[5,5]undecan-3-one, 4-(5-methoxypyridin-2-yl)-9-(4-{3-[(3S)-3-methylpiperidin-1-yl]propoxy}phenyl)-1-oxa-4,9-diazaspiro[5,5]undecan-3-one, 4-(5-fluoropyridin-2-yl)-9-(4-{3-[(3S)-3-methylpiperidin-1-yl]propoxy}phenyl)-1-oxa-4,9-diazaspiro[5,5]undecan-3-one, 5-[9-(4-{3-[(3S)-3-methylpiperidin-1-yl]propoxy}phenyl)-3-oxo-1-oxa-4,9-diazaspiro[5,5]undecan-4-yl]nicotinonitrile, 9-(4-{3-[(3S)-3-methylpiperidin-1-yl]propoxy}phenyl)-4-(3-methylpyridin-2-yl)-1-oxa-4,9-diazaspiro[5,5]undecan-3-one, 4-[1-(difluoromethyl)-6-oxo-1,6-dihydropyridin-3-yl]-9-(4-{3-[(3S)-3-methylpiperidin-1-yl]propoxy}phenyl)-1-oxa-4,9-diazaspiro[5,5]undecan-3-one, 4-(1-isopropyl-6-oxo-1,6-dihydropyridin-3-yl)-9-(4-{3-[(3S)-3-methylpiperidin-1-yl]propoxy}phenyl)-1-oxa-4,9-diazaspiro[5,5]undecan-3-one, 9-[4-(3-piperidin-1-ylpropoxy)phenyl]-4-pyrazin-2-yl-1-oxa-4,9-diazaspiro[5,5]undecan-3-one,
4-(3,4-difluorophenyl)-9-[4-(3-pyrrolidin-1-ylpropoxy)phenyl]-1-oxa-4,9-diazaspiro[5,5]undecan-3-one,
4-(2,4-difluorophenyl)-9-[4-(3-pyrrolidin-1-ylpropoxy)phenyl]-1-oxa-4,9-diazaspiro[5,5]undecan-3-one,
9-[4-(3-pyrrolidin-1-ylpropoxy)phenyl]-4-[6-(trifluoromethyl)pyridin-3-yl]-1-oxa-4,9-diazaspiro[5,5]undecan-3-one,
4-(6-isopropoxypyridin-3-yl)-9-[4-(3-pyrrolidin-1-ylpropoxy)phenyl]-1-oxa-4,9-diazaspiro[5,5]undecan-3-one,
4-(2-ethoxypyrimidin-5-yl)-9-[4-{3-[(2R)-2-methylpyrrolidin-1-yl]propoxy}phenyl)-1-oxa-4,9-diazaspiro[5,5]undecan-3-one,
4-(5-methoxypyrazin-2-yl)-9-[4-{3-[(2R)-2-methylpyrrolidin-1-yl]propoxy}phenyl)-1-oxa-4,9-diazaspiro[5,5]undecan-3-one,
4-(4-chlorophenyl)-9-[4-{3-[(2R)-2-methylpyrrolidin-1-yl]propoxy}phenyl)-1-oxa-4,9-diazaspiro[5,5]undecan-3-one,
9-[4-{3-[(2R)-2-methylpyrrolidin-1-yl]propoxy}phenyl)-4-[4-(trifluoromethyl)phenyl]-1-oxa-4,9-diazaspiro[5,5]undecan-3-one,
4-[9-(4-{3-[(2R)-2-methylpyrrolidin-1-yl]propoxy}phenyl)-3-oxo-1-oxa-4,9-diazaspiro[5,5]undecan-4-yl]benzonitrile,
9-(4-{3-[(2R)-2-methylpyrrolidin-1-yl]propoxy}phenyl)-4-[4-methylsulfonyl)phenyl]-1-oxa-4,9-diazaspiro[5,5]undecan-3-one,
9-(4-{3-[(2R)-2-methylpyrrolidin-1-yl]propoxy}phenyl)-4-pyrazin-2-yl-1-oxa-4,9-diazaspiro[5,5]undecan-3-one,
4-(2-methoxypyrimidin-5-yl)-9-(4-{3-[(2R)-2-methylpyrrolidin-1-yl]propoxy}phenyl)-1-oxa-4,9-diazaspiro[5,5]undecan-3-one,
4-(3-methylpyridin-2-yl)-9-(4-{3-[(2R)-2-methylpyrrolidin-1-yl]propoxy}phenyl)-1-oxa-4,9-diazaspiro[5,5]undecan-3-one,
4-(3-methoxypyridin-2-yl)-9-(4-{3-[(2R)-2-methylpyrrolidin-1-yl]propoxy}phenyl)-1-oxa-4,9-diazaspiro[5,5]undecan-3-one,
9-(4-{3-[(2R)-2-methylpyrrolidin-1-yl]propoxy}phenyl)-4-pyridin-3-yl-1-oxa-4,9-diazaspiro[5,5]undecan-3-one,
9-(4-{3-[(2R)-2-methylpyrrolidin-1-yl]propoxy}phenyl)-4-[5-(trifluoromethyl)pyridin-3-yl]-1-oxa-4,9-diazaspiro[5,5]undecan-3-one,
4-(1-methyl-1H-pyrazol-3-yl)-9-(4-{3-[(2R)-2-methylpyrrolidin-1-yl]propoxy}phenyl)-1-oxa-4,9-diazaspiro[5,5]undecan-3-one,
4-(1-methyl-1H-pyrazol-4-yl)-9-(4-{3-[(2R)-2-methylpyrrolidin-1-yl]propoxy}phenyl)-1-oxa-4,9-diazaspiro[5,5]undecan-3-one,
4-(5-methoxypyridin-3-yl)-9-(4-{3-[(2R)-2-methylpyrrolidin-1-yl]propoxy}phenyl)-1-oxa-4,9-diazaspiro[5,5]undecan-3-one,
5-[9-(4-{3-[(2R)-2-methylpyrrolidin-1-yl]propoxy}phenyl)-3-oxo-1-oxa-4,9-diazaspiro[5,5]undecan-4-yl]nicotinonitrile,
9-(4-{3-[(2S)-2-methylpyrrolidin-1-yl]propoxy}phenyl)-4-pyridin-3-yl-1-oxa-4,9-diazaspiro[5,5]undecan-3-one,
4-(2-methoxypyrimidin-5-yl)-9-(4-{3-[(2S)-2-methylpyrrolidin-1-yl]propoxy}phenyl)-1-oxa-4,9-diazaspiro[5,5]undecan-3-one,
5-[9-(4-{3-[(2S)-2-methylpyrrolidin-1-yl]propoxy}phenyl)-3-oxo-1-oxa-4,9-diazaspiro[5,5]undecan-4-yl]nicotinonitrile,
4-(5-methoxypyridin-3-yl)-9-(4-{3-[(2S)-2-methylpyrrolidin-1-yl]propoxy}phenyl)-1-oxa-4,9-diazaspiro[5,5]undecan-3-one,
4-(5-methoxypyrazin-2-yl)-9-(4-{3-[(2S)-2-methylpyrrolidin-1-yl]propoxy}phenyl)-1-oxa-4,9-diazaspiro[5,5]undecan-3-one,
4-(1-methyl-1H-pyrazol-4-yl)-9-(4-{3-[(2S)-2-methylpyrrolidin-1-yl]propoxy}phenyl)-1-oxa-4,9-diazaspiro[5,5]undecan-3-one,
3-ethyl-8-(4-{3-[(2R)-2-methylpyrrolidin-1-yl]propoxy}phenyl)-1-oxa-3,8-diazaspiro[4,5]decan-2-one,
8-(4-{3-[(2R)-2-methylpyrrolidin-1-yl]propoxy}phenyl)-3-[4-(methylsulfonyl)phenyl]-1-oxa-3,8-diazaspiro[4,5]decan-2-one,
3-(2-ethoxypyrimidin-5-yl)-8-(4-{3-[(2R)-2-methylpyrrolidin-1-yl]propoxy}phenyl)-1-oxa-3,8-diazaspiro[4,5]decan-2-one,
3-(1-methyl-1H-pyrazol-4-yl)-8-(4-{3-[(2R)-2-methylpyrrolidin-1-yl]propoxy}phenyl)-1-oxa-3,8-diazaspiro[4,5]decan-2-one,
3-(1-methyl-1H-pyrazol-3-yl)-8-(4-{3-[(2R)-2-methylpyrrolidin-1-yl]propoxy}phenyl)-1-oxa-3,8-diazaspiro[4,5]decan-2-one,
5-[8-(4-{3-[(2R)-2-methylpyrrolidin-1-yl]propoxy}phenyl)-2-oxo-1-oxa-3,8-diazaspiro[4,5]decan-3-yl]nicotinonitrile,
8-(4-{3-[(2R)-2-methylpyrrolidin-1-yl]propoxy}phenyl)-3-pyrazin-2-yl-1-oxa-3,8-diazaspiro[4,5]decan-2-one,
3-(6-methoxypyridin-3-yl)-8-(4-{3-[(2R)-2-methylpyrrolidin-1-yl]propoxy}phenyl)-1-oxa-3,8-diazaspiro[4,5]decan-2-one,
3-(2-methoxypyrimidin-5-yl)-8-(4-{3-[(2R)-2-methylpyrrolidin-1-yl]propoxy}phenyl)-1-oxa-3,8-diazaspiro[4,5]decan-2-one,
3-(5-methoxypyridin-3-yl)-8-(4-{3-[(2R)-2-methylpyrrolidin-1-yl]propoxy}phenyl)-1-oxa-3,8-diazaspiro[4,5]decan-2-one,
3-(2-methoxypyrimidin-5-yl)-8-[4-(3-piperidin-1-ylpropoxy)phenyl]-1-oxa-3,8-diazaspiro[4,5]decan-2-one,
9-{4-[(1-cyclobutylpiperidin-4-yl)oxy]phenyl}-4-(4-methoxyphenyl)-1-oxa-4,9-diazaspiro[5,5]undecan-3-one,
9-{4-[(1-cyclobutylpiperidin-4-yl)oxy]phenyl}-4-(6-methylpyridin-3-yl)-1-oxa-4,9-diazaspiro[5,5]undecan-3-one,
9-{4-[(1-cyclobutylpiperidin-4-yl)oxy]phenyl}-4-[6-(difluoromethoxy)pyridin-3-yl]-1-oxa-4,9-diazaspiro[5,5]undecan-3-one,
9-{4-[(1-cyclobutylpiperidin-4-yl)oxy]phenyl}-4-isopropyl-1-oxa-4,9-diazaspiro[5,5]undecan-3-one,
9-{4-[(1-cyclobutylpiperidin-4-yl)oxy]phenyl}-4-(6-isopropoxypyridin-3-yl)-1-oxa-4,9-diazaspiro[5,5]undecan-3-one,
9-{4-[(1-cyclobutylpiperidin-4-yl)oxy]phenyl}-4-(2-isopropoxypyrimidin-5-yl)-1-oxa-4,9-diazaspiro[5,5]undecan-3-one,
9-{4-[(1-cyclobutylpiperidin-4-yl)oxy]phenyl}-4-(1-methyl-1H-pyrazol-3-yl)-1-oxa-4,9-diazaspiro[5,5]undecan-3-one,
9-{4-[(1-cyclobutylpiperidin-4-yl)oxy]phenyl}-4-(5-methoxypyridin-3-yl)-1-oxa-4,9-diazaspiro[5,5]undecan-3-one,
9-{4-[(1-cyclobutylpiperidin-4-yl)oxy]phenyl}-4-[5-(trifluoromethyl)pyridin-3-yl]-1-oxa-4,9-diazaspiro[5,5]undecan-3-one,
9-{4-[(1-cyclobutylpiperidin-4-yl)oxy]phenyl}-4-[3-(trifluoromethyl)pyridin-2-yl]-1-oxa-4,9-diazaspiro[5,5]undecan-3-one, 9-{4-[(1-cyclobutylpiperidin-4-yl)oxy]phenyl}-4-(6-methoxypyridin-2-yl)-1-oxa-4,9-diazaspiro[5,5]undecan-3-one,
9-{4-[(1-cyclobutylpiperidin-4-yl)oxy]phenyl}-4-imidazo[1,2-a]pyridin-3-yl-1-oxa-4,9-diazaspiro[5,5]undecan-3-one,
9-{4-[(1-cyclobutylpiperidin-4-yl)oxy]phenyl}-4-[4-(methylsulfonyl)phenyl]-1-oxa-4,9-diazaspiro[5,5]undecan-3-one,
9-{4-[(1-cyclobutylpiperidin-4-yl)oxy]phenyl}-4-pyrazin-2-yl-1-oxa-4,9-diazaspiro[5,5]undecan-3-one,
9-{4-[(1-cyclobutylpiperidin-4-yl)oxy]phenyl}-4-(3-methylpyridin-2-yl)-1-oxa-4,9-diazaspiro[5,5]undecan-3-one,
9-{4-[(1-cyclobutylpiperidin-4-yl)oxy]phenyl}-4-(5-methoxypyridin-2-yl)-1-oxa-4,9-diazaspiro[5,5]undecan-3-one,
9-{4-[(1-cyclobutylpiperidin-4-yl)oxy]phenyl}-4-(4-fluorophenyl)-1-oxa-4,9-diazaspiro[5,5]undecan-3-one,
9-{4-[(1-cyclobutylpiperidin-4-yl)oxy]phenyl}-4-(1-methyl-1H-pyrazol-4-yl)-1-oxa-4,9-diazaspiro[5,5]undecan-3-one,
9-{4-[(1-cyclobutylpiperidin-4-yl)oxy]phenyl}-4-(2-methoxypyrimidin-5-yl)-1-oxa-4,9-diazaspiro[5,5]undecan-3-one,
9-{4-[(1-cyclobutylpiperidin-4-yl)oxy]phenyl}-4-(1-methyl-6-oxo-1,6-dihydropyridin-3-yl)-1-oxa-4,9-diazaspiro[5,5]undecan-3-one,
9-{4-[(1-cyclobutylpiperidin-4-yl)oxy]phenyl}-4-(2-fluoropyridin-4-yl)-1-oxa-4,9-diazaspiro[5,5]undecan-3-one,
9-{4-[(1-cyclobutylpiperidin-4-yl)oxy]phenyl}-4-(1-ethyl-6-oxo-1,6-dihydropyridin-3-yl)-1-oxa-4,9-diazaspiro[5,5]undecan-3-one,
9-{4-[(1-cyclobutylpiperidin-4-yl)oxy]phenyl}-4-(1-isopropyl-6-oxo-1,6-dihydropyridin-3-yl)-1-oxa-4,9-diazaspiro[5,5]undecan-3-one,
9-{4-[(1-cyclobutylpiperidin-4-yl)oxy]phenyl}-4-pyridin-3-yl-1-oxa-4,9-diazaspiro[5,5]undecan-3-one,
5-(9-{4-[(1-cyclobutylpiperidin-4-yl)oxy]phenyl}-3-oxo-1-oxa-4,9-diazaspiro[5,5]undecan-4-yl)nicotinonitrile,
9-{4-[(1-cyclobutylpiperidin-4-yl)oxy]phenyl}-4-(5-methoxypyrazin-2-yl)-1-oxa-4,9-diazaspiro[5,5]undecan-3-one,
4-ethyl-9-{4-[(1-isopropylpiperidin-4-yl)oxy]phenyl}-1-oxa-4,9-diazaspiro[5,5]undecan-3-one,
9-{4-[(1-isopropylpiperidin-4-yl)oxy]phenyl}-4-(2,2,2-trifluoroethyl)-1-oxa-4,9-diazaspiro[5,5]undecan-3-one,
9-{4-[(1-isopropylpiperidin-4-yl)oxy]phenyl}-4-[4-(methylsulfonyl)phenyl]-1-oxa-4,9-diazaspiro[5,5]undecan-3-one,
9-{4-[(1-isopropylpiperidin-4-yl)oxy]phenyl}-4-[5-(trifluoromethyl)pyridin-3-yl]-1-oxa-4,9-diazaspiro[5,5]undecan-3-one,
9-{4-[(1-isopropylpiperidin-4-yl)oxy]phenyl}-4-(5-methoxypyridin-3-yl)-1-oxa-4,9-diazaspiro[5,5]undecan-3-one,
9-{4-[(1-isopropylpiperidin-4-yl)oxy]phenyl}-4-pyrazin-2-yl-1-oxa-4,9-diazaspiro[5,5]undecan-3-one,
9-{4-[(1-isopropylpiperidin-4-yl)oxy]phenyl}-4-(3-methoxypyridin-2-yl)-1-oxa-4,9-diazaspiro[5,5]undecan-3-one,
9-{4-[(1-isopropylpiperidin-4-yl)oxy]phenyl}-4-(2-methoxypyrimidin-5-yl)-1-oxa-4,9-diazaspiro[5,5]undecan-3-one,
9-{4-[(1-isopropylpiperidin-4-yl)oxy]phenyl}-4-(1-methyl-1H-pyrazol-4-yl)-1-oxa-4,9-diazaspiro[5,5]undecan-3-one,
9-{4-[(1-isopropylpiperidin-4-yl)oxy]phenyl}-4-(1-methyl-1H-pyrazol-3-yl)-1-oxa-4,9-diazaspiro[5,5]undecan-3-one,
5-(9-{4-[(1-isopropylpiperidin-4-yl)oxy]phenyl}-3-oxo-1-oxa-4,9-diazaspiro[5,5]undecan-4-yl)nicotinonitrile,
4-(2-ethoxypyrimidin-5-yl)-9-{4-[(1-isopropylpiperidin-4-yl)oxy]phenyl}-1-oxa-4,9-diazaspiro[5,5]undecan-3-one,
9-{4-[(1-isopropylpiperidin-4-yl)oxy]phenyl}-4-(5-methoxypyrazin-2-yl)-1-oxa-4,9-diazaspiro[5,5]undecan-3-one,
9-{4-[(1-isopropylpiperidin-4-yl)oxy]phenyl}-4-(6-methoxypyridin-3-yl)-1-oxa-4,9-diazaspiro[5,5]undecan-3-one,
9-{6-[(1-cyclobutylpiperidin-4-yl)oxy]pyridin-3-yl}-4-(1-methyl-1H-pyrazol-3-yl)-1-oxa-4,9-diazaspiro[5,5]undecan-3-one,
9-{6-[(1-cyclobutylpiperidin-4-yl)oxy]pyridin-3-yl}-4-(1-methyl-1H-pyrazol-4-yl)-1-oxa-4,9-diazaspiro[5,5]undecan-3-one,
9-{6-[(1-cyclobutylpiperidin-4-yl)oxy]pyridin-3-yl}-4-(2-isopropoxypyrimidin-5-yl)-1-oxa-4,9-diazaspiro[5,5]undecan-3-one,
9-{6-[(1-cyclobutylpiperidin-4-yl)oxy]pyridin-3-yl}-4-pyridin-3-yl-1-oxa-4,9-diazaspiro[5,5]undecan-3-one,
5-(9-{6-[(1-cyclobutylpiperidin-4-yl)oxy]pyridin-3-yl}-3-oxo-1-oxa-4,9-diazaspiro[5,5]undecan-4-yl)nicotinonitrile,
9-{6-[(1-cyclobutylpiperidin-4-yl)oxy]pyridin-3-yl}-4-[4-(methylsulfonyl)phenyl]-1-oxa-4,9-diazaspiro[5,5]undecan-3-one,
9-{6-[(1-cyclobutylpiperidin-4-yl)oxy]pyridin-3-yl}-4-(4-methoxyphenyl)-1-oxa-4,9-diazaspiro[5,5]undecan-3-one,
9-{6-[(1-cyclobutylpiperidin-4-yl)oxy]pyridin-3-yl}-4-(6-fluoropyridin-3-yl)-1-oxa-4,9-diazaspiro[5,5]undecan-3-one,
9-{6-[(1-cyclobutylpiperidin-4-yl)oxy]pyridin-3-yl}-4-(2-fluoropyridin-4-yl)-1-oxa-4,9-diazaspiro[5,5]undecan-3-one,
9-{6-[(1-cyclobutylpiperidin-4-yl)oxy]pyridin-3-yl}-4-[6-difluoromethoxy)pyridin-3-yl]-1-oxa-4,9-diazaspiro[5,5]undecan-3-one,
9-{6-[(1-cyclobutylpiperidin-4-yl)oxy]pyridin-3-yl}-4-(4-fluorophenyl)-1-oxa-4,9-diazaspiro[5,5]undecan-3-one,
9-{6-[(1-cyclobutylpiperidin-4-yl)oxy]pyridin-3-yl}-4-(6-methoxypyridin-3-yl)-1-oxa-4,9-diazaspiro[5,5]undecan-3-one,
9-{6-[(1-cyclobutylpiperidin-4-yl)oxy]pyridin-3-yl}-4-ethyl-1-oxa-4,9-diazaspiro[5,5]undecan-3-one,
9-{6-[(1-cyclobutylpiperidin-4-yl)oxy]pyridin-3-yl}-4-(2-methoxypyrimidin-5-yl)-1-oxa-4,9-diazaspiro[5,5]undecan-3-one,
9-{6-[(1-cyclobutylpiperidin-4-yl)oxy]pyridin-3-yl}-4-(6-methylpyridin-3-yl)-1-oxa-4,9-diazaspiro[5,5]undecan-3-one,
9-{6-[(1-cyclobutylpiperidin-4-yl)oxy]pyridin-3-yl}-4-(5-methoxypyrazin-2-yl)-1-oxa-4,9-diazaspiro[5,5]undecan-3-one,
8-{4-[(1-cyclobutylpiperidin-4-yl)oxy]phenyl}-3-(6-methylpyridin-3-yl)-1-oxa-3,8-diazaspiro[4,5]decan-2-one,
5-(8-{4-[(1-cyclobutylpiperidin-4-yl)oxy]phenyl}-2-oxo-1-oxa-3,8-diazaspiro[4,5]decan-3-yl)nicotinonitrile,
8-{4-[(1-cyclobutylpiperidin-4-yl)oxy]phenyl}-3-pyridin-3-yl-1-oxa-3,8-diazaspiro[4,5]decan-2-one,
8-{4-[(1-cyclobutylpiperidin-4-yl)oxy]phenyl}-3-(1-methyl-1H-pyrazol-4-yl)-1-oxa-3,8-diazaspiro[4,5]decan-2-one, 8-{4-[(1-cyclobutylpiperidin-4-yl)oxy]phenyl}-3-(1-methyl-1H-pyrazol-3-yl)-1-oxa-3,8-diazaspiro[4,5]decan-2-one,
8-{4-[(1-cyclobutylpiperidin-4-yl)oxy]phenyl}-3-(6-methoxypyridin-3-yl)-1-oxa-3,8-diazaspiro[4,5]decan-2-one,
8-{4-[(1-cyclobutylpiperidin-4-yl)oxy]phenyl}-3-imidazo[1,2-a]pyridin-3-yl-1-oxa-3,8-diazaspiro[4,5]decan-2-one,
8-{4-[(1-cyclobutylpiperidin-4-yl)oxy]phenyl}-3-(3-methylpyridin-2-yl)-1-oxa-3,8-diazaspiro[4,5]decan-2-one,
8-{4-[(1-cyclobutylpiperidin-4-yl)oxy]phenyl}-3-(6-fluoropyridin-3-yl)-1-oxa-3,8-diazaspiro[4,5]decan-2-one,
8-{4-[(1-cyclobutylpiperidin-4-yl)oxy]phenyl}-3-[4-(methylsulfonyl)phenyl]-1-oxa-3,8-diazaspiro[4,5]decan-2-one,
8-{4-[(1-cyclobutylpiperidin-4-yl)oxy]phenyl}-3-(2-fluoropyridin-4-yl)-1-oxa-3,8-diazaspiro[4,5]decan-2-one,
8-{4-[(1-cyclobutylpiperidin-4-yl)oxy]phenyl}-3-(1-methyl-6-oxo-1,6-dihydropyridin-3-yl)-1-oxa-3,8-diazaspiro[4,5]decan-2-one,
8-{4-[(1-cyclobutylpiperidin-4-yl)oxy]phenyl}-3-(2-methoxypyrimidin-5-yl)-1-oxa-3,8-diazaspiro[4,5]decan-2-one,
3-ethyl-8-{4-[(1-isopropylpiperidin-4-yl)oxy]phenyl}-1-oxa-3,8-diazaspiro[4,5]decan-2-one,
8-{4-[(1-isopropylpiperidin-4-yl)oxy]phenyl}-3-(1-methyl-1H-pyrazol-4-yl)-1-oxa-3,8-diazaspiro[4,5]decan-2-one,
8-{4-[(1-isopropylpiperidin-4-yl)oxy]phenyl}-3-(1-methyl-1H-pyrazol-3-yl)-1-oxa-3,8-diazaspiro[4,5]decan-2-one,
5-(8-{4-[(1-isopropylpiperidin-4-yl)oxy]phenyl}-2-oxo-1-oxa-3,8-diazaspiro[4,5]decan-3-yl)nicotinonitrile,
8-{4-[(1-isopropylpiperidin-4-yl)oxy]phenyl}-3-pyrazin-2-yl-1-oxa-3,8-diazaspiro[4,5]decan-2-one,
8-{4-[(1-isopropylpiperidin-4-yl)oxy]phenyl}-3-(5-methoxypyridin-2-yl)-1-oxa-3,8-diazaspiro[4,5]decan-2-one,
8-{4-[(1-isopropylpiperidin-4-yl)oxy]phenyl}-3-(2-methoxypyrimidin-5-yl)-1-oxa-3,8-diazaspiro[4,5]decan-2-one,
8-{4-[(1-isopropylpiperidin-4-yl)oxy]phenyl}-3-(3-methoxypyrimidin-2-yl)-1-oxa-3,8-diazaspiro[4,5]decan-2-one,
8-{4-[(1-isopropylpiperidin-4-yl)oxy]phenyl}-3-(6-methoxypyridin-3-yl)-1-oxa-3,8-diazaspiro[4,5]decan-2-one,
8-{4-[(1-isopropylpiperidin-4-yl)oxy]phenyl}-3-(5-methoxypyridin-3-yl)-1-oxa-3,8-diazaspiro[4,5]decan-2-one,
8-{6-[(1-cyclobutylpiperidin-4-yl)oxy]pyridin-3-yl}-3-(3-methylpyridin-2-yl)-1-oxa-3,8-diazaspiro[4,5]decan-2-one,
8-{6-[(1-cyclobutylpiperidin-4-yl)oxy]pyridin-3-yl}-3-(5-methoxypyridin-2-yl)-1-oxa-3,8-diazaspiro[4,5]decan-2-one,
8-{6-[(1-cyclobutylpiperidin-4-yl)oxy]pyridin-3-yl}-3-(5-fluoropyridin-2-yl)-1-oxa-3,8-diazaspiro[4,5]decan-2-one,
8-{6-[(1-cyclobutylpiperidin-4-yl)oxy]pyridin-3-yl}-3-ethyl-1-oxa-3,8-diazaspiro[4,5]decan-2-one,
8-{6-[(1-cyclobutylpiperidin-4-yl)oxy]pyridin-3-yl}-3-(2,2,2-trifluoroethyl)-1-oxa-3,8-diazaspiro[4,5]decan-2-one,
8-{6-[(1-cyclobutylpiperidin-4-yl)oxy]pyridin-3-yl}-3-[4-(methylsulfonyl)phenyl]-1-oxa-3,8-diazaspiro[4,5]decan-2-one,
8-{6-[(1-cyclobutylpiperidin-4-yl)oxy]pyridin-3-yl}-3-(2-ethoxypyrimidin-5-yl)-1-oxa-3,8-diazaspiro[4,5]decan-2-one,
8-{6-[(1-cyclobutylpiperidin-4-yl)oxy]pyridin-3-yl}-3-(1-methyl-1H-pyrazol-4-yl)-1-oxa-3,8-diazaspiro[4,5]decan-2-one,
8-{6-[(1-cyclobutylpiperidin-4-yl)oxy]pyridin-3-yl}-3-(1-methyl-1H-pyrazol-3-yl)-1-oxa-3,8-diazaspiro[4,5]decan-2-one,
5-(8-{6-[(1-cyclobutylpiperidin-4-yl)oxy]pyridin-3-yl}-2-oxo-1-oxa-3,8-diazaspiro[4,5]decan-3-yl)nicotinonitrile,
8-{6-[(1-cyclobutylpiperidin-4-yl)oxy]pyridin-3-yl}-3-pyrazin-2-yl-1-oxa-3,8-diazaspiro[4,5]decan-2-one,
8-{6-[(1-cyclobutylpiperidin-4-yl)oxy]pyridin-3-yl}-3-(6-methoxypyridin-3-yl)-1-oxa-3,8-diazaspiro[4,5]decan-2-one,
8-{6-[(1-cyclobutylpiperidin-4-yl)oxy]pyridin-3-yl}-3-(2-methoxypyrimidin-5-yl)-1-oxa-3,8-diazaspiro[4,5]decan-2-one,
8-{6-[(1-cyclobutylpiperidin-4-yl)oxy]pyridin-3-yl}-3-[5-(trifluoromethyl)pyridin-3-yl]-1-oxa-3,8-diazaspiro[4,5]decan-2-one,
8-{6-[(1-cyclobutylpiperidin-4-yl)oxy]pyridin-3-yl}-3-(5-methoxypyridin-3-yl)-1-oxa-3,8-diazaspiro[4,5]decan-2-one,
8-{6-[(1-cyclobutylpiperidin-4-yl)oxy]pyridin-3-yl}-3-(5-methoxypyrazin-2-yl)-1-oxa-3,8-diazaspiro[4,5]decan-2-one,
8-{6-[(1-isopropylpiperidin-4-yl)oxy]pyridin-3-yl}-3-(2-methoxypyrimidin-5-yl)-1-oxa-3,8-diazaspiro[4,5]decan-2-one,
5-(8-{6-[(1-isopropylpiperidin-4-yl)oxy]pyridin-3-yl}-2-oxo-1-oxa-3,8-diazaspiro[4,5]decan-3-yl)nicotinonitrile,
8-{6-[(1-isopropylpiperidin-4-yl)oxy]pyridin-3-yl}-3-pyrazin-2-yl-1-oxa-3,8-diazaspiro[4,5]decan-2-one,
8-{6-[(1-isopropylpiperidin-4-yl)oxy]pyridin-3-yl}-3-(1-methyl-1H-pyrazol-4-yl)-1-oxa-3,8-diazaspiro[4,5]decan-2-one,
4-(4-methoxyphenyl)-9-[4-(3-piperidin-1-ylpropoxy)phenyl]-1-oxa-4,9-diazaspiro[5,5]undecan-3-one,
4-(3-methoxyphenyl)-9-[4-(3-piperidin-1-ylpropoxy)phenyl]-1-oxa-4,9-diazaspiro[5,5]undecan-3-one,
4-(4-fluorophenyl)-9-[4-(3-piperidin-1-ylpropoxy)phenyl]-1-oxa-4,9-diazaspiro[5,5]undecan-3-one,
4-(6-fluoropyridin-3-yl)-9-[4-(3-piperidin-1-ylpropoxy)phenyl]-1-oxa-4,9-diazaspiro[5,5]undecan-3-one,
4-(6-methoxypyridin-3-yl)-9-[4-(3-piperidin-1-ylpropoxy)phenyl]-1-oxa-4,9-diazaspiro[5,5]undecan-3-one,
4-(6-methoxypyridin-2-yl)-9-[4-(3-piperidin-1-ylpropoxy)phenyl]-1-oxa-4,9-diazaspiro[5,5]undecan-3-one,
4-methyl-9-(4-{3-[(2R)-2-methylpyrrolidin-1-yl]propoxy}phenyl)-1-oxa-4,9-diazaspiro[5,5]undecan-3-one,
4-methyl-9-(4-{3-[(2S)-2-methylpyrrolidin-1-yl]propoxy}phenyl)-1-oxa-4,9-diazaspiro[5,5]undecan-3-one,
4-ethyl-9-(4-{3-[(2R)-2-methylpyrrolidin-1-yl]propoxy}phenyl)-1-oxa-4,9-diazaspiro[5,5]undecan-3-one,
9-(4-{3-[(3S)-3-methylpiperidin-1-yl]propoxy}phenyl)-4-propyl-1-oxa-4,9-diazaspiro[5,5]undecan-3-one,
4-isopropyl-9-(4-{3-[(3S)-3-methylpiperidin-1-yl]propoxy}phenyl)-1-oxa-4,9-diazaspiro[5,5]undecan-3-one,
4-isopropyl-9-(4-{3-[(2R)-2-methylpyrrolidin-1-yl]propoxy}phenyl)-1-oxa-4,9-diazaspiro[5,5]undecan-3-one,
4-(1-ethylpropyl)-9-(4-{3-[(3S)-3-methylpiperidin-1-yl]propoxy}phenyl)-1-oxa-4,9-diazaspiro[5,5]undecan-3-one,
9-(4-{3-[(2R)-2-methylpyrrolidin-1-yl]propoxy}phenyl)-4-(2,2,2-trifluoroethyl)-1-oxa-4,9-diazaspiro[5,5]undecan-3-one, 4-cyclopropyl-9-(4-{3-[(3S)-3-methylpiperidin-1-yl]propoxy}phenyl)-1-oxa-4,9-diazaspiro[5,5]undecan-3-one, 4-cyclobutyl-9-(4-{3-[(3S)-3-methylpiperidin-1-yl]propoxy}phenyl)-1-oxa-4,9-diazaspiro[5,5]undecan-3-one, 4-cyclobutyl-9-(4-{3-[(2R)-2-methylpyrrolidin-1-yl]propoxy}phenyl)-1-oxa-4,9-diazaspiro[5,5]undecan-3-one, 4-cyclopentyl-9-(4-{3-[(3S)-3-methylpiperidin-1-yl]propoxy}phenyl)-1-oxa-4,9-diazaspiro[5,5]undecan-3-one, 4-cyclohexyl-9-(4-{3-[(3S)-3-methylpiperidin-1-yl]propoxy}phenyl)-1-oxa-4,9-diazaspiro[5,5]undecan-3-one, 4-benzyl-9-(4-{3-[(3S)-3-methylpiperidin-1-yl]propoxy}phenyl)-1-oxa-4,9-diazaspiro[5,5]undecan-3-one, 4-benzyl-9-[4-(3-pyrrolidin-1-ylpropoxy)phenyl]-1-oxa-4,9-diazaspiro[5,5]undecan-3-one, 4-benzyl-9-[4-(3-piperidin-1-ylpropoxy)phenyl]-1-oxa-4,9-diazaspiro[5,5]undecan-3-one, 4-(3-fluorophenyl)-9-[4-(3-piperidin-1-ylpropoxy)phenyl]-1-oxa-4,9-diazaspiro[5,5]undecan-3-one, 4-(2-fluorophenyl)-9-[4-(3-piperidin-1-ylpropoxy)phenyl]-1-oxa-4,9-diazaspiro[5,5]undecan-3-one, 4-(2-fluoropyridin-4-yl)-9-[4-(3-piperidin-1-ylpropoxy)phenyl]-1-oxa-4,9-diazaspiro[5,5]undecan-3-one, 4-ethyl-9-[4-(3-piperidin-1-ylpropoxy)phenyl]-1-oxa-4,9-diazaspiro[5,5]undecan-3-one, 4-ethyl-9-[4-(3-(3S)-methylpiperidin-1-ylpropoxy)phenyl]-1-oxa-4,9-diazaspiro[5,5]undecan-3-one, 4-methyl-9-[4-(3-piperidin-1-ylpropoxy)phenyl]-1-oxa-4,9-diazaspiro[5,5]undecan-3-one, 8-[4-(3-(3S)-methylpiperidin-1-ylpropoxy)phenyl]-3-phenyl-1-oxa-3,8-diazaspiro[4,5]decan-2-one, 3-(4-hydroxyphenyl)-8-[4-(3-piperidin-1-ylpropoxy)phenyl]-1-oxa-3,8-diazaspiro[4,5]decan-2-one, 9-{4-[(1-cyclobutylpiperidin-4-yl)oxy]phenyl}-4-phenyl-1-oxa-4,9-diazaspiro[5,5]undecan-3-one, 9-[4-(1-cyclobutylpiperidin-4-yloxy)phenyl]-4-ethyl-1-oxa-4,9-diazaspiro[5,5]undecan-3-one, 9-[4-(1-cyclobutylpiperidin-4-yloxy)phenyl]-4-(6-fluoropyridin-3-yl)-1-oxa-4,9-diazaspiro[5,5]undecan-3-one, 9-{4-[(1-cyclobutylpiperidin-4-yl)oxy]phenyl}-4-(6-methoxypyridin-3-yl)-1-oxa-4,9-diazaspiro[5,5]undecan-3-one, 9-{4-[(1-cyclopropylpiperidin-4-yl)oxy]phenyl}-4-(6-methoxypyridin-3-yl)-1-oxa-4,9-diazaspiro[5,5]undecan-3-one, 4-cyclobutyl-9-{4-[(1-cyclobutylpiperidin-4-yl)oxy]phenyl}-1-oxa-4,9-diazaspiro[5,5]undecan-3-one, 4-cyclobutyl-9-{4-[(1-isopropylpiperidin-4-yl)oxy]phenyl}-1-oxa-4,9-diazaspiro[5,5]undecan-3-one.

Preferred are the following:

4-(6-methoxypyridin-3-yl)-9-[4-(3-piperidin-1-ylpropoxy)phenyl]-1-oxa-4,9-diazaspiro[5,5]undecan-3-one, 9-{4-[(1-cyclobutylpiperidin-4-yl)oxy]phenyl}-4-(6-methoxypyridin-3-yl)-1-oxa-4,9-diazaspiro[5,5]undecan-3-one, 9-{4-[(1-isopropylpiperidin-4-yl)oxy]phenyl}-4-(6-methoxypyridin-3-yl)-1-oxa-4,9-diazaspiro[5,5]undecan-3-one, 4-(6-methoxypyridin-3-yl)-9-(4-{3-[(2R)-2-methylpyrrolidin-1-yl]propoxy}phenyl)-1-oxa-4,9-diazaspiro[5,5]undecan-3-one, 4-(6-methoxypyridin-3-yl)-9-(4-{3-[(3S)-3-methylpiperidin-1-yl]propoxy}phenyl)-1-oxa-4,9-diazaspiro[5,5]undecan-3-one, 4-(2-methoxypyrimidin-5-yl)-9-(4-{3-[(2R)-2-methylpyrrolidin-1-yl]propoxy}phenyl)-1-oxa-4,9-diazaspiro[5,5]undecan-3-one, 9-{4-[(1-cyclobutylpiperidin-4-yl)oxy]phenyl}-4-(1-methyl-1H-pyrazol-3-yl)-1-oxa-4,9-diazaspiro[5,5]undecan-3-one, 9-{6-[(1-cyclobutylpiperidin-4-yl)oxy]pyridin-3-yl}-4-(2-methoxypyrimidin-5-yl)-1-oxa-4,9-diazaspiro[5,5]undecan-3-one, 8-{4-[(1-cyclobutylpiperidin-4-yl)oxy]phenyl}-3-(2-methoxypyrimidin-5-yl)-1-oxa-3,8-diazaspiro[4,5]decan-2-one, 9-{4-[(1-cyclobutylpiperidin-4-yl)oxy]phenyl}-4-ethyl-1-oxa-4,9-diazaspiro[5,5]undecan-3-one, 9-{4-[(1-cyclobutylpiperidin-4-yl)oxy]phenyl}-4-(2-methoxypyrimidin-5-yl)-1-oxa-4,9-diazaspiro[5,5]undecan-3-one, 9-{4-[(1-cyclobutylpiperidin-4-yl)oxy]phenyl}-4-(1-methyl-1H-pyrazol-4-yl)-1-oxa-4,9-diazaspiro[5,5]undecan-3-one, 5-[9-(4-{3-[(2R)-2-methylpyrrolidin-1-yl]propoxy}phenyl)-3-oxo-1-oxa-4,9-diazaspiro[5,5]undecan-4-yl]nicotinonitrile,

[9-(4-{3-[(2R)-2-methylpyrrolidin-1-yl]propoxy}phenyl)-4-(2,2,2-trifluoroethyl)-1-oxa-4,9-diazaspiro[5,5]undecan-3-one, 8-{6-[(1-cyclobutylpiperidin-4-yl)oxy]pyridin-3-yl}-3-pyrazin-2-yl-1-oxa-3,8-diazaspiro[4,5]decan-2-one, 8-{6-[(1-cyclobutylpiperidin-4-yl)oxy]pyridin-3-yl}-3-(2-methoxypyrimidin-5-yl)-1-oxa-3,8-diazaspiro[4,5]decan-2-one, 4-methyl-9-(4-{3-[(2R)-2-methylpyrrolidin-1-yl]propoxy}phenyl)-1-oxa-4,9-diazaspiro[5,5]undecan-3-one, 9-{4-[(1-isopropylpiperidin-4-yl)oxy]phenyl}-4-(2-methoxypyrimidin-5-yl)-1-oxa-4,9-diazaspiro[5,5]undecan-3-one, 9-(4-{3-[(2R)-2-methylpyrrolidin-1-yl]propoxy}phenyl)-4-pyridin-3-yl-1-oxa-4,9-diazaspiro[5,5]undecan-3-one, 8-{6-[(1-cyclobutylpiperidin-4-yl)oxy]pyridin-3-yl}-3-(1-methyl-1H-pyrazol-4-yl)-1-oxa-3,8-diazaspiro[4,5]decan-2-one, 9-{4-[(1-cyclobutylpiperidin-4-yl)oxy]phenyl}-4-pyridin-3-yl-1-oxa-4,9-diazaspiro[5,5]undecan-3-one, 8-{4-[(1-isopropylpiperidin-4-yl)oxy]phenyl}-3-(2-methoxypyrimidin-5-yl)-1-oxa-3,8-diazaspiro[4,5]decan-2-one, 9-{6-[(1-cyclobutylpiperidin-4-yl)oxy]pyridin-3-yl}-4-(6-methylpyridin-3-yl)-1-oxa-4,9-diazaspiro[5,5]undecan-3-one, 4-(3-methylpyridin-2-yl)-9-(4-{3-[(2R)-2-methylpyrrolidin-1-yl]propoxy}phenyl)-1-oxa-4,9-diazaspiro[5,5]undecan-3-one, 4-cyclobutyl-9-{4-[(1-cyclobutylpiperidin-4-yl)oxy]phenyl}-1-oxa-4,9-diazaspiro[5,5]undecan-3-one, 9-{4-[(1-cyclobutylpiperidin-4-yl)oxy]phenyl}-4-(5-methoxypyridin-2-yl)-1-oxa-4,9-diazaspiro[5,5]undecan-3-one, 8-{4-[(1-cyclobutylpiperidin-4-yl)oxy]phenyl}-3-(1-methyl-1H-pyrazol-4-yl)-1-oxa-3,8-diazaspiro[4,5]decan-2-one, 9-{6-[(1-cyclobutylpiperidin-4-yl)oxy]pyridin-3-yl}-4-(6-methoxypyridin-3-yl)-1-oxa-4,9-diazaspiro[5,5]undecan-3-one, 5-(9-{4-[(1-isopropylpiperidin-4-yl)oxy]phenyl}-3-oxo-1-oxa-4,9-diazaspiro[5,5]undecan-4-yl)nicotinonitrile,
9-{4-[(1-isopropylpiperidin-4-yl)oxy]phenyl}-4-pyrazin-2-yl-1-oxa-4,9-diazaspiro[5,5]undecan-3-one,
4-ethyl-9-{4-[(1-isopropylpiperidin-4-yl)oxy]phenyl}-1-oxa-4,9-diazaspiro[5,5]undecan-3-one,
3-ethyl-8-{4-[(1-isopropylpiperidin-4-yl)oxy]phenyl}-1-oxa-3,8-diazaspiro[4,5]decan-2-one,
8-{4-[(1-isopropylpiperidin-4-yl)oxy]phenyl}-3-(1-methyl-1H-pyrazol-4-yl)-1-oxa-3,8-diazaspiro[4,5]decan-2-one,
8-{4-[(1-cyclobutylpiperidin-4-yl)oxy]phenyl}-3-(6-methylpyridin-3-yl)-1-oxa-3,8-diazaspiro[4,5]decan-2-one,
4-(3-methoxypyridin-2-yl)-9-(4-{3-[(2R)-2-methylpyrrolidin-1-yl]propoxy}phenyl)-1-oxa-4,9-diazaspiro[5,5]undecan-3-one,
8-{6-[(1-cyclobutylpiperidin-4-yl)oxy]pyridin-3-yl}-3-(2-ethoxypyrimidin-5-yl)-1-oxa-3,8-diazaspiro[4,5]decan-2-one,
9-{4-[(1-isopropylpiperidin-4-yl)oxy]phenyl}-4-(5-methoxypyridin-3-yl)-1-oxa-4,9-diazaspiro[5,5]undecan-3-one,
4-(2-ethoxypyrimidin-5-yl)-9-{4-[(1-isopropylpiperidin-4-yl)oxy]phenyl}-1-oxa-4,9-diazaspiro[5,5]undecan-3-one,
9-{4-[(1-cyclobutylpiperidin-4-yl)oxy]phenyl}-4-(5-methoxypyridin-3-yl)-1-oxa-4,9-diazaspiro[5,5]undecan-3-one,
8-{6-[(1-cyclobutylpiperidin-4-yl)oxy]pyridin-3-yl}-3-ethyl-1-oxa-3,8-diazaspiro[4,5]decan-2-one,
9-{4-[(1-isopropylpiperidin-4-yl)oxy]phenyl}-4-(5-methoxypyrazin-2-yl)-1-oxa-4,9-diazaspiro[5,5]undecan-3-one,
4-(1-methyl-1H-pyrazol-4-yl)-9-(4-{3-[(2S)-2-methylpyrrolidin-1-yl]propoxy}phenyl)-1-oxa-4,9-diazaspiro[5,5]undecan-3-one,
4-(5-methoxypyrazin-2-yl)-9-(4-{3-[(2S)-2-methylpyrrolidin-1-yl]propoxy}phenyl)-1-oxa-4,9-diazaspiro[5,5]undecan-3-one,
4-(5-methoxypyridin-3-yl)-9-(4-{3-[(2S)-2-methylpyrrolidin-1-yl]propoxy}phenyl)-1-oxa-4,9-diazaspiro[5,5]undecan-3-one,
5-[9-(4-{3-[(2S)-2-methylpyrrolidin-1-yl]propoxy}phenyl-3-oxo-1-oxa-4,9-diazaspiro[5,5]undecan-4-yl]nicotinonitrile,
4-methyl-9-(4-{3-[(2S)-2-methylpyrrolidin-1-yl]propoxy}phenyl)-1-oxa-4,9-diazaspiro[5,5]undecan-3-one, and
9-(4-{3-[(2S)-2-methylpyrrolidin-1-yl]propoxy}phenyl)-4-pyridin-3-yl-1-oxa-4,9-diazaspiro[5,5]undecan-3-one.
More preferred are the following:
4-(2-methoxypyrimidin-5-yl)-9-(4-{3-[(2R)-2-methylpyrrolidin-1-yl]propoxy}phenyl)-1-oxa-4,9-diazaspiro[5,5]undecan-3-one,
4-methyl-9-(4-{3-[(2R)-2-methylpyrrolidin-1-yl]propoxy}phenyl)-1-oxa-4,9-diazaspiro[5,5]undecan-3-one,
5-[9-(4-{3-[(2R)-2-methylpyrrolidin-1-yl]propoxy}phenyl)-3-oxo-1-oxa-4,9-diazaspiro[5,5]undecan-4-yl]nicotinonitrile,
9-{6-[(1-cyclobutylpiperidin-4-yl)oxy]pyridin-3-yl}-4-(2-methoxypyrimidin-5-yl)-1-oxa-4,9-diazaspiro[5,5]undecan-3-one,
9-{4-[(1-cyclobutylpiperidin-4-yl)oxy]phenyl}-4-pyridin-3-yl-1-oxa-4,9-diazaspiro[5,5]undecan-3-one,
8-{6-[(1-cyclobutylpiperidin-4-yl)oxy]pyridin-3-yl}-3-(1-methyl-1H-pyrazol-4-yl)-1-oxa-3,8-diazaspiro[4,5]decan-2-one,
9-{4-[(1-cyclobutylpiperidin-4-yl)oxy]phenyl}-4-ethyl-1-oxa-4,9-diazaspiro[5,5]undecan-3-one,
9-{4-[(1-cyclobutylpiperidin-4-yl)oxy]phenyl}-4-(1-methyl-1H-pyrazol-4-yl)-1-oxa-4,9-diazaspiro[5,5]undecan-3-one,
8-{4-[(1-cyclobutylpiperidin-4-yl)oxy]phenyl}-3-(1-methyl-1H-pyrazol-4-yl)-1-oxa-3,8-diazaspiro[4,5]decan-2-one,
9-{4-[(1-isopropylpiperidin-4-yl)oxy]phenyl}-4-(2-methoxypyrimidin-5-yl)-1-oxa-4,9-diazaspiro[5,5]undecan-3-one,
5-[9-{4-[(1-isopropylpiperidin-4-yl)oxy]phenyl}-3-oxo-1-oxa-4,9-diazaspiro[5,5]undecan-4-yl]nicotinonitrile, and
8-{4-[(1-isopropylpiperidin-4-yl)oxy]phenyl}-3-(1-methyl-1H-pyrazol-4-yl)-1-oxa-3,8-diazaspiro[4,5]decan-2-one.

Production Method for Compounds of Formula (I)

Compounds of formula (I) of the invention (hereinunder referred to as compounds (1)) can be produced, for example, according to the following method:

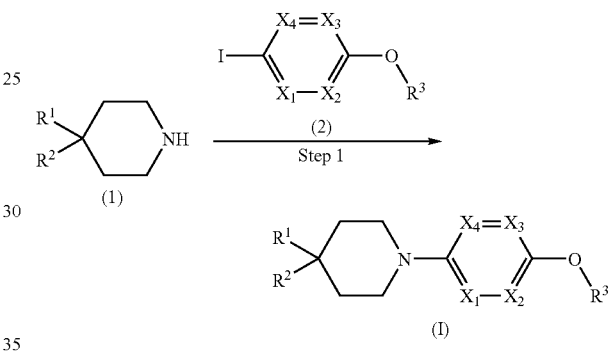

[In the formula, the symbols have the same meanings as above.]

(Step 1)

This step is a process for producing compounds (I) of the invention by reacting a compound (1) and a compound (2) in the presence of a base, using a ligand and a Pd catalyst. The reaction in this step may be attained according to a method described in literature (for example, Journal of Organic Chemistry, Vol. 66, 2001, pp. 2560-2565), or a method similar to it, or a combination of the method with an ordinary method.

The base to be used in this step includes, for example, sodium tert-butoxide, cesium carbonate et al.

The amount of the base may be generally from 1 to 5 equivalents relative to 1 equivalent of the compound (1), preferably from 1 to 2 equivalents.

The ligand to be used in this step includes, for example, 2-dicyclohexylphosphinobiphenyl, 2-dicyclohexylphosphino-2'-dimethylaminobiphenyl, 9,9-dimethyl-4,5-bis(diphenylphosphino)xanthene et al. The amount of the ligand may be generally from 0.01 to 0.1 equivalents relative to 1 equivalent of the compound (1), preferably from 0.02 to 0.1 equivalents.

The Pd catalyst to be used in this step includes, for example, $Pd(OAc)_2$, $Pd(PPh_3)_4$, $Pd_2(dba)_3$, $PdCl_2(dppf)_2$ et al. The amount of the Pd catalyst may be generally from 0.01 to 0.1 equivalents relative to 1 equivalent of the compound (1), preferably from 0.01 to 0.05 equivalents.

The solvent to be used may be any one not interfering with the reaction and includes, for example, dioxane, N,N-dimethylformamide, toluene et al. Of those, preferred are dioxane, N,N-dimethylformamide et al.

The reaction temperature may be generally from 0° C. to 150° C., preferably from 60 to 100° C.

The reaction time may be generally from 1 to 48 hours, preferably from 2 to 15 hours.

Thus obtained, the compound (I) of the invention may be isolated and purified in a known isolation and purification method of, for example, concentration, concentration under reduced pressure, solvent extraction, crystallization, reprecipitation, chromatography et al.

Compounds (I-1) of the invention may be produced according to the following method:

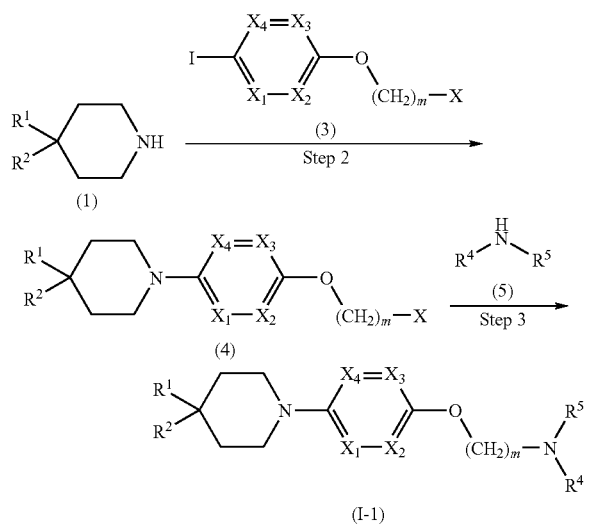

[In the formula, X represents a halogen atom, and the other symbols have the same meanings as above.]

(Step 2)

his step is a process for producing a compound (4) by reacting a compound (1) and a compound (3) in the presence of a base, using a ligand and a Pd catalyst.

The type and the amount of the base to be used in this step, the type and the amount of the ligand, and the type and the amount of the Pd catalyst may be the same as those in the step 1.

The solvent to be used may be any one not interfering with the reaction and includes, for example, 1,4-dioxane, N,N-dimethylformamide, toluene et al. Of those, preferred are 1,4-dioxane, N,N-dimethylformamide et al.

The reaction temperature may be generally from 0° C. to 150° C., preferably from 60° C. to 100° C.

The reaction time may be generally from 1 to 48 hours, preferably from 2 to 15 hours.

Thus obtained, the compound (4) in the invention may be subjected to the next step, after isolated and purified in a known isolation and purification method of, for example, concentration, concentration under reduced pressure, solvent extraction, crystallization, reprecipitation, chromatography et al, or not isolated and purified.

(Step 3)

This step is a process for producing a compound (I-1) of the invention by reacting the compound (4) obtained in the above step 2 and a compound (5).

The compound (5) to be used in this step includes, for example, dimethylamine, diethylamine, diisopropylamine, ethylmethylamine, pyrrolidine, piperidine, homopiperidine et al. The solvent to be used may be any one not interfering with the reaction and includes, for example, acetone, tetrahydrofuran, N,N-dimethylformamide, acetonitrile, toluene, and their mixed solvents. Of those, preferred are acetone, tetrahydrofuran, N,N-dimethylformamide. The reaction temperature may be generally from 0° C. to 100° C., preferably from 40° C. to 80° C. The reaction time may be generally from 1 to 48 hours, preferably from 1 to 12 hours.

Thus obtained, the compound (I-1) of the invention may be isolated and purified in a known isolation and purification method of, for example, concentration, concentration under reduced pressure, solvent extraction, crystallization, reprecipitation, chromatography et al.

A compound (I-2) of the invention may be produced according to the following method, using a compound (15) as the starting material therein. A production method for the compound (15) is first described below, and then the production method for the compound (I-2) is described.

Production Method for Compound (15):

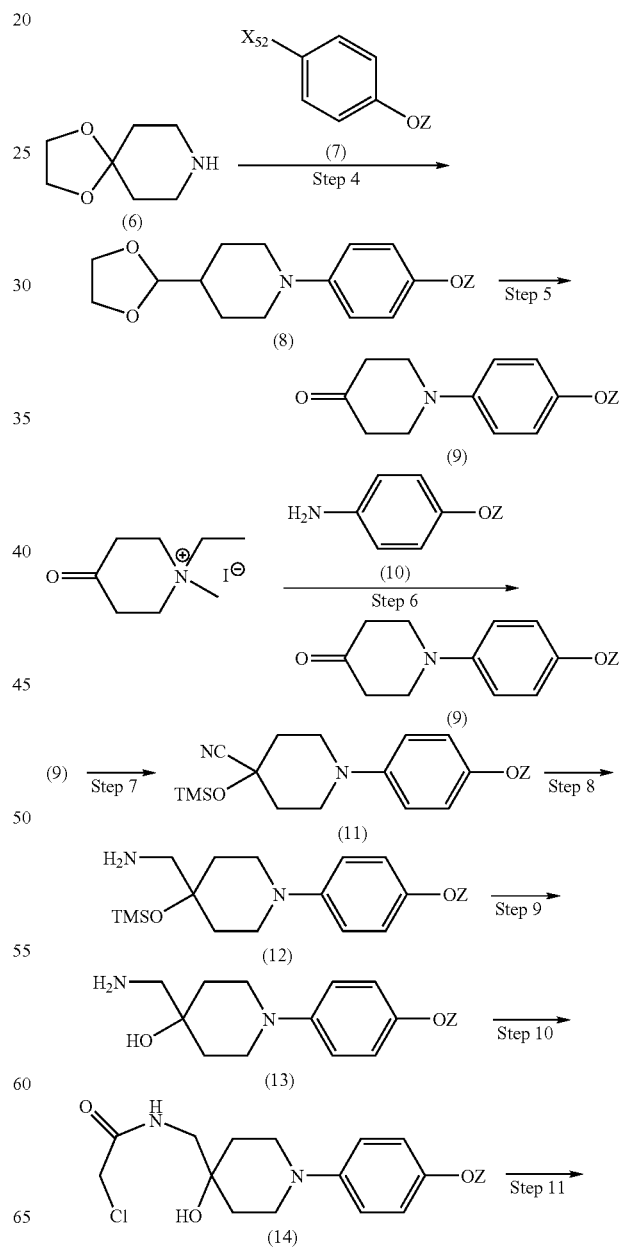

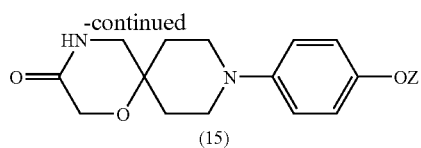

(15)

[In the formula, Z means a benzyl group or a methyl group, or means the following formula:

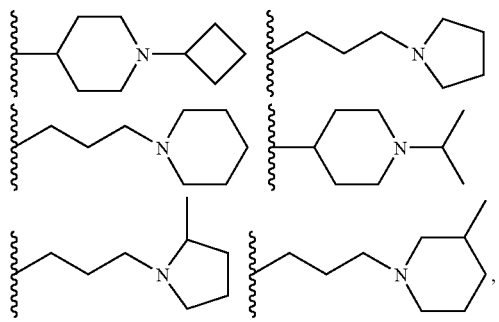

TMS means a trunethylsilyl group, $X_{52}$ represents a halogen atom, and the other symbols have the same meanings as above.]

(Step 4)

his step is a process for producing a compound (8) by reacting a compound (6) and a compound (7) in the presence of a base. The reaction in this step may be attained according to a method described in literature (for example, Journal of Organic Chemistry, Vol. 66, 2001, pp. 2560-2565), or a method similar to it, or a combination of the method with an ordinary method.

The base to be used in this step includes, for example, sodium tert-butoxide, cesium carbonate et al. The amount of the base may be generally from 1 to 5 equivalents relative to 1 equivalent of the compound (6), preferably from 1 to 2 equivalents.

In the compound (7), $X_{52}$ represents a halogen atom, concretely including, for example, a bromine atom and an iodine atom et al.

The compound (7) includes, for example, 4-benzyloxybromobenzene, 4-benzyloxyiodobenzene, 4-methoxybromobenzene, 4-methoxyiodobenzene et al.

The amount of the compound (7) may be generally from 1 to 10 equivalents relative to 1 equivalent of the compound (6), preferably from 1 to 3 equivalents.

In this reaction, a catalyst and a ligand shall be used. The catalyst is preferably a Pd catalyst, concretely including, for example, $Pd(OAc)_2$, $Pd(PPh_3)_4$, $Pd_2(dba)_3$, $PdCl_2(dppf)_2$ et al. The amount of the Pd catalyst may be generally from 0.001 to 1.0 equivalent relative to 1 equivalent of the compound (6), preferably from 0.01 to 0.05 equivalents.

The ligand includes, for example, 2-dicyclohexylphosphinobiphenyl, 2-dicyclohexylphosphino-2'-dimethylaminobiphenyl, 9,9-dimethyl-4,5-bis(diphenylphosphino)xanthene et al.

The amount of the ligand may be generally from 0.01 to 1.0 equivalent relative to 1 equivalent of the compound (6), preferably from 0.02 to 0.1 equivalents.

Not specifically defined, the reaction solvent may be any one not interfering with the reaction and includes, for example, dioxane, N,N-dimethylformamide, toluene et al. Of those, preferred are dioxane, N,N-dimethylformamide et al.

The reaction temperature may be generally from 0° C. to 150° C., preferably from 60° C. to 100° C. The reaction time may be generally from 1 to 48 hours, preferably from 2 to 15 hours.

Thus obtained, the compound (8) may be subjected to the next step, after isolated and purified in a known isolation and purification method of, for example, concentration, concentration under reduced pressure, crystallization, solvent extraction, reprecipitation, chromatography et al, or not isolated and purified.

(Step 5)

This step is a process for producing a compound (9) by removing the acetal group from the compound (8) obtained in the above step 4.

The reaction in this step may be attained according to a method described in literature (for example, Journal of Medicinal Chemistry, Vol. 29, 1986, pp. 369-375), or a method similar to it, or a combination of the method with an ordinary method.

In case where Z in the compound (8) is a benzyl group, for example, the compound (8) may be reacted with an aqueous formic acid solution, an aqueous acetic acid solution or p-toluenesulfonic acid monohydrate. Of those, preferred is an aqueous formic acid solution. The amount of formic acid to be used may be generally from 1 to 100 equivalents relative to 1 equivalent of the compound (8), preferably from 10 to 50 equivalents.

Not specifically defined, the reaction solvent may be any one not interfering with the reaction and includes, for example, water, methyl alcohol, ethyl alcohol, acetone et al. Of those, preferred is water.

The reaction temperature may be generally from 0° C. to 150° C., preferably from 50° C. to 100° C.

The reaction time may be generally from 1 to 48 hours, preferably from 5 to 15 hours.

In case where Z in the compound (8) is a methyl group, for example, the compound (8) may be reacted with concentrated hydrochloric acid, concentrated sulfuric acid, aqueous formic acid solution or aqueous acetic acid solution et al. Of those, preferred is concentrated hydrochloric acid.

The amount of concentrated hydrochloric acid to be used may be generally from 1 to 100 equivalents relative to 1 equivalent of the compound (8), preferably from 10 to 50 equivalents.

Not specifically defined, the reaction solvent may be any one not interfering with the reaction and includes, for example, water, methyl alcohol, ethyl alcohol, acetone et al. Of those, preferred is water.

The reaction temperature may be generally from 0° C. to 100° C., preferably from 25° C. to 50° C.

The reaction time may be generally from 1 to 30 hours, preferably from 5 to 15 hours.

(Step 6)

This step is a process for producing a compound (9) by reacting 1-ethyl-1-methyl-4-oxopiperidinium and a compound (10). The reaction in this step may be attained according to a method described in literature (for example, Organic Letters, Vol. 1, 1999, pp. 1261-1262; European Journal of Medicinal Chemistry, Vol. 35, 2000, pp. 839-851), or a method similar to it, or a combination of the method with an ordinary method.

The base to be used in this step includes, for example, potassium carbonate, sodium carbonate et al. The amount of the base may be generally from 1 to 5 equivalents relative to 1 equivalent of the compound (10), preferably from 1 to 2 equivalents.

The compound (10) to be used in this step includes, for example, 4-benzyloxyaniline, 4-methoxyaniline, 4-(3-piperidin-1-ylpropoxy)aniline hydrochloride, 4-{3-[(2R)-2-methylpyrrolidin-1-yl]propoxy}aniline 4-methylbenzenesulfonate, 4-[(1-cyclobutylpiperidin-4-yl)oxy]aniline 4-methylbenzenesulfonate, 4-[(1-isopropylpiperidin-4-yl)oxy]aniline, 6-[(1-cyclobutylpiperidin-4-yl)oxy]pyridine-3-aniline, 6-[(1-isopropylpiperidin-4-yl)oxy]pyridin-3-aniline et al.

The amount of 1-ethyl-1-methyl-4-oxopiperidinium may be generally from 1 to 10 equivalents relative to 1 equivalent of the compound (10), preferably from 1 to 3 equivalents.

Not specifically defined, the reaction solvent may be any one not interfering with the reaction. Ethanol-water is recommended.

The reaction temperature may be generally from 0° C. to 150° C., preferably from 80° C. to 100° C.

The reaction time may be generally from 1 to 48 hours, preferably from 4 to 10 hours.

Thus obtained, the compound (9) may be subjected to the next step, after isolated and purified in a known isolation and purification method of, for example, concentration, concentration under reduced pressure, crystallization, solvent extraction, reprecipitation, chromatography et al, or not isolated and purified.

(Step 7)

This step is a process for producing a compound (11) by reacting the compound (9) obtained in the step 5 or the step 6 and trimethylsilylcyanide (TMSCN) in the presence of a base. The reaction in this step may be attained according to a method described in literature (for example, Synthetic Communications, Vol. 24, 1994, pp. 1483-1487), or a method similar to it, or a combination of the method with an ordinary method.

The base to be used in this step includes, for example, triethylamine, N-ethyldiisopropylamine et al. The amount of the base may be generally from 0.1 to 1 equivalent relative to 1 equivalent of the compound (9), preferably from 0.1 to 0.5 equivalents.

The amount of trimethylsilylcyanide to be used may be generally from 1 to 10 equivalents relative to 1 equivalent of the compound (9), preferably from 1 to 3 equivalents.

Not specifically defined, the reaction solvent may be any one not interfering with the reaction and includes, for example, chloroform, methylene chloride et al. Of those, preferred is chloroform.

The reaction time may be generally from 1 to 48 hours, preferably from 1 to 15 hours.

The reaction temperature may be generally from 0° C. to 100° C., preferably from 0° C. to 25° C.

Thus obtained, the compound (11) may be subjected to the next step, after isolated and purified in a known isolation and purification method of, for example, concentration, concentration under reduced pressure, crystallization, solvent extraction, reprecipitation, chromatography et al, or not isolated and purified.

(Step 8)

This step is a process for producing a compound (12) by reducing the cyano group in the compound (11) obtained in the above step 7.

The reducing agent to be used in this step includes LiAlH$_4$, Raney Ni et al. The amount of the reducing agent may be generally from 1 to 10 equivalents relative to 1 equivalent of the compound (11), preferably from 1 to 2 equivalents.

Not specifically defined, the reaction solvent may be any one not interfering with the reaction and includes, for example, diethyl ether, tetrahydrofuran, 1,4-dioxane, 1,2-dimethoxyethane et al. Of those, preferred is tetrahydrofuran.

The reaction time may be generally from 30 minutes to 48 hours, preferably from 30 minutes to 2 hours. The reaction temperature may be generally from 0° C. to 100° C., preferably from 0° C. to 25° C.

Thus obtained, the compound (12) may be subjected to the next step, after isolated and purified in a known isolation and purification method of, for example, concentration, concentration under reduced pressure, crystallization, solvent extraction, reprecipitation, chromatography et al, or not isolated and purified.

(Step 9)

This step is a process for producing a compound (13) by removing TMS (trimethylsilyl) group from the compound (12) obtained in the above step 8.

The removal of the TMS group may be attained, for example, by processing the compound (12) with 6 N hydrochloric acid in a solvent such as methanol.

The amount of 6 N hydrochloric acid to be used may be generally from 1 to 10 equivalents relative to 1 equivalent of the compound (12), preferably from 2 to 6 equivalents.

Not specifically defined, the reaction solvent may be any one not interfering with the reaction and includes, for example, methanol, ethanol et al. Of those, preferred is methanol.

The reaction time may be generally from 1 to 48 hours, preferably from 1 to 2 hours.

The reaction temperature may be generally from 0° C. to 100° C., preferably from 10° C. to 30° C.

Thus obtained, the compound (13) may be subjected to the next step, after isolated and purified in a known isolation and purification method of, for example, concentration, concentration under reduced pressure, crystallization, solvent extraction, reprecipitation, chromatography et al, or not isolated and purified.

(Step 10)

This step is a process for producing a compound (14) by reacting the compound (13) obtained in the above step 9 and 2-chloroacetyl chloride in the presence of a base. The reaction in this step may be attained according to a method described in literature (for example, Journal of Medicinal Chemistry, Vol. 26, 1983, pp. 855-861), or a method similar to it, or a combination of the method with an ordinary method.

The base to be used in this step includes, for example, potassium carbonate, sodium carbonate, cesium carbonate, pyridine, triethylamine, diisopropylethylamine et al. The amount of the base may be generally from 1 to 10 equivalents relative to 1 equivalent of the compound (13), preferably from 2 to 3 equivalents.

The amount of 2-chloroacetyl chloride may be generally from 1 to 10 equivalents relative to 1 equivalent of the compound (13), preferably from 1 to 2 equivalents.

Not specifically defined, the reaction solvent may be any one not interfering with the reaction and includes, for example, ethyl acetate, acetonitrile, tetrahydrofuran et al. Of those, preferred is a mixed solvent of acetonitrile and water.

The reaction time may be generally from 30 minutes to 10 hours, preferably from 30 minutes to 2 hours.

The reaction temperature may be generally from 0° C. to 100° C., preferably from 0° C. to 25° C.

Thus obtained, the compound (14) may be subjected to the next step, after isolated and purified in a known isolation and purification method of, for example, concentration, concentration under reduced pressure, crystallization, solvent extraction, reprecipitation, chromatography et al, or not isolated and purified.

(Step 11)

This step is a process for producing a compound (15) through intramolecular cyclization of the compound (14) in the presence of a base. The reaction in this step may be attained according to a method described in literature (for example, Journal of Medicinal Chemistry, Vol. 26, 1983, pp. 855-861), or a method similar to it, or a combination of the method with an ordinary method.

The base to be used in this step includes, for example, potassium tert-butoxide, sodium tert-pentoxide et al.
The amount of the base may be generally from 1 to 10 equivalents relative to 1 equivalent of the compound (14), preferably from 1 to 3 equivalents.

Not specifically defined, the reaction solvent may be any one not interfering with the reaction and includes, for example, N,N-dimethylformamide, tetrahydrofuran, tert-butyl alcohol, 2-methyl-2-butyl alcohol. Of those, preferred is a mixed solvent of N,N-dimethylformamide and 2-methyl-2-butyl alcohol et al. The reaction time may be generally from 30 minutes to 15 hours, preferably from 30 minutes to 1 hour. The reaction temperature may be generally from 0° C. to 100° C., preferably from 0° C. to 25° C.

Thus obtained, the compound (15) may be subjected to the next step, after isolated and purified in a known isolation and purification method of, for example, concentration, concentration under reduced pressure, crystallization, solvent extraction, reprecipitation, chromatography et al, or not isolated and purified.

Production Method for Compound (1-2):

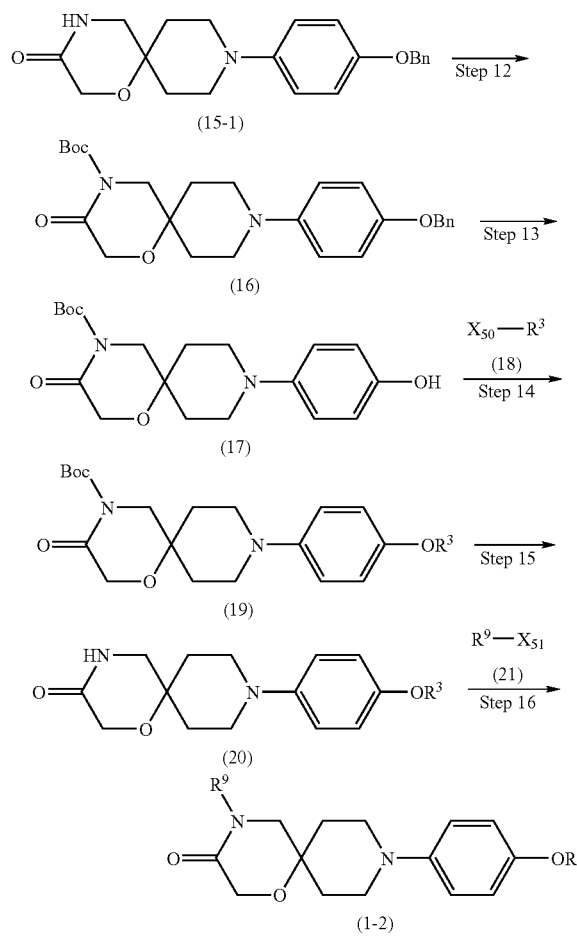

[In the formula, Bn means a benzyl group; $X_{50}$ and $X_{51}$ each mean a halogen atom; and the other symbols have the same meanings as above.]

(Step 12)

This step is a process for producing a compound (16) by introducing a Boc group into the amido group of a compound (15-1), or that is, the compound (15) where Z is a benzyl group.

The introduction of Boc group may be attained according to a method described in literature (for example, Protective Groups in Organic Synthesis, written by T. W. Green, 2nd Ed., by John Wiley & Sons, 1991), or a method similar to it, or a combination of the method with an ordinary method. Concretely, for the Boc group introduction, for example, the compound (15-1) is reacted with $(Boc)_2O$ generally in an amount of from 1 to 3 equivalents relative to 1 equivalent of the compound (15-1), in the presence of a base such as triethylamine generally in an amount of from 1 to 3 equivalents relative to 1 equivalent of the compound (15-1) in a solvent such as chloroform, thereby producing the compound (16). In general, from 0.1 to 1 equivalent of 4-dimethylaminopyridine may be present in the reaction system.

Thus obtained, the compound (16) may be subjected to the next step, after isolated and purified in a known isolation and purification method of, for example, concentration, concentration under reduced pressure, crystallization, solvent extraction, reprecipitation, chromatography et al, or not isolated and purified.

(Step 13)

This step is a process for producing a compound (17) by removing the benzyl group from the compound (16) obtained in the above step 12.

The benzyl group removal may be attained according to a method described in the above-mentioned Protective Groups in Organic Synthesis, or a method similar to it, or a combination of the method with an ordinary method.

The benzyl group removal may be attained, for example, by processing the compound (16) with a catalytic amount of Pd—C in a solvent such as methanol in a hydrogen atmosphere.

Thus obtained, the compound (17) may be subjected to the next step, after isolated and purified in a known isolation and purification method of, for example, concentration, concentration under reduced pressure, crystallization, solvent extraction, reprecipitation, chromatography et al, or not isolated and purified.

(Step 14)

This step is a process for producing a compound (19) by reacting the compound (17) obtained in the above step 13 and a compound (18) in the presence of a base.

The base to be used in this step includes, for example, potassium carbonate, cesium carbonate, sodium carbonate et al. The amount of the base may be generally from 1 to 10 equivalents relative to 1 equivalent of the compound (17), preferably from 3 to 5 equivalents.

$X_{50}$ in the formula of the compound (18) represents a halogen atom, concretely including, for example, an iodine atom, a bromine atom, a chlorine atom.

The compound (18) concretely includes, for example, 1-(3-chloropropyl)piperidine hydrochloride, 1-(3-bromopropyl)piperidine hydrobromide, 1-(3-iodopropyl)piperidine, 1-(3-chloropropyl)pyrrolidine hydrochloride, 1-(3-bromopropyl)pyrrolidine hydrobromide, 1-(3-iodopropyl)pyrrolidine, (3S)-1-(3-bromopropyl)-3-methylpiperidine hydrobromide, (2S)-1-(3-bromopropyl)-2-methylpyrrolidine hydrobromide, (2R)-1-(3-bromopropyl)-2-methylpyrrolidine hydrobromide.

The solvent to be used in this reaction may be any one not interfering with the reaction and includes, for example, acetone, tetrahydrofuran, N,N-dimethylformamide, acetonitrile, toluene et al. Of those, preferred are acetone, tetrahydrofuran, N,N-dimethylformamide.

The reaction temperature may be generally from 0° C. to 150° C., preferably from 25° C. to 80° C. The reaction time may be generally from 1 to 48 hours, preferably from 5 to 15 hours.

Thus obtained, the compound (19) in the invention may be isolated and purified in a known isolation and purification method of, for example, concentration, concentration under reduced pressure, solvent extraction, crystallization, reprecipitation, chromatography et al.

(Step 15)

This step is a process for producing a compound (20) by removing the Boc group from the compound (19) obtained in the above step 14.

The Boc group removal may be attained according to a method described in the above-mentioned Protective Groups in Organic Synthesis, or a method similar to it, or a combination of the method with an ordinary method.

Concretely, for example, the Boc group-having compound (19) may be reacted with an acid such as trifluoroacetic acid (hereinafter referred to as "TFA"). The amount of TFA to be used may be generally from 1 to 10 equivalents relative to 1 equivalent of the compound (19), preferably from 2 to 3 equivalents. The solvent to be used may be any one not interfering with the reaction and includes, for example, chloroform, methylene chloride, ethyl acetate, acetonitrile, 1,4-dioxane et al. Of those, preferred are chloroform, methylene chloride. The reaction temperature may be generally from 0° C. to 100° C., preferably from 0° C. to 25° C. The reaction time may be generally from 10 minutes to 48 hours, preferably from 30 minutes to 2 hours.

Thus obtained, the compound (20) may be isolated and purified in a known isolation and purification method of, for example, concentration, concentration under reduced pressure, solvent extraction, crystallization, reprecipitation, chromatography et al.

(Step 16)

This step is a process for producing a compound (I-2) of the invention by reacting the compound (20) obtained in the above step 15 and a compound (21). The reaction in this step may be attained according to a method described in literature (for example, Journal of American Chemical Society, Vol. 124, 2002, pp. 7421-7428), or a method similar to it, or a combination of the method with an ordinary method.

The compound (21) to be used in this step includes, for example, bromobenzene, 2-bromofluorobenzene, 3-bromofluorobenzene, 4-bromofluorobenzene, 2-bromopyridine, 3-bromopyridine, 4-bromopyridine et al. The amount of the compound (21) to be used may be generally from 1 to 10 equivalents relative to 1 equivalent of the compound (20), preferably from 1 to 2 equivalents.

Copper(I) iodide, potassium phosphate and N,N'-dimethyldiaminoethane are used in the reaction system to attain the reaction.

The amount of copper(I) iodide to be used may be generally from 0.01 to 10 equivalents relative to 1 equivalent of the compound (20), preferably from 0.5 to 1.0 equivalent.

The amount of potassium phosphate to be used may be generally from 1 to 10 equivalents relative to 1 equivalent of the compound (20), preferably from 1 to 3 equivalents.

The amount of N,N'-dimethyldiaminoethane to be used may be generally from 0.01 to 10 equivalents relative to 1 equivalent of the compound (20), preferably from 0.5 to 1.0 equivalent.

Not specifically defined, the reaction solvent may be any one not interfering with the reaction and includes, for example, toluene, 1,4-dioxane, tetrahydrofuran, N,N-dimethylformamide et al. Of those, preferred are 1,4-dioxane, N,N-dimethylformamide. The reaction temperature may be generally from 0° C. to 150° C., preferably from 80° C. to 120° C. The reaction time may be generally from 1 to 48 hours, preferably from 5 to 15 hours.

Thus obtained, the compound (I-2) may be isolated and purified in a known isolation and purification method of, for example, concentration, concentration under reduced pressure, crystallization, solvent extraction, reprecipitation, chromatography et al.

The compound (I-2) of the invention may also be produced, for example, according to the following method.

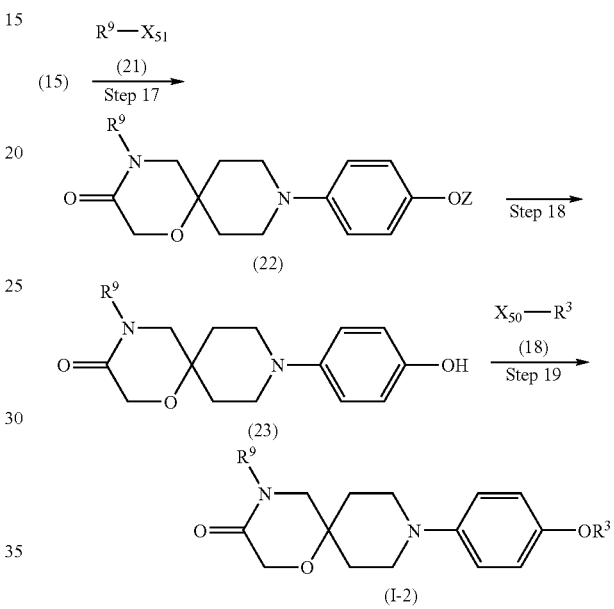

[In the formula, the symbols have the same meanings as above.]

(Step 17)

his step is a process for producing a compound (22) by reacting a compound (15) and a compound (21). The reaction in this step may be attained according to a method described in literature (for example, Journal of American Chemical Society, Vol. 124, 2002, pp. 7421-7428), or a method similar to it, or a combination of the method with an ordinary method.

The compound (21) to be used in this step includes, for example, bromobenzene, 2-bromofluorobenzene, 3-bromofluorobenzene, 4-bromofluorobenzene, 2-bromopyridine, 3-bromopyridine, 4-bromopyridine et al.

Copper(I) iodide, potassium phosphate and N,N'-dimethyldiaminoethane are made to exist in the reaction system to attain the reaction.

The amount of copper(I) iodide, potassium phosphate and N,N'-dimethyldiaminoethane to be used may be the same as in the above step 16; and the reaction solvent, the reaction time and the reaction temperature may be the same as in the above step 8.

Thus obtained, the compound (22) may be subjected to the next step, after isolated and purified in a known isolation and purification method of, for example, concentration, concentration under reduced pressure, crystallization, solvent extraction, reprecipitation, chromatography et al, or not isolated and purified, or not isolated and purified.

(Step 18)

This step is a process for producing a compound (23) by removing the protective group of the hydroxyl group of the compound (22) obtained in the above step 17.

The reaction in this step may be attained according to a method described in the above-mentioned Protective Groups in Organic Synthesis, or a method similar to it, or a combination of the method with an ordinary method.

In case where the protective group of the hydroxyl group is a benzyl group, 1 equivalent of the compound (22) may be processed with from 0.1 to 1 equivalent, preferably from 0.1 to 0.5 equivalents of 10% Pd—C in a hydrogen atmosphere in methanol, tetrahydrofuran, ethyl acetate or their mixed solvent, thereby obtaining the compound (23). In case where the protective group of the hydroxyl group is a methyl group, the compound (22) may be processed with boron tribromide generally in an amount of from 1 to 4 equivalents relative to 1 equivalent of the compound (22), preferably from 2 to 4 equivalents, in a solvent such as chloroform, methylene chloride, thereby obtaining the compound (23).

Thus obtained, the compound (23) may be subjected to the next step, after isolated and purified in a known isolation and purification method of, for example, concentration, concentration under reduced pressure, crystallization, solvent extraction, reprecipitation, chromatography et al, or not isolated and purified, or not isolated and purified.

(Step 19)

This step is a process for producing a compound (I-2) of the invention by reacting the compound (23) obtained in the above step 18 and a compound (18) in the presence of a base. The reaction in this step may be the same as in the above step 14 in point of the type and the amount of the compound (18), the reaction solvent, the reaction temperature and the reaction time, except that the compound (23) is used in place of the compound (17).

Thus obtained, the compound (I-2) of the invention may be isolated and purified in a known isolation and purification method of, for example, concentration, concentration under reduced pressure, crystallization, solvent extraction, reprecipitation, chromatography et al, A compound (I-3) of the invention may be produced, for example, according to the following method.

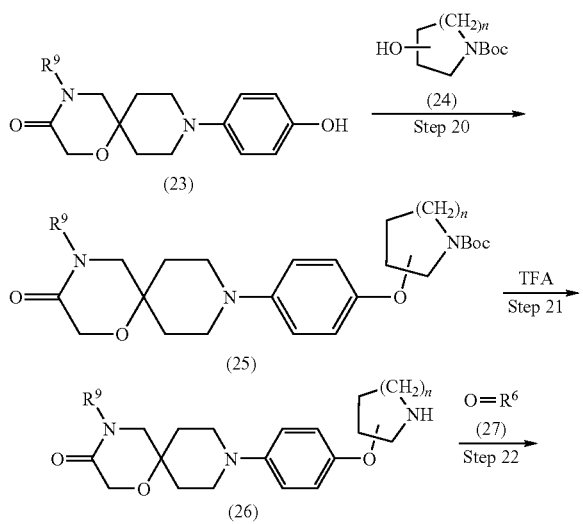

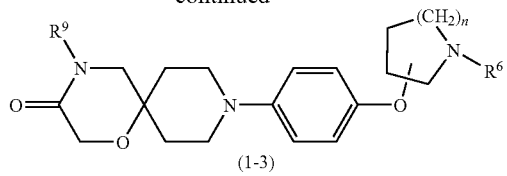

[In the formula, n indicates an integer of from 0 to 4; and the other symbols have the same meanings as above.]

(Step 20)

his step is a process for producing a compound (25) by reacting a compound (23) and a compound (24). The reaction in this step is a Mitsunobu reaction, and the Mitsunobu reaction may be attained in the presence of a phosphine compound and an azo compound, according to a method described in literature (for example, Mitsunobu, O., "The use of diethyl azodicarboxylate and triphenylphosphine in synthesis and transformation of natural products", Synthesis, Vol. 1, 1981, pp. 1-28), or a method similar to it, or a combination of the method with an ordinary method.

The amount of the compound (24) to be used may be generally from 0.5 to 10 equivalents relative to 1 equivalent of the compound (23), preferably from 1 to 3 equivalents.

The phosphine compound to be used includes triphenyl phosphine, triethyl phosphine et al.

The amount of the phosphine compound to be used may be generally from 0.5 to 10 equivalents relative to 1 equivalent of the compound (23), preferably from 1 to 3 equivalents.

The azo compound to be used includes diethyl azodicarboxylate, diisopropyl azodicarboxylate et al. The amount of the azo compound to be used may be generally from 0.5 to 10 equivalents relative to 1 equivalent of the compound (23), preferably from 1 to 3 equivalents.

The reaction time may be generally from 1 to 48 hours, preferably from 4 to 12 hours. The reaction temperature may be generally from room temperature to the boiling point of the reaction solvent, preferably from 15° C. to 30° C.

Not specifically defined, the reaction solvent may be any one not interfering with the reaction and includes, for example, tetrahydrofuran, toluene et al.

Thus obtained, the compound (25) may be subjected to the next step, after isolated and purified in a known isolation and purification method of, for example, concentration, concentration under reduced pressure, crystallization, solvent extraction, reprecipitation, chromatography et al, or not isolated and purified.

(Step 21)

This step is a process for producing a compound (26) by removing the Boc group from the compound (25).

The reaction in this step may be attained according to a method described in the above-mentioned Protective Groups in Organic Synthesis, or a method similar to it, or a combination of the method with an ordinary method.

For example, the compound (25) is processed with from 1 to 10 equivalents, relative to 1 equivalent of the compound (25), preferably from 2 to 4 equivalents of TFA in a reaction solvent such as methylene chloride, methanol et al, thereby producing the compound (26).

Thus obtained, the compound (26) may be subjected to the next step, after isolated and purified in a known isolation and purification method of, for example, concentration, concentration under reduced pressure, crystallization, solvent extraction, reprecipitation, chromatography et al, or not isolated and purified.

(Step 22)

his step is a process for producing a compound (I-3) of the invention by reacting the compound (26) and a compound (27).

The reaction in this step is so-called reductive amination. The amount of the compound (27) to be used may be generally from 1 to 10 equivalents relative to 1 equivalent of the compound (26), preferably from 2 to 4 equivalents.

The compound (27) includes cyclobutanone, cyclopentanone et al.

The reducing agent to be used includes an organic metal reagent such as sodium borohydride, sodium cyanoborohydride, sodium triacetoxyborohydride et al. The amount of the reducing agent may be generally from 1 to 5 equivalents relative to 1 equivalent of the compound (26), preferably from 1 to 3 equivalents. A catalytic amount of $ZnCl_2$ may be present in the reaction system.

The reaction may be effected generally in an inert solvent. The inert solvent is preferably methanol, ethanol, benzene, toluene, xylene, methylene chloride, chloroform, dimethoxyethane, tetrahydrofuran, dioxane, dimethylformamide and their mixed solvents.

The reaction temperature may be generally from room temperature to the boiling point of the reaction solvent, preferably from 20° C. to 100° C. The reaction time may be generally from 30 minutes to 7 days, preferably from 3 hours to 2 days.

Thus obtained, the compound (I-3) of the invention may be isolated and purified in a known isolation and purification method of, for example, concentration, concentration under reduced pressure, solvent extraction, crystallization, reprecipitation, chromatography et al.

Compounds (I-4) and (I-5) of the invention may be produced, for example, according to the following method.

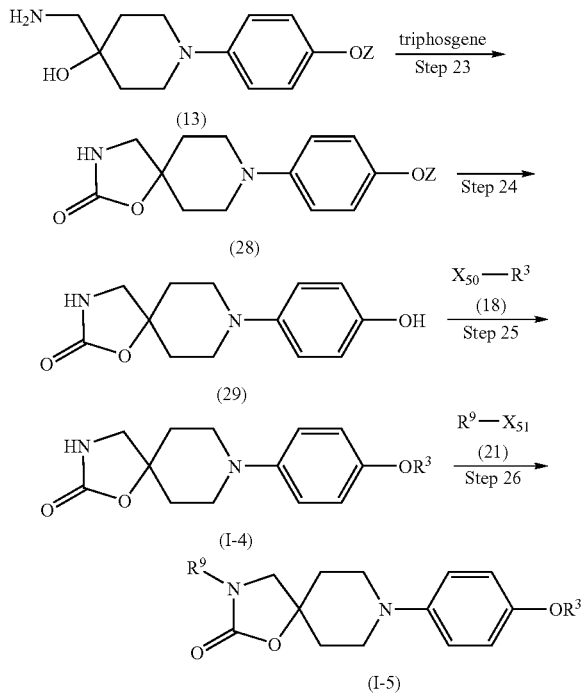

[In the formula, the symbols have the same meanings as above.]

(Step 23)

This step is a process for producing a compound (28) by reacting a compound (13) and triphosgene. The reaction in this step may be attained according to a method described in literature (for example, Synthetic Communications, Vol. 24, 1994, pp. 1483-1487), or a method similar to it, or a combination of the method with an ordinary method.

The amount of triphosgene to be used in this step may be generally from 1 to 10 equivalents relative to 1 equivalent of the compound (13), preferably from 1 to 2 equivalents.

Not specifically defined, the reaction solvent may be any one not interfering with the reaction and includes, for example, an inert solvent such as chloroform, methylene chloride, 1,2-dichloroethane, carbon tetrachloride, tetrahydrofuran, diethyl ether, toluene et al, or their mixed solvents. Of those, preferred are chloroform, methylene chloride, 1,2-dichloroethane. The reaction temperature may be generally from 40° C. to 100° C., preferably from 10° C. to 30° C. The reaction time may be generally from 1 to 48 hours, preferably from 1 to 15 hours.

Thus obtained, the compound (28) may be subjected to the next step, after isolated and purified in a known isolation and purification method of, for example, concentration, concentration under reduced pressure, crystallization, solvent extraction, reprecipitation, chromatography et al, or not isolated and purified.

In case where Z in the compound (13) is the following formula,

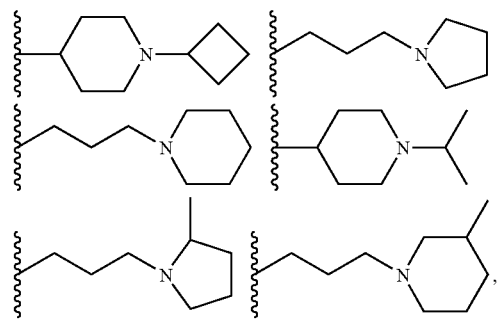

the reaction gives a compound (I-4), and then this may be subjected to the step 26 to obtain a compound (I-5).

In case where Z is a benzyl or methyl group, the compound (I-4) may be obtained after the following step 24 and step 25.

(Step 24)

This step is a process for producing a compound (29) by removing the protective group of the hydroxyl group in the compound (28) obtained in the above step 23.

The reaction in this step may be attained according to a method described in the above-mentioned Protective Groups in Organic Synthesis, or a method similar to it, or a combination of the method with an ordinary method.

The protective group removal in this step may be attained according to the method of the above step 18, or a method similar to it, or a combination of the method with an ordinary method.

Thus obtained, the compound (29) may be subjected to the next step, after isolated and purified in a known isolation and purification method of, for example, concentration, concentration under reduced pressure, crystallization, solvent extraction, reprecipitation, chromatography et al, or not isolated and purified.

(Step 25)

This step is a process for producing a compound (14) of the invention by reacting the compound (29) obtained in the above step 24 and a compound (18).

The reaction in this step may be attained according to the method of the above step 19, or a method similar to it, or a combination of the method with an ordinary method, except that the compound (29) is used in place of the compound (23). Thus obtained, the compound (14) may be subjected to the next step, after isolated and purified in a known isolation and purification method of, for example, concentration, concentration under reduced pressure, crystallization, solvent extraction, reprecipitation, chromatography et al, or not isolated and purified.

(Step 26)

This step is a process for producing a compound (I-5) of the invention by reacting the compound (I-4) obtained in the above step 25 and a compound (21).

The reaction in this step may be attained according to the method of the above step 17, or a method similar to it, or a combination of the method with an ordinary method, except that the compound (I-4) is used in place of the compound (15).

Thus obtained, the compound (I-5) may be isolated and purified in a known isolation and purification method of, for example, concentration, concentration under reduced pressure, crystallization, solvent extraction, reprecipitation, chromatography et al.

The compound (I-5) of the invention may also be produced, for example, according to the following method.

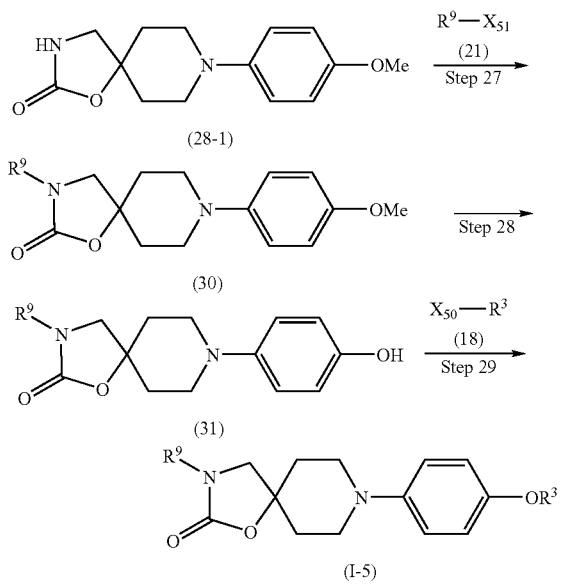

[In the formula, the symbols have the same meanings as above.]

(Step 27)

his step is a process for producing a compound (30) by reacting a compound (28-1), or that is, the compound (28) obtained in the above step 23 where Z is methyl, and a compound (21).

The reaction in this step may be attained according to the method of the above step 17, or a method similar to it, or a combination of the method with an ordinary method, except that the compound (28-1) is used in place of the compound (15).

Thus obtained, the compound (30) may be subjected to the next step, after isolated and purified in a known isolation and purification method of, for example, concentration, concentration under reduced pressure, crystallization, solvent extraction, reprecipitation, chromatography et al, or not isolated and purified.

(Step 28)

This step is a process for producing a compound (31) by removing the protective group of the hydroxyl group of the compound (30) obtained in the above step 27.

The reaction in this step may be attained according to a method described in the above-mentioned Protective Groups in Organic Synthesis, or a method similar to it, or a combination of the method with an ordinary method.

The protective group removal in this step may be attained according to the method of the above step 18, or a method similar to it, or a combination of the method with an ordinary method.

Thus obtained, the compound (31) may be subjected to the next step, after isolated and purified in a known isolation and purification method of, for example, concentration, concentration under reduced pressure, crystallization, solvent extraction, reprecipitation, chromatography et al, or not isolated and purified.

(Step 29)

This step is a process for producing a compound (I-5) of the invention by reacting the compound (31) obtained in the above step 28 and a compound (18).

The reaction in this step may be attained according to the method of the above step 19, or a method similar to it, or a combination of the method with an ordinary method, except that the compound (31) is used in place of the compound (23). Thus obtained, the compound (I-5) may be isolated and purified in a known isolation and purification method of, for example, concentration, concentration under reduced pressure, crystallization, solvent extraction, reprecipitation, chromatography et al.

A compound (I-6) of the invention may be produced, for example, according to the following method.

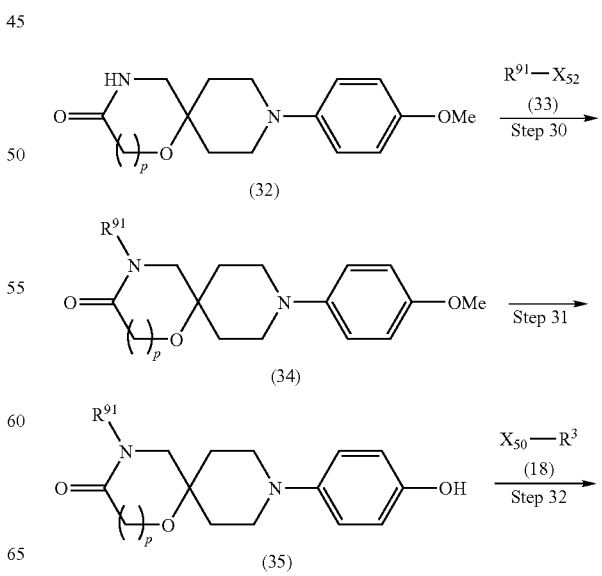

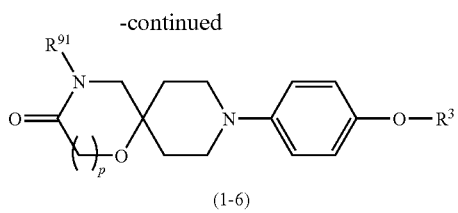

(1-6)

[In the formula, p indicates 0 or 1; $R^{91}$ represents a lower alkyl group; $X_{52}$ represents a bromine atom or an iodine atom; and the other symbols have the same meanings as above.]

(Step 30)

This step is a process for producing a compound (34) by reacting a compound (32) and a compound (33) in the presence of a base.

The compound (33) for use in this step includes, for example, methyl iodide, ethyl bromide et al.

The amount of the compound (33) may be generally from 1 to 10 equivalents relative to 1 equivalent of the compound (32), preferably from 1 to 2 equivalents.

The base to be used in this step includes, for example, sodium hydride, lithium hydride, potassium tert-butoxide et al. The amount of the base may be generally from 1 to 10 equivalents relative to 1 equivalent of the compound (32), preferably from 1 to 2 equivalents.

Not specifically defined, the reaction solvent may be any one not interfering with the reaction and includes, for example, N,N-dimethylformamide, tetrahydrofuran, 1,4-dioxane, acetonitrile et al. Of those, preferred is N,N-dimethylformamide.

The reaction temperature may be generally from 0° C. to 100° C., preferably from 10° C. to 30° C.

The reaction time may be generally from 1 to 48 hours, preferably from 5 to 15 hours.

Thus obtained, the compound (34) may be subjected to the next step, after isolated and purified in a known isolation and purification method of, for example, concentration, concentration under reduced pressure, crystallization, solvent extraction, reprecipitation, chromatography et al, or not isolated and purified.

(Step 31)

This step is a process for producing a compound (35) by removing the protective group of the hydroxyl group of the compound (34) obtained in the above step 30.

The reaction in this step may be attained according to a method described in the above-mentioned Protective Groups in Organic Synthesis, or a method similar to it, or a combination of the method with an ordinary method.

Thus obtained, the compound (35) may be subjected to the next step, after isolated and purified in a known isolation and purification method of, for example, concentration, concentration under reduced pressure, crystallization, solvent extraction, reprecipitation, chromatography et al, or not isolated and purified.

(Step 32)

This step is a process for producing a compound (I-6) of the invention by reacting the compound (35) obtained in the above step 31 and a compound (18).

The reaction in this step may be attained according to the method of the above step 19, or a method similar to it, or a combination of the method with an ordinary method, except that the compound (35) is used in place of the compound (23). Thus obtained, the compound (I-6) may be isolated and purified in a known isolation and purification method of, for example, concentration, concentration under reduced pressure, crystallization, solvent extraction, reprecipitation, chromatography et al.

A compound (I-7) of the invention may be produced, for example, according to the following method.

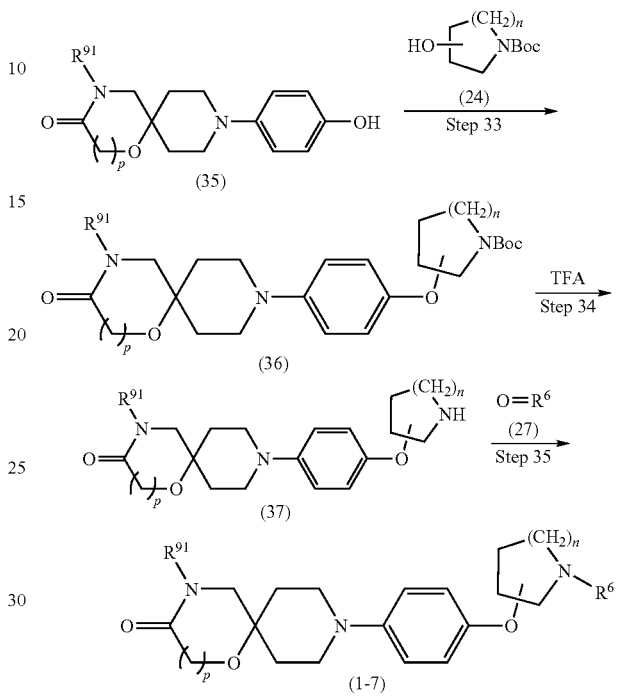

[In the formula, the symbols have the same meanings as above.]

(Step 33)

This step is a process for producing a compound (36) by reacting the compound (35) obtained in the above step 31 and a compound (24). The reaction in this step may be attained according to the method of the above step 20, or a method similar to it, or a combination of the method with an ordinary method, except that the compound (35) is used in place of the compound (23).

Thus obtained, the compound (36) may be subjected to the next step, after isolated and purified in a known isolation and purification method of, for example, concentration, concentration under reduced pressure, crystallization, solvent extraction, reprecipitation, chromatography et al, or not isolated and purified.

(Step 34)

This step is a process for producing a compound (37) by removing the Boc group from the compound (36) obtained in the above step 33. This may be attained according to a method described in the above-mentioned Protective Groups in Organic Synthesis, or a method similar to it, or a combination of the method with an ordinary method. Concretely, it may be attained according to the method of the above step 21, or a method similar to it, or a combination of the method with an ordinary method.

Thus obtained, the compound (37) may be subjected to the next step, after isolated and purified in a known isolation and purification method of, for example, concentration, concentration under reduced pressure, crystallization, solvent extraction, reprecipitation, chromatography et al, or not isolated and purified.

(Step 35)

This step is a process for producing a compound (I-7) of the invention by reacting the compound (37) obtained in the above step 34 and a compound (27).

The reaction in this step is so-called reductive amination.

The compound (27) to be used may be generally from 1 to 10 equivalents relative to 1 equivalent of the compound (37), preferably from 2 to 4 equivalents.

The compound (27) includes cyclobutanone, cyclopentanone et al.

The reducing agent to be used includes an organic metal reagent such as sodium borohydride, sodium cyanoborohydride, sodium triacetoxyborohydride et al. The amount of the reducing agent may be generally from 1 to 5 equivalents relative to 1 equivalent of the compound (37), preferably from 1 to 3 equivalents.

A catalytic amount of $ZnCl_2$ may be present in the reaction system.

The reaction may be effected generally in an inert solvent. The inert solvent is preferably methanol, ethanol, benzene, toluene, xylene, methylene chloride, chloroform, dimethoxyethane, tetrahydrofuran, dioxane, dimethylformamide and their mixed solvents.

The reaction temperature may be generally from 0° C. to the boiling point of the reaction solvent, preferably from 20° C. to 100° C. The reaction time may be generally from 30 minutes to 7 days, preferably from 3 hours to 2 days.

Thus obtained, the compound (I-7) may be isolated and purified in a known isolation and purification method of, for example, concentration, concentration under reduced pressure, solvent extraction, crystallization, reprecipitation, chromatography et al.

The compounds of formula (I), or that is, the compounds (I-1), the compounds (I-2), the compounds (I-3), the compounds (14), the compounds (I-5), the compounds (I-6) and the compounds (I-7) of the invention obtained according to the above methods may be readily isolated and purified in an ordinary separation and purification method. The method includes, for example, solvent extraction, recrystallization, reprecipitation, column chromatography, preparative thin-layer chromatography.

These compounds may be converted into pharmaceutically-acceptable salts or esters in an ordinary manner; and on the contrary, such salts or esters may be converted into the corresponding free compounds in an ordinary manner.

The novel piperidine derivatives of the invention may exist as pharmaceutically-acceptable salts, and the salts may be produced in an ordinary manner, using the compounds of formula (I). The acid addition salts include, for example, hydrohalides (e.g., hydrochlorides, hydrofluorides, hydrobromides, hydroiodides), inorganic acid salts (e.g., nitrates, perchlorates, sulfates, phosphates, carbonates), lower alkylsulfonates (e.g., methanesulfonates, trifluoromethanesulfonates, ethanesulfonates), arylsulfonates (e.g., benzenesulfonates, p-toluenesulfonates), organic acid salts (e.g., fumarates, succinates, citrates, tartrates, oxalates, maleates), and amino acid salts (e.g., glutamates, aspartates).

The base addition salts include, for example, alkali metal salts (e.g., sodium salts, potassium salts), alkaline earth metal salts (e.g., calcium salts, magnesium salts), ammonium salts, and organic base (e.g., guanidine, triethylamine, dicyclohexylamine) addition salts. Further, the compounds of the invention may be in any form of hydrates or solvates of their free compounds or salts.

The compounds of formula (I) and their pharmaceutically-acceptable salts may be administered orally or parenterally.

In clinical use of the compounds of the invention, pharmaceutically-acceptable additives may be added thereto to formulate various preparations in accordance with the intended administration route thereof. Various additives generally used in the field of pharmaceutical compositions may be used herein, including, for example, gelatin, lactose, white sugar, titanium oxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, and hydroxypropylcyclodextrin et al.

A mixture of the compound of the invention and the above additives may be used as solid preparations (e.g., tablets, capsules, granules, powders, suppositories) and liquid preparations (e.g., syrups, elixirs, injections). These preparations can be produced in an ordinary method known in the filed of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto. The preparations may contain the compound of the invention in an amount of from 1.0 to 100% by weight, preferably from 1.0 to 60% by weight of the preparation.

The compounds of the invention may be formulated into preparations, for example, according to the following Formulation Examples.

FORMULATION EXAMPLE 1

10 parts of the compound of Example 1 to be described hereinunder, 15 parts of heavy magnesium oxide and 75 parts of lactose are uniformly mixed to prepare a powdery or granular preparation having a particle size of at most 350 μm. The preparation is encapsulated to give capsules.

FORMULATION EXAMPLE 2

45 parts of the compound of Example 1 to be described hereinunder, 15 parts of starch, 16 parts of lactose, 21 parts of crystalline cellulose, 3 parts of polyvinyl alcohol and 30 parts of distilled water are uniformly mixed, then ground, granulated and dried, and then sieved to give a granular preparation having a particle diameter of from 1410 to 177 μm.

FORMULATION EXAMPLE 3

A granular preparation is prepared in the same manner as in Formulation Example 2. 96 parts of the granular preparation is mixed with 3 parts of calcium stearate, and shaped under compression into tablets having a diameter of 10 mm.

FORMULATION EXAMPLE 4

90 parts of the granular preparation obtained according to the method of Formulation Example 2 is mixed with 10 parts of crystalline cellulose and 3 parts of calcium stearate, and shaped under compression into tablets having a diameter of 8 mm. These are coated with a mixed suspension of syrup gelatin and precipitated calcium carbonate to give sugar-coated tablets.

These preparations may contain any other therapeutically-effective drug, as described below.

In their use, the compounds of the invention may be combined with any other drug effective for treatment (prevention or therapy) of metabolic disorders or dietary disorders. The individual ingredients to be combined may be administered at different times or at the same time, either as one preparation or as divided different preparations. The combination of the compound of the invention with any other drug effective for treatment of metabolic disorders or dietary disorders includes, in principle, combinations thereof with any and every drug effective for treatment of metabolic disorders or dietary disorders.

The compounds of the invention may also be combined with any other drug effective for hypertension, obesity-related hypertension, hypertension-related disorders, cardiomegaly, left ventricle hypertrophy, metabolic disorders, obesity, obesity-related disorders (these are hereinafter referred to as "co-drugs"). Combined with the compound of the invention, such co-drugs may be administered at the same time or at different times or successively in order in prevention or treatment of the above-mentioned disorders. When the compound of the invention is used simultaneously with one or more co-drugs, then it may be in a pharmaceutical composition for one-dose administration. However, in such combination therapy, the composition containing the compound of the invention and the co-drug may be administered to subjects simultaneously, or separately or successively. The composition and the co-drug may be packed separately. They may be administered at different times.

The dose of the co-drug may depend on the clinical use thereof, and may be suitably determined in accordance with the administration subject, the administration route, the diseases and the combination. The form of the co-drug for administration is not specifically defined, and it may be combined with the compound of the invention when they are administered. The administration mode includes, for example, the following: (1) A compound of the invention is combined with a co-drug to give a single preparation for single administration; (2) a compound of the invention and a co-drug are separately formulated into different two preparations, and the two preparations are simultaneously administered in one administration route; (3) a compound of the invention and a co-drug are separately formulated into different two preparations, and they are administered at different times in one and the same administration route; (4) a compound of the invention and a co-drug are separately formulated into different two preparations, and they are administered at the same time in two different administration routes; (5) a compound of the invention and a co-drug are separately formulated into different two preparations, and they are administered at different times in different administration routes (for example, a compound of the invention and a co-drug are administered in that order, or in an order contrary to this). The blend ratio of the compound of the invention and the co-drug may be suitably determined depending on the administration subject, the administration route, and the disease for the administration.

The co-drugs usable in the invention include therapeutical drugs for diabetes, therapeutical drugs for hyperlipemia, therapeutical drugs for hypertension, and anti-obesity drugs. Two or more such co-drugs may be combined in any desired ratio.

The therapeutical drugs for diabetes include, for example, the following:
1) PPAR (peroxisome proliferator-activated receptor)-γ agonists such as glitazones (e.g., ciglitazone, darglitazone, englitazone, isaglitazone, MCC-555, pioglitazone, rosiglitazone, troglitazone, BRL49653, CLX-0921, 5-BTZD), GW-0207, LG-100641, LY-300512;
2) biguanides such as metformin, buformin, phenformin;
3) protein tyrosine phosphatase-1B inhibitors;
4) sulfonylureas such as acetohexamide, chloropropamide, diabinese, glibenclamide, glipizide, glyburide, glimepiride, gliclazide, glipentide, gliquidone, glisolamide, trazamide, tolubutamide;
5) meglitinides such as repaglinide, nateglinide;
6) α-glucoside hydrolase inhibitors such as acarbose, adiposine, camiglibose, emiglitate, miglitol, voglibose, pradimicin-Q, salbostatin, CKD-711, MDL-25,673, MDL-73,945, MOR14;
7) α-amylase inhibitors such as tendamistat, trestatin, A13688;
8) insulin secretion promoters such as linogliride, A-4166;
9) fatty acid oxidation inhibitors such as clomoxir, etomoxir;
10) A2 antagonists such as midaglizole, isaglidole, deriglidole, idazoxan, earoxan, fluparoxan;
11) insulin or insulin mimetics such as biota, LP-100, novalapid, insulin determir, insulin lispro, insulin glargine, insulin zinc, Lys-Pro-insulin, GLP-1 (73-7), GLP1 (7-36)-NH$_2$;
12) non-thiazolidinediones such as JT-501, farglitazar;
13) PPARα/γ dual-agonists such as CLX-0940, GW-1536, GW-1929, GW-2433, KRP-297, L-796449, LR-90, SB219994;
14) other insulin sensitizes, and
15) VPAC2 receptor agonists.

The therapeutical drugs for hyperlipemia include, for example, the following:
1) bile acid absorption promoters such as cholesterylamine, colesevelem, colestipol, crosslinked dextran dialkylaminoalkyl derivatives, Colestid®, LoCholest®, Questran®;
2) HMG-CoA reductase inhibitors such as atorvastatin, itavastatin, fluvastatin, lovastatin, pravastatin, rivastatin, rosuvastatin, simvastatin, ZD-4522;
3) HMG-CoA synthase inhibitors;
4) cholesterol absorption inhibitors such as snatol ester, β-sitosterol, sterol glucoside, ezetimibe;
5) ACAT (acyl-CoA-cholesterol acyltransferase) inhibitors such as avasimibe, eflucimibe, KY-505, SMP-709;
6) CETP inhibitors such as JTT705, torcetrapib, CP532632, BAY-63-2149, SC-591, SC-795;
7) squalane synthetase inhibitors;
8) antioxidants such as probucol;
9) PPARα agonists such as beclofibrate, benzafibrate, syprofibrate, clofibrate, etofibrate, fenofibrate, gemcabene, gemfibrozil, GW-7647, BM-170744, LY-518674, fibric acid derivatives (e.g., Atromid®, Lopid®, Tricor®);
10) FXR receptor antagonists such as GW-4064, SR-103912;
11) LXR receptor agonists such as GW3965, T9013137, XTCO-179628;
12) lipoprotein synthesis inhibitors such as niacin;
13) renin-angiotensin system inhibitors;
14) PPARδ partial agonists;
15) bile acid resorption inhibitors such as BARA1453, SC435, PHA384640, S-435, AZD7706;
16) PPARδ agonists such as GW501516, GW590735;
17) triglyceride synthesis inhibitors;
18) MTTP (microsomic triglyceride transportation) inhibitors such as inplitapide, LAB687, CP346086;
19) transcription modifying factors;
20) squalane epoxidase inhibitors;
21) LDL (low-density lipoprotein) receptor inducers,
22) platelet agglutination inhibitors;

23) 5-LO (5-lipoxygenase)/FLAP (5-lipoxygenase activated protein) inhibitors; and
24) niacin receptor agonists.

The therapeutical drugs for hypertension include, for example, the following:
1) thiazide diuretics such as chlorothialidon, chlorothiazide, dichlorofenamide, hydrofluorothiazide, indapamide, hydrochlorothiazide; loop diuretics such as bumetanide, ethacrynic acid, flosemide, tolusemide; sodium diuretics such as amyloride, triamuteren; aldosterone antagonist diuretics such as spironolactone, epilenone;
2) β-adrenaline blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, probanolol, sotalol, tartatolol, tilisolol, timolol;
3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, verapamil;
4) angiotensin converting enzyme inhibitors such as benazepril, captopril, cilazapril, delapril, enalapril, fosinopril, imidapril, rosinopril, moexipril, quinapril, quinaprilat, ramipril, perindopril, perindoropril, quanipril, spirapril, tenocapril, trandolapril, zofenopril;
5) neutral endopeptidase inhibitors such as omapatrilat, cadoxatril, ecadotril, fosidotril, sampatrilat, AVE7688, ER4030;
6) endotheline antagonists such as tezosentan, A308165, YM62899;
7) vasodilators such as hydraladine, clonidine, minoxidil, nicotinyl alcohol;
8) angiotensin II receptor antagonists such as candesartan, eporsartan, iribesartan, losartan, pratosartan, tasosartan, telmisartan, valsartan, EXP-3137, FI6828K, RNH6270;
9) α/β adrenalin blockers such as nipradilol, arotinolol, amoslalol;
10) α 1 blockers such as terazosin, urapidil, purazosin, bunazosin, trimazosin, doxazosin, naphthopidil, indolamin, WHIP164, XEN010;
11) α2 agonists such as lofexidine, tiamenidine, moxonidine, rilmenidine, guanobenz; and
12) aldosterone inhibitors.

The anti-obesity drugs include, for example, the following:
1) 5HT (serotonin) transporter inhibitors such as paroxetine, fluoxetine, fenfluramine, fluvoxamine, sertraline, imipuramine;
2) NE (norepinephrine) transporter inhibitors such as GW320659, desipramin, talsupram, nomifensin;
3) CB-1 (cannabinoid-1 receptor) antagonists/inverse-agonists such as limonabant (Sanofi Synthelabo), SR-147778 (Sanofi Synthelabo), BAY-65-2520 (Bayer), SLV-319 (Sorbei), as well as compounds disclosed in U.S. Pat. No. 5,532,237, U.S. Pat. No. 4,973,587, U.S. Pat. No. 5,013,837, U.S. Pat. No. 5,081,122, U.S. Pat. No. 5,112,820, U.S. Pat. No. 5,292,736, U.S. Pat. No. 5,624,941, U.S. Pat. No. 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887 and EP-658546;
4) glerin antagonists such as compounds disclosed in WO01/87355, WO02/08250;
5) histamine(H3) antagonists/inverse-agonists such as thioperamide, 3-1H-imidazol-4-yl)propyl N-(pentenyl)carbonate, clobenpropit, iodofenpropit, imoproxyfen, GT2395, A331440, compounds disclosed in WO02/15905, O-[3-(1H-imidazol-4-yl)propanol]carbamate, piperazine-containing H3-receptor antagonists (Lazewska, D. et al., Pharmazie, 56: 927-32 (2001)), benzophenone derivatives Sasse, A. et al., Arch. PharnL (Weinheim) 334: 45-52 (2001)), substituted N-phenylcarbamates (Reidemeister, S. et al., Pharmazie, 55: 83-6 (2000)), proxyfen derivatives (Sasse, A. et al., J. Med. Chem., 43: 3335-43 (2000));
6) MCH-1R (melamine concentrating hormone receptor 1) antagonists such as T-226296 (Takeda), SNP-7941 (Synaptic), other compounds disclosed in WO01/82925, WO01/87834, WO02/051809, WO02/06245, WO02/076929, WO02/076947, WO02/04433, WO02/51809, WO02/083134, WO02/094799, WO03/004027 and JP-A-2001-226269;
7) MCH-2R (melamine concentrating hormone receptor 2) agonists/antagonists;
8) NPY1 (neuropeptide YY1) antagonists such as BIBP3226, J-115814, BIB03304, LY-357897, CP-671906, GI-264879, and other compounds disclosed in U.S. Pat. No. 6,001,836, WO96/14307, WO01/23387, WO99/51600, WO01/85690, WO01/85098, WO01/85173 and WO01/89528;
9) NPY5 (neuropeptide YY5) antagonists such as 152804, GW-569180A, GW-594884A, GW-587081X, GW-548118X, FR235,208, FR226928, FR240662, FR252384, 1229U91, GI-264879A, CGP71683A, LY-377897, LY366377, PD-160170, SR-120562A, SR-120819A, JCF-104, H409/22, and other compounds disclosed in U.S. Pat. No. 6,140,354, U.S. Pat. No. 6,191,160, U.S. Pat. No. 6,258,837, U.S. Pat. No. 6,313,298, U.S. Pat. No. 6,337,332, U.S. Pat. No. 6,329,395, U.S. Pat. No. 340,683, U.S. Pat. No. 6,326,375, U.S. Pat. No. 6,329,395, U.S. Pat. No. 6,337,332, U.S. Pat. No. 6,335,345, EP-01010691, EP-01044970, WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO1/85730, WO01/07409, WO01/02379, WO01/02379, WO01/23388, WO01/23389, WO01/44201, WO01/62737, WO01/62738, WO01/09120, WO02/20488, WO02/22592, WO02/48152, WO02/49648, WO02/094789, and compounds disclosed in Norman et al., J. Med. Chem., 43:4288-4312 (2000);
10) reptins such as human recombinant reptin (PEG-OB, Hoffman La Roche), recombinant methionylreptin (Amgen);
11) reptin derivatives such as compounds disclosed in U.S. Pat. No. 5,552,524, U.S. Pat. No. 5,552,523, U.S. Pat. No. 5,552,522, U.S. Pat. No. 5,521,283, WO96/23513, WO96/23514, WO96/23515, WO96/23516, WO96/23517, 96/23518, WO96/23519 and WO96/23520;
12) opioid antagonists such as narmefen (Revex®), 3-methoxynartorexone, naloxone, nartorexone, compounds disclosed in WO00/21509;
13) aurexin antagonists such as SB-334867A, and other compounds disclosed in WO01/96302, WO01/68609, WO02/51232, WO02/51838 and WO03/023561;
14) BRS3 (bonbesin receptor subtype-3) agonists;
15) CCK-A (cholecystokinin A) agonists such as AR-R15849, GI-181771, JMV-180, A-71378, A-71623, SR-146131, and other compounds disclosed in U.S. Pat. No. 5,739,106;
16) CNTF (ciliary neurotrophic factors) such as GI-181771 (Glaxo-Smith Kline), SR146131 (Sanofi Synthelabo), butabindide, PD 170,292, PS149164 (Pfizer);

17) CNTF derivatives such as axokine (Regeneron), and other compounds disclosed in WO94/09134, WO98/22128, WO99/43813;
18) GHS (growth hormone secretion receptor) agonists such as NN703, hexarelin, MK-0677, SM-130686, CP-424,391, L-692,429, L-163,255, and compounds disclosed in U.S. Pat. No. 6,358,951, US Patent Application Nos. 2002/049196, 2002/022637, WO01/56592, WO02/32888;
19) 5HT2c (serotonin receptor-2c) agonists such as BVT933, DPCA37215, IK264, PNU22394, WAY161503, R-1065, YM348, and other compounds disclosed in U.S. Pat. No. 3,914,250, WO02/36596, WO02/48124, WO02/10169, WO01/66548, WO02/44152, WO02/51844, WO02/40456 and WO02/40457;
20) Mc3r (melanocortin-3 receptor) agonists;
21) Mc4r (melanocortin-4 receptor) agonists such as CHIR86036 (Chiron), ME-10142, ME-10145 (Melacure), and other compounds disclosed in WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949 and WO03/009847;
22) monoamine re-uptake inhibitors such as sibutramine (Meridia®/Reductil®) and its salts, and other derivatives disclosed in U.S. Pat. No. 4,746,680, U.S. Pat. No. 4,806,570, U.S. Pat. No. 5,436,272, US Patent Application No. 2002/0006964, WO01/27068 and WO01/62341;
23) serotonin re-uptake inhibitors such as dexfenfluramine, fluoxetine, and other compounds disclosed in U.S. Pat. No. 6,365,633, WO01/27060 and WO01/162341;
24) GLP1 (glucagon-like peptide-1) agonists;
25) topiramate (Topimax®);
26) phytopharm compound 57 (e.g., CP644,673);
27) ACC2 (acetyl CoA carboxylase-2) inhibitors;
28) β3 (adrenalin receptor-3) agonists such as AD9677/TAK677 (Dai-Nippon Pharmaceutical/Takeda Chemical), CL-316,243, SB418790, BRL-37344, L-796568, BMS-196085, BRL-35135A, CGP12177A, BTA-243, W427353, trecadrine, Zeneca D7114, SR59119A, and other compounds disclosed in U.S. Pat. No. 5,705,515, U.S. Pat. No. 5,451,677, WO01/74782 and WO02/32897;
29) DGAT1 (diacylglycerol acyltransferase-1) inhibitors;
30) DGAT2 (diacylglycerol acyltransferase-2) inhibitors,
31) FAS (fatty acid synthetase) inhibitors such as cerulenin, C75;
32) PDE (phosphodiesterase) inhibitors such as theophylline, pentoxifylline, zaprinast, sildenafil, aminone, milrinone, cilostamide, rolipram and cilomilast;
33) thyroid hormone-β agonists such as KB-2611 (KaroBio BMS), and other compounds disclosed in WO02/15845, JP-A-2000-256190;
34) UCP (uncoupling protein)-1, 2, or 3 activators such as phytanic acid, 4-[(E)-2-(5,6,7,8-tetrahydro-5,5,8,8-tetramethyl-2-naphthalenyl-1-propenyl]benzoic acid (TTNPB), retinoic acid, and other compounds disclosed in WO99/00123;
35) acylestrogens such as oleoylestrone (disclosed in del Mar-Grasa, M. et al., Obesity Research, 9:202-9 (2001));
36) glucocorticoid antagonists;
37) 11-β HSD1 (11-β-hydroxysteroid dehydrogenase-1) inhibitors such as BVT3498, BVT2733, and other compounds disclosed in WO01/90091, WO01/90090, WO01/90092;
38) SCD1 (stearoyl-CoA desaturase-1) inhibitors;
39) DP-IV (dipeptidyl peptidase-IV) inhibitors such as isoleucine thiazolidide, valine pyrrolidide, NVP-DPP728, AF237, P93/01, TSL225, TMC-2A/2B/2C, FE999011, P9310/K364, VIP0177, SDZ274-444, and other compounds disclosed in WO03/004498, WO03/004496, EP1258476, WO02/083128, WO02/062764, WO03/000250, WO03/002530, WO03/002531, WO03/002553, WO03/002593, WO03/000180 and WO03/000181;
40) lipase inhibitors such as tetrahydroliptatin (Orlistat/Xenical®), Triton WR1339, RHC80267, lipstatin, tea saponin, diethylumbelliferyl phosphate, FL-386, WAY-121898, Bay-N-3176, valilactone, esteracin, ebelactone A, ebelactone B, RHC80267, and other compounds disclosed in WO01/77094, U.S. Pat. No. 4,598,089, U.S. Pat. No. 4,452,813, U.S. Pat. No. 5,512,565, U.S. Pat. No. 5,391,571, U.S. Pat. No. 5,602,151, U.S. Pat. No. 4,405,644, U.S. Pat. No. 4,189,438 and U.S. Pat. No. 4,242,453;
41) fatty acid transporter inhibitors;
42) dicarboxylate transporter inhibitors;
43) glucose transporter inhibitors;
44) phosphate transporter inhibitors;
45) melanocortin agonists such as melanotan II, and other compounds disclosed in WO99/64002 and WO00/746799;
46) melanin concentrating hormone antagonists;
47) galanin antagonists;
48) CCK agonists;
49) corticotropin release hormones;
50) PDE3 (phosphodiesterase 3B) agonists.

The compounds of the invention may be combined with one or more of the above-mentioned co-drugs. The combination of the compound of the invention with one or more co-drugs selected from a group consisting of drugs for diabetes and drugs for hyperlipemia is useful for prevention or remedy of metabolic disorders. In particular, a combination of the compound of the invention with a drug for hypertension and an anti-obesity drug along with a drug for diabetes or a drug for hyperlipemia is useful for prevention or remedy of metabolic disorders owing to the synergistic effect thereof.

When the compounds of the invention are used in clinical sites, then the dose and the administration frequency thereof may vary depending on the sex, the age, the body weight and the condition of the patient and on the type and the scope of the treatment of the patient. In oral administration, in general, the dose may be from 0.01 to 100 mg/kg-adult/day, preferably from 0.03 to 1 mg/kg-adult/day, and it may be administered all at a time or may be administered in a few times as divided into a few portions. In parenteral administration, its dose may be from 0.001 to 10 mg/kg-adult/day, preferably from 0.001 to 0.1 mg/kg-adult/day, and it may be administered all at a time or may be administered in a few times as divided into a few portions. Ordinary physicians, veterinarians and clinicians may readily determine the effective dose necessary for retarding, inhibiting or stopping the development of diseases.

EXAMPLES

The invention is described more concretely with reference to the following Examples and Reference Examples, which, however, do not whatsoever restrict the invention.

For the thin-layer chromatography of the compounds in the Examples, used was a plate of Silicagel 60F245 (Merck); and for detection, used was a UV detector. For silica gel column chromatography, used were filled silica gel columns (FLASH+™ cartridge, KP-Sil FLASH12+M, FLASH25+M or FLASH40+M (Biotage Japan)). As a reversed-phase preparative HPLC column, used was YMC-Comb Prep ProC18 (YMC). For mass spectrometry, used was QuattroII (Micromass) according to an electrospray ionization (ESI) process.

In NMR spectrometry, dimethyl sulfoxide was used for the internal standard in measurement in a heavy dimethyl sulfoxide solution. Using a spectrometer of Gemini-200 (200 MHz; Varian), Gemini-300 (300 MHz; Varian), Mercury 400 (400 MHz; Varian) or Inova 400 (400 MHz; Varian), the sample was analyzed for the total δ value in ppm.

In LC-MS to determine the retention time and the molecular weight in Examples 2-4 to 2-27, the column used was Wakopak Comb ODS fast (diameter: 2.0 mm×30 mm). The condition is as follows: The liquid A is 0.1% TFA/water, the liquid B is 0.1% TFA/acetonitrile. A/B is 95/5 to 40/60, and the mode is 6 minute linear concentration gradient elution. The flow rate is 0.8 ml/min.

The meanings of the abbreviations in the following Examples are mentioned below.
i-Bu: isobutyl group
n-Bu: n-butyl group
t-Bu: t-butyl group
Me: methyl group
Et: ethyl group
Ph: phenyl group
i-Pr: isopropyl group
n-Pr: n-propyl group
$CDCl_3$: heavy chloroform
$CD_3OD$: heavy methanol
DMSO-d6: heavy dimethylsulfoxide The meanings of the abbreviations in nuclear magnetic resonance spectra are mentioned below.
s: singlet
d: doublet
dd: double-doublet
t: triplet
m: multiplet
br: broad
q: quartet
J: coupling constant
Hz: hertz Example 1

Production of 1'-[4-(3-piperidin-1-ylpropoxy)phenyl]-3H-spiro[2-benzofuran-1,4'-piperidine]

3H-spiro[2-benzofuran-1,4'-piperidin] (131 mg, 0.695 mmol), 1-[3-(4-iodophenoxy)propyl]piperidine (200 mg, 0.58 mmol) prepared in Reference Example (2), sodium tert-butoxide (78 mg, 0.812 mmol), $Pd_2(dba)_3$ (5 mg, 0.0058 mmol), 9,9-dimethyl-4,5-bis(diphenylphosphino)xanthene (7 mg, 0.0116 mmol) were mixed, and stirred overnight in 1,4-dioxane in a nitrogen atmosphere at 60° C. The reaction solution was filtered under suction through Celite, diluted with ethyl acetate, washed with water and saturated saline in that order, and the organic layer was dried with sodium sulfate. The solvent was evaporated off under reduced pressure, and the resulting residue was purified through preparative thin-layer chromatography (eluate: chloroform/methanol=10/1) to obtain the entitled compound as a colorless solid (60.5 mg, 26%).

$^1$H-NMR (400 MHz, $CDCl_3$) δ: 1.43 (2H, brs), 1.56-1.61 (4H, m), 1.87 (2H, d, J=12.0 Hz), 1.92-1.99 (2H, m), 2.08-2.16 (2H, m), 2.39-2.48 (6H, m), 3.10 (2H, t, J=12.4 Hz), 3.43 (2H, d, J=11.2 Hz), 3.96 (2H, t, (J=6.4 Hz), 5.09 (2H, s), 6.83 (2H, d, J=8.8 Hz), 6.96 (2H, d, J=8.8 Hz), 7.13-7.15 (1H, m), 7.21-7.28 (3H, m)

Example 1-1

Production of 4-phenyl-1-[4-(3-piperidin-1-ylpropoxy)phenyl]piperidin-4-ol

The entitled compound was obtained as a colorless solid, according to the same method as in Example 1 or according to a method similar to it but using 4-phenylpiperidin-4-ol in place of 3H-spiro[2-benzofuran-1,4'-piperidine].

$^1$H-NMR (400 MHz, $CDCl_3$) δ: 1.43 (2H, brs), 1.56-1.61 (4H, m), 1.87 (2H, d, J=13.2 Hz), 1.91-1.97 (2H, m), 2.26-2.48 (8H, m), 3.14 (2H, t, J=12.4 Hz), 3.40 (2H, d, J=13.2 Hz), 3.95 (2H, t, J=6 Hz), 6.83 (2H, d, J=8.8 Hz), 6.95 (2H, d, J=8.8 Hz), 7.26 (1H, t, J=8.0 Hz), 7.36 (2H, t, J=8.0 Hz), 7.53 (2H, dd, J=3.6, 2.0 Hz)

Example 1-2

Production of 3-phenyl-8-[4-(3-piperidin-1-ylpropoxy)phenyl]-1-oxa-3,8-diazaspiro[4,5]decan-2-one The entitled compound was obtained as a colorless solid, according to the same method as in Example 1 or according to a method similar to it but using 3-phenyl-1-oxa-3,8-diazaspiro[4,5]decan-2-one in place of 3H-spiro[2-benzofuran-1,4'-piperidine].

$^1$H-NMR (400 MHz, $CD_3OD$) δ: 1.49-1.51 (2H, m), 1.61-1.67 (4H, m), 1.89-2.15 (6H, m), 2.52-2.59 (6H, m), 3.15-3.21 (2H, m), 3.24-3.26 (2H, m), 3.32-3.98 (4H, m), 6.83 (2H, d, J=9.2 Hz), 6.98 (2H, d, J=9.2 Hz), 7.13 (1H, t, J=7.2 Hz), 7.36 (2H, t, J=7.6 Hz), 7.57 (2H, d, J=8.8 Hz)

Example 2

Production of 1'-[4-(3-piperidin-1-ylpropoxy)phenyl]-3H-spiro[2-benzofuran-1,4'-piperidine]-3-one 3H-spiro[2-benzofuran-1,4'-piperidin]-3-one (164 mg, 0.81 mmol), 1-(3-chloropropoxy)-4-iodobenzene (200 mg, 0.674 mmol) prepared in Reference Example (1), sodium tert-butoxide (91 mg, 0.943 mmol), $Pd_2(dba)_3$ (3 mg, 0.00337 mmol) and 9,9-dimethyl-4,5-bis(diphenylphosphino)xanthene (8 mg, 0.0134 mmol) were mixed, and stirred for 2.5 hours in 1,4-dioxane in a nitrogen atmosphere at 60° C. After cooling, the reaction solution was filtered under suction through Celite, diluted with chloroform, washed with water and saturated saline in that order, and the organic layer was dried with sodium sulfate. The solvent was evaporated off under reduced pressure, and the resulting residue was suspended in diethyl ether, and then filtered under suction to obtain a chloro-form as a yellow solid (90 mg, 36%).

The above chloro-form (80 mg) was mixed with piperidine (1 ml), and stirred at 100° C. for 6 hours. After cooling, the reaction solution was concentrated, and the resulting residue was dissolved in chloroform, washed with water and saturated saline in that order, and the organic layer was dried with sodium sulfate. The solvent was evaporated off under reduced pressure, and the resulting residue was purified through reversed-phase preparative HPLC (liquid A: 0.1% TFA/water, liquid B: 0.1% TFA/acetonitrile, A/B=90/10 to 50/50, 8 minute linear concentration gradient elution, flow rate 40 ml/min), and a fraction containing the intended product was collected to obtain the entitled compound as a pale yellow solid (34.5 mg, 38%).

$^1$H-NMR (400 MHz, $CDCl_3$) δ: 1.45 (2H, brs), 1.58-1.63 (4H, m), 1.83 (2H, d, J=13.6 Hz), 1.94-2.01 (2H, m), 2.34-2.51 (8H, m), 3.23 (2H, t, J=12.4 Hz), 3.52 (2H, d, J=12.0

Hz), 3.98 (2H, t, J=6.8 Hz), 6.86 (2H, d, J=8.8 Hz), 6.97 (2H, d, J=8.8 Hz), 7.43 (1H, d, J=7.2 Hz), 7.535 (1H, t, J=7.2 Hz), 7.68 (1H, t, J=7.2 Hz), 7.90 (1H, d, J=7.2 Hz)

Example 2-1

Production of 4-phenyl-9-[4-(3-pyrrolidin-1-ylpropoxy)phenyl]-1-oxa-4,9-diazaspiro[5,5]undecan-3-one The entitled compound was obtained as a yellow solid, according to the same method as in Example 2 or according to a method similar to it but using 4-phenyl-4,9-diazaspiro[5,5]undecan-3-one in place of 3H-spiro[2-benzofuran-1,4'-piperidin]-3-one.

$^1$H-NMR (400 MHz, CDCl$_3$) δ: 1.78-2.03 (8H, m), 2.14 (2H, d, J=13.2 Hz), 2.54 (4H, brs), 2.61-2.65 (2H, m), 3.08 (2H, td, J=11.6, 2.4 Hz), 3.27 (2H, dt, J=9.3, 2.7 Hz), 3.48 (1H, dt, J=17.2, 7.2 Hz), 3.64 (2H, s), 3.98 (2H, t, J=6.0 Hz), 4.35 (2H, s), 6.83 (2H, d, J=8.8 Hz), 6.91 (2H, d, J=8.8 Hz), 7.25-7.31 (3H, m), 7.39-7.43 (2H, m)

Example 2-2

Production of 9-[4-(3-((2S-2-methylpyrrolidin-1-yl)propoxy)phenyl]-4-phenyl-1-oxa-4,9-diazaspiro[5,5]undecan-3-one The entitled compound was obtained as a yellow solid, according to the same method as in Example 2 or according to a method similar to it but using 4-phenyl-4,9-diazaspiro[5,5]undecan-3-one in place of 3H-spiro[2-benzofuran-1,4'-piperidin]-3-one and using (2S)-2-methylpyrrolidine hydrobromide, which had been produced according to the method described in a reference (Journal of Organic Chemistry, J. O. C., 1989, Vol. 54, p. 209) and using D-prolinol as the starting material, in place of piperidine.

$^1$H-NMR (400 z, CDCl$_3$) δ: 1.12 (3H, brs), 1.46-2.00 (9H, m), 2.12-2.35 (4H, m), 2.98-3.11 (3H, m), 3.25-3.29 (3H, m), 3.64 (2H, s), 3.96-4.01 (2H, m), 4.36 (2H, s), 6.84 (2H, d, J=9.2 Hz), 6.93 (2H, d, J=9.2 Hz), 7.27-7.31 (3H, m), 7.41-7.44 (2H, m)

Example 2-3

Production of 9-[4-(3-((3S)-3-methylpiperidin-1-yl)propoxy)phenyl]-4-phenyl-1-oxa-4,9-diazaspiro[5,5]undecan-3-one The entitled compound was obtained as a yellow solid, according to the same method as in Example 2 or according to a method similar to it but using 4-phenyl-4,9-diazaspiro[5,5]undecan-3-one in place of 3H-spiro[2-benzofuran-1,4'-piperidin]-3-one and using (3S)-3-methylpiperidine-(2S)-hydroxy(phenyl)acetate, which had been produced according to the method described in a reference (Journal of Organic Chemistry, J. O. C., 1987, Vol. 52, p. 5467) and using 3-methylpiperidine as the starting material, in place of piperidine.

$^1$H-NMR (400 MHz, CDCl$_3$) δ: 0.87 (3H, d, J=6.8 Hz), 1.61-2.03 (11H, m), 1.98-2.01 (2H, m), 2.14 (2H, d, J=13.2 Hz), 2.55 (2H, brs), 2.92 (2H, brs), 3.04-3.11 (2H, m), 3.24-3.30 (2H, m), 3.64 (2H, s), 3.97 (2H, t, J=6.3 Hz), 4.36 (2H, s), 6.81-6.85 (2H, m), 6.91-6.95 (2H, m), 7.26-7.31 (3H, m)

Example 2-4

Production of 4-(4-fluorophenyl)-1-[4-(3-piperidin-1-ylpropoxy)phenyl]piperidin-4-ol trifluoroacetate The entitled compound was obtained as a pale yellow solid, according to the same method as in Example 2 or according to a method similar to it but using 4-(4-fluorophenyl)piperidin-4-ol in place of 3H-spiro[2-benzofuran-1,4'-piperidin]-3-one.

Retention time: 3.16 min
m/z: 413.3 [M+H]$^+$

Example 2-5

Production of 1-[4-(3-piperidin-1-ylpropoxy)phenyl]-4-pyridin-3-ylpiperidin-4-ol trifluoroacetate The entitled compound was obtained as a pale yellow solid, according to the same method as in Example 2 or according to a method similar to it but using 4-pyridin-3-ylpiperidin-4-ol in place of 3H-spiro[2-benzofuran-1,4'-piperidin]-3-one.

Retention time: 1.98 min
m/z: 396.3 [M+H]$^+$

Example 2-6

Production of 4-(4-methoxyphenyl)-1-[4-(3-piperidin-1-ylpropoxy)phenyl]piperidin-4-ol trifluoroacetate The entitled compound was obtained as a pale yellow solid, according to the same method as in Example 2 or according to a method similar to it but using 4-(4-methoxyphenyl)piperidin-4-ol in place of 3H-spiro[2-benzofuran-1,4'-piperidin]-3-one.

Retention time: 3.08 min
m/z: 425.3 [M+H]$^+$

Example 2-7

Production of 5-fluoro-1'-[4-(3-piperidin-1-ylpropoxy)phenyl]-3H-spiro[2-benzofuran-1,4'-piperidine]trifluoroacetate The entitled compound was obtained as a pale yellow solid, according to the same method as in Example 2 or according to a method similar to it but using 5-fluoro-3H-spiro[2-benzofuran-1,4'-piperidine] in place of 3H-spiro[2-benzofuran-1,4'-piperidin]-3-one.

Retention time: 3.71 min
m/z: 425.3 [N+H]$^+$

Example 2-8

Production of 5-fluoro-1'-[4-(3-piperidin-1-ylpropoxy)phenyl]-3H-spiro[2-benzofuran-1,4'-piperidin]-3-one trifluoroacetate The entitled compound was obtained as a pale yellow solid, according to the same method as in Example 2 or according to a method similar to it but using 5-fluoro-3H-spiro[2-benzofuran-1,4'-piperidin]-3-one in place of 3H-spiro[2-benzofuran-1,4'-piperidin]-3-one.

Retention time: 3.42 min
m/z: 439.3 [M+H]$^+$

Example 2-9

Production of 7-fluoro-1'-[4-(3-piperidin-1-ylpropoxy)phenyl]-3H-spiro[2-benzofuran-1,4'-piperidin]-3-one trifluoroacetate The entitled compound was obtained as a pale yellow solid, according to the same method as in Example 2 or according to a method similar to it but using 7-fluoro-3H-spiro[2-benzofuran-1,4'-piperidin]-3-one in place of 3H-spiro[2-benzofuran-1,4'-piperidin]-3-one.
Retention time: 3.32 min
m/z: 439.3 [M+H]$^+$

Example 2-10

Production of 5-methoxy-1'-[4-(3-piperidin-1-ylpropoxy)phenyl]-3H-spiro[2-benzofuran-1,4'-piperidin]-3-one trifluoroacetate The entitled compound was obtained as a pale yellow solid, according to the same method as in Example 2 or according to a method similar to it but using 5-methoxy-3H-spiro[2-benzofuran-1,4'-piperidin]-3-one in place of 3H-spiro[2-benzofuran-1,4'-piperidin]-3-one.
Retention time: 3.58 min
m/z: 451.3 [M+H]$^+$

Example 2-11

Production of 6-methoxy-1'-[4-(3-piperidin-1-ylpropoxy)phenyl]-3H-spiro[2-benzofuran-1,4'-piperidin]-3-one trifluoroacetate The entitled compound was obtained as a pale yellow solid, according to the same method as in Example 2 or according to a method similar to it but using 6-methoxy-3H-spiro[2-benzofuran-1,4'-piperidin]-3-one in place of 3H-spiro[2-benzofuran-1,4'-piperidin]-3-one.
Retention time: 3.56 min
m/z: 451.3 [M+H]$^+$

Example 2-12

Production of 7-methoxy-1'-[4-(3-piperidin-1-ylpropoxy)phenyl]-3H-spiro[2-benzofuran-1,4'-piperidin]-3-one trifluoroacetate The entitled compound was obtained as a pale yellow solid, according to the same method as in Example 2 or according to a method similar to it but using 7-methoxy-3H-spiro[2-benzofuran-1,4'-piperidin]-3-one in place of 3H-spiro[2-benzofuran-1,4'-piperidin]-3-one.
Retention time: 3.60 min
m/z: 451.3 [M+H]$^+$

Example 2-13

Production of 1'-[4-(3-piperidin-1-ylpropoxy)phenyl]-1H-spiro[furo[3,4-c]pyridine-3,4'-piperidin]-1-one trifluoroacetate The entitled compound was obtained as a pale yellow solid, according to the same method as in Example 2 or according to a method similar to it but using 1H-spiro[furo[3,4-c]pyridine-3,4'-piperidin]-1-one in place of 3H-spiro[2-benzofuran-1,4'-piperidin]-3-one.
Retention time: 3.11 min
m/z: 422.3 [M+H]$^+$

Example 2-14

Production of 1-(methylsulfonyl)-1'-[4-(3-piperidin-1-ylpropoxy)phenyl]-1,2-dihydrospiro[indole-3,4'-piperidine]trifluoroacetate The entitled compound was obtained as a pale yellow solid, according to the same method as in Example 2 or according to a method similar to it but using 1-(methylsulfonyl)-1,2-dihydrospiro[indole-3,4'-piperidine] in place of 3H-spiro[2-benzofuran-1,4'-piperidin]-3-one.
Retention time: 3.76 min
m/z: 484.3 [M+H]$^+$

Example 2-15

Production of 1-(ethylsulfonyl)-7-fluoro-1'-[4-(3-piperidin-1-ylpropoxy)phenyl]-1,2-dihydrospiro[indole-3,4'-piperidine]trifluoroacetate The entitled compound was obtained as a pale yellow solid, according to the same method as in Example 2 or according to a method similar to it but using 1-(ethylsulfonyl)-7-fluoro-1,2-dihydrospiro[indole-3,4'-piperidine] in place of 3H-spiro[2-benzofuran-1,4'-piperidin]-3-one.
Retention time: 3.98 min
m/z: 516.3 [M+H]$^+$

Example 2-16

Production of 1-(ethylsulfonyl)-5-fluoro-1'-[4-(3-piperidin-1-ylpropoxy)phenyl]-1,2-dihydrospiro[indole-3,4'-piperidine]trifluoroacetate The entitled compound was obtained as a pale yellow solid, according to the same method as in Example 2 or according to a method similar to it but using 1-(ethylsulfonyl)-5-fluoro-1,2-dihydrospiro[indole-3,4'-piperidine] in place of 3H-spiro[2-benzofuran-1,4'-piperidin]-3-one.
Retention time: 4.17 min
m/z: 516.3 [M+H]$^+$

Example 2-17

Production of 4-tert-butoxy-1'-[4-(3-piperidin-1-ylpropoxy)phenyl]-3H-spiro[2-benzofuran-1,4'-piperidin]-3-one trifluoroacetate The entitled compound was obtained as a pale yellow solid, according to the same method as in Example 2 or according to a method similar to it but using 4-tert-butoxy-3H-spiro[2-benzofuran-1,4'-piperidin]-3-one in place of 3H-spiro[2-benzofuran-1,4'-piperidin]-3-one.
Retention time: 4.39 min
m/z: 493.4 [M+H]$^+$

Example 2-18

Production of 1-(ethylsulfonyl)-1'-[4-(3-piperidin-1-ylpropoxy)phenyl]-1,2-dihydrospiro[indole-3,4'-piperidine]trifluoroacetate The entitled compound was obtained as a pale yellow solid, according to the same method as in Example 2 or according to a method similar to it but using 1-(ethylsulfonyl)-1,2-dihydrospiro[indole-3,4'-piperidine] in place of 3H-spiro[2-benzofuran-1,4'-piperidin]-3-one.
Retention time: 4.06 min
m/z: 498.3 [M+H]$^+$

Example 2-19

Production of 3,3-dimethyl-1'-[4-(3-piperidin-1-ylpropoxy)phenyl]-3H-spiro[2-benzofuran-1,4'-piperidine]trifluoroacetate The entitled compound was obtained as a pale yellow solid, according to the same method as in Example 2 or according to a method similar to it but using 3,3-dimethyl-3H-spiro[2-benzofuran-1,4'-piperidine] in place of 3H-spiro[2-benzofuran-1,4'-piperidin]-3-one.
Retention time: 4.00 min
m/z: 435.4 [M+H]$^+$

Example 2-20

Production of 3-methyl-1'-[4-(3-piperidin-1-ylpropoxy)phenyl]-3H-spiro[2-benzofuran-1,4'-piperidine]trifluoroacetate The entitled compound was obtained as a pale yellow solid, according to the same method as in Example 2 or according to a method similar to it but using 3-methyl-3H-spiro[2,-benzofuran-1,4'-piperidine] in place of 3H-spiro[2-benzofuran-1,4'-piperidin]-3-one.
Retention time: 3.78 min
m/z: 421.4 [M+H]$^+$

Example 2-21

Production of 1'-[4-(3-piperidin-1-ylpropoxy)phenyl]-3,4-dihydrospiro[chromene-2,4'-piperidine] trifluoroacetate The entitled compound was obtained as a pale yellow solid, according to the same method as in Example 2 or according to a method similar to it but using 3,4-dihydrospiro[chromene-2,4'-piperidine] in place of 3H-spiro[2-benzofuran-1,4'-piperidin]-3-one.
Retention time: 3.93 min
m/z: 421.4 [M+H]$^+$

Example 2-22

Production of Phenyl {1-[4-(3-piperidin-1-ylpropoxy)phenyl]piperidin-4-yl}methanone Trifluoroacetate The entitled compound was obtained as a pale yellow solid, according to the same method as in Example 2 or according to a method similar to it but using phenyl(piperidin-4-yl)methanone in place of 3H-spiro[2-benzofuran-1,4'-piperidin]-3-one.
Retention time: 3.29 min
m/z: 407.3 [M+H]$^+$

Example 2-23

Production of 4-phenyl-1-[4-(3-piperidin-1-ylpropoxy)phenyl]piperidine-4-carbonitrile trifluoroacetate The entitled compound was obtained as a pale yellow solid, according to the same method as in Example 2 or according to a method similar to it but using 4-phenylpiperidine-4-carbonitrile in place of 3H-spiro[2-benzofuran-1,4'-piperidin]-3-one.
Retention time: 3.82 min
m/z: 404.4 [M+H]$^+$

Example 2-24

Production of 4-benzyl-1-[4-(3-piperidin-1-ylpropoxy)phenyl]piperidine-4-carbonitrile trifluoroacetate The entitled compound was obtained as a pale yellow solid, according to the same method as in Example 2 or according to a method similar to it but using 4-benzylpiperidine-4-carbonitrile in place of 3H-spiro[2-benzofuran-1,4'-piperidin]-3-one.
Retention time: 3.78 min
m/z: 418.4 [M+H]$^+$

Example 2-25

Production of 4-methyl-4-phenyl-1-[4-(3-piperidin-1-ylpropoxy)phenyl]piperidine Trifluoroacetate The entitled compound was obtained as a pale yellow solid, according to the same method as in Example 2 or according to a method similar to it but using 4-methyl-4-phenylpiperidine in place of 3H-spiro[2-benzofuran-1,4'-piperidin]-3-one.
Retention time: 3.56 min
m/z: 393.4 [M+H]$^+$

Example 2-26

Production of 4,4-diphenyl-1-[4-(3-piperidin-1-ylpropoxy)phenyl]piperidine Trifluoroacetate The entitled compound was obtained as a pale yellow solid, according to the same method as in Example 2 or according to a method similar to it but using 4,4-diphenylpiperidine in place of 3H-spiro[2-benzofuran-1,4'-piperidin]-3-one.
Retention time: 4.28 min
m/z: 455.4 [M+H]$^+$

Example 2-27

Production of 4-(3-methoxyphenyl)-1-[4-(3-piperidin-1-ylpropoxy)phenyl]piperidin-4-ol Trifluoroacetate The entitled compound was obtained as a pale yellow solid, according to the same method as in Example 2 or according to a method similar to it but using 4-(3-methoxyphenyl)piperidin-4-ol in place of 3H-spiro[2-benzofuran-1,4'-piperidin]-3-one.
Retention time: 3.03 min
m/z: 425.4 [M+H]$^+$

Example 3

Production of 4-(4-fluorophenyl)-9-[4-(3-[(3S)-3-methylpiperidin-1-yl]propoxy)phenyl]-1-oxa-4,9-diazaspiro[5,5]undecan-3-one 9-(4-{3-[(3S)-3-methylpiperidin-1-yl]propoxy}phenyl)-1-oxa-4,9-diazaspiro[5,5]undecan-3-one (100 mg, 0.25 mmol) obtained in Reference Example 12-1, 1-bromo-4- fluorobenzene (52 mg, 0.25 mmol), potassium phosphate (10 mg, 0.50 mmol), copper iodide (23 mg, 0.125 mmol), N,N'-dimethyldiaminoethane (22 mg, 0.25 mmol) were mixed in 1,4-dioxane, and stirred overnight with heating in a sealed tube at 110° C. The reaction solution was diluted with ethyl acetate, washed with water and saturated saline in that order, and the organic layer was dried with sodium sulfate. The solvent was concentrated under reduced pressure, and the residue was purified through reversed-phase preparative HPLC (liquid A, 0.1% TFA/water; liquid B, 0.1% TFA/acetonitrile; A/B=90/10 to 50/50; 8-minute linear concentration gradient elution; flow rate, 40 ml/min) to collect a fraction containing the intended product. Then, the solvent was concentrated under reduced pressure, and the residue was neutralized with aqueous 2 N sodium hydroxide solution added thereto. This was extracted by addition of ethyl acetate thereto, and the organic layer was washed with saturated saline and dried with sodium sulfate. The solvent was evaporated off under reduced pressure to obtain the entitled compound as a pale brown solid (83.7 mg, 68%).

$^1$H-NMR (400 MHz, CDCl$_3$) δ: 0.86 (3H, d, J=6.3 Hz), 1.53-1.72 (6H, m), 1.82-1.90 (3H, m), 1.93-2.00 (2H, m), 2.13 (2H, d, J=12.9 Hz), 2.46-2.50 (2H, m), 2.83-2.90 (2H, m), 3.07 (2H, t, J=10.6 Hz), 3.27 (2H, d, J=12.5 Hz), 3.60 (2H, s), 3.96 (2H, t, J=6.3 Hz), 4.35 (2H, s), 6.84 (2H, d, J=9.0 Hz), 6.92 (2H, d, J=9.0 Hz), 7.11 (2H, t, J=8.6 Hz), 7.26-7.28 (2H, m)

Example 3-1

Production of 4-(6-fluoropyridin-3-yl)-9-[4-{3-[(3S)-3-methylpiperidin-1-yl]propoxy}phenyl]-1-oxa-4,9-diazaspiro[5,5]undecan-3-one The entitled compound was obtained as a pale yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 5-bromo-2-fluoropyridine in place of 1-bromo-4-fluorobenzene.

$^1$H-NMR (400 MHz. CDCl$_3$) δ: 0.86 (3H, d, J=6.7 Hz), 1.61-1.73 (6H, m), 1.82-1.89 (3H, m), 1.97 (2H, brs), 2.11-2.16 (2H, m), 2.52 (2H, s), 2.90 (2H, brs), 3.05 (2H, t, J=10.6 Hz), 3.27 (2H, d, J=12.1 Hz), 3.64 (2H, s), 3.96 (2H, t, J=6.3 Hz), 4.36 (2H, s), 6.82 (2H, d, J=9.0 Hz), 6.91 (2H, d, J=9.0 Hz), 6.99 (1H, dd, J=8.6, 3.1 Hz), 7.80-7.85 (1H, m), 8.17 (1H, s)

Example 3-2

Production of 4-(methoxyphenyl)-9-[4-{3-[(3S)-3-methylpiperidin-1-yl]propoxy}phenyl]-1-oxa-4,9-diazaspiro[5,5]undecan-3-one The entitled compound was obtained as a pale yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 1-bromo-4-methoxybenzene in place of 1-bromo-4-fluorobenzene.

$^1$H-NMR (400 MHz, CDCl$_3$) δ: 0.86 (3H, d, J=6.3 Hz), 1.53-1.72 (10H, m), 1.82-2.00 (5H, m), 2.13 (2H, d, J=13.3 Hz), 2.48 (2H, t, J=7.0 Hz), 2.90-2.82 (2H, m), 3.07 (2H, t, J=10.4 Hz), 3.26 (2H, d, J=12.1 Hz), 3.59 (2H, s), 3.81 (3H, s), 3.96 (2H, t, J=6.5 Hz), 4.34 (2H, s), 6.84 (2H, d, J=9.0 Hz), 6.91-6.95 (4H, m), 7.20 (2H, d, J=9.0 Hz)

Example 3-3

Production of 4-(4-methylphenyl)-9-[4-{3-[(3S)-3-methylpiperidin-1-yl]propoxy}phenyl]-1-oxa-4,9-diazaspiro[5,5]undecan-3-one The entitled compound was obtained as a pale yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 1-bromo-4-methylbenzene in place of 1-bromo-4-fluorobenzene.

$^1$H-NMR (400 MHz, CDCl$_3$) δ: 0.86 (4H, d, J=6.8 Hz), 1.53-1.72 (10H, m), 1.82-1.90 (3H, m), 1.93-2.00 (2H, m), 2.13 (2H, d, J=12.9 Hz), 2.36 (3H, s), 2.48 (2H, t, J=7.4 Hz), 2.86 (2H, t, J=12.7 Hz), 3.07 (2H, t, J=10.6 Hz), 3.26 (2H, d, J=12.1 Hz), 3.61 (2H, s), 3.96 (2H, t, J=6.5 Hz), 4.35 (2H, s), 6.84 (2H, d, J=9.0 Hz), 6.93 (2H, d, J=9.0 Hz), 7.17 (2H, d, J=8.2 Hz), 7.23 (2H, d, J=8.2 Hz)

Example 3-4

Production of 4-(6-methoxypyridin-3-yl)-9-[4-{3-[(3S)-3-methylpiperidin-1-yl]propoxy}phenyl]-1-oxa-4,9-diazaspiro[5,5]undecan-3-one The entitled compound was obtained as a brown solid, according to the same method as in Example 3 or according to a method similar to it but using 9-(4-{3-[(3S-3-methylpiperidin-1-yl]propoxy}phenyl)-1-oxa-4,9-diazaspiro[5,5]undecan-3-one obtained in Reference Example 12-1, and 5-bromo-2-methoxypyridine in place of 1-bromo-4-fluorobenzene.

$^1$H-NMR (400 MHz, CDCl$_3$) δ: 0.87 (3H, d, J=6.3 Hz), 1.54-1.72 (6H, m), 1.83-1.90 (3H, m), 1.93-2.00 (2H, m), 2.13 (2H, d, J=12.9 Hz), 2.49 (2H, t, J=7.4 Hz), 2.83-2.91 (2H, m), 3.07 (2H, t, J=10.6 Hz), 3.27 (2H, d, J=12.5 Hz), 3.60 (2H, s), 3.94-3.98 (5H, m), 4.36 (2H, s), 6.78-6.85 (3H, m), 6.93 (2H, d, J=9.0 Hz), 7.55 (1H, dd, J=9.0, 2.7 Hz), 8.10 (1H, d, J=2.3 Hz)

Example 3-5

Production of 9-[4-{3-[(3S)-3-methylpiperidin-1-yl]propoxy}phenyl]-4-(2-methylpyridin-5-yl)-1-oxa-4,9-diazaspiro[5,5]undecan-3-one The entitled compound was obtained as a pale yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 5-bromo-2-methylpyridine in place of 1-bromo-4-fluorobenzene.

$^1$H-NMR (400 MHz, CDCl$_3$) δ: 0.87 (3H, d, J=6.3 Hz), 1.56-1.73 (6H, m), 1.83-2.00 (5H, m), 2.14 (2H, d, J=13.3 Hz), 2.49 (2H, t, J=7.2 Hz), 2.57 (3H, s), 2.84-2.90 (2H, m), 3.07 (2H, t, J=10.4 Hz), 3.26-3.29 (2H, m), 3.64 (2H, s), 3.96 (2H, t, J=6.5 Hz), 4.37 (2H, s), 6.84 (2H, d, J=9.0 Hz), 6.93 (2H, d, J=9.0 Hz), 7.22 (1H, d, J=8.2 Hz), 7.58 (1H, dd, J=8.2, 2.3 Hz), 8.46 (1H, d, J=2.7 Hz)

Example 3-6

Production of 4-(3,4-difluorophenyl)-9-[4-{3-[(3S)-3-methylpiperidin-1-yl]propoxy}phenyl]-1-oxa-4,9-diazaspiro[5,5]undecan-3-one The entitled compound was obtained as a pale yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 4-bromo-1,2-difluorobenzene in place of 1-bromo-4-fluorobenzene.

$^1$H-NMR (400 MHz, CDCl$_3$) δ: 0.87 (3H, d, J=6.3 Hz), 1.54-1.73 (6H, m), 1.82-1.89 (3H, m), 1.93-2.00 (2H, m), 2.11 (2H, d, J=12.1 Hz), 2.49 (2H, t, J=8.2 Hz), 2.87 (2H, t, J=13.5 Hz), 3.06 (2H, t, J=10.6 Hz), 3.27 (2H, d, J=12.5 Hz), 3.60 (2H, s), 3.96 (2H, t, J=6.3 Hz), 4.35 (2H, s), 6.84 (2H, d, J=9.0 Hz), 6.92 (2H, d, J=9.4 Hz), 7.05 (1H, d, J=9.0 Hz), 7.17-7.24 (2H, m)

Example 3-7

Production of 4-(2,4-difluorophenyl)-9-(4-{3-[(3S)-3-piperidin-1-yl]propoxy}phenyl)-1-oxa-4,9-diazaspiro[5,5]undecan-3-one The entitled compound was obtained as a pale yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 1-bromo-2,4-difluorobenzene in place of 1-bromo-4-fluorobenzene.

$^1$H-NMR (400 MHz, CDCl$_3$) δ: 0.87 (3H, d, J=6.3 Hz), 1.54-1.73 (6H, m), 1.84-2.00 (5H, m), 2.15 (2H, d, J=13.3 Hz), 2.49 (2H, t, J=7.4 Hz), 2.84-2.91 (2H, m), 3.08 (2H, t, J=10.4 Hz), 3.26 (2H, d, J=12.1 Hz), 3.56 (2H, s), 3.96 (2H, t, J=6.5 Hz), 4.37 (2H, s), 6.84 (2H, d, J=9.0 Hz), 6.94 (4H, q, J=6.3 Hz), 7.26 (1H, s)

Example 3-8

Production of 4-phenyl-9-[4-(3-piperidin-1-ylpropoxy)phenyl]-1-oxa-4,9-diazaspiro[5,5]undecan-3-one The entitled compound was obtained as a white solid, according to the same method as in Example 3 or according to a method similar to it but using 9-[4-(3-piperidin-1-ylpropoxy)phenyl]-1-oxa-4,9-diazaspiro[5,5]undecan-3-one obtained in Reference Example 12, and bromobenzene in place of 1-bromo-4-fluorobenzene.

$^1$H-NMR (400 MHz, CDCl$_3$) δ: 1.43 (2H, m), 1.56-1.60 (4H, m), 1.84-1.99 (4H, m), 2.13 (2H, d, J=13.2 Hz), 2.40-2.48 (6H, m), 3.05-3.10 (2H, m), 3.26 (2H, d, J=12.4 Hz), 3.64 (2H, s), 3.96 (2H, t, J=6.4 Hz), 4.36 (2H, s), 6.84 (2H, d, J=9.2 Hz), 6.93 (2H, d, J=9.2 Hz), 7.28-7.31 (3H, m), 7.41-7.45 (2H, m)

Example 3-9

Production of 9-[4-(3-piperidin-1-ylpropoxy)phenyl]-4-pyridin-4-yl-1-oxa-4,9-diazaspiro[5,5]undecan-3-one The entitled compound was obtained as a pale yellow solid, according to the same method as in Example 3 or according to a method similar to it but using 9-[4-(3-piperidin-1-ylpropoxy)phenyl]-1-oxa-4,9-diazaspiro[5,5]undecan-3-one obtained in Reference Example 12, and 4-bromopyridine in place of 1-bromo-4-fluorobenzene.

$^1$H-NMR (400 MHz, CDCl$_3$) δ: 1.43-1.45 (2H, m), 1.56-1.61 (4H, m), 1.82-1.90 (2H, m), 1.91-1.98 (2H, m), 2.11 (2H, d, J=12.4 Hz), 2.39 (4H, brs), 2.44-2.48 (2H, m), 3.06 (2H, td, J=11.6, 2.0 Hz), 3.28 (2H, dt, J=12.4, 4.0 Hz), 3.68 (2H, s), 3.96 (2H, t, J=6.4 Hz), 4.37 (2H, s), 6.84 (2H, d, J=8.0 Hz), 6.92 (2H, d, J=8.0 Hz), 7.39-7.41 (2H, m), 8.62-8.64 (2H, m)

Example 3-10

Production of 9-[4-(3-piperidin-1-ylpropoxy)phenyl]-4-pyridin-2-yl-1-oxa-4,9-diazaspiro[5,5]undecan-3-one The entitled compound was obtained as a pale yellow solid, according to the same method as in Example 3 or according to a method similar to it but using 9-[4-(3-piperidin-1-ylpropoxy)phenyl]-1-oxa-4,9-diazaspiro[5,5]undecan-3-one obtained in Reference Example 12, and 2-bromopyridine in place of 1-bromo-4-fluorobenzene.

$^1$H-NMR (400 MHz, DMSO-d$_6$) δ: 1.44 (2H, brs), 1.58-1.61 (4H, m), 1.85-1.98 (4H, m), 2.07 (2H, d, J=13.6 Hz), 2.41 (4H, brs), 2.48 (2H, t, J=7.6 Hz), 3.04-3.11 (2H, m), 3.25-3.28 (2H, m), 3.96 (2H, t, J=6.4 Hz), 4.01 (2H, s), 4.37 (2H, s), 6.83 (2H, d, J=8.8 Hz), 6.92 (2H, d, J=8.8 Hz), 7.11-7.14 (1H, m), 7.70-7.74 (1H, m), 8.09 (1H, d, J=8.4 Hz), 8.42-8.43 (1H, m)

Example 3-11

Production of 4-[6-(difluoromethoxy)pyridin-3-yl]-9-(4-{3-[(3S)-3-methylpiperidin-1-yl]propoxy}phenyl)-1-oxa-4,9-diazaspiro[5,5]undecan-3-one The entitled compound was obtained as a yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 5-bromo-2-(difluoromethoxy)pyridine obtained in Reference Example 16 in place of 1-bromo-4-fluorobenzene.

$^1$H-NMR (400 MHz, CDCl$_3$) δ: 0.87 (3H, d, J=6.8 Hz), 1.57-1.72 (6H, m), 1.83-1.90 (3H, m), 1.95-2.00 (2H, m), 2.13 (2H, d, J=12.7 Hz), 2.46-2.50 (2H, m), 2.83-2.90 (2H, m), 3.07 (2H, td, J=11.2, 2.4 Hz), 3.28 (2H, dt, J=12.2, 3.9 Hz), 3.63 (2H, s), 3.96 (2H, t, J=6.6 Hz), 4.37 (2H, s), 6.84 (2H, dt, J=9.3, 3.4 Hz), 6.92 (2H, dt, J=9.3, 3.9 Hz), 6.96 (1H, d, J=8.8 Hz), 7.44 (1H, t, J=73.2 Hz), 7.74 (1H, dd, J=8.8, 2.9 Hz), 8.17 (1H, d, J=2.4 Hz)

Example 3-12

Production of 4-(6-isopropoxypyridin-3-yl)-9-(4-{3-[(3S)-3-methylpiperidin-1-yl]propoxy}phenyl)-1-oxa-4,9-diazaspiro[5,5]undecan-3-one The entitled compound was obtained as a yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 5-bromo-2-isopropoxypyridine obtained in Reference Example 17 in place of 1-bromo-4-fluorobenzene.

¹H-NMR (400 MHz, CDCl₃) δ: 0.87 (3H, d, J=6.3 Hz), 1.34 (6H, d, J=6.3 Hz), 1.57-1.73 (6H, m), 1.82-1.90 (3H, m), 1.95-1.99 (2H, m), 2.13 (2H, d, J=13.2 Hz), 2.48 (2H, brs), 2.87 (2H, brs), 3.07 (2H, td, J=11.2, 2.4 Hz), 3.27 (2H, dt, J=12.7, 4.4 Hz), 3.60 (2H, s), 3.96 (2H, t, J=6.3 Hz), 4.35 (2H, s), 5.24-5.31 (1H, m), 6.72 (1H, d, J=8.8 Hz), 6.84 (2H, dt, J=9.3, 3.4 Hz), 6.93 (2H, dt, J=9.3, 3.4 Hz), 7.51 (1H, dd, J=8.8, 2.4 Hz), 8.07 (1H, d, J=2.9 Hz)

Example 3-13

Production of 4-(6-isopropoxypyridin-3-yl)-9-[4-(3-piperidin-1-ylpropoxy)phenyl]-1-oxa-4,9-diazaspiro[5,5]undecan-3-one The entitled compound was obtained as a yellow solid, according to the same method as in Example 3 or according to a method similar to it but using 9-[4-(3-piperidin-1-ylpropoxy)phenyl]-1-oxa-4,9-diazaspiro[5,5]undecan-3-one obtained in Reference Example 12, and 5-bromo-2-isopropoxypyridine obtained in Reference Example 17 in place of 1-bromo-4-fluorobenzene.

¹H-NMR (400 MHz, CDCl₃) δ: 1.34 (6H, d, J=6.3 Hz), 1.44 (2H, brs), 1.58-1.61 (4H, m), 1.83-1.90 (2H, m), 1.92-1.99 (2H, m), 2.13 (2H, d, J=13.2 Hz), 2.39-2.49 (6H, m), 3.07 (2H, td, J=11.6, 2.4 Hz), 3.27 (2H, dt, J=12.2, 3.7 Hz), 3.60 (2H, s), 3.96 (2H, t, J=6.6 Hz), 4.35 (2H, s), 5.24-5.31 (1H, m), 6.72 (1H, d, J=8.8 Hz), 6.84 (2H, dt, J=9.3, 3.4 Hz), 6.92 (2H, dt, J=9.3, 3.4 Hz), 7.51 (1H, dd, J=8.8, 2.9 Hz), 8.06 (1H, d, J=2.4 Hz)

Example 3-14

Production of 4-[6-(difluoromethoxy)pyridin-3-yl]-9-[4-(3-piperidin-1-ylpropoxy)phenyl]-1-oxa-4,9-diazaspiro[5,5]undecan-3-one The entitled compound was obtained as a white solid, according to the same method as in Example 3 or according to a method similar to it but using 9-[4-(3-piperidin-1-ylpropoxy)phenyl]-1-oxa-4,9-diazaspiro[5,5]undecan-3-one obtained in Reference Example 12, and 5-bromo-2-(difluoromethoxy)pyridine obtained in Reference Example 16 in place of 1-bromo-4-fluorobenzene.

¹H-NMR (400 MHz, CDCl₃) δ: 1.44 (2H, s), 1.56-1.62 (4H, m), 1.83-1.90 (2H, m), 1.92-1.99 (2H, m), 2.13 (2H, d, J=13.2 Hz), 2.40-2.48 (6H, m), 3.07 (2H, td, J=11.7, 2.4 Hz), 3.28 (2H, dt, J=12.2, 3.9 Hz), 3.63 (2H, s), 3.96 (2H, t, J=6.3 Hz), 4.37 (2H, s), 6.84 (2H, dt, J=9.3, 3.4 Hz), 6.91 (2H, dt, J=9.3, 3.4 Hz), 6.96 (1H, d, J=8.8 Hz), 7.44 (1H, t, J=73.7 Hz), 7.74 (1H, dd, J=8.5, 2.7 Hz), 8.17 (1H, d, J=2.0 Hz)

Example 3-15

Production of 4-(2-methoxypyrimidin-5-yl)-9-[4-(3-piperidin-1-ylpropoxy)phenyl]-1-oxa-4,9-diazaspiro[5,5]undecan-3-one The entitled compound was obtained as a pale yellow solid, according to the same method as in Example 3 or according to a method similar to it but using 9-[4-(3-piperidin-1-ylpropoxy)phenyl]-1-oxa-4,9-diazaspiro[5,5]undecan-3-one obtained in Reference Example 12, and 5-iodo-2-methoxypyrimidine in place of 1-bromo-4-fluorobenzene.

¹H-NMR (400 MHz, CDCl₃) δ: 1.44 (2H, s), 1.56-1.62 (4H, m), 1.83-1.90 (2H, m), 1.92-1.99 (2H, m), 2.13 (2H, d, J=13.2 Hz), 2.40-2.48 (6H, m), 3.07 (2H, td, J=11.7, 2.4 Hz), 3.28 (2H, dt, J=12.2, 3.9 Hz), 3.63 (2H, s), 3.96 (2H, t, J=6.3 Hz), 4.37 (2H, s), 6.84 (2H, dt, J=9.3, 3.4 Hz), 6.91 (2H, dt, J=9.3, 3.4 Hz), 6.96 (1H, d, J=8.8 Hz), 7.44 (1H, t, J=73.7 Hz), 7.74 (1H, dd, J=8.5, 2.7 Hz), 8.17 (1H, d, J=2.0 Hz)

Example 3-16

Production of 4-(2-methoxypyrimidin-5-yl)-9-[4-{3-[(3S)-3-methylpiperidin-1-yl]propoxy}phenyl-1-oxa-4,9-diazaspiro[5,5]undecan-3-one The entitled compound was obtained as a white solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 5-iodo-2-methoxypyrimidine in place of 1-bromo-4-fluorobenzene.

¹H-NMR (400 MHz, CDCl₃) δ: 0.86 (3H, d, J=6.3 Hz), 1.55-1.72 (6H, m), 1.84-1.91 (3H, m), 1.94-2.00 (2H, m), 2.14 (2H, d, J=13.2 Hz), 2.46-2.50 (2H, brm), 2.83-2.89 (2H, brm), 3.06 (2H, td, J=11.7, 2.4 Hz), 3.28 (2H, dt, J=12.2, 3.9 Hz), 3.63 (2H, s), 3.96 (2H, t, J=6.6 Hz), 4.03 (3H, s), 4.37 (2H, s), 6.84 (2H, dt, J=9.3, 3.4 Hz), 6.93 (2H, dt, J=9.3, 3.4 Hz), 8.53 (2H, s)

Example 3-17

Production of 4-(6-methoxypyridin-3-yl)-9-[4-(3-pyrrolidin-1-ylpropoxy)phenyl]-1-oxa-4,9-diazaspiro[5,5]undecan-3-one The entitled compound was obtained as a pale yellow solid, according to the same method as in Example 3 or according to a method similar to it but using 9-[4-(3-pyrrolidin-1-ylpropoxy)phenyl]-1-oxa-4,9-diazaspiro[5,5]undecan-3-one obtained in Reference Example 12-2, and 5-bromo-2-methoxypyridine in place of 1-bromo-4-fluorobenzene.

¹H-NMR (400 MHz, CDCl₃) δ: 1.79-1.90 (6H, m), 1.97-2.04 (2H, m), 2.13 (2H, d, J=12.7 Hz), 2.56 (4H, s), 2.64 (2H, t, J=7.3 Hz), 3.07 (2H, td, J=11.7, 2.3 Hz), 3.27 (2H, dt, J=12.7, 3.9 Hz), 3.60 (2H, s), 3.94 (3H, s), 3.98 (2H, t, J=6.6 Hz), 4.35 (2H, s), 6.79 (1H, d, J=8.8 Hz), 6.84 (2H, dt, J=9.3, 3.4 Hz), 6.93 (2H, dt, J=9.3, 3.4 Hz), 7.54 (1H, dd, J=8.8, 2.4 Hz), 8.10 (1H, d, J=2.9 Hz)

Example 3-18

Production of 4-(2-methoxypyridin-5-yl)-9-[4-{3-[(2S)-2-methylpyrrolidin-1-yl]propoxy}phenyl)-1-oxa-4,9-diazaspiro[5,5]undecan-3-one The entitled compound was obtained as a colorless oily substance, according to the same method as in Example 3 or according to a method similar to it but using 9-(4-{3-[(2S)-2-methylpyrrolidin-1-yl]propoxy}phenyl)-1-oxa-4,9-diazaspiro[5,5]undecan-3-one obtained in Reference Example 12-3, and 5-bromo-2-methoxypyridine in place of 1-bromo-4-fluorobenzene.

¹H-NMR (400 MHz, CDCl₃) δ: 1.10 (3H, d, J=6.3 Hz), 1.38-1.47 (1H, m), 1.58-2.01 (7H, m), 2.09-2.32 (5H, m), 2.94-3.01 (1H, m), 3.03-3.10 (2H, m), 3.16-3.21 (1H, m), 3.24-3.29 (2H, m), 3.60 (2H, s), 3.94 (3H, s), 3.95-4.01 (2H, m), 4.35 (2H, s), 6.79 (1H, d, J=8.8 Hz), 6.84 (2H, d, J=9.3 Hz), 6.93 (2H, d, J=9.3 Hz), 7.54 (1H, dd, J=8.8, 2.4 Hz), 8.10 (1H, d, J=2.9 Hz)

Example 3-19

Production of 4-(6-methoxypyridin-3-yl)-9-(4-{3-[(2R)-2-methylpyrrolidin-1-yl]propoxy}phenyl)-1-oxa-4,9-diazaspiro[5,5]undecan-3-one The entitled compound was obtained as a brown viscous substance, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 5-bromo-2-methoxypyridine in place of 1-bromo-4-fluorobenzene.

$^1$H-NMR (400 MHz, CDCl$_3$) δ: 1.10 (3H, d, J=6.3 Hz), 1.42 (1H, brs), 1.61-2.01 (7H, m), 2.08-2.31 (5H, m), 2.94-3.01 (1H, m), 3.07 (2H, td, J=11.2, 2.9 Hz), 3.15-3.21 (1H, m), 3.27 (2H, dt, J=11.7, 3.9 Hz), 3.60 (2H, s), 3.94 (3H, s), 3.95-4.01 (2H, m), 4.35 (2H, s), 6.79 (1H, d, J=8.8 Hz), 6.85 (2H, dt, J=9.3, 3.4 Hz), 6.93 (2H, dt, J=9.3, 3.4 Hz), 7.55 (1H, dd, J=8.8, 2.9 Hz), 8.10 (1H, d, J=2.9 Hz)

Example 3-20

Production of 4-(4-fluorophenyl)-9-(4-{3-[(2R)-2-methylpyrrolidin-1-yl]propoxy}phenyl)-1-oxa-4,9-diazaspiro[5,5]undecan-3-one The entitled compound was obtained as a pale yellow oily substance, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4 and 1-bromo-4-fluorobenzene.

$^1$H-NMR (400 MHz, CDCl$_3$) δ: 1.09 (3H, d, J=6.3 Hz), 1.39-1.46 (1H, m), 1.58-2.01 (7H, m), 2.07-2.21 (4H, m), 2.24-2.32 (1H, m), 2.93-3.01 (1H, m), 3.04-3.10 (2H, m), 3.15-3.20 (1H, m), 3.25-3.29 (2H, m), 3.60 (2H, s), 3.95-4.01 (2H, m), 4.35 (2H, s), 6.85 (2H, d, J=8.8 Hz), 6.93 (2H, d, J=8.8 Hz), 7.08-7.14 (2H, m), 7.25-7.29 (2H, m)

Example 3-21

Production of 4-(4-methoxyphenyl)-9-(4-{3-[(2R)-2-methylpyrrolidin-1-yl]propoxy}phenyl)-1-oxa-4,9-diazaspiro[5,5]undecan-3-one The entitled compound was obtained as a pale yellow oily substance, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 1-bromo-4-methoxybenzene in place of 1-bromo-4-fluorobenzene.

$^1$H-NMR (400 MHz, CDCl$_3$) δ: 1.09 (3H, d, J=6.3 Hz), 1.37-1.46 (1H, m), 1.57-2.01 (7H, m), 2.07-2.21 (4H, m), 2.25-2.32 (1H, m), 2.93-3.00 (1H, m), 3.04-3.11 (2H, m), 3.15-3.20 (1H, m), 3.24-3.29 (2H, m), 3.59 (2H, s), 3.81 (3H, s), 3.95-4.01 (2H, m), 4.34 (2H, s), 6.84 (2H, d, J=8.8 Hz), 6.92-6.95 (4H, m), 7.20 (2H, d, J=8.8 Hz)

Example 3-22

Production of 4-(1,3-benzodioxol-5-yl)-9-(4-{3-[(2R)-2-methylpyrrolidin-1-yl]propoxy}phenyl)-1-oxa-4,9-diazaspiro[5,5]undecan-3-one The entitled compound was obtained as a white solid, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 5-bromo-1,3-benzodioxole in place of 1-bromo-4-fluorobenzene.

$^1$H-NMR (400 MHz, CDCl$_3$) δ: 1.09 (3H, d, J=5.9 Hz), 1.39-1.46 (1H, m), 1.56-2.00 (7H, m), 2.07-2.31 (5H, m), 2.93-3.00 (1H, m), 3.03-3.10 (2H, m), 3.15-3.20 (1H, m), 3.24-3.28 (2H, m), 3.57 (2H, s), 3.94-4.01 (2H, m), 4.33 (2H, s), 5.99 (2H, s), 6.71 (1H, dd, J=8.3, 2.4 Hz), 6.78 (1H, d, J=2.0 Hz), 6.82-6.86 (3H, m), 6.93 (2H, d, J=9.3 Hz)

Example 3-23

Production of 4-(2-methoxypyridin-4-yl)-9-(4-{3-[(3S)-3-methylpiperidin-1-yl]propoxy}phenyl)-1-oxa-4,9-diazaspiro[5,5]undecan-3-one The entitled compound was obtained as a white solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 4-bromo-2-methoxypyridine in place of 1-bromo-4-fluorobenzene.

$^1$H-NMR (400 MHz, CDCl$_3$) δ: 0.86 (3H, d, J=6.3 Hz), 1.51-1.72 (6H, m), 1.80-1.88 (3H, m), 1.92-1.99 (2H, m), 2.09 (2H, d, J=13.2 Hz), 2.46 (2H, t, J=7.6 Hz), 2.81-2.88 (2H, m), 3.05 (2H, td, J=11.2, 2.4 Hz), 3.27 (2H, dt, J=11.2, 3.9 Hz), 3.64 (2H, s), 3.94-3.97 (5H, m), 4.35 (2H, s), 6.75 (1H, d, J=1.5 Hz), 6.84 (2H, dt, J=9.3, 3.4 Hz), 6.92 (2H, dt, J=9.3, 3.4 Hz), 7.04 (1H, dd, J=2.0, 5.9 Hz), 8.16 (1H, d, J=5.9 Hz)

Example 3-24

Production of 4-(1-methyl-6-oxo-1,6-dihydropyridin-3-yl)-9-(4-{3-[(3S)-3-methylpiperidin-1-yl]propoxy}phenyl)-1-oxa-4,9-diazaspiro[5,5]undecan-3-one The entitled compound was obtained as a yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 5-bromo-1-methylpyridin-2(1H)-one in place of 1-bromo-4-fluorobenzene.

$^1$H-NMR (400 MHz, CDCl$_3$) δ: 0.85 (3H, t, J=6.6 Hz), 1.51-1.71 (6H, m), 1.81-1.88 (3H, m), 1.92-1.99 (2H, m), 2.09 (2H, d, J=13.2 Hz), 2.47 (2H, t, J=7.6 Hz), 2.81-2.89 (2H, m), 3.05 (2H, td, J=11.7, 2.4 Hz), 3.27 (2H, dt, J=12.2, 3.4 Hz), 3.52 (2H, s), 3.55 (3H, s), 3.96 (2H, t, J=6.6 Hz), 4.32 (2H, s), 6.62 (1H, d, J=9.8 Hz), 6.84 (2H, dt, J=9.3, 3.4 Hz), 6.92 (2H, dt, J=9.3, 3.4 Hz), 7.25-7.28 (1H, m), 7.39 (1H, d, J=2.9 Hz)

Example 3-25

Production of 4-(2-methoxypyridin-4-yl)-9-[4-(3-piperidin-1-ylpropoxy)phenyl]-1-oxa-4,9-diazaspiro[5,5]undecan-3-one The entitled compound was obtained as a brown viscous substance, according to the same method as in Example 3 or according to a method similar to it but using 9-[4-(3-piperidin-1-ylpropoxy)phenyl]-1-oxa-4,9-diazaspiro[5,5]undecan-3-one obtained in Reference Example 12, and 4-iodo-2-methoxypyridine in place of 1-bromo-4-fluorobenzene.

¹H-NMR (400 MHz, CDCl₃) δ: 1.43 (2H, s), 1.56-1.61 (4H, m), 1.81-1.88 (2H, m), 1.92-1.99 (2H, m), 2.09 (2H, d, J=12.7 Hz), 2.39-2.48 (6H, m), 3.05 (2H, td, J=11.2, 2.4 Hz), 3.27 (2H, dt, J=12.2, 3.9 Hz), 3.64 (2H, s), 3.95-3.97 (5H, m), 4.35 (2H, s), 6.75 (1H, d, J=2.0 Hz), 6.84 (2H, dt, J=9.3, 3.4 Hz), 6.92 (2H, dt, J=9.3, 3.4 Hz), 7.04 (1H, dd, J=5.4, 2.0 Hz), 8.16 (1H, d, J=5.9 Hz)

Example 3-26

Production of 4-(1-methyl-6-oxo-1,6-dihydropyridin-3-yl)-9-[4-(3-piperidin-1-ylpropoxy)phenyl]-1-oxa-4,9-diazaspiro[5,5]undecan-3-one The entitled compound was obtained as a pale brown solid, according to the same method as in Example 3 or according to a method similar to it but using 9-[4-(3-piperidin-1-ylpropoxy)phenyl]-1-oxa-4,9-diazaspiro[5,5]undecan-3-one obtained in Reference Example 12, and 5-bromo-1-methylpyridin-2(1H)-one in place of 1-bromo-4-fluorobenzene.

¹H-NMR (400 MHz, CDCl₃) δ: 1.44 (2H, s), 1.57-1.63 (4H, m), 1.81-1.88 (2H, m), 1.93-1.99 (2H, m), 2.09 (2H, d, J=13.2 Hz), 2.40-2.49 (6H, m), 3.05 (2H, td, J=11.7, 2.4 Hz), 3.27 (2H, dt, J=12.2, 3.4 Hz), 3.52 (2H, s), 3.55 (3H, s), 3.96 (2H, t, J=6.6 Hz), 4.32 (2H, s), 6.62 (1H, d, J=9.8 Hz), 6.84 (2H, dt, J=9.3, 3.4 Hz), 6.91 (2H, dt, J=9.3, 3.4 Hz), 7.25-7.28 (1H, m), 7.39 (1H, d, J=2.9 Hz)

Example 3-27

Production of 9-(4-{3-[(2R)-2-methylpyrrolidin-1-yl]propoxy}phenyl)-4-pyridin-2-yl-1-oxa-4,9-diazaspiro[5,5]undecan-3-one The entitled compound was obtained as a pale yellow solid, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 2-bromopyridine in place of 1-bromo-4-fluorobenzene.

¹H-NMR (400 MHz, CDCl₃) δ: 1.10 (3H, d, J=6.3 Hz), 1.38-1.47 (1H, m), 1.57-2.01 (7H, m), 2.05-2.21 (4H, m), 2.25-2.31 (1H, m), 2.94-3.01 (1H, m), 3.04-3.11 (2H, m), 3.15-3.20 (1H, m), 3.25-3.30 (2H, m), 3.95-4.01 (4H, m), 4.37 (2H, s), 6.84 (2H, d, J=8.8 Hz), 6.93 (2H, d, J=8.8 Hz), 7.13 (1H, ddd, J=7.3, 4.9, 1.0 Hz), 7.73 (1H, ddd, J=8.8, 6.8, 1.5 Hz), 8.09 (1H, d, J=8.3 Hz), 8.43 (1H, dq, J=4.9, 1.0 Hz)

Example 3-28

Production of 4-(5-methylpyridin-2-yl)-9-(4-{3-[(2R)-2-methylpyrrolidin-1-yl]propoxy}phenyl)-1-oxa-4,9-diazaspiro[5,5]undecan-3-one The entitled compound was obtained as a pale brown solid, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 2-bromo-5-methylpyridine in place of 1-bromo-4-fluorobenzene.

¹H-NMR (400 MHz, CDCl₃) δ: 1.09 (3H, d, J=5.9 Hz), 1.37-1.47 (1H, m), 1.64-1.82 (2H, m), 1.85-2.01 (5H, m), 2.05-2.12 (3H, m), 2.14-2.22 (1H, m), 2.26-2.33 (4H, m), 2.94-3.01 (1H, m), 3.04-3.10 (2H, m), 3.15-3.20 (1H, m), 3.24-3.29 (2H, m), 3.95-4.01 (4H, m), 4.35 (2H, s), 6.84 (2H, d, J=8.8 Hz), 6.93 (2H, d, J=9.3 Hz), 7.54 (1H, dd, J=9.0, 2.2 Hz), 7.93 (1H, d, J=8.8 Hz), 8.24 (1H, s)

Example 3-29

Production of 4-(4-methylpyridin-2-yl)-9-(4-{3-[(2R)-2-methylpyrrolidin-1-yl]propoxy}phenyl)-1-oxa-4,9-diazaspiro[5,5]undecan-3-one The entitled compound was obtained as a pale brown solid, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 2-bromo-4-methylpyridine in place of 1-bromo-4-fluorobenzene.

¹H-NMR (400 MHz, CDCl₃) δ: 1.10 (3H, d, J=6.3 Hz), 1.37-1.47 (1H, m), 1.57-1.81 (2H, m), 1.84-2.01 (5H, m), 2.04-2.12 (3H, m), 2.15-2.22 (1H, m), 2.25-2.32 (1H, m), 2.39 (3H, s), 2.94-3.01 (1H, m), 3.04-3.10 (2H, m), 3.15-3.20 (1H, m), 3.24-3.29 (2H, m), 3.95-4.01 (4H, m), 4.36 (2H, s), 6.84 (2H, d, J=9.3 Hz), 6.92 (2H, d, J=9.3 Hz), 6.96 (1H, d, J=4.4 Hz), 7.87 (1H, s), 8.28 (1H, d, J=4.9 Hz)

Example 3-30

Production of 4-(3-methylpyridin-2-yl)-9-(4-{3-[(2R)-2-methylpyrrolidin-1-yl]propoxy}phenyl)-1-oxa-4,9-diazaspiro[5,5]undecan-3-one The entitled compound was obtained as a pale orange oily substance, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 2-bromo-3-methylpyridine in place of 1-bromo-4-fluorobenzene.

¹H-NMR (400 MHz, CDCl₃) δ: 1.10 (3H, d, J=5.9 Hz), 1.38-1.47 (1H, m), 1.57-1.81 (2H, m), 1.88-2.01 (5H, m), 2.08-2.22 (4H, m), 2.24-2.32 (4H, m), 2.94-3.01 (1H, m), 3.06-3.12 (2H, m), 3.16-3.21 (1H, m), 3.25-3.31 (2H, m), 3.34-3.47 (1H, brs), 3.94-4.10 (3H, m), 4.36 (2H, s), 6.85 (2H, d, J=9.3 Hz), 6.93 (2H, d, J=9.3 Hz), 7.21 (1H, dd, J=7.6, 4.6 Hz), 7.61 (1H, dd, J=7.3, 1.5 Hz), 8.38 (1H, dd, J=4.6, 1.2 Hz)

Example 3-31

Production of 4-(5-methoxypyridin-2-yl)-9-(4-{3-[(2R)-2-methylpyrrolidin-1-yl]propoxy}phenyl)-1-oxa-4,9-diazaspiro[5,5]undecan-3-one The entitled compound was obtained as a pale yellow solid, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 2-bromo-5-methoxypyridine in place of 1-bromo-4-fluorobenzene.

¹H-NMR (400 z, CDCl₃) δ: 1.10 (3H, d, J=5.9 Hz), 1.38-1.48 (1H, m), 1.56-1.81 (2H, m), 1.85-2.01 (5H, m), 2.06-2.23 (4H, m), 2.27-2.33 (1H, m), 2.94-3.01 (1H, m), 3.04-3.11 (2H, m), 3.16-3.21 (1H, m), 3.24-3.29 (2H, m), 3.87 (3H, s), 3.93 (2H, s), 3.95-4.01 (2H, m), 4.35 (2H, s), 6.84 (2H, d,

Example 3-32

Production of 4-(6-methoxypyridin-2-yl)-9-(4-{3-[(2R)-2-methylpyrrolidin-1-yl]propoxy}phenyl)-1-oxa-4,9-diazaspiro[5,5]undecan-3-one The entitled compound was obtained as a pale yellow oily substance, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 2-bromo-6-methoxypyridine in place of 1-bromo-4-fluorobenzene.

$^1$H-NMR (400 MHz, CDCl$_3$) δ: 1.10 (3H, d, J=5.9 Hz), 1.38-1.47 (1H, m), 1.58-1.80 (5H, m), 1.85-2.00 (5H, m), 2.05-2.22 (4H, m), 2.25-2.33 (1H, m), 2.94-3.01 (1H, m), 3.04-3.11 (2H, m), 3.16-3.21 (1H, m), 3.24-3.30 (2H, m), 3.89 (3H, s), 3.95-4.01 (4H, m), 4.35 (2H, s), 6.57 (1H, dd, J=7.8, 1.0 Hz), 6.84 (2H, d, J=9.3 Hz), 6.93 (2H, d, J=9.3 Hz), 7.60-7.68 (2H, m)

Example 3-33

Production of 9-(4-{3-[(2R)-2-methylpyrrolidin-1-yl]propoxy}phenyl)-4-(3-thienyl)-1-oxa-4,9-diazaspiro[5,5]undecan-3-one The entitled compound was obtained as a pale yellow oily substance, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 3-bromothiophene in place of 1-bromo-4-fluorobenzene.

$^1$H-NMR (400 MHz, CDCl$_3$) δ: 1.12 (3H, d, J=6.3 Hz), 1.42-1.49 (1H, m), 1.59-2.02 (7H, m), 2.08-2.25 (4H, m), 2.31-2.38 (1H, m), 2.96-3.08 (3H, m), 3.18-3.30 (3H, m), 3.67 (2H, s), 3.95-4.01 (2H, m), 4.34 (2H, s), 6.84 (2H, d, J=9.3 Hz), 6.93 (2H, d, J=8.8 Hz), 7.31-7.33 (3H, m)

Example 3-34

Production of 9-(4-{3-[(2R)-2-methylpyrrolidin-1-yl]propoxy}phenyl)-4-(2-thienyl)-1-oxa-4,9-diazaspiro[5,5]undecan-3-one The entitled compound was obtained as a pale yellow oily substance, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 2-bromothiophene in place of 1-bromo-4-fluorobenzene.

$^1$H-NMR (400 MHz, CDCl$_3$) δ: 1.11 (3H, d, J=5.9 Hz), 1.40-1.48 (1H, m), 1.57-1.81 (2H, m), 1.85-2.02 (5H, m), 2.09-2.24 (4H, m), 2.27-2.35 (1H, m), 2.95-3.08 (3H, m), 3.17-3.22 (1H, m), 3.26-3.31 (2H, m), 3.74 (2H, s), 3.95-4.01 (2H, m), 4.40 (2H, s), 6.67 (1H, dd, J=3.9, 1.5 Hz), 6.85 (2H, d, J=9.3 Hz), 6.91-6.94 (3H, m), 7.01 (1H, dd, J=5.9, 1.5 Hz)

Example 3-35

Production of 4-(4-methoxyphenyl)-9-[4-(3-pyrrolidin-1-ylpropoxy)phenyl]-1-oxa-4,9-diazaspiro[5,5]undecan-3-one The entitled compound was obtained as a pale yellow solid, according to the same method as in Example 3 or according to a method similar to it but using 9-[4-(3-pyrrolidin-1-ylpropoxy)phenyl]-1-oxa-4,9-diazaspiro[5,5]undecan-3-one obtained in Reference Example 12-2, and 1-bromo-4-methoxybenzene in place of 1-bromo-4-fluorobenzene.

$^1$H-NMR (400 MHz, CDCl$_3$) δ: 1.82-1.89 (6H, m), 2.02-2.15 (4H, m), 2.66-2.74 (6H, m), 3.07 (2H, td, J=11.7, 2.4 Hz), 3.27 (2H, dt, J=12.2, 3.9 Hz), 3.59 (2H, s), 3.81 (3H, s), 3.99 (2H, t, J=6.3 Hz), 4.34 (2H, s), 6.83 (2H, dt, J=9.3, 3.4 Hz), 6.91-6.96 (4H, m), 7.20 (2H, dt, J=9.3, 3.4 Hz)

Example 3-36

Production of 4-(6-fluoropyridin-3-yl)-9-[4-(3-pyrrolidin-1-ylpropoxy)phenyl]-1-oxa-4,9-diazaspiro[5,5]undecan-3-one The entitled compound was obtained as a yellow solid, according to the same method as in Example 3 or according to a method similar to it but using 9-[4-(3-pyrrolidin-1-ylpropoxy)phenyl]-1-oxa-4,9-diazaspiro[5,5]undecan-3-one obtained in Reference Example 12-2, and 5-bromo-2-fluoropyridine in place of 1-bromo-4-fluorobenzene.

$^1$H-NMR (400 MHz, CDCl$_3$) δ: 1.84-1.91 (6H, m), 2.05-2.15 (4H, m), 2.69-2.75 (6H, m), 3.07 (2H, td, J=11.7, 2.4 Hz), 3.29 (2H, dt, J=12.2, 3.9 Hz), 3.65 (2H, s), 3.99 (2H, t, J=6.3 Hz), 4.37 (2H, s), 6.84 (2H, dt, J=9.3, 3.4 Hz), 6.93 (2H, dt, J=9.3, 3.4 Hz), 7.00 (1H, dd, J=8.8, 3.4 Hz), 7.81-7.86 (1H, m), 8.18-8.19 (1H, m)

Example 3-37

Production of 4-[6-(difluoromethoxy)pyridin-3-yl]-9-[4-(3-pyrrolidin-1-ylpropoxy)phenyl]-1-oxa-4,9-diazaspiro[5,5]undecan-3-one The entitled compound was obtained as a white solid, according to the same method as in Example 3 or according to a method similar to it but using 9-[4-(3-pyrrolidin-1-ylpropoxy)phenyl]-1-oxa-4,9-diazaspiro[5,5]undecan-3-one obtained in Reference Example 12-2, and 5-bromo-2-(difluoromethoxy)pyridine obtained in Reference Example 16 in place of 1-bromo-4-fluorobenzene.

$^1$H-NMR (400 MHz, CDCl$_3$) δ: 1.77-1.81 (4H, m), 1.83-1.90 (2H, m), 1.95-2.02 (2H, m), 2.13 (2H, d, J=12.7 Hz), 2.51-2.54 (4H, m), 2.61 (2H, t, J=7.6 Hz), 3.06 (2H, td, J=11.7, 2.4 Hz), 3.28 (2H, dt, J=12.7, 2.9 Hz), 3.63 (2H, s), 3.98 (2H, t, J=6.6 Hz), 4.37 (2H, s), 6.84 (2H, dt, J=9.3, 3.4 Hz), 6.93 (2H, dt, J=9.3, 3.4 Hz), 6.96 (1H, d, J=8.8 Hz), 7.44 (1H, t, J=72.7 Hz), 7.74 (1H, dd, J=8.8, 2.4 Hz), 8.16 (1H, d, J=2.4 Hz)

Example 3-38

Production of 5-[9-(4-{3-[(2R)-2-methylpyrrolidin-1-yl]propoxy}phenyl)-3-oxo-1-oxa-4,9-diazaspiro[5,5]undecan-4-yl]nicotinonitrile The entitled compound was obtained as a white solid, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 5-bromonicotinonitrile in place of 1-bromo-4-fluorobenzene.

$^1$H-NMR (400 MHz, CDCl$_3$) δ: 1.10 (3H, d, J=5.9 Hz), 1.41-1.47 (1H, m), 1.58-1.79 (2H, m), 1.84-2.01 (5H, m), 2.11-2.33 (5H, m), 2.95-3.09 (3H, m), 3.16-3.22 (1H, m), 3.27-3.32 (2H, m), 3.71 (2H, s), 3.94-4.01 (2H, m), 4.40 (2H, s), 6.85 (2H, d, J=9.3 Hz), 6.93 (2H, d, J=8.8 Hz), 8.10 (1H, dd, J=2.2, 1.1 Hz), 8.76 (1H, d, J=1.5 Hz), 8.85 (1H, d, J=2.4 Hz)

Example 3-39

Production of 9-(4-{3-[(2R)-2-methylpyrrolidin-1-yl]propoxy}phenyl)-4-(1,3-thiazol-2-yl)-1-oxa-4,9-diazaspiro[55]undecan-3-one The entitled compound was obtained as a brown oily substance, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 2-bromo-1,3-thiazole in place of 1-bromo-4-fluorobenzene.

$^1$H-NMR (400 MHz, CDCl$_3$) δ: 1.14 (3H, d, J=6.3 Hz), 1.43-1.52 (1H, m), 1.59-2.09 (9H, m), 2.14-2.30 (2H, m), 2.34-2.46 (1H, m), 2.98-3.09 (3H, m), 3.22-3.31 (3H, m), 3.94-4.02 (2H, m), 4.16 (2H, s), 4.46 (2H, s), 6.84 (2H, d, J=9.3 Hz), 6.93 (2H, d, J=9.3 Hz), 7.08 (1H, d, J=3.4 Hz), 7.53 (1H, d, J=3.4 Hz)

Example 3-40

Production of 3-(4-fluorophenyl)-8-[4-(3-piperidin-1-ylpropoxy)phenyl]-1-oxa-3,8-diazaspiro[4,5]decan-2-one The entitled compound was obtained as a pale yellow solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15 and 1-bromo-4-fluorobenzene.

$^1$H-NMR (400 MHz, CDCl$_3$) δ: 1.44 (2H, brs), 1.58-1.59 (4H, m), 1.94-2.05 (4H, m), 2.15 (2H, d, J=13.6 Hz), 2.40 (4H, brs), 2.47 (2H, t, J=7.2 Hz), 3.24-3.27 (4H, m), 3.78 (2H, s), 3.97 (2H, t, J=6.4 Hz), 6.84 (2H, d, J=8.8 Hz), 6.92 (2H, d, J=8.8 Hz), 7.08 (2H, t, J=8.0 Hz), 7.52 (2H, dd, J=9.2, 4.8 Hz)

Example 3-41

Production of 8-[4-(3-piperidin-1-ylpropoxy)phenyl]-3-(pyridin-2-yl)-1-oxa-3,8-diazaspiro[4,5]decan-2-one The entitled compound was obtained as a white solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15, and 2-bromopyridine in place of 1-bromo-4-fluorobenzene.

$^1$H-NMR (400 MHz, CDCl$_3$) δ: 1.43-1.45 (2H, m), 1.56-1.60 (4H, m), 1.93-2.06 (4H, m), 2.13-2.17 (2H, m), 2.39 (4H, brs), 2.46 (2H, t, J=7.6 Hz), 3.22-3.26 (4H, m), 3.95 (2H, t, J=6.0 Hz), 4.04 (2H, s), 6.82 (2H, d, J=8.8 Hz), 6.91 (2H, d, J=8.8 Hz), 7.01-7.04 (1H, m), 7.67-7.72 (1H, m), 8.23 (1H, d, J=8.4 Hz), 8.29-8.31 (1H, m)

Example 3-42

Production of 8-[4-(3-piperidin-1-ylpropoxy)phenyl]-3-(pyridin-4-yl)-1-oxa-3,8-diazaspiro[4,5]decan-2-one The entitled compound was obtained as a white solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15, and 4-bromopyridine in place of 1-bromo-4-fluorobenzene.

$^1$H-NMR (400 MHz, CDCl$_3$) δ: 1.45-1.46 (2H, m), 1.57-1.63 (4H, m), 1.94-2.08 (4H, m), 2.16 (2H, dd, J=2.3, 12.8 Hz), 2.40 (4H, brs), 2.45-2.49 (2H, m), 3.24-3.28 (4H, m), 3.79 (2H, s), 3.96 (2H, t, J=6.4 Hz), 6.84 (2H, d, J=9.2 Hz), 6.92 (2H, d, J=9.2 Hz), 7.49 (2H, d, J=6.0 Hz), 8.54 (2H, d, J=6.0 Hz)

Example 3-43

Production of 3-(6-fluoropyridin-3-yl)-8-[4-(3-piperidin-1-ylpropoxy)phenyl]-1-oxa-3,8-diazaspiro[4,5]decan-2-one The entitled compound was obtained as a pale yellow solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15, and 5-bromo-2-fluoropyridine in place of 1-bromo-4-fluorobenzene.

$^1$H-NMR (400 MHz, CDCl$_3$) δ: 1.44 (2H, brs), 1.58-1.63 (4H, m), 1.94-2.08 (4H, m), 2.16 (2H, d, J=12.8 Hz), 2.41 (4H, brs), 2.46-2.50 (2H, m), 3.21-3.31 (4H, m), 3.81 (2H, s), 3.97 (2H, t, J=6.4 Hz), 6.85 (2H, d, J=8.8 Hz), 6.93 (2H, d, J=8.8 Hz), 6.99 (1H, dd, J=3.2, 8.8 Hz), 8.09-8.10 (1H, m), 8.39-8.44 (1H, m)

Example 3-44

Production of 8-[4-(3-piperidin-1-ylpropoxy)phenyl]-3-[6-(trifluoromethyl)pyridin-3-yl]-1-oxa-3,8-diazaspiro[4,5]decan-2-one The entitled compound was obtained as a pale yellow solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15, and 5-bromo-2-(trifluoromethyl)pyridine in place of 1-bromo-4-fluorobenzene.

$^1$H-NMR (400 MHz, CDCl$_3$) δ: 1.44 (2H, brs), 1.57-1.62 (4H, m), 1.93-2.09 (4H, m), 2.17 (2H, d, J=13.2 Hz), 2.40 (4H, brs), 2.45-2.49 (2H, m), 3.21-3.32 (4H, m), 3.87 (2H, s), 3.97 (2H, t, J=6.4 Hz), 6.85 (2H, d, J=9.2 Hz), 6.93 (2H, d, J=9.2 Hz), 7.71 (1H, d, J=8.8 Hz), 8.45 (1H, dd, J=8.8, 2.8 Hz), 8.67 (1H, d, J=2.4 Hz)

Example 3-45

Production of 3-(2-fluorophenyl)-8-[4-(3-piperidin-1-ylpropoxy)phenyl]-1-oxa-3,8-diazaspiro[4,5]decan-2-one The entitled compound was obtained as a pale brown solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15, and 1-bromo-2-fluorobenzene in place of 1-bromo-4-fluorobenzene.

$^1$H-NMR (400 MHz, CDCl$_3$) δ: 1.44 (2H, brs), 1.57-1.63 (4H, m), 1.95-2.06 (4H, m), 2.20 (2H, d, J=13.2 Hz), 2.41 (4H, brs), 2.48 (2H, t, J=7.2 Hz), 3.24-3.27 (4H, m), 3.82 (2H, s), 3.96 (2H, t, J=6.4 Hz), 6.76 (2H, d, J=8.8 Hz), 6.93 (2H, d, J=8.8 Hz), 7.12-7.26 (2H, m), 7.56 (1H, td, J=7.8, 1.6 Hz)

Example 3-46

Production of 3-(2-fluoropyridin-4-yl)-8-[4-(3-piperidin-1-ylpropoxy)phenyl]-1-oxa-3,8-diazaspiro[4,5]decan-2-one The entitled compound was obtained as a pale yellow solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15, and 2-fluoro-4-iodopyridine in place of 1-bromo-4-fluorobenzene.

$^1$H-NMR (400 MHz, CDCl$_3$) δ: 1.44 (2H, brs), 1.59-1.61 (4H, m), 1.95-2.08 (4H, m), 2.15 (2H, d, J=12.8 Hz), 2.41 (4H, brs), 2.48 (2H, t, J=7.2 Hz), 3.21-3.28 (4H, m), 3.79 (2H, s), 3.97 (2H, t, J=6.0 Hz), 6.85 (2H, d, J=9.2 Hz), 6.93 (2H, d, J=9.2 Hz), 7.15 (1H, d, J=1.6 Hz), 7.42 (1H, dd, J=6.0, 2.0 Hz), 8.16 (1H, d, J=6.0 Hz)

Example 3-47

Production of 3-[6-(difluoromethyl)pyridin-3-yl]-8-[4-(3-piperidin-1-ylpropoxy)phenyl]-1-oxa-3,8-diazaspiro[4,5]decan-2-one The entitled compound was obtained as a pale yellow solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15, and 5-bromo-2-(difluoromethyl)pyridine in place of 1-bromo-4-fluorobenzene.

$^1$H-NMR (400 MHz, CDCl$_3$) δ: 1.44 (2H, brs), 1.56-1.62 (4H, m), 1.97-2.09 (4H, m), 2.17 (2H, d, J=14.0 Hz), 2.40 (4H, brs), 2.45-2.49 (2H, t, J=7.2 Hz), 3.21-3.32 (4H, m), 3.86 (2H, s), 3.97 (2H, t, J=6.4 Hz), 6.64 (1H, t, J=55.2 Hz), 6.85 (2H, d, J=9.2 Hz), 6.93 (2H, d, J=9.2 Hz), 7.67 (1H, d, J=8.8 Hz), 8.36 (1H, dd, J=8.4, 2.4 Hz), 8.64-8.65 (1H, m)

Example 3-48

Production of 3-(5-fluoropyridin-2-yl)-8-[4-(3-piperidin-1-ylpropoxy)phenyl]-1-oxa-3,8-diazaspiro[4,5]decan-2-one The entitled compound was obtained as a pale yellow solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15, and 2-bromo-5-fluoropyridine in place of 1-bromo-4-fluorobenzene.

$^1$H-NMR (400 MHz, CDCl$_3$) δ: 1.44 (2H, brs), 1.56-1.62 (4H, m), 1.92-2.07 (4H, m), 2.13-2.16 (2H, m), 2.40 (4H, brs), 3.23-3.26 (4H, m), 3.96 (2H, t, J=6.4 Hz), 4.02 (2H, s), 6.84 (2H, d, J=9.2 Hz), 6.93 (2H, d, J=9.2 Hz), 7.44-7.49 (1H, m), 8.16 (1H, d, J=2.8 Hz), 8.27 (1H, dd, H=9.2, 4.0 Hz)

Example 3-49

Production of 3-(6-fluoropyridin-2-yl)-8-[4-(3-piperidin-1-ylpropoxy)phenyl]-1-oxa-3,8-diazaspiro[4,5]decan-2-one The entitled compound was obtained as a brown solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15, and 2-bromo-6-fluoropyridine in place of 1-bromo-4-fluorobenzene.

$^1$H-NMR (400 MHz, CDCl$_3$) δ: 1.44 (2H, brs), 1.58-1.62 (4H, m), 1.95-2.07 (4H, m), 2.14 (2H, d, J=13.2 Hz), 2.42 (4H, brs), 3.23-3.25 (4H, m), 3.97 (2H, t, J=6.4 Hz), 4.01 (2H, s), 6.65 (1H, dd, H=8.0, 2.8 Hz), 6.84 (2H, d, J=9.2 Hz), 6.93 (2H, d, J=9.2 Hz), 7.81 (1H, quint., J=8.0 Hz), 8.12 (1H, dd, H=8.4, 2.0 Hz)

Example 3-50

Production of 3-(3-fluorophenyl)-8-[4-(3-piperidin-1-ylpropoxy)phenyl]-1-oxa-3,8-diazaspiro[4,5]decan-2-one The entitled compound was obtained as a pale brown solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15, and 1-bromo-3-fluorobenzene in place of 1-bromo-4-fluorobenzene.

$^1$H-NMR (400 MHz, CDCl$_3$) δ: 1.45 (2H, brs), 1.60-1.62 (4H, m), 1.96-2.06 (4H, m), 2.14 (2H, d, J=13.2 Hz), 2.43 (4H, brs), 2.49-2.50 (2H, m), 3.24-3.26 (4H, m), 3.78 (2H, s), 3.97 (2H, t, J=6.4 Hz), 6.83-6.86 (3H, m), 6.93 (2H, d, J=9.2 Hz), 7.25 (1H, d, J=8.4 Hz), 7.30-7.36 (1H, m), 7.45 (1H, dt, H=11.2, 2.4 Hz)

Example 3-51

Production of 3-(4-methoxyphenyl)-8-[4-(3-piperidin-1-ylpropoxy)phenyl]-1-oxa-3,8-diazaspiro[4,5]decan-2-one The entitled compound was obtained as a yellow solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15, and 1-bromo-4-methoxybenzene in place of 1-bromo-4-fluorobenzene.

$^1$H-NMR (400 MHz, CDCl$_3$) δ: 1.47 (2H, brs), 1.65 (4H, brs), 1.97-2.04 (4H, m), 2.15 (2H, d, J=12.8 Hz), 2.47-2.58 (6H, m), 3.25-3.27 (4H, m), 3.77 (2H, s), 3.81 (3H, s), 3.97 (2H, t, J=6.0 Hz), 6.84 (2H, d, J=8.8 Hz), 6.91-6.94 (4H, m), 7.45 (2H, d, H=9.2 Hz)

Example 3-52

Production of 3-(3-methoxyphenyl)-8-[4-(3-piperidin-1-ylpropoxy)phenyl]-1-oxa-3,8-diazaspiro[4,5]decan-2-one The entitled compound was obtained as a brown solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15, and 1-bromo-3-methoxybenzene in place of 1-bromo-4-fluorobenzene.

¹H-NMR (400 MHz, CDCl₃) δ: 1.48 (2H, brs), 1.66 (4H, brs), 1.98-2.05 (4H, m), 2.14 (2H, d, J=13.2 Hz), 2.50-2.57 (6H, m), 3.25-3.27 (4H, m), 3.78 (2H, s), 3.83 (3H, s), 3.97 (2H, t, J=6.4 Hz), 6.70 (2H, dd, J=7.6, 2.0 Hz), 6.84 (2H, d, J=8.8 Hz), 6.92 (2H, d, J=8.8 Hz), 7.04 (1H, dd, H=7.6, 2.4 Hz) 7.26-7.30 (2H, m)

Example 3-53

Production of 3-(6-methoxypyridin-3-yl)-8-[4-(3-piperidin-1-ylpropoxy)phenyl]-1-oxa-3,8-diazaspiro [4,5]decan-2-one The entitled compound was obtained as a pale yellow solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15, and 5-bromo-2-methoxypyridine in place of 1-bromo-4-fluorobenzene.

¹H-NMR (400 MHz, CDCl₃) δ: 1.44 (2H, brs), 1.57-1.61 (4H, m), 1.95-2.06 (4H, m), 2.16 (2H, d, J=13.2 Hz), 2.42 (4H, brs), 2.48 (2H, t, J=7.6 Hz), 3.24-3.28 (4H, m), 3.77 (2H, s), 3.93 (3H, s), 3.97 (2H, t, J=6.4 Hz), 6.78 (2H, d, J=8.8 Hz), 6.84 (2H, d, J=9.2 Hz), 6.93 (2H, d, J=9.2 Hz), 8.06 (1H, d, H=2.8 Hz), 8.11 (1H, dd, J=8.8, 2.8 Hz)

Example 3-54

Production of 3-(6-methylpyridin-3-yl)-8-[4-(3-piperidin-1-ylpropoxy)phenyl]-1-oxa-3,8-diazaspiro[4,5]decan-2-one The entitled compound was obtained as a pale yellow solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15, and 5-bromo-2-methylpyridine in place of 1-bromo-4-fluorobenzene.

¹H-NMR (400 MHz, CDCl₃) δ: 1.44 (2H, brs), 1.58-1.61 (4H, m), 1.95-2.08 (4H, m), 2.16 (2H, d, J=12.8 Hz), 2.41 (4H, brs), 2.46-2.50 (2H, m), 2.54 (3H, s), 3.24-3.29 (4H, m), 3.81 (2H, s), 3.97 (2H, t, J=6.4 Hz), 6.85 (2H, d, J=8.8 Hz), 6.93 (2H, d, J=9.2 Hz), 7.18 (1H, d, J=8.8 Hz), 8.14 (1H, dd, H=8.8, 2.8 Hz), 8.41 (1H, d, J=2.8 Hz)

Example 3-55

Production of 3-(2-methoxyphenyl)-8-[4-(3-piperidin-1-ylpropoxy)phenyl]-1-oxa-3,8-diazaspiro[4,5] decan-2-one The entitled compound was obtained as a brown solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15, and 1-bromo-2-methoxybenzene in place of 1-bromo-4-fluorobenzene.

¹H-NMR (400 MHz, CDCl₃) δ: 1.45 (2H, brs), 1.63 (4H, brs), 1.99-2.04 (4H, m), 2.21 (2H, d, J=13.2 Hz), 2.45-2.52 (6H, m), 3.24-3.27 (4H, m), 3.73 (2H, s), 3.87 (3H, s), 3.97 (2H, t, J=6.4 Hz), 6.84 (2H, d, J=8.8 Hz), 6.93 (2H, d, J=8.8 Hz), 6.95-6.99 (2H, m), 7.29 (1H, td, J=8.2, 1.6 Hz), 7.37 (1H, dd, J=8.0, 1.6 Hz)

Example 3-56

Production of 8-[4-(3-piperidin-1-ylpropoxy)phenyl]-3-[4-(trifluoromethoxy)phenyl]-1-oxa-3,8-diazaspiro[4,5]decan-2-one The entitled compound was obtained as a pale yellow solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15, and 1-bromo-4-(trifluoromethoxy)benzene in place of 1-bromo-4-fluorobenzene.

¹H-NMR (400 MHz, CDCl₃) δ: 1.44 (2H, brs), 1.59-1.62 (4H, m), 1.93-2.06 (4H, m), 2.15 (2H, d, J=13.2 Hz), 2.41 (4H, brs), 3.24-3.26 (4H, m), 3.80 (2H, s), 3.97 (2H, t, J=6.0 Hz), 6.85 (2H, d, J=9.2 Hz), 6.93 (2H, d, J=9.2 Hz), 7.24 (2H, d, J=8.4 Hz), 7.59 (2H, d, J=8.4 Hz)

Example 3-57

Production of 4-(1-ethyl-6-oxo-1,6-dihydropyridin-3-yl)-9-(4-{3-[(3S)-3-methylpiperidin-1-yl] propoxy}phenyl)-1-oxa-4,9-diazaspiro[5,5]undecan-3-one The entitled compound was obtained as a yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 5-bromo-1-ethylpyridin-2(1H)-one in place of 1-bromo-4-fluorobenzene.

¹H-NMR (400 MHz, CDCl₃) δ: 0.85 (3H, t, J=6.6 Hz), 1.38 (3H, t, J=7.3 Hz), 1.51-1.75 (6H, m), 1.80-1.90 (3H, m), 1.91-2.02 (2H, m), 2.10 (2H, d, J=13.2 Hz), 2.48 (2H, t, J=7.6 Hz), 2.80-2.91 (2H, brm), 3.06 (2H, td, J=11.7, 2.4 Hz), 3.27 (2H, dt, J=12.2, 3.9 Hz), 3.52 (2H, s), 3.93-4.02 (4H, m), 4.32 (2H, s), 6.60 (1H, d, J=9.8 Hz), 6.84 (2H, d, J=9.3 Hz), 6.92 (2H, d, J=9.3 Hz), 7.25 (1H, dd, J=9.8, 2.9 Hz), 7.38 (1H, d, J=2.9 Hz)

Example 3-58

Production of 9-(4-{3-[(3S)-3-methylpiperidin-1-yl] propoxy}phenyl)-4-pyrazin-2-yl-1-oxa-4,9-diazaspiro[5,5]undecan-3-one The entitled compound was obtained as a yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 2-iodopyrazine in place of 1-bromo-4-fluorobenzene.

¹H-NMR (400 MHz, CDCl₃) δ: 0.85 (3H, t, J=6.3 Hz), 1.53-1.72 (6H, m), 1.79-2.01 (5H, m), 2.08 (2H, d, J=13.2 Hz), 2.48 (2H, t, J=7.6 Hz), 2.84-2.88 (2H, brm), 3.08 (2H, td, J=11.2, 2.9 Hz), 3.27 (2H, dt, J=12.7, 3.4 Hz), 3.94-3.98 (4H, m), 4.41 (2H, s), 6.84 (2H, d, J=9.3 Hz), 6.93 (2H, d, J=9.3 Hz), 8.38 (2H, s), 9.53 (1H, d, J=1.0 Hz)

Example 3-59

Production of 9-(4-{3-[(3S-3-methylpiperidin-1-yl] propoxy}phenyl)-4-pyridin-2-yl-1-oxa-4,9-diazaspiro[5,5]undecan-3-one The entitled compound was obtained as a yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 2-bromopyridine in place of 1-bromo-4-fluorobenzene.

$^1$H-NMR (400 MHz, CDCl$_3$) δ: 0.86 (3H, d, J=6.3 Hz), 1.48-1.75 (6H, m), 1.78-2.13 (7H, m), 2.48 (2H, brs), 2.86 (2H, brs), 3.08 (2H, td, J=11.7, 2.4 Hz), 3.27 (2H, dt, J=12.7, 4.4 Hz), 3.96 (2H, t, J=6.3 Hz), 4.01 (2H, s), 4.37 (2H, s), 6.83 (2H, d, J=9.3 Hz), 6.93 (2H, d, J=9.3 Hz), 7.13 (1H, dd, J=7.3, 4.9 Hz), 7.72 (1H, td, J=8.3, 2.0 Hz), 8.09 (1H, d, J=8.3 Hz), 8.43 (1H, dd, J=4.9, 1.5 Hz)

Example 3-60

Production of 4-(3-methoxypyridin-2-yl)-9-(4-{3-[(3S)-3-methylpiperidin-1-yl]propoxy}phenyl)-1-oxa-4,9-diazaspiro[5,5]undecan-3-one The entitled compound was obtained as a yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 2-bromo-3-methoxypyridine in place of 1-bromo-4-fluorobenzene.

$^1$H-NMR (400 MHz, CDCl$_3$) δ: 0.86 (3H, d, J=6.8 Hz), 1.49-1.76 (6H, m), 1.79-2.03 (5H, m), 2.17 (2H, d, J=13.7 Hz), 2.48 (2H, t, J=7.3 Hz), 2.79-2.94 (2H, m), 3.09 (2H, td, J=11.2, 2.9 Hz), 3.26 (2H, dt, J=12.2, 3.9 Hz), 3.66 (2H, brs), 3.88 (3H, s), 3.96 (2H, t, J=6.3 Hz), 4.36 (2H, s), 6.84 (2H, d, J=8.8 Hz), 6.92 (2H, d, J=8.8 Hz), 7.24-7.34 (4H, m), 8.12 (1H, dd, J=4.4, 2.0 Hz)

Example 3-61

Production of 4-(1-ethyl-5-methyl-6-oxo-1,6-dihydropyridin-3-yl)-9-(4-{3-[(3S)-3-methylpiperidin-1-yl]propoxy}phenyl)-1-oxa-4,9-diazaspiro[5,5]undecan-3-one The entitled compound was obtained as a yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 5-bromo-1-ethyl-3-methylpyridin-2(1H)-one in place of 1-bromo-4-fluorobenzene.

$^1$H-NMR (400 MHz, CDCl$_3$) δ: 0.87 (3H, d, J=6.8 Hz), 1.37 (3H, t, J=7.3 Hz), 1.48-1.75 (6H, m), 1.79-1.90 (3H, m), 1.92-2.02 (2H, m), 2.10 (2H, d, J=12.7 Hz), 2.16 (3H, s), 2.48 (2H, brs), 2.78-2.94 (2H, brm), 3.06 (2H, td, J=11.7, 2.4 Hz), 3.28 (2H, dt, J=12.2, 3.9 Hz), 3.52 (2H, s), 3.95-4.01 (4H, m), 4.32 (2H, s), 6.84 (2H, d, J=8.8 Hz), 6.92 (2H, d, J=8.8 Hz), 7.11-7.14 (1H, m), 7.23 (1H, d, J=2.9 Hz).

Example 3-62

Production of 4-(1-ethyl-5-methoxy-6-oxo-1,6-dihydropyridin-3-yl)-9-(4-{3-[(3S)-3-methylpiperidin-1-yl]propoxy}phenyl)-1-oxa-4,9-diazaspiro[5,5]undecan-3-one The entitled compound was obtained as a yellow solid, according to the same method as in Example 3 or according to a method similar to it but using 9-(4-{3-[(3S)-3-methylpiperidin-1-yl]propoxy}phenyl-1-oxa-4,9-diazaspiro[5,5]undecan-3-one obtained in Reference Example 12-1, and 5-bromo-1-ethyl-3-methoxypyridin-2(1H) one in place of 1-bromo-4-fluorobenzene.

$^1$H-NMR (400 MHz, CDCl$_3$) δ: 0.87 (3H, d, J=6.3 Hz), 1.37 (3H, t, J=7.3 Hz), 1.50-1.76 (6H, m), 1.79-2.05 (5H, m), 2.11 (2H, d, J=13.2 Hz), 2.49 (2H, brs), 2.87 (2H, brs), 3.06 (2H, td, J=11.2, 2.4 Hz), 3.29 (2H, d, J=12.2 Hz), 3.54 (2H, s), 3.83 (3H, s), 4.06-3.93 (4H, m), 4.32 (2H, s), 6.52 (1H, d, J=2.4 Hz), 6.84 (2H, d, J=9.3 Hz), 6.97-6.89 (3H, m)

Example 3-63

Production of 4-(5-methoxypyridin-2-yl)-9-(4-{3-[(3S)-3-methylpiperidin-1-yl]propoxy}phenyl)-1-oxa-4,9-diazaspiro[5,5]undecan-3-one The entitled compound was obtained as a yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 2-bromo-5-methoxypyridin in place of 1-bromo-4-fluorobenzene.

$^1$H-NMR (400 MHz, CDCl$_3$) δ: 0.86 (3H, d, J=6.3 Hz), 1.48-1.76 (5H, m), 1.78-2.02 (6H, m), 2.07 (2H, d, J=13.2 Hz), 2.47 (2H, t, J=7.3 Hz), 2.79-2.92 (2H, m), 3.07 (2H, td, J=11.2, 2.0 Hz), 3.26 (2H, dt, J=12.7, 4.4 Hz), 3.87 (3H, s), 3.93 (2H, s), 3.96 (2H, t, J=6.3 Hz), 4.35 (2H, s), 6.84 (2H, d, J=9.3 Hz), 6.92 (2H, d, J=9.3 Hz), 7.29-7.25 (1H, m), 7.92 (1H, d, J=8.8 Hz), 8.10 (1H, d, J=2.9 Hz)

Example 3-64

Production of 4-(5-fluoropyridin-2-yl)-9-(4-{3-[(3S)-3-methylpiperidin-1-yl]propoxy}phenyl)-1-oxa-4,9-diazaspiro[5,5]undecan-3-one The entitled compound was obtained as a pale yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 2-bromo-5-fluoropyridine in place of 1-bromo-4-fluorobenzene.

$^1$H-NMR (400 MHz, CDCl$_3$) δ: 0.86 (3H, d, J=6.3 Hz), 1.49-1.75 (6H, m), 1.79-2.01 (5H, m), 2.06 (2H, d, J=13.7 Hz), 2.48 (2H, t, J=7.6 Hz), 2.79-2.93 (2H, brm), 3.07 (2H, td, J=11.2, 2.9 Hz), 3.27 (2H, dt, J=12.7, 3.9 Hz), 3.93-3.99 (4H, m), 4.36 (2H, s), 6.84 (2H, d, J=9.3 Hz), 6.92 (2H, d, J=9.3 Hz), 7.42-7.49 (1H, m), 8.11 (1H, dd, J=9.0, 4.1 Hz), 8.26 (1H, d, J=3.4 Hz)

Example 3-65

Production of 5-[9-(4-{3-[(3S)-3-methylpiperidin-1-yl]propoxy}phenyl)-3-oxo-1-oxa-4,9-diazaspiro[5,5]undecan-4-yl]nicotinonitrile The entitled compound was obtained as a white solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 5-bromonicotinonitrile in place of 1-bromo-4-fluorobenzene.

$^1$H-NMR (400 MHz, CDCl$_3$) δ: 0.88 (3H, t, J=8.5 Hz), 1.48-1.76 (6H, m), 1.78-2.02 (5H, m), 2.14 (2H, d, J=13.2 Hz), 2.48 (2H, J=7.6 Hz), 2.80-2.92 (2H, m), 3.06 (2H, td,

J=1.7, 2.3 Hz), 3.30 (2H, d, J=12.2 Hz), 3.71 (2H, s), 3.96 (2H, t, J=6.3 Hz), 4.40 (2H, s), 6.85 (2H, d, J=9.3 Hz), 6.93 (2H, d, J=9.3 Hz), 8.10 (1H, t, J=2.2 Hz), 8.76 (1H, d, J=2.0 Hz), 8.85 (1H, d, J=2.4 Hz)

Example 3-66

Production of 9-(4-{3-[(3S)-3-methylpiperidin-1-yl]propoxy}phenyl)-4-(3-methylpyridin-2-yl)-1-oxa-4,9-diazaspiro[5,5]undecan-3-one The entitled compound was obtained as a pale yellow oily substance, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 2-bromo-3-methylpyridine in place of 1-bromo-4-fluorobenzene.

$^1$H-NMR (400 MHz, CDCl$_3$) δ: 0.85 (3H, t, J=6.8 Hz), 1.49-1.75 (6H, m), 1.79-2.01 (5H, m), 2.07 (2H, d, J=13.2 Hz), 2.47 (2H, t, J=7.6 Hz), 2.86 (2H, t, J=13.4 Hz), 3.07 (2H, td, J=11.2, 2.9 Hz), 3.26 (2H, dt, J=12.7, 3.4 Hz), 3.87 (3H, s), 3.93 (2H, s), 3.96 (2H, t, J=6.3 Hz), 4.35 (2H, s), 6.83 (2H, d, J=9.3 Hz), 6.92 (2H, d, J=9.3 Hz), 7.29-7.25 (1H, m), 7.92 (1H, d, J=9.3 Hz), 8.10 (1H, d, J=2.9 Hz)

Example 3-67

Production of 4-[1-(difluoromethyl)-6-oxo-1,6-dihydropyridin-3-yl]-9-(4-{3-[(3S)-3-methylpiperidin-1-yl]propoxy}phenyl)-1-oxa-4,9-diazaspiro[5,5]undecan-3-one The entitled compound was obtained as a pale yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 5-bromo-1-(difluoromethyl)pyridin-2(1H)-one in place of 1-bromo-4-fluorobenzene.

$^1$H-NMR (400 MHz, CDCl$_3$) δ: 0.86 (3H, d, J=6.3 Hz), 1.50-1.75 (6H, m), 1.79-1.91 (3H, m), 1.92-2.03 (2H, m), 2.10 (2H, d, J=12.2 Hz), 2.48 (2H, t, J=6.8 Hz), 2.77-2.95 (2H, brm), 3.05 (2H, td, J=11.7, 2.4 Hz), 3.28 (2H, dt, J=12.2, 3.4 Hz), 3.55 (2H, s), 3.96 (2H, t, J=6.6 Hz), 4.33 (2H, s), 6.60 (1H, d, J=9.3 Hz), 6.84 (2H, d, J=8.8 Hz), 6.92 (2H, d, J=8.8 Hz), 7.40 (1H, dd, J=10.2, 2.9 Hz), 7.45 (1H, d, J=2.9 Hz), 7.66 (1H, t, J=60.0 Hz)

Example 3-68

Production of 4-(1-isopropyl-6-oxo-1,6-dihydropyridin-3-yl)-9-(4-{3-[(3S)-3-methylpiperidin-1-yl]propoxy}phenyl)-1-oxa-4,9-diazaspiro[5,5]undecan-3-one The entitled compound was obtained as a pale yellow solid, according to the same method as in Example 3 or according to a method similar to it but using 9-(4-{3-[(3S)-3-methylpiperidin-1-yl]propoxy}phenyl)-1-oxa-4,9-diazaspiro[5,5]undecan-3-one obtained in Reference Example 12-1, and 5-bromo-1-isopropylpyridin-2(1H)-one in place of 1-bromo-4-fluorobenzene.

$^1$H-NMR (400 MHz, CDCl$_3$) δ: 0.86 (3H, d, J=6.3 Hz), 1.37 (6H, d, J=6.8 Hz), 1.49-1.75 (6H, m), 1.80-1.91 (3H, m), 1.92-2.03 (2H, m), 2.10 (2H, d, J=12.7 Hz), 2.49 (2H, t, J=6.3 Hz), 2.79-2.95 (2H, brm), 3.06 (2H, td, J=11.2, 2.4 Hz), 3.28 (2H, dt, J=12.2, 3.4 Hz), 3.53 (2H, s), 3.96 (2H, t, J=6.3 Hz), 4.32 (2H, s), 5.21-5.28 (1H, m), 6.60 (1H, d, J=9.8 Hz), 6.84 (2H, d, J=9.3 Hz), 6.92 (2H, d, J=9.3 Hz), 7.22 (1H, dd, J=9.8, 2.9 Hz), 7.40 (1H, d, J=2.4 Hz)

Example 3-69

Production of 9-[4-(3-piperidin-1-ylpropoxy)phenyl]-4-pyrazin-2-yl-1-oxa-4,9-diazaspiro[5,5]undecan-3-one The entitled compound was obtained as a yellow oily substance, according to the same method as in Example 3 or according to a method similar to it but using 9-[4-(3-piperidin-1-ylpropoxy)phenyl]-1-oxa-4,9-diazaspiro[5,5]undecan-3-one obtained in Reference Example 12, and 2-iodopyrazine in place of 1-bromo-4-fluorobenzene.

$^1$H-NMR (400 MHz, CDCl$_3$) δ: 1.39-1.48 (2H, brm), 1.54-1.69 (4H, m), 1.84-2.01 (4H, m), 2.08 (2H, d, J=13.2 Hz), 2.35-2.51 (6H, m), 3.08 (2H, td, J=11.2, 2.0 Hz), 3.27 (2H, dt, J=12.2, 4.4 Hz), 3.93-3.99 (4H, m), 4.41 (2H, s), 6.84 (2H, d, J=9.3 Hz), 6.93 (2H, d, J=8.8 Hz), 8.38 (2H, s), 9.53 (1H, d, J=1.0 Hz)

Example 3-70

Production of 4-(3,4-difluorophenyl)-9-[4-(3-pyrrolidin-1-ylpropoxy)phenyl]-1-oxa-4,9-diazaspiro[5,5]undecan-3-one The entitled compound was obtained as a yellow solid, according to the same method as in Example 3 or according to a method similar to it but using 9-[4-(3-pyrrolidin-1-ylpropoxy)phenyl]-1-oxa-4,9-diazaspiro[5,5]undecan-3-one obtained in Reference Example 12-2, and 4-bromo-1,2-difluorobenzene in place of 1-bromo-4-fluorobenzene.

$^1$H-NMR (400 MHz, CDCl$_3$) δ: 1.79-1.99 (6H, m), 2.03-2.17 (4H, m), 2.59-2.86 (6H, brm), 3.06 (2H, td, J=11.7, 2.4 Hz), 3.28 (2H, dt, J=12.2, 3.9 Hz), 3.60 (2H, s), 4.00 (2H, t, J=6.1 Hz), 4.34 (2H, s), 6.83 (2H, d, J=9.3 Hz), 6.92 (2H, d, J=9.3 Hz), 7.01-7.08 (1H, m), 7.25-7.16 (2H, m)

Example 3-71

Production of 4-(2,4-difluorophenyl)-9-[4-(3-pyrrolidin-1-ylpropoxy)phenyl]-1-oxa-4,9-diazaspiro[5,5]undecan-3-one The entitled compound was obtained as a yellow solid, according to the same method as in Example 3 or according to a method similar to it but using 9-[4-(3-pyrrolidin-1-ylpropoxy)phenyl]-1-oxa-4,9-diazaspiro[5,5]undecan-3-one obtained in Reference Example 12-2, and 1-bromo-2,4-difluorobenzene in place of 1-bromo-4-fluorobenzene.

$^1$H-NMR (400 MHz, CDCl$_3$) δ: 1.81-2.03 (6H, m), 2.14 (4H, d, J=12.7 Hz), 2.64-2.98 (6H, m), 3.08 (2H, td, J=11.2, 2.4 Hz), 3.27 (2H, dt, J=12.2, 3.9 Hz), 3.56 (2H, s), 4.00 (2H, t, J=5.9 Hz), 4.37 (2H, s), 6.83 (2H, d, J=9.3 Hz), 6.90-6.98 (4H, m), 7.30-7.21 (1H, m).

Example 3-72

Production of 9-[4-(3-pyrrolidin-1-ylpropoxy)phenyl]-4-[6-(trifluoromethyl)pyridin-3-yl]-1-oxa-4,9-diazaspiro[5,5]undecan-3-one The entitled compound was obtained as a yellow solid, according to the same method as in Example 3 or according to a method similar to it but using 9-[4-(3-pyrrolidin-1-ylpropoxy)phenyl]-1-oxa-4,9-diazaspiro[5,5]undecan-3-one obtained in Reference Example 12-2, and 5-bromo-2-(trifluoromethyl)pyridine in place of 1-bromo-4-fluorobenzene.

$^1$H-NMR (400 MHz, CDCl$_3$) δ: 1.82-1.98 (6H, m), 2.14 (4H, d, J=12.7 Hz), 2.81 (6H, s), 3.07 (2H, t, J=10.5 Hz), 3.29 (2H, d, J=12.2 Hz), 3.72 (2H, s), 4.00 (2H, t, J=6.1 Hz), 4.40 (2H, s), 6.83 (2H, d, J=8.8 Hz), 6.93 (2H, d, J=8.8 Hz), 7.74 (1H, d, J=8.8 Hz), 7.96 (1H, dd, J=8.3, 2.4 Hz), 8.75 (1H, d, J=2.4 Hz)

Example 3-73

Production of 4-(6-isopropoxypyridine-3-yl)-9-[4-(3-pyrrolidin-1-ylpropoxy)phenyl]-1-oxa-4,9-diazaspiro[5,5]undecan-3-one The entitled compound was obtained as a yellow solid, according to the same method as in Example 3 or according to a method similar to it but using 9-[4-(3-pyrrolidin-1-ylpropoxy)phenyl]-1-oxa-4,9-diazaspiro[5,5]undecan-3-one obtained in Reference Example 12-2, and 5-bromo-2-isopropoxypyridine produced in Reference Example 17 in place of 1-bromo-4-fluorobenzene.

$^1$H-NMR (400 MHz, CDCl$_3$) δ: 1.34 (6H, d, J=6.3 Hz), 1.76-1.92 (6H, m), 1.97-2.04 (2H, m), 2.13 (2H, d, J=13.2 Hz), 2.57 (4H, brs), 2.65 (2H, t, J=7.3 Hz), 3.07 (2H, td, J=11.2, 2.4 Hz), 3.27 (2H, dt, J=12.2, 3.9 Hz), 3.60 (2H, s), 3.99 (2H, t, J=6.3 Hz), 4.35 (2H, s), 5.24-5.31 (1H, m), 6.72 (1H, d, J=8.8 Hz), 6.84 (2H, d, J=9.3 Hz), 6.93 (2H, d, J=9.3 Hz), 7.51 (1H, dd, J=8.8, 2.9 Hz), 8.06 (1H, d, J=2.0 Hz)

Example 3-74

Production of 4-(2-ethoxypyrimidin-5-yl)-9-[4-{3-[(2R)-2-methylpyrrolidin-1-yl]propoxy}phenyl)-1-oxa-4,9-diazaspiro[5,5]undecan-3-one The entitled compound was obtained as a yellow solid, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 5-bromo-2-ethoxypyrimidine in place of 1-bromo-4-fluorobenzene.

$^1$H-NMR (400 MHz, CDCl$_3$) δ: 1.11 (3H, d, J=5.4 Hz), 1.44 (3H, t, J=7.1 Hz), 1.53-2.05 (8H, m), 2.05-2.55 (5H, m), 2.90-3.12 (3H, m), 3.19 (1H, brs), 3.28 (2H, dt, J=12.2, 3.9 Hz), 3.62 (2H, s), 3.93-4.04 (2H, m), 4.37 (2H, s), 4.44 (2H, q, J=7.2 Hz), 6.85 (2H, d, J=9.3 Hz), 6.92 (2H, d, J=9.3 Hz), 8.51 (2H, s)

Example 3-75

Production of 4-(5-methoxypyrazin-2-yl)-9-[4-{3-[(2R)-2-methylpyrrolidin-1-yl]propoxy}phenyl)-1-oxa-4,9-diazaspiro[5,5]undecan-3-one The entitled compound was obtained as a brown oily substance, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 2-bromo-5-methoxypyrazine in place of 1-bromo-4-fluorobenzene.

$^1$H-NMR (400 MHz, CDCl$_3$) δ: 1.11 (3H, d, J=4.9 Hz), 1.34-2.53 (13H, m), 2.92-3.13 (3H, m), 3.14-3.31 (3H, m), 3.88 (2H, s), 3.92-4.04 (5H, m), 4.38 (2H, s), 6.84 (2 Hd, J=9.3 Hz), 6.93 (2H, d, J=9.3 Hz), 8.03 (1H, d, J=1.5 Hz), 8.84 (1H, d, J=1.5 Hz).

Example 3-76

Production of 4-(4-chlorophenyl)-9-[4-{3-[(2R)-2-methylpyrrolidin-1-yl]propoxy}phenyl)-1-oxa-4,9-diazaspiro[5,5]undecan-3-one The entitled compound was obtained as a pale yellow oily substance, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 1-bromo-4-chlorobenzene in place of 1-bromo-4-fluorobenzene.

$^1$H-NMR (400 MHz, CDCl$_3$) δ: 1.10 (3H, d, J=5.9 Hz), 1.38-1.47 (1H, m), 1.56-2.01 (7H, m), 2.08-2.23 (4H, m), 2.25-2.33 (1H, m), 2.94-3.01 (1H, m), 3.03-3.10 (2H, m), 3.15-3.21 (1H, m), 3.24-3.29 (2H, m), 3.61 (2H, s), 3.95-4.01 (2H, m), 4.34 (2H, s), 6.84 (2H, d, J=9.3 Hz), 6.92 (2H, d, J=9.3 Hz), 7.25 (2H, d, J=8.8 Hz), 7.39 (2H, d, J=8.8 Hz)

Example 3-77

Production of 9-(4-{3-[(2R)-2-methylpyrrolidin-1-yl]propoxy}phenyl)-4-[4-(trifluoromethyl)phenyl]-1-oxa-4,9-diazaspiro[5,5]undecan-3-one The entitled compound was obtained as a white solid, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 1-bromo-4-(trifluoromethyl)benzene in place of 1-bromo-4-fluorobenzene.

$^1$H-NMR (400 MHz, CDCl$_3$) δ: 1.10 (3H, d, J=6.3 Hz), 1.38-1.47 (1H, m), 1.58-2.00 (7H, m), 2.08-2.23 (4H, m), 2.27-2.32 (1H, m), 2.94-3.01 (1H, m), 3.04-3.10 (2H, m), 3.15-3.21 (1H, m), 3.26-3.30 (2H, m), 3.67 (2H, s), 3.94-4.01 (2H, m), 4.37 (2H, s), 6.85 (2H, d, J=8.8 Hz), 6.93 (2H, d, J=9.3 Hz), 7.47 (2H, d, J=8.3 Hz), 7.68 (2H, d, J=8.8 Hz)

Example 3-78

Production of 4-[9-(4-{3-[(2R)-2-methylpyrrolidin-1-yl]propoxy}phenyl)-3-oxo-1-oxa-4,9-diazaspiro[5,5]undecan-4-yl]benzonitrile The entitled compound was obtained as a white solid, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 4-bromobenzonitrile in place of 1-bromo-4-fluorobenzene.

$^1$H-NMR (400 MHz, CDCl$_3$) δ: 1.10 (3H, d, J=6.3 Hz), 1.38-1.47 (1H, m), 1.58-2.01 (7H, m), 2.08-2.32 (5H, m), 2.94-3.01 (1H, m), 3.03-3.10 (2H, m), 3.15-3.21 (1H, m), 3.25-3.31 (2H, m), 3.67 (2H, s), 3.96-4.01 (2H, m), 4.37 (2H, s), 6.84 (2H, d, J=9.3 Hz), 6.92 (2H, d, J=9.3 Hz), 7.50 (2H, d, J=8.8 Hz), 7.71 (2H, d, J=8.3 Hz)

Example 3-79

Production of 9-(4-{3-[(2R)-2-methylpyrrolidin-1-yl]propoxy}phenyl)-4-[4-(methylsulfonyl)phenyl]-1-oxa-4,9-diazaspiro[5,5]undecan-3-one The entitled compound was obtained as a white solid, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 1-bromo-4-(methylsulfonyl)benzene in place of 1-bromo-4-fluorobenzene.

$^1$H-NMR (400 MHz, CDCl$_3$) δ: 1.14 (3H, d, J=6.3 Hz), 1.43-2.05 (7H, m), 2.11-2.40 (5H, m), 2.99-3.10 (3H, m), 3.06 (3H, s), 3.23-3.31 (3H, m), 3.69 (2H, s), 3.94-4.03 (2H, m), 4.38 (2H, s), 6.84 (2H, d, J=8.8 Hz), 6.92 (2H, d, J=9.3 Hz), 7.58 (2H, d, J=8.8 Hz), 8.00 (2H, d, J=8.8 Hz)

Example 3-80

Production of 9-(4-{3-[(2R)-2-methylpyrrolidin-1-yl]propoxy}phenyl)-4-pyrazin-2-yl-1-oxa-4,9-diazaspiro[5,5]undecan-3-one The entitled compound was obtained as a pale yellow oily substance, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 2-iodopyrazine in place of 1-bromo-4-fluorobenzene.

$^1$H-NMR (400 MHz, CDCl$_3$) δ: 1.11 (3H, d, J=5.9 Hz), 1.39-1.48 (1H, m), 1.58-2.02 (7H, m), 2.05-2.34 (5H, m), 2.95-3.02 (1H, m), 3.05-3.11 (2H, m), 3.17-3.22 (1H, m), 3.25-3.30 (2H, m), 3.95-4.00 (4H, m), 4.41 (2H, s), 6.84 (2H, d, J=9.3 Hz), 6.93 (2H, d, J=9.3 Hz), 8.38 (2H, s), 9.53 (1H, s)

Example 3-81

Production of 4-(2-methoxypyrimidin-5-yl)-9-(4-{3-[(2R)-2-methylpyrrolidin-1-yl]propoxy}phenyl)-1-oxa-4,9-diazaspiro[5,5]undecan-3-one The entitled compound was obtained as a pale yellow solid, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 5-iodo-2-methoxypyrimidine in place of 1-bromo-4-fluorobenzene.

$^1$H-NMR (400 MHz, CDCl$_3$) δ: 1.10 (3H, d, J=6.3 Hz), 1.38-1.48 (1H, m), 1.57-2.01 (7H, m), 2.09-2.23 (4H, m), 2.27-2.33 (1H, m), 2.94-3.01 (1H, m), 3.03-3.09 (2H, m), 3.16-3.21 (1H, m), 3.26-3.31 (2H, m), 3.63 (2H, s), 3.94-4.01 (2H, m), 4.03 (3H, s), 4.37 (2H, s), 6.85 (2H, d, J=9.3 Hz), 6.93 (2H, d, J=9.3 Hz), 8.53 (2H, s)

Example 3-82

Production of 4-(3-methylpyridin-2-yl)-9-(4-{3-[(2R)-2-methylpyrrolidin-1-yl]propoxy}phenyl)-1-oxa-4,9-diazaspiro[5,5]undecan-3-one The entitled compound was obtained as a pale orange oily substance, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 2-bromo-3-methylpyridine in place of 1-bromo-4-fluorobenzene.

$^1$H-NMR (400 MHz, CDCl$_3$) δ: 1.64 (3H, d, J=6.3 Hz), 2.01-2.54 (7H, m), 2.83-3.06 (4H, m), 3.20-3.30 (2H, m), 3.42 (3H, s), 3.49-3.72 (6H, m), 3.93-3.98 (2H, m), 4.13-4.18 (2H, m), 4.40 (2H, s), 7.02 (2H, d, J=8.8 Hz), 7.27-7.31 (1H, m), 7.70 (1H, d, J=7.8 Hz), 7.81 (2H, d, J=8.8 Hz), 8.39 (1H, d, J=6.0 Hz)

Example 3-83

Production of 4-(3-methoxypyridin-2-yl)-9-(4-{3-[(2R)-2-methylpyrrolidin-1-yl]propoxy}phenyl)-1-oxa-4,9-diazaspiro[5,5]undecan-3-one The entitled compound was obtained as a pale brown solid, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 2-bromo-3-methoxypyridine in place of 1-bromo-4-fluorobenzene.

$^1$H-NMR (400 MHz, CDCl$_3$) δ: 1.16 (3H, d, J=5.9 Hz), 1.46-2.06 (8H, m), 2.14-2.31 (4H, m), 2.39-2.45 (1H, m), 2.99-3.12 (3H, m), 3.23-3.28 (3H, m), 3.66 (2H, brs), 3.88 (3H, s), 3.94-4.03 (2H, m), 4.36 (2H, s), 6.84 (2H, d, J=9.3 Hz), 6.93 (2H, d, J=8.8 Hz), 7.26-7.33 (2H, m), 8.12 (1H, dd, J=4.4, 2.0 Hz)

Example 3-84

Production of 9-(4-{3-[(2R)-2-methylpyrrolidin-1-yl]propoxy}phenyl)-4-pyridin-3-yl-1-oxa-4,9-diazaspiro[5,5]undecan-3-one The entitled compound was obtained as a pale yellow solid, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 3-bromopyridine in place of 1-bromo-4-fluorobenzene.

$^1$H-NMR (400 MHz, CDCl$_3$) δ: 1.10 (3H, d, J=5.9 Hz), 1.38-1.48 (1H, m), 1.53-2.01 (7H, m), 2.08-2.24 (4H, m), 2.27-2.34 (1H, m), 2.94-3.01 (1H, m), 3.04-3.10 (2H, m), 3.15-3.22 (1H, m), 3.25-3.32 (2H, m), 3.68 (2H, s), 3.94-4.01 (2H, m), 4.38 (2H, s), 6.85 (2H, d, J=8.8 Hz), 6.93 (2H, d, J=9.3 Hz), 7.37 (1H, dd, J=8.3, 4.9 Hz), 7.73 (1H, dq, J=8.3, 1.3 Hz), 8.53 (1H, dd, J=4.9, 1.5 Hz), 8.61 (1H, d, J=2.4 Hz)

Example 3-85

Production of 9-(4-{3-[(2R)-2-methylpyrrolidin-1-yl]propoxy}phenyl)-4-[5-(trifluoromethyl)pyridin-3-yl]-1-oxa-4,9-diazaspiro[5,5]undecan-3-one The entitled compound was obtained as a pale yellow solid, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 3-bromo-5-(trifluoromethyl)pyridine in place of 1-bromo-4-fluorobenzene.

$^1$H-NMR (400 MHz, CDCl$_3$) δ: 1.10 (3H, d, J=5.9 Hz), 1.39-1.48 (1H, m), 1.57-1.82 (2H, m), 1.85-2.01 (5H, m), 2.10-2.24 (4H, m), 2.27-2.34 (1H, m), 2.94-3.01 (1H, m), 3.03-3.10 (2H, m), 3.15-3.21 (1H, m), 3.27-3.32 (2H, m), 3.71 (2H, s), 3.94-4.03 (2H, m), 4.40 (2H, s), 6.85 (2H, d, J=8.8 Hz), 6.93 (2H, d, J=9.3 Hz), 8.00 (1H, s), 8.78 (1H, s), 8.84 (1H, d, J=2.4 Hz)

Example 3-86

Production of 4-(1-methyl-1H-pyrazol-3-yl)-9-(4-{3-[(2R)-2-methylpyrrolidin-1-yl]propoxy}phenyl)-1-oxa-4,9-diazaspiro[5,5]undecan-3-one The entitled compound was obtained as a white solid, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 3-iodo-1-methyl-1H-pyrazole in place of 1-bromo-4-fluorobenzene.

$^1$H-NMR (400 MHz, CDCl$_3$) δ: 1.10 (3H, d, J=5.9 Hz), 1.38-1.47 (1H, m), 1.57-2.01 (7H, m), 2.04-2.23 (4H, m), 2.26-2.32 (1H, m), 2.93-3.00 (1H, m), 3.02-3.09 (2H, m), 3.15-3.20 (1H, m), 3.24-3.29 (2H, m), 3.84 (3H, s), 3.87 (2H, s), 3.93-4.01 (2H, m), 4.33 (2H, s), 6.83-6.85 (3H, m), 6.92 (2H, d, J=8.8 Hz), 7.29 (1H, d, J=2.0 Hz)

Example 3-87

Production of 4-(1-methyl-1H-pyrazol-4-yl)-9-(4-{3-[(2R)-2-methylpyrrolidin-1-yl]propoxy}phenyl-1-oxa-4,9-diazaspiro[5,5]undecan-3-one The entitled compound was obtained as a pale brown solid, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 4-bromo-1-methyl-1H-pyrazole in place of 1-bromo-4-fluorobenzene.

$^1$H-NMR (400 Hz, CDCl$_3$) δ: 1.10 (3H, d, J=5.9 Hz), 1.40-1.48 (1H, m), 1.57-2.01 (7H, m), 2.06-2.23 (5H, m), 2.26-2.33 (1H, m), 2.94-2.99 (1H, m), 3.01-3.08 (2H, m), 3.16-3.21 (1H, m), 3.24-3.30 (2H, m), 3.59 (2H, s), 3.90 (3H, s), 3.95-4.01 (2H, m), 4.32 (2H, s), 6.84 (2H, d, J=9.3 Hz), 6.92 (2H, d, J=9.3 Hz), 7.47 (1H, s), 8.03 (1H, s)

Example 3-88

Production of 4-(5-methoxypyridin-3-yl)-9-(4-{3-[(2R)-2-methylpyrrolidin-1-yl]propoxy}phenyl)-1-oxa-4,9-diazaspiro[5,5]undecan-3-one The entitled compound was obtained according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 3-bromo-5-methoxypyridine in place of 1-bromo-4-fluorobenzene.

$^1$H-NMR (400 MHz, CDCl$_3$) δ1.10 (3H, d, J=6.3 Hz), 1.40-1.48 (1H, m), 1.53-2.01 (7H, m), 2.08-2.32 (5H, m), 2.94-2.99 (1H, m), 3.04-3.10 (2H, m), 3.15-3.22 (1H, m), 3.25-3.31 (2H, m), 3.67 (2H, s), 3.88 (3H, s), 3.95-4.01 (2H, m), 4.37 (2H, s), 6.85 (2H, d, J=9.3 Hz), 6.93 (2H, d, J=9.3 Hz), 7.28 (1H, t, J=2.4 Hz), 8.20 (1H, d, J=2.0 Hz), 8.24 (1H, d, J=2.4 Hz)

Example 3-89

Production of 5-[9-(4-{3-[(2R)-2-methylpyrrolidin-1-yl]propoxy}phenyl)-3-oxo-1-oxa-4,9-diazaspiro[5,5]undecan-4-yl]nicotinonitrile The entitled compound was obtained as a pale orange solid, according to the same method as in Example 3 or according to a method similar to it but using 9-(4-{3-[(2R)-2-methylpyrrolidin-1-yl]propoxy}phenyl)-1-oxa-4,9-diazaspiro[5,5]undecan-3-one obtained in Reference Example 12-4, and 5-bromonicotinonitrile in place of 1-bromo-4-fluorobenzene.

$^1$H-NMR (CDCl$_3$) δ: 1.10 (3H, d, J=5.9 Hz), 1.41-1.47 (1H, m), 1.58-1.79 (2H, m), 1.84-2.01 (5H, m), 2.11-2.33 (5H, m), 2.95-3.09 (3H, m), 3.16-3.22 (1H, m), 3.27-3.32 (2H, m), 3.71 (2H, s), 3.94-4.01 (2H, m), 4.40 (2H, s), 6.85 (2H, d, J=9.3 Hz), 6.93 (2H, d, J=8.8 Hz), 8.10 (1H, dd, J=2.2, 1.1 Hz), 8.76 (1H, d, J=1.5 Hz), 8.85 (1H, d, J=2.4 Hz)

Example 3-90

Production of 9-(4-{3-[(2S)-2-methylpyrrolidin-1-yl]propoxy}phenyl)-4-pyridin-3-yl-1-oxa-4,9-diazaspiro[5,5]undecan-3-one The entitled compound was obtained as a pale brown solid, according to the same method as in Example 3 or according to a method similar to it but using 9-(4-{3-[(2S)-2-methylpyrrolidin-1-yl]propoxy}phenyl)-1-oxa-4,9-diazaspiro[5,5]undecan-3-one obtained in Reference Example 12-3, and 3-bromopyridine in place of 1-bromo-4-fluorobenzene.

$^1$H-NMR (400 MHz, CDCl$_3$) δ: 1.11 (3H, d, J=5.9 Hz), 1.40-1.49 (1H, m), 1.58-2.02 (7H, m), 2.11-2.24 (4H, m), 2.28-2.36 (1H, m), 2.95-3.10 (3H, m), 3.17-3.22 (1H, m), 3.25-3.31 (2H, m), 3.68 (2H, s), 3.95-4.02 (2H, m), 4.38 (2H, s), 6.85 (2H, d, J=8.8 Hz), 6.93 (2H, d, J=9.3 Hz), 7.37 (1H, dd, J=8.3, 4.9 Hz), 7.73 (1H, dq, J=8.3, 1.5 Hz), 8.53 (1H, dd, J=4.9, 1.5 Hz), 8.61 (1H, d, J=2.4 Hz).

Example 3-91

Production of 4-(2-methoxypyrimidin-5-yl)-9-(4-{3-[(2S)-2-methylpyrrolidin-1-yl]propoxy}phenyl)-1-oxa-4,9-diazaspiro[5,5]undecan-3-one The entitled compound was obtained as a white solid, according to the same method as in Example 3 or according to a method similar to it but using 9-(4-{3-[(2S)-2-methylpyrrolidin-1-yl]propoxy}phenyl)-1-oxa-4,9-diazaspiro[5,5]undecan-3-one obtained in Reference Example 12-3, and 5-iodo-2-methoxypyrimidine in place of 1-bromo-4-fluorobenzene.

$^1$H-NMR (400 MHz, CDCl$_3$) δ: 1.09 (3H, d, J=5.9 Hz), 1.38-1.47 (1H, m), 1.57-1.79 (2H, m), 1.83-2.01 (5H, m), 2.07-2.22 (4H, m), 2.25-2.31 (1H, m), 2.93-3.00 (1H, m), 3.03-3.10 (2H, m), 3.15-3.20 (1H, m), 3.26-3.31 (2H, m), 3.63 (2H, s), 3.95-4.01 (2H, m), 4.03 (3H, s), 4.37 (2H, s), 6.85 (2H, d, J=9.3 Hz), 6.93 (2H, d, J=9.3 Hz), 8.53 (2H, s)

Example 3-92

Production of 5-[9-(4-{3-[(2S)-2-methylpyrrolidin-1-yl]propoxy}phenyl)-3-oxo-1-oxa-4,9-diazaspiro[5,5]undecan-4-yl]nicotinonitrile The entitled compound was obtained as a pale brown solid, according to the same method as in Example 3 or according to a method similar to it but using 9-(4-{3-[(2S)-2-methylpyrrolidin-1-yl]propoxy}phenyl)-1-oxa-4,9-diazaspiro[5,5]undecan-3-one obtained in Reference Example 12-3, and 5-bromonicotinonitrile in place of 1-bromo-4-fluorobenzene.

$^1$H-NMR (400 MHz, CDCl$_3$) δ: 1.14 (3H, d, J=6.3 Hz), 1.46-2.06 (8H, m), 2.11-2.36 (5H, m), 2.98-3.10 (3H, m), 3.20-3.32 (3H, m), 3.71 (2H, s), 3.95-4.02 (2H, m), 4.40 (2H, s), 6.85 (2H, d, J=9.3 Hz), 6.93 (2H, d, J=9.3 Hz), 8.10 (1H, s), 8.76 (1H, d, J=1.5 Hz), 8.85 (1H, d, J=2.4 Hz).

Example 3-93

Production of 4-(5-methoxypyridin-3-yl)-9-(4-{3-[(2S)-2-methylpyrrolidin-1-yl]propoxy}phenyl)-1-oxa-4,9-diazaspiro[5,5]undecan-3-one The entitled compound was obtained as a pale brown solid, according to the same method as in Example 3 or according to a method similar to it but using 9-(4-{3-[(2S)-2-methylpyrrolidin-1-yl]propoxy}phenyl)-1-oxa-4,9-diazaspiro[5,5]undecan-3-one obtained in Reference Example 12-3, and 3-bromo-5-methoxypyridine in place of 1-bromo-4-fluorobenzene.

$^1$H-NMR (400 MHz, CDCl$_3$) δ: 1.12 (3H, d, J=6.3 Hz), 1.41-1.50 (1H, m), 1.59-2.03 (7H, m), 2.12-2.26 (4H, m), 2.32-2.37 (1H, m), 2.96-3.10 (3H, m), 3.18-3.31 (3H, m), 3.66 (2H, s), 3.88 (3H, s), 3.94-4.03 (2H, m), 4.37 (2H, s), 6.85 (2H, d, J=8.8 Hz), 6.93 (2H, d, J=9.3 Hz), 7.28 (1H, t, J=2.4 Hz), 8.20 (1H, d, J=2.0 Hz), 8.24 (1H, d, J=2.4 Hz).

Example 3-94

Production of 4-(5-methoxypyrazin-2-yl)-9-(4-{3-[(2S-2-methylpyrrolidin-1-yl]propoxy}phenyl)-1-oxa-4,9-diazaspiro[5,5]undecan-3-one The entitled compound was obtained as a pale brown oily substance, according to the same method as in Example 3 or according to a method similar to it but using 9-(4-{3-[(2S)-2-methylpyrrolidin-1-yl]propoxy}phenyl)-1-oxa-4,9-diazaspiro[5,5]undecan-3-one obtained in Reference Example 12-3, and 2-bromo-5-methoxypyrazine in place of 1-bromo-4-fluorobenzene. $^1$H-NMR (400 MHz, CDCl$_3$) δ: 1.12 (3H, d, J=6.3 Hz), 1.41-1.50 (1H, m), 1.63-2.03 (7H, m), 2.06-2.25 (4H, m), 2.30-2.37 (1H, m), 2.96-3.11 (3H, m), 3.18-3.29 (3H, m), 3.88 (2H, s), 3.94-4.02 (2H, m), 3.99 (3H, s), 4.38 (2H, s), 6.84 (2H, d, J=8.8 Hz), 6.93 (2H, d, J=9.3 Hz), 8.04 (1H, d, J=1.5 Hz), 8.84 (1H, d, J=1.5 Hz).

Example 3-95

Production of 4-(1-methyl-1H-pyrazol-4-yl)-9-(4-{3-[(2S)-2-methylpyrrolidin-1-yl]propoxy}phenyl)-1-oxa-4,9-diazaspiro[5,5]undecan-3-one The entitled compound was obtained as a pale brown solid, according to the same method as in Example 3 or according to a method similar to it but using 9-(4-{3-[(2S)-2-methylpyrrolidin-1-yl]propoxy}phenyl)-1-oxa-4,9-diazaspiro[5,5]undecan-3-one obtained in Reference Example 12-3, and 4-bromo-1-methyl-1H-pyrazole in place of 1-bromo-4-fluorobenzene.

$^1$H-NMR (400 MHz, CDCl$_3$) δ: 1.13 (3H, d, J=5.9 Hz), 1.43-1.50 (1H, m), 1.64-2.03 (7H, m), 2.07-2.26 (4H, m), 2.32-2.38 (1H, m), 2.96-3.07 (3H, m), 3.19-3.31 (3H, m), 3.59 (2H, s), 3.90 (3H, s), 3.94-4.03 (2H, m), 4.32 (2H, s), 6.84 (2H, d, J=9.3 Hz), 6.92 (2H, d, J=9.3 Hz), 7.47 (1H, s), 8.04 (1H, s)

Example 3-96

Production of 3-ethyl-8-(4-{3-[(2R)-2-methylpyrrolidin-1-yl]propoxy}phenyl)-1-oxa-3,8-diazaspiro[4,5]decan-2-one 8-(4-{3-[(2R)-2-Methylpyrrolidin-1-yl]propoxy}phenyl)-1-oxa-3,8-diazaspiro[4,5]decan-2-one (100 mg, 0.268 mmol) obtained in Reference Example 13-5 was dissolved in N,N-dimethylformamide, and at 0° C., sodium hydride (16 mg, 0.402 mmol) and bromoethane (32 mg, 0.295 mmol) were added thereto, and stirred overnight at room temperature. Water was added to it, the solvent was evaporated off under reduced pressure, then the residue was dissolved in ethyl acetate, washed with water and saturated saline in that order. The organic layer was dried with sodium sulfate, then the solvent was evaporated off under reduced pressure, and the residue was purified through thin-layer chromatography (eluate: chloroform/methanol=9/1) to obtain the entitled compound (17 mg, 16%) as a yellow solid.

$^1$H-NMR (400 MHz, CDCl$_3$) δ: 1.08-1.22 (6H, m), 1.38-2.59 (13H, m), 2.99 (1H, brs), 3.16-3.22 (5H, m), 3.31-3.37 (4H, m), 3.93-4.03 (2H, m), 6.83 (2H, d, J=9.3 Hz), 6.90 (2H, d, J=9.3 Hz)

Example 3-97

Production of 8-(4-{3-[(2R)-2-methylpyrrolidin-1-yl]propoxy}phenyl)-3-[4-methylsulfonyl)phenyl]-1-oxa-3,8-diazaspiro[4,5]decan-2-one The entitled compound was obtained as a brown solid, according to the same method as in Example 3 or according to a method similar to it but using 8-(4-{3-[(2R)-2-methylpyrrolidin-1-yl]propoxy}phenyl)-1-oxa-3,8-diazaspiro[4,5]decan-2-one obtained in Reference Example 13-5, and 1-bromo-4-(methylsulfonyl)benzene in place of 1-bromo-4-fluorobenzene.

$^1$H-NMR (400 MHz, CDCl$_3$) δ: 1.13 (3H, s), 1.38-2.57 (13H, m), 2.95-3.09 (4H, m), 3.18-3.34 (5H, m), 3.85 (2H, s), 3.94-4.05 (2H, m), 6.85 (2H, d, J=9.3 Hz), 6.93 (2H, d, J=9.3 Hz), 7.78 (2H, d, J=9.3 Hz), 7.96 (2H, d, J=9.3 Hz)

Example 3-98

Production of 3-(2-ethoxypyrimidine-5-yl)-8-(4-{3-[(2R)-2-methylpyrrolidin-1-yl]propoxy}phenyl)-1-oxa-3,8-diazaspiro[4,5]decan-2-one The entitled compound was obtained as a pale brown solid, according to the same method as in Example 3 or according to a method similar to it but using 8-(4-{3-[(2R)-2-methylpyrrolidin-1-yl]propoxy}phenyl)-1-oxa-3,8-diazaspiro[4,5]decan-2-one obtained in Reference Example 13-5, and 5-bromo-2-ethoxypyrimidine in place of 1-bromo-4-fluorobenzene.

$^1$H-NMR (400 MHz, CDCl$_3$) δ: 1.12 (3H, s), 1.43 (3H, t, J=7.1 Hz), 1.51-2.56 (13H, m), 3.00 (1H, brs), 3.14-3.35 (5H, m), 3.77 (2H, s), 3.95-4.02 (2H, m), 4.42 (2H, q, J=7.0 Hz), 6.85 (2H, d, J=9.3 Hz), 6.93 (2H, d, J=9.3 Hz), 8.74 (2H, s)

Example 3-99

Production of 3-(1-methyl-1H-pyrazol-4-yl)-8-(4-{3-[(2R)-2-methylpyrrolidin-1-yl]propoxy}phenyl)-1-oxa-3,8-diazaspiro[4,5]decan-2-one The entitled compound was obtained as a pale yellow solid, according to the same method as in Example 3 or according to a method similar to it but using 8-(4-{3-[(2R)-2-methylpyrrolidin-1-yl]propoxy}phenyl)-1-oxa-3,8-diazaspiro[4,5]decan-2-one obtained in Reference Example 13-5, and 4-bromo-1-methyl-1H-pyrazole in place of 1-bromo-4-fluorobenzene.
$^1$H-NMR (400 MHz, CDCl$_3$) δ: 1.09 (3H, dd, J=13.7, 6.3 Hz), 1.35-2.52 (13H, m), 3.13-3.31 (1H, m), 3.17-3.26 (5H, m), 3.66 (2H, s), 3.90 (3H, s), 3.93-4.04 (2H, m), 6.85 (2H, d, J=9.3 Hz), 6.92 (2H, d, J=9.3 Hz), 7.36 (1H, s), 7.77 (1H, s)

Example 3-100

Production of 3-(1-methyl-1H-pyrazol-3-yl)-8-(4-{3-[(2R)-2-methylpyrrolidin-1-yl]propoxy}phenyl)-1-oxa-3,8-diazaspiro[4,5]decan-2-one The entitled compound was obtained as a brown solid, according to the same method as in Example 3 or according to a method similar to it but using 8-(4-{3-[(2R)-2-methylpyrrolidin-1-yl]propoxy}phenyl)-1-oxa-3,8-diazaspiro[4,5]decan-2-one obtained in Reference Example 13-5, and 3-iodo-1-methyl-1H-pyrazole in place of 1-bromo-4-fluorobenzene.
$^1$H-NMR (400 MHz, CDCl$_3$) δ: 1.11 (3H, d, J=6.3 Hz), 1.43 (1H, brs), 1.56-2.51 (12H, m), 2.92-3.04 (1H, m), 3.13-3.32 (5H, m), 3.82 (3H, s), 3.87 (2H, s), 3.93-4.04 (2H, m), 6.64 (1H, d, J=2.4 Hz), 6.84 (2H, d, J=9.3 Hz), 6.92 (2H, d, J=9.3 Hz), 7.28 (1H, d, J=2.0 Hz)

Example 3-101

Production of 5-[8-(4-{3-[(2R)-2-methylpyrrolidin-1-yl]propoxy}phenyl)-2-oxo-1-oxa-3,8-diazaspiro[4,5]decan-3-yl]nicotinonitrile The entitled compound was obtained as a brown solid, according to the same method as in Example 3 or according to a method similar to it but using 8-(4-{3-[(2R)-2-methylpyrrolidin-1-yl]propoxy}phenyl)-1-oxa-3,8-diazaspiro[4,5]decan-2-one obtained in Reference Example 13-5, and 5-bromonicotinonitrile in place of 1-bromo-4-fluorobenzene.
$^1$H-NMR (400 MHz CDCl$_3$) δ: 1.11 (3H, d, J=5.9 Hz), 1.37-1.49 (1H, brm), 1.50-2.51 (12H, m), 2.93-3.03 (1H, m), 3.15-3.35 (5H, m), 3.85 (2H, s), 3.94-4.04 (2H, m), 6.86 (2H, d, J=9.3 Hz), 6.93 (2H, d, J=9.3 Hz), 8.55-8.53 (1H, m), 8.64 (1H, d, J=1.5 Hz), 8.82 (1H, d, J=2.9 Hz)

Example 3-102

Production of 8-(4-{3-[(2R)-2-methylpyrrolidin-1-yl]propoxy}phenyl)-3-pyrazin-2-yl-1-oxa-3,8-diazaspiro[4,5]decan-2-one The entitled compound was obtained as a brown solid, according to the same method as in Example 3 or according to a method similar to it but using 8-(4-{3-[(2R)-2-methylpyrrolidin-1-yl]propoxy}phenyl)-1-oxa-3,8-diazaspiro[4,5]decan-2-one obtained in Reference Example 13-5, and 2-iodopyrazine in place of 1-bromo-4-fluorobenzene.
$^1$H-NMR (400 MHz, CDCl$_3$) δ: 1.12 (3H, d, J=5.9 Hz), 1.36-2.55 (13H, m), 2.94-3.06 (1H, brm), 3.13-3.35 (5H, m), 3.94-4.05 (4H, m), 6.85 (2H, d, J=9.3 Hz), 6.93 (2H, d, J=9.3 Hz), 8.26-8.30 (1H, m), 8.33 (1H, d, J=2.4 Hz), 9.60 (1H, d, J=1.5 Hz)

Example 3-103

Production of 3-(6-methoxypyridin-3-yl)-8-(4-{3-[(2R)-2-methylpyrrolidin-1-yl]propoxy}phenyl)-1-oxa-3,8-diazaspiro[4,5]decan-2-one The entitled compound was obtained as a white solid, according to the same method as in Example 3 or according to a method similar to it but using 8-(4-{3-[(2R)-2-methylpyrrolidin-1-yl]propoxy}phenyl)-1-oxa-3,8-diazaspiro[4,5]decan-2-one obtained in Reference Example 13-5, and 5-bromo-2-methoxypyridine in place of 1-bromo-4-fluorobenzene.
$^1$H-NMR (400 MHz, CDCl$_3$) δ: 1.11 (3H, d, J=5.9 Hz), 1.36-2.52 (13H, m), 2.93-3.03 (1H, m), 3.15-3.32 (5H, m), 3.77 (2H, s), 3.93 (3H, s), 3.94-4.04 (2H, m), 6.79 (1H, d, J=8.3 Hz), 6.85 (2H, d, J=9.3 Hz), 6.93 (2H, d, J=9.3 Hz), 8.06 (1H, d, J=2.4 Hz), 8.11 (1H, dd, J=9.3, 2.9 Hz)

Example 3-104

Production of 3-(2-methoxypyrimidin-5-yl)-8-(4-{3-[(2R)-2-methylpyrrolidin-1-yl]propoxy}phenyl)-1-oxa-3,8-diazaspiro[4,5]decan-2-one The entitled compound was obtained as a yellow solid, according to the same method as in Example 3 or according to a method similar to it but using 8-(4-{3-[(2R)-2-methylpyrrolidin-1-yl]propoxy}phenyl)-1-oxa-3,8-diazaspiro[4,5]decan-2-one obtained in Reference Example 13-5, and 5-iodo-2-methoxypyrimidine in place of 1-bromo-4-fluorobenzene.
$^1$H-NMR (400 MHz, CDCl$_3$) δ: 1.12 (3H, d, J=4.9 Hz), 1.33-2.46 (13H, m), 2.93-3.05 (1H, brm), 3.14-3.33 (5H, m), 3.78 (2H, s), 3.97-4.02 (5H, m), 6.85 (2H, d, J=9.3 Hz), 6.93 (2H, d, J=9.3 Hz), 8.76 (2H, s)

Example 3-105

Production of 3-(5-methoxypyridin-3-yl)-8-(4-{3-[(2R)-2-methylpyrrolidin-1-yl]propoxy}phenyl)-1-oxa-3,8-diazaspiro[4,5]decan-2-one The entitled compound was obtained as a pale brown solid, according to the same method as in Example 3 or according to a method similar to it but using 8-(4-{3-[(2R)-2-methylpyrrolidin-1-yl]propoxy}phenyl)-1-oxa-3,8-diazaspiro[4,5]decan-2-one obtained in Reference Example 13-5, and 3-bromo-5-methoxypyridine in place of 1-bromo-4-fluorobenzene.
$^1$H-NMR (400 MHz, CDCl$_3$) δ: 1.11 (3H, d, J=5.9 Hz), 1.35-2.58 (13H, m), 2.93-3.03 (1H, brm), 3.15-3.33 (5H, m), 3.82 (2H, s), 3.89 (3H, s), 3.94-4.04 (2H, m), 6.85 (2H, d, J=9.3 Hz), 6.93 (2H, d, J=9.3 Hz), 7.96 (1H, t, J=2.4 Hz), 8.08 (1H, d, J=2.4 Hz), 8.12 (1H, d, J=2.4 Hz)

Example 3-106

Production of 3-(2-methoxypyrimidin-5-yl)-8-[4-(3-piperidin-1-ylpropoxy)phenyl]-1-oxa-3,8-diazaspiro[4,5]decan-2-one The entitled compound was obtained as a white solid, according to the same method as in Example 3 or according to a method similar to it but using 8-[4-(3-piperidin-1-ylpropoxy)phenyl]-1-oxa-3,8-diazaspiro[4,5]decan-2-one obtained in Reference Example 15, and 5-iodo-2-methoxypyrimidine in place of 1-bromo-4-fluorobenzene.

$^1$H-NMR (400 MHz, CDCl$_3$) δ: 1.45 (2H, brs), 1.60 (4H, brs), 1.93-2.10 (4H, m), 2.17 (2H, d, J=13.2 Hz), 2.31-2.55 (6H, m), 3.21-3.30 (4H, m), 3.77 (2H, s), 3.97 (2H, t, J=6.3 Hz), 4.02 (3H, s), 6.85 (2H, d, J=9.3 Hz), 6.93 (2H, d, J=9.3 Hz), 8.76 (2H, s)

Example 3-107

Production of 9-{4-[(1-cyclobutylpiperidin-4-yl)oxy]phenyl}-4-(4-methoxyphenyl)-1-oxa-4,9-diazaspiro[5,5]undecan-3-one The entitled compound was obtained as a white oily substance, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 1-iodo-4-methoxybenzene in place of 1-bromo-4-fluorobenzene.

$^1$H-NMR (400 MHz, CDCl$_3$) δ: 1.58-2.14 (16H, m), 2.55-2.87 (3H, m), 3.03-3.13 (2H, m), 3.23-3.32 (2H, m), 3.59 (2H, s), 3.81 (3H, s), 4.24 (1H, brs), 4.34 (2H, s), 6.84 (2H, d, J=8.8 Hz), 6.91 (2H, d, J=8.8 Hz), 6.94 (2H, d, J=9.1 Hz), 7.20 (2H, d, J=9.1 Hz)

Example 3-108

Production of 9-{4-[(1-cyclobutylpiperidin-4-yl)oxy]phenyl}-4-(6-methylpyridin-3-yl)-1-oxa-4,9-diazaspiro[5,5]undecan-3-one The entitled compound was obtained as a yellow solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 5-bromo-2-methylpyridine in place of 1-bromo-4-fluorobenzene.

$^1$H-NMR (400 MHz, CDCl$_3$) δ: 1.41-2.26 (16H, m), 2.52-2.79 (3H, m), 3.00-3.15 (2H, m), 3.21-3.37 (2H, m), 3.64 (2H, s), 4.22 (1H, brs), 4.36 (2H, s), 6.84 (2H, d, J=9.1 Hz), 6.91 (2H, d, J=9.1 Hz), 7.21 (1H, d, J=8.3 Hz), 7.58 (1H, dd, J=8.3, 2.4 Hz), 8.46 (1H, d, J=2.4 Hz)

Example 3-109

Production of 9-{4-[(1-cyclobutylpiperidin-4-yl)oxy]phenyl}-4-[6-(difluoromethoxy)pyridin-3-yl]-1-oxa-4,9-diazaspiro[5,5]undecan-3-one The entitled compound was obtained as a pale orange solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 5-bromo-2-(difluoromethoxy)pyridine obtained in Reference Example 16 in place of 1-bromo-4-fluorobenzene.

$^1$H-NMR (400 MHz, CDCl$_3$) δ: 1.48-2.27 (16H, m), 2.52-2.87 (3H, m), 3.00-3.15 (2H, m), 3.24-3.34 (2H, m), 3.63 (2H, s), 4.22 (1H, brs), 4.36 (2H, s), 6.85 (2H, d, J=9.1 Hz), 6.91 (2H, d, J=9.1 Hz), 6.96 (1H, d, J=8.8 Hz), 7.43 (1H, t, J=72.7 Hz), 7.74 (1H, dd, J=8.8, 2.7 Hz), 8.16 (1H, d, J=2.7 Hz)

Example 3-110

Production of 9-{4-[(1-cyclobutylpiperidin-4-yl)oxy]phenyl}-4-isopropyl-1-oxa-4,9-diazaspiro[5,5]undecan-3-one The entitled compound was obtained as a pale orange solid, according to the same method as in Example 3-96 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 2-bromopropane in place of bromoethane.

$^1$H-NMR (400 MHz, CDCl$_3$) δ: 1.12 (6H, d, J=6.8 Hz), 1.55-2.30 (16H, m), 2.57-2.84 (3H, m), 2.98-3.07 (2H, m), 3.10 (2H, s), 3.19-3.28 (2H, m), 4.17 (2H, s), 4.22 (1H, brs), 4.93 (1H, septet, J=6.8 Hz), 6.84 (2H, d, J=9.1 Hz), 6.90 (2H, d, J=9.1 Hz)

Example 3-111

Production of 9-{4-[(1-cyclobutylpiperidin-4-yl)oxy]phenyl}-4-(6-isopropoxypyridine-3-yl)-1-oxa-4,9-diazaspiro[5,5]undecan-3-one The entitled compound was obtained as a pale orange solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 5-bromo-2-isopropoxypyridine obtained in Reference Example 17 in place of 1-bromo-4-fluorobenzene.

$^1$H-NMR (400 MHz, CDCl$_3$) δ: 1.34 (6H, d, J=6.3 Hz), 1.50-2.30 (16H, m), 2.55-2.85 (3H, m), 3.03-3.12 (2H, m), 3.22-3.32 (2H, m), 3.59 (2H, s), 4.23 (1H, brs), 4.35 (2H, s), 5.27 (1H, septet, J=6.3 Hz), 6.72 (1H, d, J=8.8 Hz), 6.85 (2H, d, J=9.1 Hz), 6.91 (2H, d, J=9.1 Hz), 7.51 (1H, dd, J=8.8, 2.7 Hz), 8.06 (1H, d, J=2.7 Hz)

Example 3-112

Production of 9-{4-[(1-cyclobutylpiperidin-4-yl)oxy]phenyl}-4-(2-isopropoxypyrimidin-5-yl)-1-oxa-4,9-diazaspiro[5,5]undecan-3-one The entitled compound was obtained as a pale orange solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 5-bromo-2-isopropoxypyrimidine in place of 1-bromo-4-fluorobenzene.

$^1$H-NMR (400 MHz, CDCl$_3$) δ: 1.40 (6H, d, J=6.3 Hz), 1.46-2.28 (16H, m), 2.54-2.85 (3H, m), 2.99-3.14 (2H, m), 3.21-3.35 (2H, m), 3.62 (2H, s), 4.24 (1H, brs), 4.37 (2H, s), 5.26 (1H, septet, J=6.3 Hz), 6.85 (2H, d, J=9.1 Hz), 6.91 (2H, d, J=9.1 Hz), 8.49 (2H, s)

Example 3-113

Production of 9-{4-[(1-cyclobutylpiperidin-4-yl)oxy]phenyl}-4-(1-methyl-1H-pyrazol-3-yl)-1-oxa-4,9-diazaspiro[5,5]undecan-3-one The entitled compound was obtained as an orange solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 3-iodo-1-methyl-1H-pyrazole in place of 1-bromo-4-fluorobenzene.
$^1$H-NMR (400 MHz, CDCl$_3$) δ: 1.40-2.36 (16H, m), 2.50-2.87 (3H, m), 2.98-3.14 (2H, m), 3.20-3.37 (2H, m), 3.83 (3H, s), 3.87 (2H, s), 4.22 (1H, brs), 4.33 (2H, s), 6.83 (1H, d, J=2.4 Hz), 6.84 (2H, d, J=9.3 Hz), 6.91 (2H, d, J=8.8 Hz), 7.29 (1H, d, J=2.4 Hz)

Example 3-114

Production of 9-{4-[(1-cyclobutylpiperidin-4-yl)oxy]phenyl}-4-(5-methoxypyridin-3-yl)-1-oxa-4,9-diazaspiro[5,5]undecan-3-one The entitled compound was obtained as an orange solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 3-bromo-5-methoxypyridine in place of 1-bromo-4-fluorobenzene.
$^1$H-NMR (400 MHz, CDCl$_3$) δ: 1.50-2.29 (16H, m), 2.54-2.86 (3H, m), 3.00-3.15 (2H, m), 3.21-3.36 (2H, m), 3.66 (2H, s), 3.88 (3H, s), 4.23 (1H, brs), 4.37 (2H, s), 6.85 (2H, d, J=9.3 Hz), 6.92 (2H, d, J=9.3 Hz), 7.28 (1H, dd, J=2.9, 2.0 Hz), 8.19 (1H, d, J=2.0 Hz), 8.24 (1H, d, J=2.9 Hz)

Example 3-115

Production of 9-{4-[(1-cyclobutylpiperidin-4-yl)oxy]phenyl}-4-[5-(trifluoromethyl)pyridin-3-yl]-1-oxa-4,9-diazaspiro[5,5]undecan-3-one The entitled compound was obtained as a pale yellow solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 3-bromo-5-trifluoromethyl)pyridine in place of 1-bromo-4-fluorobenzene.
$^1$H-NMR (400 MHz, CDCl$_3$) δ: 1.47-2.24 (16H, m), 2.56-2.84 (3H, m), 3.01-3.14 (2H, m), 3.26-3.36 (2H, m), 3.71 (2H, s), 4.22 (1H, brs), 4.40 (2H, s), 6.85 (2H, d, J=9.3 Hz), 6.92 (2H, d, J=9.3 Hz), 8.00 (1H, dd, J=2.0, 1.0 Hz), 8.78 (1H, d, J=1.0 Hz), 8.84 (1H, d, J=2.0 Hz)

Example 3-116

Production of 9-{4-[(1-cyclobutylpiperidin-4-yl)oxy]phenyl}-4-[3-(trifluoromethyl)pyridin-2-yl]-1-oxa-4,9-diazaspiro[5,5]undecan-3-one The entitled compound was obtained as a colorless oily substance, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 2-bromo-3-(trifluoromethyl)pyridine in place of 1-bromo-4-fluorobenzene.
$^1$H-NMR (400 MHz, CDCl$_3$) δ: 1.43-2.38 (16H, m), 2.55-2.94 (3H, m), 3.01-3.17 (2H, m), 3.21-3.36 (2H, m), 3.46 (1H, d, J=11.7 Hz), 3.88 (1H, d, J=11.7 Hz), 4.15-4.46 (1H, m), 4.32 (1H, d, J=17.8 Hz), 4.40 (1H, d, J=17.8 Hz), 6.84 (2H, d, J=9.3 Hz), 6.92 (2H, d, J=9.3 Hz), 7.48 (1H, dd, J=7.7, 5.0 Hz), 8.11 (1H, d, J=7.7 Hz), 8.77 (1H, d, J=5.0 Hz)

Example 3-117

Production of 9-{4-[(1-cyclobutylpiperidin-4-yl)oxy]phenyl}-4-(6-methoxypyridin-2-yl)-1-oxa-4,9-diazaspiro[5,5]undecan-3-one The entitled compound was obtained as a yellow solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 2-bromo-6-methoxypyridine in place of 1-bromo-4-fluorobenzene.
$^1$H-NMR (400 MHz, CDCl$_3$) δ: 1.49-2.23 (16H, m), 2.55-2.84 (3H, m), 3.03-3.14 (2H, m), 3.23-3.33 (2H, m), 3.89 (3H, s), 4.00 (2H, s), 4.23 (1H, brs), 4.35 (2H, s), 6.58 (1H, dd, J=7.8, 1.0 Hz), 6.85 (2H, d, J=9.1 Hz), 6.92 (2H, d, J=9.1 Hz), 7.62 (1H, t, J=7.8 Hz), 7.67 (1H, dd, J=7.8, 1.0 Hz)

Example 3-118

Production of 9-{4-[(1-cyclobutylpiperidin-4-yl)oxy]phenyl}-4-imidazo[1,2-a]pyridin-3-yl-1-oxa-4,9-diazaspiro[5,5]undecan-3-one The entitled compound was obtained as a brown solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 3-iodoimidazo[1,2-a]pyridine in place of 1-bromo-4-fluorobenzene.
$^1$H-NMR (400 MHz, CDCl$_3$) δ: 1.45-2.29 (16H, m), 2.53-2.85 (3H, m), 3.02-3.17 (2H, m), 3.24-3.38 (2H, m), 3.70 (2H, s), 4.23 (1H, brs), 4.46 (2H, s), 6.82-6.96 (2H, m), 6.86 (2H, d, J=9.3 Hz), 6.92 (2H, d, J=9.3 Hz), 7.56 (1H, s), 7.62-7.67 (1H, m), 7.71-7.76 (1H, m)

Example 3-119

Production of 9-{4-[(1-cyclobutylpiperidin-4-yl)oxy]phenyl}-4-[4-methylsulfonyl)phenyl]-1-oxa-4,9-diazaspiro[5,5]undecan-3-one The entitled compound was obtained as a pale brown solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 1-bromo-4-(methylsulfonyl)benzene in place of 1-bromo-4-fluorobenzene.
$^1$H-NMR (400 MHz, CDCl$_3$) δ: 1.52-2.35 (16H, m), 2.55-2.85 (3H, m), 3.03-3.12 (5H, m), 3.08 (3H, s), 3.26-3.34 (2H, m), 3.69 (2H, s), 4.22 (1H, brs), 4.38 (2H, s), 6.85 (2H, d, J=9.1 Hz), 6.91 (2H, d, J=9.1 Hz), 7.58 (2H, d, J=8.6 Hz), 8.00 (2H, d, J=8.6 Hz)

Example 3-120

Production of 9-{4-[(1-cyclobutylpiperidin-4-yl)oxy]phenyl}-4-pyrazin-2-yl-1-oxa-4,9-diazaspiro[5,5]undecan-3-one The entitled compound was obtained as a pale yellow solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 2-iodopyrazine in place of 1-bromo-4-fluorobenzene.

$^1$H-NMR (400 MHz, CDCl$_3$) δ: 1.46-2.26 (16H, m), 2.54-2.87 (3H, m), 3.02-3.14 (2H, m), 3.22-3.34 (2H, m), 3.98 (2H, s), 4.23 (1H, brs), 4.41 (2H, s), 6.85 (2H, d, J=9.3 Hz), 6.92 (2H, d, J=9.3 Hz), 8.38 (2H, s), 9.53 (1H, s)

Example 3-121

Production of 9-{4-[(1-cyclobutylpiperidin-4-yl)oxy]phenyl}-4-(3-methylpyridin-2-yl)-1-oxa-4,9-diazaspiro[5,5]undecan-3-one The entitled compound was obtained as an orange solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 2-bromo-3-methylpyridine in place of 1-bromo-4-fluorobenzene.

$^1$H-NMR (400 MHz, CDCl$_3$) δ: 1.47-2.21 (16H, m), 2.28 (3H, s), 2.54-2.85 (3H, m), 3.04-3.16 (2H, m), 3.22-3.36 (2H, m), 3.87-4.18 (2H, brm), 4.22 (1H, brs), 4.36 (2H, s), 6.85 (2H, d, J=9.3 Hz), 6.92 (2H, d, J=9.3 Hz), 7.21 (1H, dd, J=7.0, 4.8 Hz), 7.62 (1H, d, J=7.0 Hz), 8.37 (1H, d, J=4.8 Hz)

Example 3-122

Production of 9-{4-[(1-cyclobutylpiperidin-4-yl)oxy]phenyl}-4-(5-methoxypyridin-2-yl)-1-oxa-4,9-diazaspiro[5,5]undecan-3-one The entitled compound was obtained as a white solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 2-bromo-5-methoxypyridine in place of 1-bromo-4-fluorobenzene.

$^1$H-NMR (400 MHz, CDCl$_3$) δ: 1.48-2.24 (16H, m), 2.51-2.85 (3H, m), 3.02-3.16 (2H, m), 3.22-3.34 (2H, m), 3.87 (3H, s), 3.94 (2H, s), 4.21 (1H, brs), 4.35 (2H, s), 6.84 (2H, d, J=9.3 Hz), 6.91 (2H, d, J=9.3 Hz), 7.27 (1H, dd, J=8.8, 2.9 Hz), 7.92 (1H, d, J=8.8 Hz), 8.10 (1H, d, J=2.9 Hz)

Example 3-123

Production of 9-{4-[(1-cyclobutylpiperidin-4-yl)oxy]phenyl}-4-(4-fluorophenyl)-1-oxa-4,9-diazaspiro[5,5]undecan-3-one The entitled compound was obtained as a brown solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2 and 1-bromo-4-fluorobenzene.

$^1$H-NMR (400 MHz, CDCl$_3$) δ: 1.46-2.24 (16H, m), 2.58-2.90 (3H, m), 3.03-3.13 (2H, m), 3.24-3.32 (2H, m), 3.60 (2H, s), 4.26 (1H, brs), 4.34 (2H, s), 6.84 (2H, d, J=9.1 Hz), 6.91 (2H, d, J=9.1 Hz), 7.10-7.12 (2H, m), 7.26-7.28 (2H, m)

Example 3-124

Production of 9-{4-[(1-cyclobutylpiperidin-4-yl)oxy]phenyl}-4-(1-methyl-1H-pyrazol-4-yl)-1-oxa-4,9-diazaspiro[5,5]undecan-3-one The entitled compound was obtained as an orange solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 4-bromo-1-methyl-1H-pyrazole in place of 1-bromo-4-fluorobenzene.

$^1$H-NMR (400 MHz, CDCl$_3$) δ: 1.47-2.27 (16H, m), 2.52-2.91 (3H, m), 2.94-3.12 (2H, m), 3.18-3.36 (2H, m), 3.59 (2H, s), 3.90 (3H, s), 4.24 (1H, brs), 4.32 (2H, s), 6.84 (2H, d, J=9.1 Hz), 6.91 (2H, d, J=9.1 Hz), 7.46 (1H, s), 8.04 (1H, s)

Example 3-125

Production of 9-{4-[(1-cyclobutylpiperidin-4-yl)oxy]phenyl}-4-(2-methoxypyrimidin-5-yl)-1-oxa-4,9-diazaspiro[5,5]undecan-3-one The entitled compound was obtained as a pale orange solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 5-iodo-2-methoxypyrimidine in place of 1-bromo-4-fluorobenzene.

$^1$H-NMR (400 MHz, CDCl$_3$) δ: 1.46-2.38 (16H, m), 2.50-2.87 (3H, m), 3.00-3.12 (2H, m), 3.25-3.35 (2H, m), 3.63 (2H, s), 4.03 (3H, s), 4.23 (1H, brs), 4.37 (2H, s), 6.85 (2H, d, J=8.8 Hz), 6.91 (2H, d, J=9.3 Hz), 8.53 (2H, s)

Example 3-126

Production of 9-{4-[(1-cyclobutylpiperidin-4-yl)oxy]phenyl}-4-(1-methyl-6-oxo-1,6-dihydropyridin-3-yl)-1-oxa-4,9-diazaspiro[5,5]undecan-3-one The entitled compound was obtained as a white solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 5-bromo-1-methylpyridin-2(1H)-one in place of 1-bromo-4-fluorobenzene.

$^1$H-NMR (400 MHz, CDCl$_3$) δ: 1.46-2.26 (16H, m), 2.53-2.85 (3H, m), 3.00-3.11 (2H, m), 3.23-3.33 (2H, m), 3.51 (2H, s), 3.54 (3H, s), 4.23 (1H, brs), 4.31 (2H, s), 6.61 (1H, d, J=9.6 Hz), 6.84 (2H, d, J=8.9 Hz), 6.91 (2H, d, J=8.9 Hz), 7.26 (1H, dd, J=9.6, 2.9 Hz), 7.39 (1H, d, J=2.9 Hz)

Example 3-127

Production of 9-{4-[(1-cyclobutylpiperidin-4-yl)oxy]phenyl}4-(2-fluoropyridin-4-yl)-1-oxa-4,9-diazaspiro[5,5]undecan-3-one The entitled compound was obtained as a pale orange solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 4-iodo-2-fluoropyridine in place of 1-bromo-4-fluorobenzene.

$^1$H-NMR (400 MHz, CDCl$_3$) δ: 1.50-2.26 (16H, m), 2.50-2.87 (3H, m), 2.97-3.12 (2H, m), 3.21-3.37 (2H, m), 3.68 (2H, s), 4.23 (1H, brs), 4.38 (2H, s), 6.85 (2H, d, J=8.8 Hz), 6.91 (2H, d, J=8.8 Hz), 7.11 (1H, d, J=2.5 Hz), 7.34 (1H, dd, J=5.6, 2.5 Hz), 8.23 (1H, d, J=5.6 Hz)

Example 3-128

Production of 9-{4-[(1-cyclobutylpiperidin-4-yl)oxy]phenyl}-4-(1-ethyl-6-oxo-1,6-dihydropyridin-3-yl)-1-oxa-4,9-diazaspiro[5,5]undecan-3-one The entitled compound was obtained as a pale brown solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 5-bromo-1-ethylpyridin-2(1H)-one in place of 1-bromo-4-fluorobenzene.

$^1$H-NMR (400 MHz, CDCl$_3$) δ: 1.38 (3H, t, J=7.2 Hz), 1.45-2.30 (16H, m), 2.51-2.88 (3H, m), 2.98-3.14 (2H, m), 3.20-3.37 (2H, m), 3.53 (2H, s), 3.98 (2H, q, J=7.2 Hz), 4.23 (1H, brs), 4.32 (2H, s), 6.60 (1H, d, J=9.8 Hz), 6.85 (2H, d, J=9.3 Hz), 6.91 (2H, d, J=9.3 Hz), 7.25 (1H, dd, J=9.8, 2.4 Hz), 7.38 (1H, d, J=2.4 Hz)

Example 3-129

Production of 9-{4-[(1-cyclobutylpiperidin-4-yl)oxy]phenyl}-4-(1-isopropyl-6-oxo-1,6-dihydropyridin-3-yl)-1-oxa-4,9-diazaspiro[5,5]undecan-3-one The entitled compound was obtained as a brown oily substance, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 5-bromo-1-isopropylpyridin-2(1H)-one in place of 1-bromo-4-fluorobenzene.

$^1$H-NMR (400 MHz, CDCl$_3$) δ: 1.37 (6H, d, J=6.8 Hz), 1.44-2.06 (16H, m), 2.51-2.85 (3H, m), 2.99-3.12 (2H, m), 3.22-3.35 (2H, m), 3.53 (2H, s), 4.23 (1H, brs), 4.32 (2H, s), 5.25 (1H, septet, J=6.8 Hz), 6.60 (1H, d, J=9.8 Hz), 6.85 (2H, d, J=9.0 Hz), 6.91 (2H, d, J=9.0 Hz), 7.22 (1H, dd, J=9.8, 2.7 Hz), 7.40 (1H, d, J=2.7 Hz)

Example 3-130

Production of 9-{4-[(1-cyclobutylpiperidin-4-yl)oxy]phenyl}-4-pyridin-3-yl-1-oxa-4,9-diazaspiro[5,5]undecan-3-one The entitled compound was obtained as a yellow solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 3-bromopyridine in place of 1-bromo-4-fluorobenzene.

$^1$H-NMR (400 MHz, CDCl$_3$) δ: 1.28-2.28 (16H, m), 2.45-2.85 (3H, m), 2.99-3.10 (2H, m), 3.21-3.31 (2H, m), 3.64 (2H, s), 4.19 (1H, brs), 4.34 (2H, s), 6.81 (2H, d, J=9.1 Hz), 6.88 (2H, d, J=9.1 Hz), 7.29-7.36 (1H, m), 7.65-7.72 (1H, m), 8.46-8.52 (1H, m), 8.56-8.59 (1H, m)

Example 3-131

Production of 5-(9-{4-[(1-cyclobutylpiperidin-4-yl)oxy]phenyl}-3-oxo-1-oxa-4,9-diazaspiro[5,5]undecan-4-yl)nicotinonitrile The entitled compound was obtained as a pale yellow solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 5-bromonicotinonitrile in place of 1-bromo-4-fluorobenzene.

$^1$H-NMR (400 MHz, CDCl$_3$) δ: 1.41-2.25 (16H, m), 2.45-2.87 (3H, m), 2.98-3.09 (2H, m), 3.22-3.32 (2H, m), 3.67 (2H, s), 4.19 (1H, brs), 4.36 (2H, s), 6.81 (2H, d, J=9.1 Hz), 6.88 (2H, d, J=9.1 Hz), 8.03-8.08 (1H, m), 8.70-8.74 (1H, m), 8.80-8.83 (1H, m)

Example 3-132

Production of 9-{4-[(1-cyclobutylpiperidin-4-yl)oxy]phenyl}-4-(5-methoxypyrazin-2-yl)-1-oxa-4,9-diazaspiro[5,5]undecan-3-one The entitled compound was obtained as a pale yellow solid, according to the same method as in Example 3 or according to a method similar to it but using 9-{4-[(1-cyclobutylpiperidin-4-yl)oxy]phenyl}-1-oxa-4,9-diazaspiro[5,5]undecan-3-one obtained in Reference Example 9-2, and 2-bromo-5-methoxypyrazine in place of 1-bromo-4-fluorobenzene.

$^1$H-NMR (400 MHz, CDCl$_3$) δ: 1.59-2.09 (16H, m), 2.63-2.74 (3H, m), 3.08 (2H, td, J=11.2, 2.9 Hz), 3.28 (2H, dt, J=12.7, 3.4 Hz), 3.88 (2H, s), 3.99 (3H, s), 4.21 (1H, brs), 4.37 (2H, s), 6.84 (2H, d, J=9.3 Hz), 6.91 (2H, d, J=9.3 Hz), 8.03 (1H, d, J=1.5 Hz), 8.84 (1H, d, J=1.5 Hz)

Example 3-133

Production of 4-ethyl-9-{4-[(1-isopropylpiperidin-4-yl)oxy]phenyl}-1-oxa-4,9-diazaspiro[5,5]undecan-3-one The entitled compound was obtained as a white solid, according to the same method as in Example 3-96 or according to a method similar to it but using 9-{4-[(1-isopropylpiperidin-4-yl)oxy]phenyl}-1-oxa-4,9-diazaspiro[5,5]undecan-3-one obtained in Reference Example 9-3 and bromoethane.

$^1$H-NMR (400 MHz, CDCl$_3$) δ: 1.07 (6H, d, J=6.3 Hz), 1.15 (3H, t, J=7.3 Hz), 1.72-1.85 (4H, m), 2.00 (4H, d, J=13.2 Hz), 2.37 (2H, brs), 2.80 (3H, brs), 3.02 (2H, td, J=11.7, 2.8 Hz), 3.20-3.28 (4H, m), 3.46 (2H, q, J=7.3 Hz), 4.13-4.23 (3H, m), 6.84 (2H, d, J=9.3 Hz), 6.90 (2H, d, J=9.3 Hz)

Example 3-134

Production of 9-{4-[(1-isopropylpiperidin-4-yl)oxy]phenyl}-4-(2,2,2-trifluoroethyl)-1-oxa-4,9-diazaspiro[5,5]undecan-3-one The entitled compound was obtained as a yellow solid, according to the same method as in Example 3-96 or according to a method similar to it but using 9-{4-[(1-isopropylpiperidin-4-yl)oxy]phenyl}-1-oxa-4,9-diazaspiro[5,5]undecan-3-one obtained in Reference Example 9-3, and 2,2,2-trifluoroethyl trifluoromethanesulfonate in place of bromoethane.

$^1$H-NMR (400 MHz, CDCl$_3$) δ: 1.07 (6H, d, J=5.4 Hz), 1.76-1.86 (4H, m), 2.02 (4H, d, J=13.2 Hz), 2.39 (2H, brs), 2.81 (3H, brs), 3.02 (2H, td, J=11.7, 2.8 Hz), 3.25 (2H, dt, J=12.2, 3.9 Hz), 3.42 (2H, s), 4.06 (2H, q, J=8.9 Hz), 4.20 (1H, brs), 4.27 (2H, s), 6.85 (2H, d, J=9.3 Hz), 6.90 (2H, d, J=9.3 Hz)

Example 3-135

Production of 9-{4-[(1-isopropylpiperidin-4-yl)oxy]phenyl}-4-[4-(methylsulfonyl)phenyl]-1-oxa-4,9-diazaspiro[5,5]undecan-3-one The entitled compound was obtained as a pale yellow solid, according to the same method as in Example 3 or according to a method similar to it but using 9-{4-[(1-isopropylpiperidin-4-yl)oxy]phenyl}-1-oxa-4,9-diazaspiro[5,5]undecan-3-one obtained in Reference Example 9-3, and 1-bromo-4-(methylsulfonyl)benzene in place of 1-bromo-4-fluorobenzene.

$^1$H-NMR (400 MHz, CDCl$_3$) δ: 1.09 (6H, s), 1.73-1.93 (4H, m), 1.94-2.20 (4H, m), 2.40 (2H, brs), 2.82 (3H, brs), 3.03-3.12 (5H, m), 3.30 (2H, d, J=12.7 Hz), 3.69 (2H, s), 4.21 (1H, brs), 4.38 (2H, s), 6.85 (2H, d, J=9.3 Hz), 6.91 (2H, d, J=9.3 Hz), 7.58 (2H, d, J=8.8 Hz), 8.00 (2H, d, J=8.8 Hz)

Example 3-136

Production of 9-{4-[(1-isopropylpiperidin-4-yl)oxy]phenyl}-4-[5-(trifluoromethyl)pyridin-3-yl]-1-oxa-4,9-diazaspiro[5,5]undecan-3-one The entitled compound was obtained as a pale yellow solid, according to the same method as in Example 3 or according to a method similar to it but using 9-{4-[(1-isopropylpiperidin-4-yl)oxy]phenyl}-1-oxa-4,9-diazaspiro[5,5]undecan-3-one obtained in Reference Example 9-3, and 3-bromo-5-(trifluoromethyl)pyridine in place of 1-bromo-4-fluorobenzene.

$^1$H-NMR (400 MHz, CDCl$_3$) δ: 1.07 (6H, d, J=5.4 Hz), 1.72-2.08 (6H, m), 2.15 (2H, d, J=12.7 Hz), 2.38 (2H, brs), 2.80 (3H, brs), 3.08 (2H, td, J=11.2, 2.4 Hz), 3.31 (2H, dt, J=12.7, 3.9 Hz), 3.71 (2H, s), 4.20 (1H, brs), 4.40 (2H, s), 6.86 (2H, d, J=9.3 Hz), 6.92 (2H, d, J=9.3 Hz), 8.00 (1H, t, J=2.0 Hz), 8.78 (s, 1H), 8.84 (1H, d, J=2.4 Hz)

Example 3-137

Production of 9-{4-[(1-isopropylpiperidin-4-yl)oxy]phenyl}-4-(5-methoxypyridin-3-yl)-1-oxa-4,9-diazaspiro[5,5]undecan-3-one The entitled compound was obtained as a brown oily substance, according to the same method as in Example 3 or according to a method similar to it but using 9-{4-[(1-isopropylpiperidin-4-yl)oxy]phenyl}-1-oxa-4,9-diazaspiro[5,5]undecan-3-one obtained in Reference Example 9-3, and 3-bromo-5-methoxypyridine in place of 1-bromo-4-fluorobenzene.

$^1$H-NMR (400 MHz, CDCl$_3$) δ: 1.08 (6H, brs), 1.73-2.09 (6H, m), 2.13 (2H, d, J=13.2 Hz), 2.39 (2H, brs), 2.80 (3H, brs), 3.08 (2H, td, J=11.2, 2.0 Hz), 3.29 (2H, dt, J=12.7, 3.4 Hz), 3.66 (2H, s), 3.88 (3H, s), 4.20 (1H, brs), 4.37 (2H, s), 6.85 (2H, d, J=9.3 Hz), 6.92 (2H, d, J=9.3 Hz), 7.28 (1H, t, J=2.2 Hz), 8.20 (1H, d, J=2.0 Hz), 8.24 (1H, d, 2.4 Hz)

Example 3-138

Production of 9-{4-[(1-isopropylpiperidin-4-yl)oxy]phenyl}-4-pyrazin-2-yl-1-oxa-4,9-diazaspiro[5,5]undecan-3-one The entitled compound was obtained as a pale brown solid, according to the same method as in Example 3 or according to a method similar to it but using 9-{4-[(1-isopropylpiperidin-4-yl)oxy]phenyl}-1-oxa-4,9-diazaspiro[5,5]undecan-3-one obtained in Reference Example 9-3, and 2-iodopyrazine in place of 1-bromo-4-fluorobenzene.

$^1$H-NMR (400 MHz, CDCl$_3$) δ: 1.07 (6H, d, J=6.3 Hz), 1.73-1.94 (4H, m), 1.95-2.13 (4H, m), 2.38 (2H, brs), 2.70-2.86 (3H, brs), 3.09 (2H, td, J=11.2, 2.9 Hz), 3.29 (2H, dt, J=12.2, 4.4 Hz), 3.98 (2H, s), 4.19 (1H, brs), 4.41 (2H, s), 6.85 (2H, d, J=9.3 Hz), 6.92 (2H, d, J=9.3 Hz), 8.38 (2H, s), 9.53 (1H, s)

Example 3-139

Production of 9-{4-[(1-isopropylpiperidin-4-yl)oxy]phenyl}-4-(3-methoxypyridin-2-yl)-1-oxa-4,9-diazaspiro[5,5]undecan-3-one The entitled compound was obtained as a yellow oily substance, according to the same method as in Example 3 or according to a method similar to it but using 9-{4-[(1-isopropylpiperidin-4-yl)oxy]phenyl}-1-oxa-4,9-diazaspiro[5,5]undecan-3-one obtained in Reference Example 9-3, and 2-bromo-3-methoxypyridine in place of 1-bromo-4-fluorobenzene.

$^1$H-NMR (400 MHz, CDCl$_3$) δ: 1.07 (6H, d, J=5.9 Hz), 1.73-2.09 (6H, m), 2.17 (2H, d, J=13.7 Hz), 2.39 (2H, brs), 2.70-2.86 (3H, brm), 3.10 (2H, td, J=11.2, 2.4 Hz), 3.27 (2H, dt, J=12.2, 3.9 Hz), 3.70 (2H, brs), 3.88 (3H, s), 4.19 (1H, brs), 4.36 (2H, s), 6.85 (2H, d, J=9.3 Hz), 6.92 (2H, d, J=9.3 Hz), 7.34-7.27 (2H, m), 8.12 (1H, dd, J=4.4, 2.0 Hz)

Example 3-140

Production of 9-{4-[(1-isopropylpiperidin-4-yl)oxy]phenyl}-4-(2-methoxypyrimidin-5-yl)-1-oxa-4,9-diazaspiro[5,5]undecan-3-one The entitled compound was obtained as a pale brown solid, according to the same method as in Example 3 or according to a method similar to it but using 9-{4-[(1-isopropylpiperidin-4-yl)oxy]phenyl}-1-oxa-4,9-diazaspiro[5,5]undecan-3-one obtained in Reference Example 9-3, and 5-iodo-2-methoxypyrimidine in place of 1-bromo-4-fluorobenzene.

$^1$H-NMR (400 z, CDCl$_3$) δ: 1.07 (6H, d, J=6.3 Hz), 1.75-1.92 (4H, m), 2.01 (2H, brs), 2.14 (2H, d, J=13.2 Hz), 2.40 (2H, brs), 2.72-2.89 (3H, brm), 3.07 (2H, td, J=1.7, 2.4 Hz), 3.30 (2H, dt, J=12.7, 3.4 Hz), 3.63 (2H, s), 4.03 (3H, s), 4.20 (1H, brs), 4.37 (2H, s), 6.85 (2H, d, J=9.3 Hz), 6.92 (2H, d, J=9.3 Hz), 8.53 (2H, s)

Example 3-141

Production of 9-{4-[(1-isopropylpiperidin-4-yl)oxy]phenyl}-4-(1-methyl-1H-pyrazol-4-yl)-1-oxa-4,9-diazaspiro[5,5]undecan-3-one The entitled compound was obtained as a yellow solid, according to the same method as in Example 3 or according to a method similar to it but using 9-{4-[(1-isopropylpiperidin-4-yl)oxy]phenyl}-1-oxa-4,9-diazaspiro[5,5]undecan-3-one obtained in Reference Example 9-3, and 4-bromo-1-methyl-1H-pyrazole in place of 1-bromo-4-fluorobenzene.

$^1$H-NMR (400 MHz, CDCl$_3$) δ: 1.06 (6H, d, J=6.3 Hz), 1.73-1.93 (4H, m), 1.95-2.11 (4H, m), 2.32-2.42 (2H, m), 2.69-2.84 (3H, m), 3.06 (2H, td, J=11.7, 2.4 Hz), 3.28 (2H, dt, J=12.2, 3.9 Hz), 3.83 (3H, s), 3.87 (2H, s), 4.18 (1H, brs), 4.33 (2H, s), 6.87-6.82 (3H, m), 6.91 (2H, d, J=9.3 Hz), 7.29 (1H, d, J=2.4 Hz)

Example 3-142

Production of 9-{4-[(1-isopropylpiperidin-4-yl)oxy]phenyl}-4-(1-methyl-1H-pyrazol-3-yl)-1-oxa-4,9-diazaspiro[5,5]undecan-3-one The entitled compound was obtained as a pale yellow solid, according to the same method as in Example 3 or according to a method similar to it but using 9-{4-[(1-isopropylpiperidin- 4-yl)oxy]phenyl}-1-oxa-4,9-diazaspiro[5,5]undecan-3-one obtained in Reference Example 9-3, and 3-iodo-1-methyl-1H-pyrazole in place of 1-bromo-4-fluorobenzene.

$^1$H-NMR (400 MHz, CDCl$_3$) δ: 1.06 (6H, d, J=6.3 Hz), 1.73-1.91 (4H, m), 1.93-2.14 (4H, m), 2.38 (2H, brs), 2.69-2.85 (3H, brm), 3.05 (2H, td, J=11.7, 2.4 Hz), 3.28 (2H, dt, J=12.7, 3.9 Hz), 3.59 (2H, s), 3.90 (3H, s), 4.19 (1H, brs), 4.32 (2H, s), 6.85 (2H, d, J=9.3 Hz), 6.91 (2H, d, J=9.3 Hz), 7.46 (1H, s), 8.03 (1H, s)

Example 3-143

Production of 5-(9-{4-[(1-isopropylpiperidin-4-yl)oxy]phenyl}-3-oxo-1-oxa-4,9-diazaspiro[5,5]undecan-4-yl)nicotinonitrile The entitled compound was obtained as a yellow solid, according to the same method as in Example 3 or according to a method similar to it but using 9-{4-[(1-isopropylpiperidin-4-yl)oxy]phenyl}-1-oxa-4,9-diazaspiro[5,5]undecan-3-one obtained in Reference Example 9-3, and 5-bromonicotinonitrile in place of 1-bromo-4-fluorobenzene.

$^1$H-NMR (400 MHz, CDCl$_3$) δ: 1.07 (6H, d, J=6.3 Hz), 1.73-1.93 (4H, m), 1.99 (2H, brs), 2.14 (2H, d, J=12.7 Hz), 2.38 (2H, brs), 2.71-2.84 (3H, brm), 3.07 (2H, td, J=11.7, 2.4 Hz), 3.31 (2H, dt, J=12.7, 3.9 Hz), 3.71 (2H, s), 4.19 (1H, brs), 4.39 (2H, s), 6.86 (2H, d, J=9.3 Hz), 6.92 (2H, d, J=9.3 Hz), 8.10 (1H, t, J=2.2 Hz), 8.76 (1H, d, J=2.0 Hz), 8.85 (1H, d, J=2.4 Hz)

Example 3-144

Production of 4-(2-ethoxypyrimidin-5-yl)-9-{4-[(1-isopropylpiperidin-4-yl)oxy]phenyl}-1-oxa-4,9-diazaspiro[5,5]undecan-3-one The entitled compound was obtained as a yellow solid, according to the same method as in Example 3 or according to a method similar to it but using 9-{4-[(1-isopropylpiperidin-4-yl)oxy]phenyl}-1-oxa-4,9-diazaspiro[5,5]undecan-3-one obtained in Reference Example 9-3, and 5-bromo-2-ethoxypyrimidine in place of 1-bromo-4-fluorobenzene.

$^1$H-NMR (400 MHz, CDCl$_3$) δ: 1.08 (6H, brs), 1.44 (3H, t, J=7.1 Hz), 1.74-2.19 (8H, m), 2.40 (2H, brs), 2.71-2.90 (3H, brm), 3.07 (2H, td, J=1.7, 2.4 Hz), 3.30 (2H, dt, J=12.2, 3.9 Hz), 3.62 (2H, s), 4.21 (1H, s), 4.37 (2H, s), 4.44 (2H, q, J=7.2 Hz), 6.85 (2H, d, J=9.3 Hz), 6.92 (2H, d, J=9.3 Hz), 8.51 (2H, s)

Example 3-145

Production of 9-{4-[(1-isopropylpiperidin-4-yl)oxy]phenyl}-4-(5-methoxypyrazin-2-yl)-1-oxa-4,9-diazaspiro[5,5]undecan-3-one The entitled compound was obtained as a brown oily substance, according to the same method as in Example 3 or according to a method similar to it but using 9-{4-[(1-isopropylpiperidin-4-yl)oxy]phenyl}-1-oxa-4,9-diazaspiro[5,5]undecan-3-one obtained in Reference Example 9-3, and 2-bromo-5-methoxypyrazine in place of 1-bromo-4-fluorobenzene.

$^1$H-NMR (400 MHz, CDCl$_3$) δ: 1.07 (6H, d, J=6.3 Hz), 1.72-1.95 (4H, m), 1.95-2.13 (4H, m), 2.39 (2H, brs), 2.70-2.86 (3H, brm), 3.08 (2H, td, J=11.2, 2.0 Hz), 3.28 (2H, dt, J=12.2, 4.4 Hz), 3.88 (2H, s), 3.99 (3H, s), 4.19 (1H, brs), 4.37 (2H, s), 6.85 (2H, d, J=9.3 Hz), 6.92 (2H, d, J=9.3 Hz), 8.03 (1H, d, J=1.5 Hz), 8.84 (1H, d, J=1.5 Hz)

Example 3-146

Production of 9-{4-[(1-isopropylpiperidin-4-yl)oxy]phenyl}-4-(6-methoxypyridin-3-yl)-1-oxa-4,9-diazaspiro[5,5]undecan-3-one The entitled compound was obtained as a pale orange oily substance, according to the same method as in Example 3 or according to a method similar to it but using 9-{4-[(1-isopropylpiperidin-4-yl)oxy]phenyl}-1-oxa-4,9-diazaspiro[5,5]undecan-3-one obtained in Reference Example 9-3, and 5-bromo-2-methoxypyridine in place of 1-bromo-4-fluorobenzene.

$^1$H-NMR (400 MHz, CDCl$_3$) δ: 1.18-1.35 (6H, m), 1.70-2.47 (8H, m), 2.76-3.36 (9H, m), 3.60 (2H, s), 3.94 (3H, s), 4.36 (2H, s), 4.36-4.47 (1H, m), 6.79 (1H, d, J=8.8 Hz), 6.84 (2H, d, J=9.3 Hz), 6.93 (2H, d, J=9.3 Hz), 7.54 (1H, dd, J=8.8, 2.2 Hz), 8.10 (1H, d, J=2.2 Hz)

Example 3-147

Production of 9-{6-[(1-cyclobutylpiperidin-4-yl)oxy]pyridin-3-yl}-4-(1-methyl-1H-pyrazol-3-yl)-1-oxa-4,9-diazaspiro[5,5]undecan-3-one The entitled compound was obtained as a white solid, according to the same method as in Example 3 or according to a method similar to it but using 9-{6-[(1-cyclobutylpiperidin-4-yl)oxy]pyridin-3-yl}-1-oxa-4,9-diazaspiro[5,5]undecan-3-one obtained in Reference Example 9-4, and 3-iodo-1-methyl-1H-pyrazole in place of 1-bromo-4-fluorobenzene.

$^1$H-NMR (400 MHz, CDCl$_3$) δ: 1.44-2.30 (16H, m), 2.57-2.92 (3H, m), 2.99-3.13 (2H, m), 3.20-3.31 (2H, m), 3.84 (3H, s), 3.88 (2H, s), 4.33 (2H, s), 4.99 (1H, brs), 6.65 (1H, d, J=8.8 Hz), 6.84 (1H, d, J=2.0 Hz), 7.29 (1H, d, J=2.0 Hz), 7.31 (1H, dd, J=8.8, 2.7 Hz), 7.80 (1H, d, J=2.7 Hz)

Example 3-148

Production of 9-{6-[(1-cyclobutylpiperidin-4-yl)oxy]pyridin-3-yl}-4-(1-methyl-1H-pyrazol-4-yl)-1-oxa-4,9-diazaspiro[5,5]undecan-3-one The entitled compound was obtained as a pale orange solid, according to the same method as in Example 3 or according to a method similar to it but using 9-{6-[(1-cyclobutylpiperidin-4-yl)oxy]pyridin-3-yl}-1-oxa-4,9-diazaspiro[5,5]undecan-3-one obtained in Reference Example 9-4, and 4-bromo-1-methyl-1H-pyrazole in place of 1-bromo-4-fluorobenzene.

$^1$H-NMR (CDCl$_3$) δ: 1.49-2.26 (16H, m), 2.58-2.85 (3H, m), 2.99-3.11 (2H, m), 3.20-3.30 (2H, m), 3.60 (2H, s), 3.90 (3H, s), 4.32 (2H, s), 4.97 (1H, brs), 6.66 (1H, d, J=8.9 Hz), 7.30 (1H, dd, J=8.9, 3.1 Hz), 7.46 (1H, d, J=1.0 Hz), 7.80 (1H, d, J=3.1 Hz), 8.04 (1H, d, J=1.0 Hz)

Example 3-149

Production of 9-{6-[(1-cyclobutylpiperidin-4-yl)oxy]pyridin-3-yl}-4-(2-isopropoxypyrimidin-5-yl)-1-oxa-4,9-diazaspiro[5,5]undecan-3-one The entitled compound was obtained as an orange oily substance, according to the same method as in Example 3 or according to a method similar to it but using 9-{6-[(1-cyclobutylpiperidin-4-yl)oxy]pyridin-3-yl}-1-oxa-4,9-diazaspiro[5,5]undecan-3-one obtained in Reference Example 9-4, and 5-bromo-2-isopropoxypyrimidine in place of 1-bromo-4-fluorobenzene.

¹H-NMR (400 MHz, CDCl₃) δ: 1.40 (6H, d, J=6.3 Hz), 1.47-2.27 (16H, m), 2.56-2.85 (3H, m), 2.99-3.14 (2H, m), 3.21-3.32 (2H, m), 3.62 (2H, s), 4.37 (2H, s), 4.97 (1H, brs), 5.27 (1H, septet, J=6.3 Hz), 6.66 (1H, d, J=9.2 Hz), 7.30 (1H, dd, J=9.2, 3.1 Hz), 7.81 (1H, d, J=3.1 Hz), 8.49 (2H, s)

Example 3-150

Production of 9-{6-[(1-cyclobutylpiperidin-4-yl)oxy]pyridin-3-yl}-4-pyridin-3-yl-1-oxa-4,9-diazaspiro[5,5]undecan-3-one The entitled compound was obtained according to the same method as in Example 3 or according to a method similar to it but using 9-{6-[(1-cyclobutylpiperidin-4-yl)oxy]pyridin-3-yl}-1-oxa-4,9-diazaspiro[5,5]undecan-3-one obtained in Reference Example 9-4, and 3-bromopyridine in place of 1-bromo-4-fluorobenzene.

¹H-NMR (400 MHz, CDCl₃) δ: 1.52-2.29 (16H, m), 2.57-2.86 (3H, m), 3.00-3.15 (2H, m), 3.20-3.33 (2H, m), 3.68 (2H, s), 4.38 (2H, s), 4.98 (1H, brs), 6.66 (1H, d, J=8.8 Hz), 7.31 (1H, dd, J=8.8, 2.9 Hz), 7.35-7.40 (1H, m), 7.69-7.76 (1H, m), 7.81 (1H, d, J=2.9 Hz), 8.50-8.56 (1H, m), 8.59-8.64 (1H, m)

Example 3-151

Production of 5-(9-{6-[(1-cyclobutylpiperidin-4-yl)oxy]pyridin-3-yl}-3-oxo-1-oxa-4,9-diazaspiro[5,5]undecan-4-yl)nicotinonitrile The entitled compound was obtained as a white solid, according to the same method as in Example 3 or according to a method similar to it but using 9-{6-[(1-cyclobutylpiperidin-4-yl)oxy]pyridin-3-yl}-1-oxa-4,9-diazaspiro[5,5]undecan-3-one obtained in Reference Example 9-4, and 5-bromonicotinonitrile in place of 1-bromo-4-fluorobenzene.

¹H-NMR (400 MHz, CDCl₃) δ: 1.48-2.24 (16H, m), 2.57-2.82 (3H, m), 3.00-3.15 (2H, m), 3.21-3.35 (2H, m), 3.71 (2H, s), 4.40 (2H, s), 4.97 (1H, brs), 6.66 (1H, d, J=8.9 Hz), 7.30 (1H, dd, J=8.9, 3.1 Hz), 7.81 (1H, d, J=3.1 Hz), 8.09 (1H, dd, J=2.4, 2.0 Hz), 8.76 (1H, d, J=2.0 Hz), 8.85 (1H, d, J=2.4 Hz)

Example 3-152

Production of 9-{6-[(1-cyclobutylpiperidin-4-yl)oxy]pyridin-3-yl}-4-[4-(methylsulfonyl)phenyl]-1-oxa-4,9-diazaspiro[5,5]undecan-3-one The entitled compound was obtained as a white solid, according to the same method as in Example 3 or according to a method similar to it but using 9-{6-[(1-cyclobutylpiperidin-4-yl)oxy]pyridin-3-yl}-1-oxa-4,9-diazaspiro[5,5]undecan-3-one obtained in Reference Example 9-4, and 1-bromo-4-(methylsulfonyl)benzene in place of 1-bromo-4-fluorobenzene.

¹H-NMR (400 MHz, CDCl₃) δ: 1.44-2.24 (16H, m), 2.49-2.87 (3H, m), 2.97-3.10 (2H, m), 3.03 (3H, s), 3.17-3.29 (2H, m), 3.66 (2H, s), 4.35 (2H, s), 4.95 (1H, brs), 6.62 (1H, d, J=9.2 Hz), 7.27 (1H, dd, J=9.2, 2.7 Hz), 7.54 (2H, d, J=8.7 Hz), 7.77 (1H, d, J=2.7 Hz), 7.96 (2H, d, J=8.7 Hz)

Example 3-153

Production of 9-{6-[(1-cyclobutylpiperidin-4-yl)oxy]pyridin-3-yl}-4-(4-methoxyphenyl)-1-oxa-4,9-diazaspiro[5,5]undecan-3-one The entitled compound was obtained as a yellow solid, according to the same method as in Example 3 or according to a method similar to it but using 9-{6-[(1-cyclobutylpiperidin-4-yl)oxy]pyridin-3-yl}-1-oxa-4,9-diazaspiro[5,5]undecan-3-one obtained in Reference Example 9-4, and 1-iodo-4-methoxybenzene in place of 1-bromo-4-fluorobenzene.

¹H-NMR (400 MHz, CDCl₃) δ: 1.44-2.32 (16H, m), 2.57-2.86 (3H, m), 3.02-3.14 (2H, m), 3.18-3.30 (2H, m), 3.59 (2H, s), 3.82 (3H, s), 4.34 (2H, s), 4.99 (1H, brs), 6.66 (1H, d, J=8.9 Hz), 6.94 (2H, d, J=9.3 Hz), 7.20 (2H, d, J=9.3 Hz), 7.30 (1H, dd, J=8.9, 3.1 Hz), 7.81 (1H, d, J=3.1 Hz)

Example 3-154

Production of 9-{6-[(1-cyclobutylpiperidin-4-yl)oxy]pyridin-3-yl}-4-(6-fluoropyridin-3-yl)-1-oxa-4,9-diazaspiro[5,5]undecan-3-one The entitled compound was obtained as a brown solid, according to the same method as in Example 3 or according to a method similar to it but using 9-{6-[(1-cyclobutylpiperidin-4-yl)oxy]pyridin-3-yl}-1-oxa-4,9-diazaspiro[5,5]undecan-3-one obtained in Reference Example 9-4, and 5-bromo-2-fluoropyridine in place of 1-bromo-4-fluorobenzene.

¹H-NMR (400 MHz, CDCl₃) δ: 1.47-2.30 (16H, m), 2.58-2.88 (3H, m), 3.01-3.13 (2H, m), 3.22-3.32 (2H, m), 3.69 (2H, s), 4.39 (2H, s), 4.99 (1H, brs), 6.67 (1H, d, J=8.8 Hz), 7.09-7.13 (1H, m), 7.31 (1H, dd, J=8.8, 2.9 Hz), 7.31-7.37 (1H, m), 7.81 (1H, d, J=2.9 Hz), 8.21-8.26 (1H, m)

Example 3-155

Production of 9-{6-[(1-cyclobutylpiperidin-4-yl)oxy]pyridin-3-yl}-4-(2-fluoropyridin-4-yl)-1-oxa-4,9-diazaspiro[5,5]undecan-3-one The entitled compound was obtained as a pale yellow solid, according to the same method as in Example 3 or according to a method similar to it but using 9-{6-[(1-cyclobutylpiperidin-4-yl)oxy]pyridin-3-yl}-1-oxa-4,9-diazaspiro[5,5]undecan-3-one obtained in Reference Example 94, and 4-iodo-2-fluoropyridine in place of 1-bromo-4-fluorobenzene.

¹H-NMR (400 MHz, CDCl₃) δ: 1.42-2.35 (16H, m), 2.60-2.87 (3H, m), 3.02-3.14 (2H, m), 3.22-3.32 (2H, m), 3.66 (2H, s), 4.37 (2H, s), 4.98 (1H, brs), 6.67 (1H, d, J=8.8 Hz), 6.97-7.04 (1H, m), 7.31 (1H, dd, J=8.8, 2.9 Hz), 7.81 (1H, d, J=2.9 Hz), 7.82-7.88 (1H, m), 8.17-8.22 (1H, m)

Example 3-156

Production of 9-{6-[(1-cyclobutylpiperidin-4-yl)oxy]pyridin-3-yl}-4-[6-(difluoromethoxy)pyridin-3-yl]-1-oxa-4,9-diazaspiro[5,5]undecan-3-one The entitled compound was obtained as a brown solid, according to the same method as in Example 3 or according to a method similar to it but using 9-{6-[(1-cyclobutylpiperidin-4-yl)oxy]pyridin-3-yl}-1-oxa-4,9-diazaspiro[5,5]undecan-3-one obtained in Reference Example 9-4, and 5-bromo-2-(difluoromethoxy)pyridine obtained in Reference Example 16 in place of 1-bromo-4-fluorobenzene.

¹H-NMR (400 MHz, CDCl₃) δ: 1.40-2.30 (16H, m), 2.57-2.93 (3H, m), 3.02-3.13 (2H, m), 3.20-3.31 (2H, m), 3.63 (2H, s), 4.36 (2H, s), 5.00 (1H, brs), 6.66 (1H, d, J=9.1 Hz), 6.96 (1H, d, J=9.1 Hz), 7.30 (1H, dd, J=9.1, 2.9 Hz), 7.43 (1H, t, J=72.7 Hz), 7.74 (1H, dd, J=9.1, 2.5 Hz), 7.81 (1H, d, J=2.9 Hz), 8.16 (1H, d, J=2.5 Hz)

Example 3-157

Production of 9-{6-[(1-cyclobutylpiperidin-4-yl)oxy]pyridin-3-yl}-4-(4-fluorophenyl)-1-oxa-4,9-diazaspiro[5,5]undecan-3-one The entitled compound was obtained as a pale brown solid, according to the same method as in Example 3 or according to a method similar to it but using 9-{6-[(1-cyclobutylpiperidin-4-yl)oxy]pyridin-3-yl}-1-oxa-4,9-diazaspiro[5,5]undecan-3-one obtained in Reference Example 9-4 and 1-bromo-4-fluorobenzene.
¹H-NMR (400 MHz, CDCl₃) δ: 1.41-2.40 (16H, m), 2.57-2.90 (3H, m), 3.01-3.15 (2H, m), 3.19-3.31 (2H, m), 3.61 (2H, s), 4.34 (2H, s), 4.99 (1H, brs), 6.66 (1H, d, J=9.2 Hz), 7.10 (2H, d, J=8.8 Hz), 7.12 (2H, d, J=8.8 Hz), 7.30 (1H, dd, J=9.2, 3.3 Hz), 7.81 (1H, d, J=3.3 Hz)

Example 3-158

Production of 9-{6-[(1-cyclobutylpiperidin-4-yl)oxy]pyridin-3-yl}-4-(6-methoxypyridin-3-yl)-1-oxa-4,9-diazaspiro[5,5]undecan-3-one The entitled compound was obtained as a pale orange solid, according to the same method as in Example 3 or according to a method similar to it but using 9-{6-[(1-cyclobutylpiperidin-4-yl)oxy]pyridin-3-yl}-1-oxa-4,9-diazaspiro[5,5]undecan-3-one obtained in Reference Example 94, and 5-bromo-2-methoxypyridine in place of 1-bromo-4-fluorobenzene.
H-NMR (400 MHz, CDCl₃) δ: 1.47-2.30 (16H, m), 2.58-2.86 (3H, m), 3.01-3.13 (2H, m), 3.19-3.31 (2H, m), 3.60 (2H, s), 3.94 (3H, s), 4.35 (2H, s), 4.98 (1H, brs), 6.66 (1H, d, J=8.9 Hz), 6.79 (1H, d, J=8.8 Hz), 7.30 (1H, dd, J=8.9, 3.1 Hz), 7.54 (1H, dd, J=8.8, 2.7 Hz), 7.81 (1H, d, J=3.1 Hz), 8.10 (1H, d, J=2.7 Hz)

Example 3-159

Production of 9-{6-[(1-cyclobutylpiperidin-4-yl)oxy]pyridin-3-yl}-4-ethyl-1-oxa-4,9-diazaspiro[5,5]undecan-3-one The entitled compound was obtained as a pale yellow oily substance, according to the same method as in Example 3-96 or according to a method similar to it but using 9-{6-[(1-cyclobutylpiperidin-4-yl)oxy]pyridin-3-yl}-1-oxa-4,9-diazaspiro[5,5]undecan-3-one obtained in Reference Example 9-4 and bromoethane.
¹H-NMR (400 MHz, CDCl₃) δ: 1.16 (3H, t, J=7.3 Hz), 1.43-2.35 (16H, m), 2.54-2.90 (3H, m), 2.96-3.09 (2H, m), 3.14-3.23 (2H, m), 3.23 (2H, s), 3.46 (2H, q, J=7.3 Hz), 4.16 (2H, s), 4.98 (1H, brs), 6.65 (1H, d, J=9.2 Hz), 7.29 (1H, dd, J=9.2, 3.1 Hz), 7.79 (1H, d, J=3.1 Hz)

Example 3-160

Production of 9-{6-[(1-cyclobutylpiperidin-4-yl)oxy]pyridin-3-yl}-4-(2-methoxypyrimidin-5-yl)-1-oxa-4,9-diazaspiro[5,5]undecan-3-one The entitled compound was obtained as a pale yellow solid, according to the same method as in Example 3 or according to a method similar to it but using 9-{6-[(1-cyclobutylpiperidin-4-yl)oxy]pyridin-3-yl}-1-oxa-4,9-diazaspiro[5,5]undecan-3-one obtained in Reference Example 9-4, and 5-iodo-2-methoxypyrimidine in place of 1-bromo-4-fluorobenzene.
¹H-NMR (400 MHz, CDCl₃) δ: 1.48-2.24 (16H, m), 2.56-2.88 (3H, m), 2.99-3.15 (2H, m), 3.20-3.34 (2H, m), 3.63 (2H, s), 4.03 (3H, s), 4.37 (2H, s), 4.97 (1H, brs), 6.66 (1H, d, J=8.9 Hz), 7.30 (1H, dd, J=8.9, 3.1 Hz), 7.81 (1H, d, J=3.1 Hz), 8.53 (2H, s)

Example 3-161

Production of 9-{6-[(1-cyclobutylpiperidin-4-yl)oxy]pyridin-3-yl}-4-(6-methylpyridin-3-yl)-1-oxa-4,9-diazaspiro[5,5]undecan-3-one The entitled compound was obtained as a pale brown solid, according to the same method as in Example 3 or according to a method similar to it but using 9-{6-[(1-cyclobutylpiperidin-4-yl)oxy]pyridin-3-yl}-1-oxa-4,9-diazaspiro[5,5]undecan-3-one obtained in Reference Example 9-4, and 5-bromo-2-methylpyridine in place of 1-bromo-4-fluorobenzene.
¹H-NMR (400 MHz, CDCl₃) δ: 1.48-2.28 (16H, m), 2.57 (3H, s), 2.60-2.87 (3H, m), 3.00-3.14 (2H, m), 3.19-3.32 (2H, m), 3.64 (2H, s), 4.36 (2H, s), 4.98 (1H, brs), 6.66 (1H, d, J=8.8 Hz), 7.21 (1H, d, J=8.3 Hz), 7.30 (1H, dd, J=8.8, 2.9 Hz), 7.58 (1H, dd, J=8.3, 2.7 Hz), 7.81 (1H, d, J=2.9 Hz), 8.45 (1H, d, J=2.7 Hz)

Example 3-162

Production of 9-{6-[(1-cyclobutylpiperidin-4-yl)oxy]pyridin-3-yl}-4-(5-methoxypyrazin-2-yl)-1-oxa-4,9-diazaspiro[5,5]undecan-3-one The entitled compound was obtained as a white solid, according to the same method as in Example 3 or according to a method similar to it but using 9-{6-[(1-cyclobutylpiperidin-4-yl)oxy]pyridin-3-yl}-1-oxa-4,9-diazaspiro[5,5]undecan-3-one obtained in Reference Example 9-4, and 2-bromo-5-methoxypyrazine in place of 1-bromo-4-fluorobenzene.
¹H-NMR (400 MHz, CDCl₃) δ: 1.54-2.25 (16H, m), 2.60-2.82 (3H, brm), 3.08 (2H, td, J=11.2, 2.9 Hz), 3.25 (2H, dt, J=12.7, 4.4 Hz), 3.89 (2H, s), 3.99 (3H, s), 4.37 (2H, s), 4.97 (1H, brs), 6.66 (1H, d, J=9.3 Hz), 7.30 (1H, dd, J=9.0, 3.2 Hz), 7.81 (1H, d, J=2.9 Hz), 8.03 (1H, d, J=1.5 Hz), 8.84 (1H, d, J=1.5 Hz)

Example 3-163

Production of 8-{4-[(1-cyclobutylpiperidin-4-yl)oxy]phenyl}-3-(6-methylpyridin-3-yl)-1-oxa-3,8-diazaspiro[4,5]decan-2-one The entitled compound was obtained as a pale orange solid, according to the same method as in Example 3 or according to a method similar to it but using 8-{4-[(1-cyclobutylpiperidin-4-yl)oxy]phenyl}-1-oxa-3,8-diazaspiro[4,5]decan-2-one obtained in Reference Example 13-1, and 5-bromo-2-methylpyridine in place of 1-bromo-4-fluorobenzene.
¹H-NMR (400 MHz, CDCl₃) δ: 1.52-2.25 (16H, m), 2.54 (3H, s), 2.57-2.83 (3H, m), 3.18-3.36 (4H, m), 3.81 (2H, s), 4.22 (1H, brs), 6.85 (2H, d, J=9.1 Hz), 6.92 (2H, d, J=9.1 Hz), 7.18 (1H, d, J=8.8 Hz), 8.14 (1H, dd, J=8.8, 2.9 Hz), 8.41 (1H, d, J=2.9 Hz)

Example 3-164

Production of 5-(8-{4-[(1-cyclobutylpiperidin-4-yl)oxy]phenyl}-2-oxo-1-oxa-3,8-diazaspiro[4,5]decan-3-yl)nicotinonitrile The entitled compound was obtained as a white solid, according to the same method as in Example 3 or according to a method similar to it but using 8-{4-[(1-cyclobutylpiperidin-4-yl)oxy]phenyl}-1-oxa-3,8-diazaspiro[4,5]decan-2-one obtained in Reference Example 13-1, and 5-bromonicotinonitrile in place of 1-bromo-4-fluorobenzene.
$^1$H-NMR (400 MHz, CDCl$_3$) δ: 1.49-2.27 (16H, m), 2.52-2.86 (3H, m), 3.18-3.39 (4H, m), 3.85 (2H, s), 4.22 (1H, brs), 6.86 (2H, d, J=9.3 Hz), 6.92 (2H, d, J=9.3 Hz), 8.54 (1H, dd, J=2.6, 1.9 Hz), 8.64 (1H, d, J=1.9 Hz), 8.81 (1H, d, J=2.6 Hz)

Example 3-165

Production of 8-{4-[(1-cyclobutylpiperidin-4-yl)oxy]phenyl}-3-pyridin-3-yl-1-oxa-3,8-diazaspiro[4,5]decan-2-one The entitled compound was obtained as a pale yellow solid, according to the same method as in Example 3 or according to a method similar to it but using 8-{4-[(1-cyclobutylpiperidin-4-yl)oxy]phenyl}-1-oxa-3,8-diazaspiro[4,5]decan-2-one obtained in Reference Example 13-1, and 3-bromopyridine in place of 1-bromo-4-fluorobenzene.
$^1$H-NMR (400 MHz, CDCl$_3$) δ: 1.40-2.31 (16H, m), 2.50-2.92 (3H, m), 3.17-3.38 (4H, m), 3.84 (2H, s), 4.24 (1H, brs), 6.85 (2H, d, J=9.3 Hz), 6.92 (2H, d, J=9.3 Hz), 7.33 (1H, dd, J=8.4, 4.4 Hz), 8.24 (1H, ddd, J=8.4, 2.4, 1.5 Hz), 8.41 (1H, dd, J=4.4, 1.5 Hz), 8.59 (1H, d, J=2.4 Hz)

Example 3-166

Production of 8-{4-[(1-cyclobutylpiperidin-4-yl)oxy]phenyl}-3-(1-methyl-1H-pyrazol-4-yl)-1-oxa-3,8-diazaspiro[4,5]decan-2-one The entitled compound was obtained as a white solid, according to the same method as in Example 3 or according to a method similar to it but using 8-{4-[(1-cyclobutylpiperidin-4-yl)oxy]phenyl}-1-oxa-3,8-diazaspiro[4,5]decan-2-one obtained in Reference Example 13-1, and 4-bromo-1-methyl-1H-pyrazole in place of 1-bromo-4-fluorobenzene.
$^1$H-NMR (400 MHz, CDCl$_3$) δ: 1.46-2.25 (16H, m), 2.53-2.86 (3H, m), 3.17-3.32 (4H, m), 3.66 (2H, s), 3.89 (3H, s), 4.22 (1H, brs), 6.85 (2H, d, J=9.3 Hz), 6.91 (2H, d, J=9.3 Hz), 7.35 (1H, s), 7.77 (1H, s)

Example 3-167

Production of 8-{4-[(1-cyclobutylpiperidin-4-yl)oxy]phenyl}-3-(1-methyl-1H-pyrazol-3-yl)-1-oxa-3,8-diazaspiro[4,5]decan-2-one The entitled compound was obtained as a pale brown solid, according to the same method as in Example 3 or according to a method similar to it but using 8-{4-[(1-cyclobutylpiperidin-4-yl)oxy]phenyl}-1-oxa-3,8-diazaspiro[4,5]decan-2-one obtained in Reference Example 13-1, and 3-iodo-1-methyl-1H-pyrazole in place of 1-bromo-4-fluorobenzene.
$^1$H-NMR (400 MHz, CDCl$_3$) δ: 1.43-2.30 (16H, m), 2.53-2.91 (3H, m), 3.16-3.33 (4H, m), 3.82 (3H, s), 3.87 (2H, s), 4.24 (1H, brs), 6.64 (1H, d, J=2.2 Hz), 6.84 (2H, d, J=9.3 Hz), 6.91 (2H, d, J=9.3 Hz), 7.28 (1H, d, J=2.2 Hz)

Example 3-168

Production of 8-{4-[(1-cyclobutylpiperidin-4-yl)oxy]phenyl}-3-(6-methoxypyridin-3-yl)-1-oxa-3,8-diazaspiro[4,5]decan-2-one The entitled compound was obtained as a white solid, according to the same method as in Example 3 or according to a method similar to it but using 8-{4-[(1-cyclobutylpiperidin-4-yl)oxy]phenyl}-1-oxa-3,8-diazaspiro[4,5]decan-2-one obtained in Reference Example 13-1, and 5-bromo-2-methoxypyridine in place of 1-bromo-4-fluorobenzene.
$^1$H-NMR (400 MHz, CDCl$_3$) δ: 1.42-2.27 (16H, m), 2.51-2.85 (3H, m), 3.17-3.35 (4H, m), 3.76 (2H, s), 3.92 (3H, s), 4.22 (1H, brs), 6.79 (1H, d, J=9.4 Hz), 6.85 (2H, d, J=9.3 Hz), 6.91 (2H, d, J=9.3 Hz), 8.05 (1H, d, J=2.4 Hz), 8.11 (1H, dd, J=9.4, 2.4 Hz)

Example 3-169

Production of 8-{4-[(1-cyclobutylpiperidin-4-yl)oxy]phenyl}-3-imidazo[1,2-a]pyridin-3-yl-1-oxa-3,8-diazaspiro[4,5]decan-2-one The entitled compound was obtained according to the same method as in Example 3 or according to a method similar to it but using 8-{4-[(1-cyclobutylpiperidin-4-yl)oxy]phenyl}-1-oxa-3,8-diazaspiro[4,5]decan-2-one obtained in Reference Example 13-1, and 3-iodoimidazo[1,2-a]pyridine in place of 1-bromo-4-fluorobenzene.
$^1$H-NMR (400 MHz, CDCl$_3$) δ: 1.42-2.37 (16H, m), 2.53-2.89 (3H, m), 3.21-3.38 (4H, m), 3.81 (2H, s), 4.24 (1H, brs), 6.86 (2H, d, J=9.1 Hz), 6.89-6.96 (1H, m), 6.93 (2H, d, J=9.1 Hz), 7.21-7.32 (1H, m), 7.57-7.70 (2H, m), 7.88-7.97 (1H, m)

Example 3-170

Production of 8-{4-[(1-cyclobutylpiperidin-4-yl)oxy]phenyl}-3-(3-methylpyridin-2-yl)-1-oxa-3,8-diazaspiro[4,5]decan-2-one The entitled compound was obtained according to the same method as in Example 3 or according to a method similar to it but using 8-{4-[(1-cyclobutylpiperidin-4-yl)oxy]phenyl}-1-oxa-3,8-diazaspiro[4,5]decan-2-one obtained in Reference Example 13-1, and 2-bromo-3-methylpyridine in place of 1-bromo-4-fluorobenzene.
$^1$H-NMR (400 MHz, CDCl$_3$) δ: 1.48-2.30 (16H, m), 2.37 (3H, s), 2.52-2.86 (3H, m), 3.19-3.35 (4H, m), 4.00 (2H, s), 4.22 (1H, brs), 6.85 (2H, d, J=9.3 Hz), 6.92 (2H, d, J=9.3 Hz), 7.16 (1H, dd, J=7.4, 4.6 Hz), 7.61 (1H, d, J=7.4 Hz), 8.28 (1H, d, J=4.6 Hz)

Example 3-171

Production of 8-{4-[(1-cyclobutylpiperidin-4-yl)oxy]phenyl}-3-(6-fluoropyridin-3-yl)-1-oxa-3,8-diazaspiro[4,5]decan-2-one The entitled compound was obtained as a white solid, according to the same method as in Example 3 or according to a method similar to it but using 8-{4-[(1-cyclobutylpiperidin-4-yl)oxy]phenyl}-1-oxa-3,8-diazaspiro[4,5]decan-2-one obtained in Reference Example 13-1, and 5-bromo-2-fluoropyridine in place of 1-bromo-4-fluorobenzene.
$^1$H-NMR (400 MHz, CDCl$_3$) δ: 1.45-2.29 (16H, m), 2.51-2.83 (3H, m), 3.17-3.36 (4H, m), 3.81 (2H, s), 4.21 (1H, brs), 6.85 (2H, d, J=9.3 Hz), 6.92 (2H, d, J=9.3 Hz), 6.96-7.01 (1H, m), 8.07-8.12 (1H, m), 8.37-8.45 (1H, m)

Example 3-172

Production of 8-{4-[(1-cyclobutylpiperidin-4-yl)oxy]phenyl}-3-[4-(methylsulfonyl)phenyl]-1-oxa-3,8-diazaspiro[4,5]decan-2-one The entitled compound was obtained as a white solid, according to the same method as in Example 3 or according to a method similar to it but using 8-{4-[(1-cyclobutylpiperidin-4-yl)oxy]phenyl}-1-oxa-3,8-diazaspiro[4,5]decan-2-one obtained in Reference Example 13-1, and 1-bromo-4-(methylsulfonyl)benzene in place of 1-bromo-4-fluorobenzene.
$^1$H-NMR (400 MHz, CDCl$_3$) δ: 1.47-2.28 (16H, m), 2.54-2.82 (3H, m), 3.05 (3H, s), 3.18-3.37 (4H, m), 3.85 (2H, s), 4.22 (1H, brs), 6.86 (2H, d, J=9.3 Hz), 6.92 (2H, d, J=9.3 Hz), 7.77 (2H, d, J=8.8 Hz), 7.96 (2H, d, J=8.8 Hz)

Example 3-173

Production of 8-{4-[(1-cyclobutylpiperidin-4-yl)oxy]phenyl}-3-(2-fluoropyridin-4-yl)-1-oxa-3,8-diazaspiro[4,5]decan-2-one The entitled compound was obtained as a pale orange solid, according to the same method as in Example 3 or according to a method similar to it but using 8-{4-[(1-cyclobutylpiperidin-4-yl)oxy]phenyl}-1-oxa-3,8-diazaspiro[4,5]decan-2-one obtained in Reference Example 13-1, and 4-iodo-2-fluoropyridine in place of 1-bromo-4-fluorobenzene.
$^1$H-NMR (400 MHz, CDCl$_3$) δ: 1.43-2.23 (16H, m), 2.56-2.91 (3H, m), 3.17-3.36 (4H, m), 3.79 (2H, s), 4.20-4.36 (1H, m), 6.85 (2H, d, J=9.1 Hz), 6.92 (2H, d, J=9.1 Hz), 7.14 (1H, d, J=2.0 Hz), 7.41 (1H, dd, J=6.1, 2.0 Hz), 8.16 (1H, d, J=6.1 Hz)

Example 3-174

Production of 8-{4-[(1-cyclobutylpiperidin-4-yl)oxy]phenyl}-3-(1-methyl-6-oxo-1,6-dihydropyridin-3-yl)-1-oxa-3,8-diazaspiro[4,5]decan-2-one The entitled compound was obtained as a pale green solid, according to the same method as in Example 3 or according to a method similar to it but using 8-{4-[(1-cyclobutylpiperidin-4-yl)oxy]phenyl}-1-oxa-3,8-diazaspiro[4,5]decan-2-one obtained in Reference Example 13-1, and 5-bromo-1-methylpyridin-2(1H)-one in place of 1-bromo-4-fluorobenzene.
$^1$H-NMR (400 MHz, CDCl$_3$) δ: 1.45-2.29 (16H, m), 2.52-2.90 (2H, m), 3.16-3.34 (4H, m), 3.57 (3H, s), 3.68 (2H, s), 4.25 (1H, brs), 6.62 (1H, d, J=9.8 Hz), 6.85 (2H, d, J=9.3 Hz), 6.91 (2H, d, J=9.3 Hz), 7.47 (1H, dd, J=9.8, 2.9 Hz), 7.70 (1H, d, J=2.9 Hz)

Example 3-175

Production of 8-{4-[(1-cyclobutylpiperidin-4-yl)oxy]phenyl}-3-(2-methoxypyrimidin-5-yl)-1-oxa-3,8-diazaspiro[4,5]decan-2-one The entitled compound was obtained as a pale orange solid, according to the same method as in Example 3 or according to a method similar to it but using 8-{4-[(1-cyclobutylpiperidin-4-yl)oxy]phenyl}-1-oxa-3,8-diazaspiro[4,5]decan-2-one obtained in Reference Example 13-1, and 5-iodo-2-methoxypyrimidine in place of 1-bromo-4-fluorobenzene.
$^1$H-NMR (400 MHz, CDCl$_3$) δ: 1.51-2.45 (16H, m), 2.53-2.94 (3H, m), 3.12-3.39 (4H, m), 3.78 (2H, s), 4.02 (3H, s), 4.27 (1H, brs), 6.85 (2H, d, J=8.8 Hz), 6.92 (2H, d, J=8.8 Hz), 8.75 (2H, s)

Example 3-176

Production of 3-ethyl-8-{4-[(1-isopropylpiperidin-4-yl)oxy]phenyl}-1-oxa-3,8-diazaspiro[4,5]decan-2-one The entitled compound was obtained as a pale brown solid, according to the same method as in Example 3-96 or according to a method similar to it but using 8-{4-[(1-isopropylpiperidin-4-yl)oxy]phenyl}-1-oxa-3,8-diazaspiro[4,5]decan-2-one obtained in Reference Example 13-2 and bromoethane.
$^1$H-NMR (400 MHz, CDCl$_3$) δ: 1.07 (6H, d, J=5.9 Hz), 1.17 (3H, t, J=7.3 Hz), 1.73-2.09 (8H, m), 2.38 (2H, brs), 2.70-2.86 (3H, brm), 3.16-3.24 (4H, m), 3.31-3.37 (4H, m), 4.19 (1H, s), 6.84 (2H, d, J=9.3 Hz), 6.89 (2H, d, J=9.3 Hz)

Example 3-177

Production of 8-{4-[(1-isopropylpiperidin-4-yl)oxy]phenyl}-3-(1-methyl-1H-pyrazol-4-yl)-1-oxa-3,8-diazaspiro[4,5]decan-2-one The entitled compound was obtained as a yellow solid, according to the same method as in Example 3 or according to a method similar to it but using 8-{4-[(1-isopropylpiperidin-4-yl)oxy]phenyl}-1-oxa-3,8-diazaspiro[4,5]decan-2-one obtained in Reference Example 13-2, and 4-bromo-1-methyl-1H-pyrazole in place of 1-bromo-4-fluorobenzene.
$^1$H-NMR (400 MHz, CDCl$_3$) δ: 1.07 (6H, d, J=6.3 Hz), 1.73-1.87 (2H, brm), 1.94-2.06 (5H, m), 2.13 (2H, d, J=13.2 Hz), 2.38 (2H, brs), 2.70-2.85 (3H, brm), 3.21-3.29 (4H, m), 3.66 (2H, s), 3.89 (3H, s), 4.20 (1H, brs), 6.85 (2H, d, J=9.3 Hz), 6.91 (2H, d, J=9.3 Hz), 7.35 (1H, d, J=1.0 Hz), 7.77 (1H, s)

Example 3-178

Production of 8-{4-[(1-isopropylpiperidin-4-yl)oxy]phenyl}-3-(1-methyl-1H-pyrazol-3-yl)-1-oxa-3,8-diazaspiro[4,5]decan-2-one The entitled compound was obtained as a brown solid, according to the same method as in Example 3 or according to a method similar to it but using 8-{4-[(1-isopropylpiperidin-4-yl)oxy]phenyl}-1-oxa-3,8-diazaspiro[4,5]decan-2-one obtained in Reference Example 13-2, and 3-iodo-1-methyl-1H-pyrazole in place of 1-bromo-4-fluorobenzene.
$^1$H-NMR (400 MHz, CDCl$_3$) δ: 1.07 (6H, d, J=6.8 Hz), 1.74-1.86 (2H, brm), 1.95-2.08 (5H, m), 2.14 (2H, d, J=13.2 Hz), 2.39 (2H, brs), 2.70-2.86 (3H, brm), 3.20-3.28 (4H, m), 3.82 (3H, s), 3.87 (2H, s), 4.20 (1H, brs), 6.64 (1H, d, J=2.4 Hz), 6.85 (2H, d, J=9.3 Hz), 6.91 (2H, d, J=9.3 Hz), 7.28 (1H, d, J=2.4 Hz)

Example 3-179

Production of 5-(8-{4-[(1-isopropylpiperidin-4-yl)oxy]phenyl}-2-oxo-1-oxa-3,8-diazaspiro[4,5]decan-3-yl)nicotinonitrile The entitled compound was obtained as a brown solid, according to the same method as in Example 3 or according to a method similar to it but using 8-{4-[(1-isopropylpiperidin-4-yl)oxy]phenyl}-1-oxa-3,8-diazaspiro[4,5]decan-2-one obtained in Reference Example 13-2, and 5-bromonicotinonitrile in place of 1-bromo-4-fluorobenzene.

$^1$H-NMR (400 MHz, CDCl$_3$) δ: 1.07 (6H, d, J=6.3 Hz), 1.74-1.86 (2H, brm), 1.93-2.12 (4H, m), 2.17 (2H, d, J=13.2 Hz), 2.38 (2H, brs), 2.69-2.86 (3H, brm), 3.21-3.33 (4H, m), 3.85 (2H, s), 4.20 (1H, brs), 6.86 (2H, d, J=9.3 Hz), 6.92 (2H, d, J=9.3 Hz), 8.56-8.53 (1H, m), 8.64 (1H, d, J=2.0 Hz), 8.81 (1H, d, J=2.4 Hz)

Example 3-180

Production of 8-{4-[(1-isopropylpiperidin-4-yl)oxy]phenyl}-3-pyrazin-2-yl-1-oxa-3,8-diazaspiro[4,5]decan-2-one The entitled compound was obtained as a pale yellow solid, according to the same method as in Example 3 or according to a method similar to it but using 8-{4-[(1-isopropylpiperidin-4-yl)oxy]phenyl}-1-oxa-3,8-diazaspiro[4,5]decan-2-one obtained in Reference Example 13-2, and 2-iodopyrazine in place of 1-bromo-4-fluorobenzene.

$^1$H-NMR (400 MHz, CDCl$_3$) δ: 1.08 (6H, d, J=5.9 Hz), 1.83 (2H, brs), 1.97-2.10 (4H, m), 2.17 (2H, d, J=13.2 Hz), 2.42 (2H, brs), 2.82 (3H, brs), 3.26-3.27 (4H, m), 4.00 (2H, s), 4.22 (1H, s), 6.86 (2H, d, J=9.3 Hz), 6.92 (2H, d, J=9.3 Hz), 8.27 (1H, dd, J=2.7, 1.7 Hz), 8.33 (1H, d, J=2.4 Hz), 9.60 (1H, d, J=1.5 Hz)

Example 3-181

Production of 8-{4-[(1-isopropylpiperidin-4-yl)oxy]phenyl}-3-(5-methoxypyridin-2-yl)-1-oxa-3,8-diazaspiro[4,5]decan-2-one The entitled compound was obtained as a pale yellow solid, according to the same method as in Example 3 or according to a method similar to it but using 8-{4-[(1-isopropylpiperidin-4-yl)oxy]phenyl}-1-oxa-3,8-diazaspiro[4,5]decan-2-one obtained in Reference Example 13-2, and 2-bromo-5-methoxypyridine in place of 1-bromo-4-fluorobenzene.

$^1$H-NMR (400 MHz, CDCl$_3$) δ: 1.07 (6H, d, J=5.9 Hz), 1.82 (2H, brs), 1.97-2.06 (4H, m), 2.10-2.19 (2H, m), 2.39 (2H, brs), 2.70-2.85 (3H, brm), 3.22-3.28 (4H, m), 3.85 (3H, s), 4.01 (2H, s), 4.20 (1H, brs), 6.85 (2H, d, J=9.3 Hz), 6.92 (2H, d, J=9.3 Hz), 7.30 (1H, dd, J=9.3, 2.9 Hz), 7.99 (1H, d, J=3.4 Hz), 8.17 (1H, d, J=9.8 Hz)

Example 3-182

Production of 8-{4-[(1-isopropylpiperidin-4-yl)oxy]phenyl}-3-(2-methoxypyrimidin-5-yl)-1-oxa-3,8-diazaspiro[4,5]decan-2-one The entitled compound was obtained as a white solid, according to the same method as in Example 3 or according to a method similar to it but using 8-{4-[(1-isopropylpiperidin-4-yl)oxy]phenyl}-1-oxa-3,8-diazaspiro[4,5]decan-2-one obtained in Reference Example 13-2, and 5-iodo-2-methoxypyrimidine in place of 1-bromo-4-fluorobenzene.

$^1$H-NMR (400 MHz, CDCl$_3$) δ: 1.08 (6H, d, J=6.3 Hz), 1.82 (2H, brs), 1.97-2.10 (4H, m), 2.17 (2H, d, J=13.2 Hz), 2.41 (2H, brs), 2.73-2.88 (3H, brm), 3.19-3.35 (4H, m), 3.78 (2H, s), 4.02 (3H, s), 4.21 (1H, brs), 6.86 (2H, d, J=9.3 Hz), 6.92 (2H, d, J=9.3 Hz), 8.76 (2H, s)

Example 3-183

Production of 8-{4-[(1-isopropylpiperidin-4-yl)oxy]phenyl}-3-(3-methoxypyridin-2-yl)-1-oxa-3,8-diazaspiro[4,5]decan-2-one The entitled compound was obtained as a yellow oily substance, according to the same method as in Example 3 or according to a method similar to it but using 8-{4-[(1-isopropylpiperidin-4-yl)oxy]phenyl}-1-oxa-3,8-diazaspiro[4,5]decan-2-one obtained in Reference Example 13-2, and 2-bromo-3-methoxypyridine in place of 1-bromo-4-fluorobenzene.

$^1$H-NMR (400 MHz, CDCl$_3$) δ: 1.09 (6H, d, J=6.3 Hz), 1.84 (2H, brs), 2.03 (4H, d, J=28.3 Hz), 2.24 (2H, d, J=12.7 Hz), 2.45 (2H, brs), 2.83 (3H, brs), 3.19-3.32 (4H, m), 3.90 (2H, s), 3.91 (3H, s), 4.22 (1H, brs), 6.85 (2H, d, J=9.3 Hz), 6.91 (2H, d, J=9.3 Hz), 7.23 (1H, dd, J=8.3, 4.9 Hz), 7.31 (1H, dd, J=8.3, 1.5 Hz), 8.06 (1H, dd, J=4.4, 1.5 Hz)

Example 3-184

Production of 8-{4-[(1-isopropylpiperidin-4-yl)oxy]phenyl}-3-(6-methoxypyridin-3-yl)-1-oxa-3,8-diazaspiro[4,5]decan-2-one The entitled compound was obtained as a pale yellow solid, according to the same method as in Example 3 or according to a method similar to it but using 8-{4-[(1-isopropylpiperidin-4-yl)oxy]phenyl}-1-oxa-3,8-diazaspiro[4,5]decan-2-one obtained in Reference Example 13-2, and 5-bromo-2-methoxypyridine in place of 1-bromo-4-fluorobenzene.

$^1$H-NMR (400 MHz, CDCl$_3$) δ: 1.07 (6H, d, J=6.3 Hz), 1.82 (2H, brs), 1.99-2.06 (4H, m), 2.15 (2H, d, J=12.7 Hz), 2.40 (2H, brs), 2.73-2.85 (3H, brm), 3.20-3.34 (4H, m), 3.77 (2H, s), 3.92 (3H, s), 4.21 (1H, brs), 6.78 (1H, d, J=9.3 Hz), 6.86 (2H, d, J=9.3 Hz), 6.92 (2H, d, J=9.3 Hz), 8.06 (1H, d, J=2.4 Hz), 8.11 (1H, dd, J=8.8, 2.9 Hz)

Example 3-185

Production of 8-{4-[(1-isopropylpiperidin-4-yl)oxy]phenyl}-3-(5-methoxypyridin-3-yl-1-oxa-3,8-diazaspiro[4,5]decan-2-one The entitled compound was obtained as a pale brown solid, according to the same method as in Example 3 or according to a method similar to it but using 8-{4-[(1-isopropylpiperidin-4-yl)oxy]phenyl}-1-oxa-3,8-diazaspiro[4,5]decan-2-one obtained in Reference Example 13-2, and 3-bromo-5-methoxypyridine in place of 1-bromo-4-fluorobenzene.

$^1$H-NMR (400 MHz, CDCl$_3$) δ: 1.09 (6H, s), 1.84 (2H, brs), 2.00-2.07 (4H, m), 2.16 (2H, d, J=13.7 Hz), 2.42 (2H, brs), 2.82 (3H, brs), 3.21-3.34 (4H, m), 3.82 (2H, s), 3.89 (3H, s), 4.22 (1H, brs), 6.86 (2H, d, J=9.3 Hz), 6.92 (2H, d, J=9.3 Hz), 7.96 (1H, t, J=2.4 Hz), 8.08 (1H, d, J=2.4 Hz), 8.12 (1H, d, J=2.4 Hz)

Example 3-186

Production of 8-{6-[(1-cyclobutylpiperidin-4-yl)oxy]pyridin-3-yl}-3-(3-methylpyridin-2-yl-1-oxa-3,8-diazaspiro[4,5]decan-2-one The entitled compound was obtained as a pale yellow oily substance, according to the same method as in Example 3 or according to a method similar to it but using 8-{6-[(1-cyclobutylpiperidin-4-yl)oxy]pyridin-3-yl}-1-oxa-3,8-diazaspiro[4,5]decan-2-one obtained in Reference Example 13-3, and 2-bromo-3-methylpyridine in place of 1-bromo-4-fluorobenzene.

$^1$H-NMR (400 MHz, CDCl$_3$) δ: 1.58-2.25 (16H, m), 2.37 (3H, s), 2.59-2.82 (3H, brm), 3.22-3.29 (4H, m), 4.01 (2H, s), 4.98 (1H, brs), 6.67 (1H, d, J=8.8 Hz), 7.16 (1H, dd, J=7.8, 4.9 Hz), 7.31 (1H, dd, J=8.8, 2.9 Hz), 7.61 (1H, d, J=6.3 Hz), 7.81 (1H, d, J=2.9 Hz), 8.28 (1H, dd, J=4.9, 1.5 Hz)

Example 3-187

Production of 8-{6-[(1-cyclobutylpiperidin-4-yl)oxy]pyridin-3-yl}-3-(5-methoxypyridin-2-yl)-1-oxa-3,8-diazaspiro[4,5]decan-2-one The entitled compound was obtained as a white solid, according to the same method as in Example 3 or according to a method similar to it but using 8-{6-[(1-cyclobutylpiperidin-4-yl)oxy]pyridin-3-yl}-1-oxa-3,8-diazaspiro[4,5]decan-2-one obtained in Reference Example 13-3, and 2-bromo-5-methoxypyridine in place of 1-bromo-4-fluorobenzene.

$^1$H-NMR (400 MHz, CDCl$_3$) δ: 1.52-2.23 (16H, m), 2.60-2.81 (3H, brm), 3.21-3.28 (4H, m), 3.85 (3H, s), 4.02 (2H, s), 4.98 (1H, brs), 6.66 (1H, d, J=8.8 Hz), 7.34-7.28 (2H, m), 7.81 (1H, d, J=2.9 Hz), 7.99 (1H, d, J=2.4 Hz), 8.17 (1H, d, J=9.3 Hz)

Example 3-188

Production of 8-{6-[(1-cyclobutylpiperidin-4-yl)oxy]pyridin-3-yl}-3-(5-fluoropyridin-2-yl)-1-oxa-3,8-diazaspiro[4,5]decan-2-one The entitled compound was obtained as a pale yellow solid, according to the same method as in Example 3 or according to a method similar to it but using 8-{6-[(1-cyclobutylpiperidin-4-yl)oxy]pyridin-3-yl}-1-oxa-3,8-diazaspiro[4,5]decan-2-one obtained in Reference Example 13-3, and 2-bromo-5-fluoropyridine in place of 1-bromo-4-fluorobenzene.

$^1$H-NMR (400 MHz, CDCl$_3$) δ: 1.49-2.28 (16H, m), 2.58-2.86 (3H, brm), 3.21-3.27 (4H, m), 4.02 (2H, s), 4.98 (1H, brs), 6.67 (1H, d, J=9.3 Hz), 7.30 (1H, dd, J=8.8, 2.9 Hz), 7.50-7.43 (1H, m), 7.81 (1H, d, J=2.9 Hz), 8.16 (1H, d, J=2.9 Hz), 8.27 (1H, dd, J=9.3, 3.9 Hz)

Example 3-189

Production of 8-{6-[(1-cyclobutylpiperidin-4-yl)oxy]pyridin-3-yl}-3-ethyl-1-oxa-3,8-diazaspiro[4,5]decan-2-one The entitled compound was obtained as a white solid, according to the same method as in Example 3-96 or according to a method similar to it but using 8-{6-[(1-cyclobutylpiperidin-4-yl)oxy]pyridin-3-yl}-1-oxa-3,8-diazaspiro[4,5]decan-2-one obtained in Reference Example 13-3 and bromoethane.

$^1$H-NMR (400 MHz, CDCl$_3$) δ: 1.17 (3H, t, J=7.3 Hz), 1.54-2.24 (16H, m), 2.59-2.80 (3H, brm), 3.20 (4H, dd, J=8.0, 3.7 Hz), 3.29-3.38 (4H, m), 4.97 (1H, brs), 6.65 (1H, d, J=8.8 Hz), 7.28 (4H, dd, J=8.8, 2.9 Hz), 7.79 (1H, d, J=2.4 Hz).

Example 3-190

Production of 8-{6-[(1-cyclobutylpiperidin-4-yl)oxy]pyridin-3-yl}-3-(2,2,2-trifluoroethyl)-1-oxa-3,8-diazaspiro[4,5]decan-2-one The entitled compound was obtained as a white solid, according to the same method as in Example 3-96 or according to a method similar to it but using 8-{6-[(1-cyclobutylpiperidin-4-yl)oxy]pyridin-3-yl}-1-oxa-3,8-diazaspiro[4,5]decan-2-one obtained in Reference Example 13-3, and 2,2,2-trifluoroethyl trifluoromethanesulfonate in place of bromoethane.

$^1$H-NMR (400 MHz, CDCl$_3$) δ: 1.49-2.26 (16H, m), 2.57-2.86 (3H, brm), 3.14-3.27 (4H, m), 3.47 (2H, s), 3.89 (2H, q, J=8.8 Hz), 4.98 (1H, brs), 6.66 (1H, d, J=8.8 Hz), 7.30-7.25 (4H, m), 7.79 (1H, d, J=2.9 Hz)

Example 3-191

Production of 8-{6-[(1-cyclobutylpiperidin-4-yl)oxy]pyridin-3-yl}-3-[4-(methylsulfonyl)phenyl]-1-oxa-3,8-diazaspiro[4,5]decan-2-one The entitled compound was obtained as a pale yellow solid, according to the same method as in Example 3 or according to a method similar to it but using 8-{6-[(1-cyclobutylpiperidin-4-yl)oxy]pyridin-3-yl}-1-oxa-3,8-diazaspiro[4,5]decan-2-one obtained in Reference Example 13-3, and 1-bromo-4-methylsulfonyl)benzene in place of 1-bromo-4-fluorobenzene.

$^1$H-NMR (400 MHz, CDCl$_3$) δ: 1.56-2.26 (16H, m), 2.61-2.83 (3H, brm), 3.05 (3H, s), 3.22-3.30 (4H, m), 3.86 (2H, s), 4.98 (1H, brs), 6.67 (1H, d, J=8.8 Hz), 7.31 (1H, dd, J=8.8, 2.9 Hz), 7.77 (2H, d, J=8.8 Hz), 7.82 (1H, d, J=2.9 Hz), 7.96 (2H, d, J=8.8 Hz)

Example 3-192

Production of 8-{6-[(1-cyclobutylpiperidin-4-yl)oxy]pyridin-3-yl}-3-(2-ethoxypyrimidin-5-yl)-1-oxa-3,8-diazaspiro[4,5]decan-2-one The entitled compound was obtained as a white solid, according to the same method as in Example 3 or according to a method similar to it but using 8-{6-[(1-cyclobutylpiperidin-4-yl)oxy]pyridin-3-yl}-1-oxa-3,8-diazaspiro[4,5]decan-2-one obtained in Reference Example 13-3, and 5-bromo-2-ethoxypyrimidine in place of 1-bromo-4-fluorobenzene.

$^1$H-NMR (400 MHz, CDCl$_3$) δ: 1.44 (3H, t, J=7.1 Hz), 1.65-2.19 (16H, m), 2.60-2.82 (3H, brm), 3.19-3.32 (5H, m), 3.78 (2H, s), 4.42 (2H, q, J=7.2 Hz), 4.97 (1H, brs), 6.67 (1H, d, J=8.8 Hz), 7.30 (1H, dd, J=9.0, 3.2 Hz), 7.81 (1H, d, J=2.9 Hz), 8.74 (2H, s)

Example 3-193

Production of 8-{6-[(1-cyclobutylpiperidin-4-yl)oxy]pyridin-3-yl}-3-(1-methyl-1H-pyrazol-4-yl)-1-oxa-3,8-diazaspiro[4,5]decan-2-one The entitled compound was obtained as a brown solid, according to the same method as in Example 3 or according to a method similar to it but using 8-{6-[(1-cyclobutylpiperidin-4-yl)oxy]pyridin-3-yl}-1-oxa-3,8-diazaspiro[4,5]decan-2-one obtained in Reference Example 13-3, and 4-bromo-1-methyl-1H-pyrazole in place of 1-bromo-4-fluorobenzene.

$^1$H-NMR (400 MHz, CDCl$_3$) δ: 1.66-2.16 (16H, m), 2.61-2.83 (3H, brm), 3.21-3.28 (4H, m), 3.67 (2H, s), 3.89 (3H, s), 4.98 (1H, brs), 6.66 (1H, d, J=9.3 Hz), 7.30 (1H, dd, J=8.8, 2.9 Hz), 7.35 (1H, s), 7.77 (1H, s), 7.81 (1H, d, J=2.9 Hz)

Example 3-194

Production of 8-{6-[(1-cyclobutylpiperidin-4-yl)oxy]pyridin-3-yl}-3-(1-methyl-1H-pyrazol-3-yl)-1-oxa-3,8-diazaspiro[4,5]decan-2-one The entitled compound was obtained as a brown solid, according to the same method as in Example 3 or according to a method similar to it but using 8-{6-[(1-cyclobutylpiperidin-4-yl)oxy]pyridin-3-yl}-1-oxa-3,8-diazaspiro[4,5]decan-2-one obtained in Reference Example 13-3, and 3-iodo-1-methyl-1H-pyrazole in place of 1-bromo-4-fluorobenzene.

$^1$H-NMR (400 MHz, CDCl$_3$) δ: 1.56-2.25 (16H, m), 2.60-2.83 (3H, brm), 3.17-3.31 (4H, m), 3.82 (3H, s), 3.87 (2H, s), 4.98 (1H, brs), 6.68-6.63 (2H, m), 7.29 (2H, dd, J=9.5, 2.7 Hz), 7.80 (1H, d, J=2.4 Hz)

Example 3-195

Production of 5-(8-{6-[(1-cyclobutylpiperidin-4-yl)oxy]pyridin-3-yl}-2-oxo-1-oxa-3,8-diazaspiro[4,5]decan-3-yl)nicotinonitrile The entitled compound was obtained as a pale yellow solid, according to the same method as in Example 3 or according to a method similar to it but using 8-{6-[(1-cyclobutylpiperidin-4-yl)oxy]pyridin-3-yl}-1-oxa-3,8-diazaspiro[4,5]decan-2-one obtained in Reference Example 13-3, and 5-bromonicotinonitrile in place of 1-bromo-4-fluorobenzene.

$^1$H-NMR (400 MHz, CDCl$_3$) δ: 1.54-2.23 (16H, m), 2.61-2.81 (3H, brm), 3.20-3.33 (4H, m), 3.86 (2H, s), 4.98 (1H, brs), 6.68 (1H, d, J=9.3 Hz), 7.31 (1H, dd, J=9.0, 3.2 Hz), 7.82 (1H, d, J=2.9 Hz), 8.55-8.53 (1H, m), 8.65 (1H, d, J=2.0 Hz), 8.81 (1H, d, J=2.4 Hz)

Example 3-196

Production of 8-{6-[(1-cyclobutylpiperidin-4-yl)oxy]pyridin-3-yl}-3-pyrazin-2-yl-1-oxa-3,8-diazaspiro[4,5]decan-2-one The entitled compound was obtained as a pale yellow solid, according to the same method as in Example 3 or according to a method similar to it but using 8-{6-[(1-cyclobutylpiperidin-4-yl)oxy]pyridin-3-yl}-1-oxa-3,8-diazaspiro[4,5]decan-2-one obtained in Reference Example 13-3, and 2-iodopyrazine in place of 1-bromo-4-fluorobenzene.

$^1$H-NMR (400 MHz, CDCl$_3$) δ: 1.61-2.19 (16H, m), 2.60-2.80 (3H, brm), 3.21-3.29 (4H, m), 4.00 (2H, s), 4.97 (1H, brs), 6.67 (1H, d, J=9.0 Hz), 7.31 (1H, dd, J=9.0, 3.2 Hz), 7.82 (1H, d, J=2.2 Hz), 8.27 (1H, s), 8.34 (1H, d, J=2.5 Hz), 9.60 (1H, s)

Example 3-197

Production of 8-{6-[(1-cyclobutylpiperidin-4-yl)oxy]pyridin-3-yl}-3-(6-methoxypyridin-3-yl)-1-oxa-3,8-diazaspiro[4,5]decan-2-one The entitled compound was obtained as a white solid, according to the same method as in Example 3 or according to a method similar to it but using 8-{6-[(1-cyclobutylpiperidin-4-yl)oxy]pyridin-3-yl}-1-oxa-3,8-diazaspiro[4,5]decan-2-one obtained in Reference Example 13-3, and 5-bromo-2-methoxypyridine in place of 1-bromo-4-fluorobenzene.

$^1$H-NMR (400 MHz, CDCl$_3$) δ: 1.52-2.21 (16H, m), 2.61-2.81 (3H, brm), 3.22-3.30 (4H, m), 3.77 (2H, s), 3.93 (3H, s), 4.98 (1H, brs), 6.67 (1H, d, J=9.0 Hz), 6.79 (1H, d, J=9.2 Hz), 7.30 (1H, dd, J=9.1, 2.8 Hz), 7.81 (1H, d, J=3.1 Hz), 8.06 (1H, d, J=2.7 Hz), 8.11 (1H, dd, J=9.0, 2.9 Hz)

Example 3-198

Production of 8-{6-[(1-cyclobutylpiperidin-4-yl)oxy]pyridin-3-yl}-3-(2-methoxypyrimidin-5-yl)-1-oxa-3,8-diazaspiro[4,5]decan-2-one The entitled compound was obtained as a pale yellow solid, according to the same method as in Example 3 or according to a method similar to it but using 8-{6-[(1-cyclobutylpiperidin-4-yl)oxy]pyridin-3-yl}-1-oxa-3,8-diazaspiro[4,5]decan-2-one obtained in Reference Example 13-3, and 5-bromo-2-methoxypyrimidine in place of 1-bromo-4-fluorobenzene.

$^1$H-NMR (400 MHz, CDCl$_3$) δ: 1.60-2.19 (16H, m), 2.62-2.80 (3H, brm), 3.21-3.30 (4H, m), 3.78 (2H, s), 4.02 (3H, s), 4.98 (1H, brs), 6.67 (1H, d, J=9.0 Hz), 7.31 (1H, dd, J=9.2, 2.7 Hz), 7.81 (1H, d, J=2.7 Hz), 8.75 (2H, s)

Example 3-199

Production of 8-{6-[(1-cyclobutylpiperidin-4-yl)oxy]pyridin-3-yl}-3-[5-trifluoromethyl)pyridin-3-yl]-1-oxa-3,8-diazaspiro[4,5]decan-2-one The entitled compound was obtained as a brown solid, according to the same method as in Example 3 or according to a method similar to it but using 8-{6-[(1-cyclobutylpiperidin-4-yl)oxy]pyridin-3-yl}-1-oxa-3,8-diazaspiro[4,5]decan-2-one obtained in Reference Example 13-3, and 3-bromo-5-(trifluoromethyl)pyridine in place of 1-bromo-4-fluorobenzene.

$^1$H-NMR (400 MHz, CDCl$_3$) δ: 1.59-2.20 (16H, m), 2.61-2.83 (3H, brm), 3.19-3.35 (4H, m), 3.88 (2H, s), 4.99 (1H, brs), 6.68 (1H, d, J=8.8 Hz), 7.31 (1H, dd, J=9.0, 3.2 Hz), 7.82 (1H, d, J=2.9 Hz), 8.43 (1H, s), 8.67 (1H, s), 8.85 (1H, s)

Example 3-200

Production of 8-{6-[(1-cyclobutylpiperidin-4-yl)oxy]pyridin-3-yl}-3-(5-methoxypyridin-3-yl)-1-oxa-3,8-diazaspiro[4,5]decan-2-one The entitled compound was obtained as a brown solid, according to the same method as in Example 3 or according to a method similar to it but using 8-{6-[(1-cyclobutylpiperidin-4-yl)oxy]pyridin-3-yl}-1-oxa-3,8-diazaspiro[4,5]decan-2-one obtained in Reference Example 13-3, and 3-bromo-5-methoxypyridine in place of 1-bromo-4-fluorobenzene.

$^1$H-NMR (400 MHz, CDCl$_3$) δ: 1.61-2.18 (16H, m), 2.60-2.84 (3H, brm), 3.18-3.33 (4H, m), 3.83 (2H, s), 3.89 (3H, s), 4.99 (1H, brs), 6.67 (1H, d, J=9.3 Hz), 7.31 (1H, dd, J=9.3, 2.9 Hz), 7.82 (1H, d, J=2.9 Hz), 7.96 (1H, t, J=2.2 Hz), 8.08 (1H, d, J=2.4 Hz), 8.13 (1H, d, J=2.4 Hz).

Example 3-201

Production of 8-{6-[(1-cyclobutylpiperidin-4-yl)oxy]pyridin-3-yl}-3-(5-methoxypyrazin-2-yl)-1-oxa-3,8-diazaspiro[4,5]decan-2-one The entitled compound was obtained as a pale yellow solid, according to the same method as in Example 3 or according to a method similar to it but using 8-{6-[(1-cyclobutylpiperidin-4-yl)oxy]pyridin-3-yl}-1-oxa-3,8-diazaspiro[4,5]decan-2-one obtained in Reference Example 13-3, and 2-bromo-5-methoxypyrazine in place of 1-bromo-4-fluorobenzene.

$^1$H-NMR (400 MHz, CDCl$_3$) δ: 1.59-2.18 (16H, m), 2.58-2.82 (3H, brm), 3.18-3.30 (4H, m), 3.97 (5H, s), 4.97 (1H, brs), 6.67 (1H, d, J=9.0 Hz), 7.30 (1H, dd, J=9.0, 3.2 Hz), 7.81 (1H, d, J=2.9 Hz), 7.93 (1H, d, J=1.5 Hz), 9.03 (1H, d, J=1.5 Hz)

Example 3-202

Production of 8-{6-[(1-isopropylpiperidin-4-yl)oxy]pyridin-3-yl}-3-(2-methoxypyrimidin-5-yl)-1-oxa-3,8-diazaspiro[4,5]decan-2-one The entitled compound was obtained as a pale orange solid, according to the same method as in Example 3 or according to a method similar to it but using 8-{6-[(1-isopropylpiperidin-4-yl)oxy]pyridin-3-yl}-1-oxa-3,8-diazaspiro[4,5]decan-2-one obtained in Reference Example 13-4, and 5-bromo-2-methoxypyrimidine in place of 1-bromo-4-fluorobenzene.

$^1$H-NMR (400 MHz, CDCl$_3$) δ: 1.08 (6H, d, J=6.3 Hz), 1.72-1.89 (2H, m), 1.97-2.23 (6H, m), 2.35-2.54 (2H, m), 2.69-2.90 (3H, m), 3.18-3.33 (4H, m), 3.78 (2H, s), 4.02 (3H, s), 4.92-5.04 (1H, m), 6.68 (1H, d, J=8.9 Hz), 7.31 (1H, dd, J=8.9, 3.1 Hz), 7.82 (1H, d, J=3.1 Hz), 8.75 (2H, s)

Example 3-203

Production of 5-(8-{6-[(1-isopropylpiperidin-4-yl)oxy]pyridin-3-yl}-2-oxo-1-oxa-3,8-diazaspiro[4,5]decan-3-yl)nicotinonitrile The entitled compound was obtained as a white solid, according to the same method as in Example 3 or according to a method similar to it but using 8-{6-[(1-isopropylpiperidin-4-yl)oxy]pyridin-3-yl}-1-oxa-3,8-diazaspiro[4,5]decan-2-one obtained in Reference Example 13-4, and 5-bromonicotinonitrile in place of 1-bromo-4-fluorobenzene.

H-NMR (400 MHz, CDCl$_3$) δ: 1.10 (6H, d, J=6.3 Hz), 1.76-1.90 (2H, m), 2.01-2.24 (6H, m), 2.40-2.59 (2H, m), 2.75-2.91 (3H, m), 3.19-3.35 (4H, m), 3.86 (2H, s), 4.92-5.04 (1H, m), 6.68 (1H, d, J=9.2 Hz), 7.31 (1H, dd, J=9.2, 2.7 Hz), 7.82 (1H, d, J=2.7 Hz), 8.54 (1H, dd, J=2.8, 1.6 Hz), 8.65 (1H, d, J=1.6 Hz), 8.82 (1H, d, J=2.8 Hz)

Example 3-204

Production of 8-{6-[(1-isopropylpiperidin-4-yl)oxy]pyridin-3-yl}-3-pyrazin-2-yl-1-oxa-3,8-diazaspiro[4,5]decan-2-one The entitled compound was obtained as a white solid, according to the same method as in Example 3 or according to a method similar to it but using 8-{6-[(1-isopropylpiperidin-4-yl)oxy]pyridin-3-yl}-1-oxa-3,8-diazaspiro[4,5]decan-2-one obtained in Reference Example 13-4, and 2-iodopyrazine in place of 1-bromo-4-fluorobenzene.

$^1$H-NMR (400 MHz, CDCl$_3$) δ: 1.09 (6H, d, J=6.3 Hz), 1.72-1.92 (2H, m), 1.98-2.25 (6H, m), 2.33-2.57 (2H, m), 2.68-2.94 (3H, m), 3.19-3.31 (4H, m), 4.00 (2H, s), 4.89-5.02 (1H, m), 6.68 (1H, d, J=9.2 Hz), 7.31 (1H, dd, J=9.2, 2.9 Hz), 7.82 (1H, d, J=2.9 Hz), 8.27 (1H, dd, J=2.6, 1.6 Hz), 8.34 (1H, d, J=2.6 Hz), 9.60 (1H, d, J=1.6 Hz)

Example 3-205

Production of 8-{6-[(1-isopropylpiperidin-4-yl)oxy]pyridin-3-yl}-3-(1-methyl-1H-pyrazol-4-yl)-1-oxa-3,8-diazaspiro[4,5]decan-2-one The entitled compound was obtained as a white solid, according to the same method as in Example 3 or according to a method similar to it but using 8-{6-[(1-isopropylpiperidin-4-yl)oxy]pyridin-3-yl}-1-oxa-3,8-diazaspiro[4,5]decan-2-one obtained in Reference Example 13-4, and 4-bromo-1-methyl-1H-pyrazole in place of 1-bromo-4-fluorobenzene.

$^1$H-NMR (400 MHz, CDCl$_3$) δ: 1.10 (6H, d, J=6.3 Hz), 1.72-1.91 (2H, m), 1.94-2.23 (6H, m), 2.34-2.61 (2H, m), 2.69-2.95 (3H, m), 3.16-3.32 (4H, m), 3.67 (2H, s), 3.90 (3H, s), 4.91-5.02 (1H, m), 6.67 (1H, d, J=8.9 Hz), 7.30 (1H, dd, J=8.9, 3.1 Hz), 7.36 (1H, s), 7.77 (1H, s), 7.81 (1H, d, J=3.1 Hz)

Example 4

Production of 4-(4-methoxyphenyl)-9-[4-(3-piperidin-1-ylpropoxy)phenyl]-1-oxa-4,9-diazaspiro[5,5]undecan-3-one

(a) 9-[4-(Benzyloxy)phenyl]-4-(4-methoxyphenyl)-1-oxa-4,9-diazaspiro[5,5]undecan-3-one 9-[4-(benzyloxy)phenyl]-1-oxa-4,9-diazaspiro[5,5]undecan-3-one (500 mg, 1.42 mmol) obtained in Reference Example 9, 1-iodo-4-methoxybenzene (400 mg, 1.70 mmol), potassium phosphate (603 mg, 2.84 mmol), copper iodide (30 mg, 0.142 mmol) and N,N'-dimethylaminoethane (26 mg, 0.284 mmol) were mixed in 1,4-dioxane, and stirred overnight with heating in a sealed tube at 110° C. The reaction solution was diluted with ethyl acetate, washed with water and saturated saline in that order, and the organic layer was dried with sodium sulfate. The solvent was evaporated off, and the residue was purified through silica gel column chromatography (eluate: ethyl acetate/hexane=60/40 to 75/25) to obtain the entitled compound (530 mg, 81%) as a white solid.

(b) 9-(4-Hydroxyphenyl)-4-(4-methoxyphenyl)-1-oxa-4,9-diazaspiro[5,5]undecan-3-one The benzyloxy compound (529 mg, 1.15 mmol) obtained in (a) was dissolved in a mixed solvent of methanol/tetrahydrofuran (1/1), then 10% palladium-carbon (110 mg, 0.103 mmol) was added thereto and stirred overnight in a hydrogen atmosphere. The reaction solution was filtered through Celite, the Celite was washed with mixed solvent of chloroform/methanol, and the mother liquid was concentrated to obtain the entitled compound (350 mg, 82%) as a violet solid.

(c) 4-(4-Methoxyphenyl)-9-[4-(3-piperidin-1-ylpropoxy)phenyl]-1-oxa-4,9-diazaspiro[5,5]undecan-3-one The phenol compound (288 mg, 0.781 mmol) obtained in (b), 1-(3-bromopropyl)piperidine hydrobromide (450 mg, 1.56 mmol) produced according to a method described in a patent (U.S. Pat. No. 4,751,302), and cesium carbonate (1.02 g, 3.12 mmol) were mixed in N,N-dimethylformamide, and stirred overnight at room temperature. The reaction solution was diluted with ethyl acetate, washed with water and saturated saline in that order, and the organic layer was dried with sodium sulfate. The solvent was evaporated off under reduced pressure, and the resulting residue was purified through reversed-phase preparative HPLC (liquid A: 0.1% TFA/water, liquid B: 0.1% TFA/acetonitrile, A/B=90/10 to 50/50, 8 minute linear concentration gradient elution, flow rate 40 ml/min), and fractions containing the intended product were collected to obtain a pale yellow solid (285 mg, 74%). The solid was crystallized in a mixed solvent of ethanol/water (2/1) to obtain the entitled compound as a pale pink solid (184 mg, 48%).

$^1$H-NMR (400 MHz, CDCl$_3$) δ: 1.43 (2H, s), 1.54-1.63 (4H, m), 1.82-1.90 (2H, m), 1.92-1.99 (2H, m), 2.13 (2H, d, J=12.7 Hz), 2.39-2.48 (6H, m), 3.04-3.10 (2H, m), 3.24-3.29 (2H, m), 3.59 (2H, s), 3.81 (3H, s), 3.96 (2H, t, J=6.6 Hz), 4.34 (2H, s), 6.82-6.86 (2H, m), 6.91-6.96 (2H, m), 7.18-7.22 (2H, m), 7.26 (2H, s)

Example 4-1

Production of 4-(3-methoxyphenyl)-9-[4-(3-piperidin-1-ylpropoxy)phenyl]-1-oxa-4,9-diazaspiro[5,5]undecan-3-one (a) 9-[4-(Benzyloxy)phenyl]-4-(3-methoxyphenyl)-1-oxa-4,9-diazaspiro[5,5]undecan-3-one The entitled compound was obtained as a pale yellow solid, according to the same method as in Example 4-(a) or according to a method similar to it but using 1-bromo-3-methoxybenzene in place of 1-iodo-4-methoxybenzene.

(b) 9-(4-Hydroxyphenyl)-4-(3-methoxyphenyl)-1-oxa-4,9-diazaspiro[5,5]undecan-3-one The entitled compound was obtained as a pink solid, according to the same method as in Example 4-(b) or according to a method similar to it but using the benzyloxy compound obtained in (a).

(c) 4-(3-Methoxyphenyl)-9-[4-(3-piperidin-1-ylpropoxy)phenyl]-1-oxa-4,9-diazaspiro[5,5]undecan-3-one The entitled compound was obtained as a yellow solid, according to the same method as in Example 4-(c) or according to a method similar to it but using the phenol compound obtained in (b).

$^1$H-NMR (400 MHz, CDCl$_3$) δ: 1.44 (2H, brs), 1.58-1.60 (4H, m), 1.82-1.90 (2H, m), 1.93-2.14 (2H, m), 2.13 (2H, d, J=12.4 Hz), 2.40 (4H, brs), 2.47 (2H, t, J=11.6 Hz), 3.07 (2H, t, J=6.8 Hz), 3.26 (2H, d, J=12.4 Hz), 3.62 (2H, s), 3.82 (3H, s), 3.96 (2H, t, J=6.4 Hz), 4.35 (2H, s), 6.82-6.93 (7H, m), 7.32 (2H, t, J=9.2 Hz)

Example 4-2

Production of 4-(4-fluorophenyl)-9-[4-(3-piperidin-1-ylpropoxy)phenyl]-1-oxa-4,9-diazaspiro[5,5]undecan-3-one (a) 9-[4-(Benzyloxy)phenyl]-4-(4-fluorophenyl)-1-oxa-4,9-diazaspiro[5,5]undecan-3-one The entitled compound was obtained as a pale yellow solid, according to the same method as in Example 4-(a) or according to a method similar to it but using 1-bromo-4-fluorobenzene in place of 1-iodo-4-methoxybenzene.

(b) 4-(4-Fluorophenyl)-9-(4-hydroxyphenyl)-1-oxa-4,9-diazaspiro[5,5]undecan-3-one The entitled compound was obtained as a pink solid, according to the same method as in Example 4-(b) or according to a method similar to it but using the benzyloxy compound obtained in (a).

(c) 4-(4-Fluorophenyl)-9-[4-(3-piperidin-1-ylpropoxy)phenyl]-1-oxa-4,9-diazaspiro[5,5]undecan-3-one The entitled compound was obtained as a white solid, according to the same method as in Example 4-(c) or according to a method similar to it but using the phenol compound obtained in (b).

$^1$H-NMR (400 MHz, CDCl$_3$) δ: 1.53 (2H, s), 1.76-1.89 (6H, m), 2.13 (4H, d, J=12.7 Hz), 2.51-2.83 (6H, brm), 3.07 (2H, td, J=11.6, 2.6 Hz), 3.28 (2H, d, J=12.7 Hz), 3.60 (2H, s), 3.98 (2H, t, J=6.1 Hz), 4.35 (2H, s), 6.80-6.85 (2H, m), 6.90-6.95 (2H, m), 7.08-7.14 (2H, m), 7.24-7.30 (2H, m)

Example 4-3

Production of 4-(6-fluoropyridin-3-yl)-9-[4-(3-piperidin-1-ylpropoxy)phenyl]-1-oxa-4,9-diazaspiro[5,5]undecan-3-one (a) 9-[4-(Benzyloxy)phenyl]-4-(6-fluoropyridin-3-yl)-1-oxa-4,9-diazaspiro[5,5]undecan-3-one The entitled compound was obtained as a pale yellow solid, according to the same method as in Example 4-(a) or according to a method similar to it but using 5-bromo-2-fluoropyridine in place of 1-iodo-4-methoxybenzene.

(b) 4-(6-Fluoropyridin-3-yl)-9-(4-hydroxyphenyl)-1-oxa-4,9-diazaspiro[5,5]undecan-3-one The entitled compound was obtained as a violet solid, according to the same method as in Example 4-(b) or according to a method similar to it but using the benzyloxy compound obtained in (a).

(c) 4-(6-Fluoropyridin-3-yl)-9-[4-(3-piperidin-1-ylpropoxy)phenyl]-1-oxa-4,9-diazaspiro[5,5]undecan-3-one The entitled compound was obtained as a brown solid, according to the same method as in Example 4-(c) or according to a method similar to it but using the phenol compound obtained in (b).

$^1$H-NMR (400 MHz, CDCl$_3$) δ: 1.44 (2H, brs), 1.57-1.61 (4H, m), 1.83-1.91 (2H, m), 1.93-2.00 (2H, m), 2.13 (2H, d, J=12.4 Hz), 2.42 (4H, brs), 2.49 (2H, t, J=7.2 Hz), 3.03-3.09 (2H, m), 3.27-3.30 (2H, m), 3.95 (2H, s), 3.96 (2H, t, J=6.4 Hz), 4.37 (2H, s), 6.84 (2H, d, J=9.2 Hz), 6.92 (2H, d, J=9.2 Hz), 7.00 (1H, dd, J=8.8, 3.2 Hz), 7.81-7.86 (1H, m), 8.19 (1H, d, J=1.6 Hz)

Example 4-4

Production of 4-(6-methoxypyridin-3-yl)-9-[4-(3-piperidin-1-ylpropoxy)phenyl]-1-oxa-4,9-diazaspiro[5,5]undecan-3-one (a) 9-[4-(Benzyloxy)phenyl]-4-(6-methoxypyridin-3-yl)-1-oxa-4,9-diazaspiro[5,5]undecan-3-one The entitled compound was obtained as a pale yellow solid, according to the same method as in Example 4-(a) or according to a method similar to it but using 5-bromo-2-methoxypyridine in place of 1-iodo-4-methoxybenzene.

(b) 9-(4-Hydroxyphenyl)-4-(6-methoxypyridin-3-yl)-1-oxa-4,9-diazaspiro[5,5]undecan-3-one The entitled compound was obtained as a violet solid, according to the same method as in Example 4-(b) or according to a method similar to it but using the benzyloxy compound obtained in (a).

(c) 4-(6-Methoxypyridin-3-yl)-9-[4-(3-piperidin-1-ylpropoxy)phenyl]-1-oxa-4,9-diazaspiro[5,5]undecan-3-one The entitled compound was obtained as a white solid, according to the same method as in Example 4-(c) or according to a method similar to it but using the phenol compound obtained in (b).
$^1$H-NMR (400 MHz, CDCl$_3$) δ: 1.44 (2H, d, J=4.9 Hz), 1.56-1.61 (4H, m), 1.83-1.90 (2H, m), 1.92-1.99 (2H, m), 2.13 (2H, d, J=13.2 Hz), 2.39-2.48 (6H, m), 3.07 (2H, td, J=11.6, 2.4 Hz), 3.27 (2H, dt, J=12.2, 4.4 Hz), 3.60 (2H, s), 3.94-3.98 (5H, m), 4.35 (2H, s), 6.79 (1H, d, J=8.8 Hz), 6.84 (2H, dt, J=9.3, 3.4 Hz), 6.93 (2H, dt, J=8.8, 3.4 Hz), 7.55 (1H, dd, J=8.8, 2.9 Hz), 8.10 (1H, d, J=3.4 Hz)

Example 4-5

Production of 4-(6-methoxypyridin-2-yl)-9-[4-(3-piperidin-1-ylpropoxy)phenyl]-1-oxa-4,9-diazaspiro[5,5]undecan-3-one (a) 9-[4-(Benzyloxy)phenyl]-4-(6-methoxypyridin-2-yl)-1-oxa-4,9-diazaspiro[5,5]undecan-3-one The entitled compound was obtained as a white solid, according to the same method as in Example 4-(a) or according to a method similar to it but using 6-bromo-2-methoxypyridine in place of 1-iodo-4-methoxybenzene.

(b) 9-(4-Hydroxyphenyl)-4-(6-methoxypyridin-2-yl)-1-oxa-4,9-diazaspiro[5,5]undecan-3-one The entitled compound was obtained as a violet solid, according to the same method as in Example 4-(b) or according to a method similar to it but using the benzyloxy compound obtained in (a).

(c) 4-(6-Methoxypyridin-2-yl)-9-[4-(3-piperidin-1-ylpropoxy)phenyl]-1-oxa-4,9-diazaspiro[5,5]undecan-3-one The entitled compound was obtained as a pale yellow solid, according to the same method as in Example 4-(c) or according to a method similar to it but using the phenol compound obtained in (b).
$^1$H-NMR (400 MHz, CDCl$_3$) δ: 1.47 (2H, brs), 1.65 (4H, brs), 1.85-1.91 (2H, m), 1.92-2.08 (4H, m), 2.45-2.55 (6H, m), 3.05-3.10 (2H, m), 3.25-3.28 (2H, m), 3.89 (2H, s), 3.97 (2H, t, J=6.0 Hz), 4.00 (2H, s), 4.35 (2H, s), 6.57 (1H, dd, J=8.0, 1.2 Hz), 6.83 (2H, d, J=9.2 Hz), 6.93 (2H, d, J=9.2 Hz), 7.52-7.68 (2H, m)

Example 4-6

4-Methyl-9-(4-{3-[(2R)-2-methylpyrrolidin-1-yl]propoxy}phenyl)-1-oxa-4,9-diazaspiro[5,5]undecan-3-one (a) 9-[4-(Benzyloxy)phenyl]-4-methyl-1-oxa-4,9-diazaspiro[5,5]undecan-3-one The entitled compound was obtained according to the same method as in Example 3-96 or according to a method similar to it but using 9-[4-(benzyloxy)phenyl]-1-oxa-4,9-diazaspiro[5,5]undecan-3-one obtained in Reference Example 9 and iodomethane.

(b) 9-(4-Hydroxyphenyl)-4-methyl-1-oxa-4,9-diazaspiro[5,5]undecan-3-one

The entitled compound was obtained according to the same method as in Example 4-(b) or according to a method similar to it but using the benzyloxy compound obtained in (a).

(c) 4-Methyl-9-(4-{3-[(2R)-2-methylpyrrolidin-1-yl]propoxy}phenyl)-1-oxa-4,9-diazaspiro[5,5]undecan-3-one The entitled compound was obtained as a pale yellow solid, according to the same method as in Example 4-(c) or according to a method similar to it but using the phenol compound obtained in (b) and (2R)-1-(3-bromopropyl)-2-methylpyrrolidine hydrobromide produced in Reference Example 4-2.
$^1$H-NMR (400 MHz, CDCl$_3$) δ: 1.10 (3H, d, J=5.9 Hz), 1.39-1.48 (1H, m), 1.58-1.82 (4H, m), 1.88-2.04 (5H, m), 2.10-2.24 (2H, m), 2.27-2.35 (1H, m), 2.94-3.04 (3H, m), 3.00 (3H, s), 3.16-3.27 (3H, m), 3.24 (2H, s), 3.93-4.02 (2H, m), 4.17 (2H, s), 6.84 (2H, d, J=9.3 Hz), 6.91 (2H, d, J=9.3 Hz)

Example 4-7

Production of 4-methyl-9-(4-{3-[(2S)-2-methylpyrrolidin-1-yl]propoxy}phenyl)-1-oxa-4,9-diazaspiro[5,5]undecan-3-one The entitled compound was obtained as a pale brown solid, according to the same method as in Example 4-(c) or according to a method similar to it but using the phenol compound obtained in 4-6-(b) and (2S)-1-(3-bromopropyl)-2-methylpyrrolidine hydrobromide produced in Reference Example 4-1.
$^1$H-NMR (400 MHz, CDCl$_3$) δ: 1.11 (3H, d, J=6.3 Hz), 1.39-1.49 (1H, m), 1.60-1.83 (4H, m), 1.88-2.04 (5H, m), 2.09-2.24 (2H, m), 2.28-2.34 (1H, m), 2.95-3.04 (3H, m), 3.00 (3H, s), 3.17-3.26 (3H, m), 3.24 (2H, s), 3.93-4.03 (2H, m), 4.17 (2H, s), 6.84 (2H, d, J=9.3 Hz), 6.92 (2H, d, J=9.3 Hz).

Example 4-8

Production of 4-ethyl-9-(4-{3-[(2R)-2-methylpyrrolidin-1-yl]propoxy}phenyl)-1-oxa-4,9-diazaspiro[5,5]undecan-3-one (a) 9-[4-(Benzyloxy)phenyl]-4-ethyl-1-oxa-4,9-diazaspiro[5,5]undecan-3-one The entitled compound was obtained according to the same method as in Example 3-96 or according to a method similar to it but using 9-[4-(benzyloxy)phenyl]-1-oxa-4,9-diazaspiro[5,5]undecan-3-one obtained in Reference Example 9 and bromoethane.

(b) 4-Ethyl-9-(4-hydroxyphenyl)-1-oxa-4,9-diazaspiro[5,5]undecan-3-one

The entitled compound was obtained according to the same method as in Example 4-(b) or according to a method similar to it but using the benzyloxy compound obtained in (a).

(c) 4-Ethyl-9-(4-{3-[(2R)-2-methylpyrrolidin-1-yl]propoxy}phenyl)-1-oxa-4,9-diazaspiro[5,5]undecan-3-one The entitled compound was obtained according to the same method as in Example 4-(c) or according to a method similar to it but using the phenol compound obtained in (b) and (2R)-1-(3-bromopropyl)-2-methylpyrrolidine hydrobromide produced in Reference Example 4-2.

$^1$H-NMR (400 MHz, CDCl$_3$) δ: 1.16 (3H, t, J=7.3 Hz), 1.22 (3H, d, J=6.3 Hz), 1.53-1.62 (1H, m), 1.74-1.82 (3H, m), 1.85-1.93 (1H, m), 1.98-2.12 (5H, m), 2.29-2.43 (2H, m), 2.49-2.58 (1H, m), 2.98-3.12 (3H, m), 3.20-3.27 (2H, m), 3.23 (2H, s), 3.29-3.36 (1H, m), 3.46 (2H, q, J=7.2 Hz), 3.95-4.04 (2H, m), 4.16 (2H, s), 6.83 (2H, d, J=8.8 Hz), 6.92 (2H, d, J=9.3 Hz)

Example 4-9

Production of 9-(4-{3-[(3S)-3-methylpiperidin-1-yl]propoxy}phenyl)-4-propyl-1-oxa-4,9-diazaspiro[5,5]undecan-3-one (a) 9-[4-(Benzyloxy)phenyl]-4-propyl-1-oxa-4,9-diazaspiro[5,5]undecan-3-one The entitled compound was obtained according to the same method as in Example 3-96 or according to a method similar to it but using 9-[4-(benzyloxy)phenyl]-1-oxa-4,9-diazaspiro[5,5]undecan-3-one obtained in Reference Example 9 and 1-bromopropane.

(b) 9-(4-Hydroxyphenyl)-4-propyl-1-oxa-4,9-diazaspiro[5,5]undecan-3-one

The entitled compound was obtained according to the same method as in Example 4-(b) or according to a method similar to it but using the benzyloxy compound obtained in (a).

(c) 9-(4-{3-[(3S)-3-methylpiperidin-1-yl]propoxy}phenyl)-4-propyl-1-oxa-4,9-diazaspiro[5,5]undecan-3-one The entitled compound was obtained as a white solid according to the same method as in Example 4-(c) or according to a method similar to it but using the phenol compound obtained in (b) and (3S)-1-(3-bromopropyl)-3-methylpiperidine hydrobromide produced in Reference Example 4.

$^1$H-NMR (400 MHz, CDCl$_3$) δ: 0.81-0.90 (1H, m), 0.86 (3H, d, J=6.3 Hz), 0.93 (3H, t, J=7.3 Hz), 1.54-1.89 (10H, m), 1.94-2.02 (4H, m), 2.49 (2H, t, J=7.3 Hz), 2.83-2.91 (2H, m), 3.02 (2H, td, J=11.7, 2.4 Hz), 3.20-3.25 (2H, m), 3.22 (2H, s), 3.37 (2H, t, J=7.6 Hz), 3.96 (2H, t, J=6.3 Hz), 4.17 (2H, s), 6.83 (2H, d, J=9.3 Hz), 6.91 (2H, d, J=9.3 Hz)

Example 4-10

Production of 4-isopropyl-9-(4-{3-[(3S)-3-methylpiperidin-1-yl]propoxy}phenyl)-1-oxa-4,9-diazaspiro[5,5]undecan-3-one (a) 9-[4-(Benzyloxy)phenyl]-4-isopropyl-1-oxa-4,9-diazaspiro[5,5]undecan-3-one The entitled compound was obtained according to the same method as in Example 3-96 or according to a method similar to it but using 9-[4-(benzyloxy)phenyl]-1-oxa-4,9-diazaspiro[5,5]undecan-3-one obtained in Reference Example 9 and 2-bromopropane.

(b) 9-(4-Hydroxyphenyl)-4-isopropyl-1-oxa-4,9-diazaspiro[5,5]undecan-3-one

The entitled compound was obtained according to the same method as in Example 4-(b) or according to a method similar to it but using the benzyloxy compound obtained in (a).

(c) 4-Isopropyl-9-(4-{3-[(3S)-3-methylpiperidin-1-yl]propoxy}phenyl)-1-oxa-4,9-diazaspiro[5,5]undecan-3-one The entitled compound was obtained as a white solid according to the same method as in Example 4-(c) or according to a method similar to it but using the phenol compound obtained in (b) and (3S)-1-(3-bromopropyl)-3-methylpiperidine hydrobromide produced in Reference Example 4.

$^1$H-NMR (400 MHz, CDCl$_3$) δ: 0.86 (3H, d, J=6.3 Hz), 1.12 (6H, d, J=6.8 Hz), 1.54-1.79 (8H, m), 1.82-1.89 (1H, m), 1.93-2.00 (4H, m), 2.49 (2H, t, J=7.6 Hz), 2.84-2.91 (2H, m), 2.99-3.05 (2H, m), 3.10 (2H, s), 3.20-3.25 (2H, m), 3.96 (2H, t, J=6.3 Hz), 4.17 (2H, s), 4.88-4.98 (1H, m), 6.83 (2H, d, J=8.8 Hz), 6.91 (2H, d, J=9.3 Hz)

Example 4-11

Production of 4-isopropyl-9-(4-{3-[(2R)-2-methylpyrrolidin-1-yl]propoxy}phenyl)-1-oxa-4,9-diazaspiro[5,5]undecan-3-one The entitled compound was obtained as a white solid according to the same method as in Example 4-(c) or according to a method similar to it but using 9-(4-hydroxyphenyl)-4-isopropyl-1-oxa-4,9-diazaspiro[5,5]undecan-3-one obtained in Example 4-10-(b) and (2R)-1-(3-bromopropyl)-2-methylpyrrolidine hydrobromide produced in Reference Example 4-2.

$^1$H-NMR (400 MHz, CDCl$_3$) δ: 1.10-1.13 (9H, m), 1.38-1.48 (1H, m), 1.58-1.79 (4H, m), 1.88-1.99 (5H, m), 2.09-2.23 (2H, m), 2.27-2.34 (1H, m), 2.94-3.05 (3H, m), 3.10 (2H, s), 3.17-3.25 (3H, m), 3.95-4.01 (2H, m), 4.18 (2H, s), 4.90-4.97 (1H, m), 6.84 (2H, d, J=9.3 Hz), 6.91 (2H, d, J=9.3 Hz)

Example 4-12

Production of 4-(1-ethylpropyl)-9-(4-{3-[(3S)-3-methylpiperidin-1-yl]propoxy}phenyl-1-oxa-4,9-diazaspiro[5,5]undecan-3-one (a) 9-[4-(Benzyloxy)phenyl]-4-(1-ethylpropyl)-1-oxa-4,9-diazaspiro[5,5]undecan-3-one The entitled compound was obtained according to the same method as in Example 3-96 or according to a method similar to it but using 9-[4-(benzyloxy)phenyl]-1-oxa-4,9-diazaspiro[5,5]undecan-3-one obtained in Reference Example 9 and 3-bromopentane.

(b) 4-(1-Ethylpropyl)-9-(4-hydroxyphenyl)-1-oxa-4,9-diazaspiro[5,5]undecan-3-one The entitled compound was obtained according to the same method as in Example 4-(b) or according to a method similar to it but using the benzyloxy compound obtained in (a).

(c) 4-(1-Ethylpropyl)-9-(4-{3-[(3S)-3-methylpiperidin-1-yl]propoxy}phenyl)-1-oxa-4,9-diazaspiro[5,5]undecan-3-one The entitled compound was obtained as a pale yellow oily substance according to the same method as in Example 4-(c) or according to a method similar to it but using the phenol compound obtained in (b) and (3S)-1-(3-bromopropyl)-3-methylpiperidine hydrobromide produced in Reference Example 4.

$^{1}$H-NMR (400 MHz, CDCl$_3$) δ: 0.83-0.91 (10H, m), 1.36-1.88 (12H, m), 1.93-2.05 (4H, m), 2.48 (2H, t, J=7.6 Hz), 2.83-2.91 (2H, m), 3.00-3.06 (2H, m), 3.01 (2H, s), 3.21-3.26 (2H, m), 3.96 (2H, t, J=6.3 Hz), 4.23 (2H, s), 4.45-4.52 (1H, m), 6.83 (2H, d, J=8.8 Hz), 6.91 (2H, d, J=9.3 Hz)

Example 4-13

Production of 9-(4-{3-[(2R)-2-methylpyrrolidin-1-yl]propoxy}phenyl)-4-(2,2,2-trifluoroethyl)-1-oxa-4,9-diazaspiro[5,5]undecan-3-one (a) 9-[4-(Benzyloxy)phenyl]-4-(2,2,2-trifluoroethyl)-1-oxa-4,9-diazaspiro[5,5]undecan-3-one The entitled compound was obtained according to the same method as in Example 3-96 or according to a method similar to it but using 9-[4-(benzyloxy)phenyl]-1-oxa-4,9-diazaspiro[5,5]undecan-3-one obtained in Reference Example 9 and 2,2,2-trifluoroethyl trifluoromethanesulfonate.

(b) 9-(4-Hydroxyphenyl)-4-(2,2,2,-trifluoroethyl)-1-oxa-4,9-diazaspiro[5,5]undecan-3-one The entitled compound was obtained according to the same method as in Example 4-(b) or according to a method similar to it but using the benzyloxy compound obtained in (a).

(c) 9-(4-{3-[(2R)-2-methylpyrrolidin-1-yl]propoxy}phenyl)-4-(2,2,2-trifluoroethyl)-1-oxa-4,9-diazaspiro[5,5]undecan-3-one The entitled compound was obtained as a pale brown solid according to the same method as in Example 4-(c) or according to a method similar to it but using the phenol compound obtained in (b) and (2R)-1-(3-bromopropyl)-2-methylpyrrolidine hydrobromide produced in Reference Example 4-2.

$^{1}$H-NMR (400 MHz, CDCl$_3$) δ: 1.12 (3H, d, J=5.9 Hz), 1.41-1.50 (1H, m), 1.60-1.84 (4H, m), 1.89-2.05 (5H, m), 2.13-2.27 (2H, m), 2.33-2.38 (1H, m), 2.96-3.05 (3H, m), 3.19-3.26 (3H, m), 3.41 (2H, s), 3.93-4.01 (2H, m), 4.06 (2H, q, J=8.9 Hz), 4.27 (2H, s), 6.84 (2H, d, J=9.3 Hz), 6.91 (2H, d, J=9.3 Hz)

Example 4-14

Production of 4-cyclopropyl-9-(4-{3-[(3S)-3-methylpiperidin-1-yl]propoxy}phenyl)-1-oxa-4,9-diazaspiro[5,5]undecan-3-one (a) 1-[4-(Benzyloxy)phenyl]-4-[(cyclopropylamino)methyl]piperidin-4-ol 6-[4-(benzyloxy)phenyl]-1-oxa-6-azaspiro[2,5]octane (500 mg, 1.69 mmol) and cyclopropylamine (195 mg, 3.38 mmol) were mixed in methanol, and heated overnight under reflux. The reaction solution was diluted with ethyl acetate, washed with water and saturated saline in that order, and the organic layer was dried with sodium sulfate. The solvent was evaporated off under reduced pressure to obtain a crude product. The resulting crude product was purified through silica gel column chromatography (eluate: methanol/chloroform=1/99 to 6/94) to obtain the entitled compound (511 mg, 85%) as a yellow solid.

(b) N-({1-[4-benzyloxy)phenyl]-4-hydroxypiperidin-4-yl}methyl-2-chloro-N-cyclopropylacetamide Pyridine (460 mg, 5.78 mmol) was added to an N,N-dimethylformamide solution (5 ml) of the N-cyclopropylaminoalcohol compound (511 mg, 1.45 mmol) obtained in (a), and with stirring with cooling with ice, chloroacetyl chloride (230 mg, 2.02 mmol) was dropwise added thereto, and this was stirred overnight at room temperature. Methanol was added to the reaction solution, diluted with ethyl acetate, washed with water and saturated saline in that order. The organic layer was dried with sodium sulfate, the solvent was evaporated off under reduced pressure to obtain a crude product. The resulting crude product was purified through silica gel column chromatography (eluate: ethyl acetate/chloroform=1/99 to 6/94) to obtain the entitled compound (422 mg, 68%) as a white solid.

(c) 9-[4-(benzyloxy)phenyl]-4-cyclopropyl-1-oxa-4,9-diazaspiro[5,5]undecan-3-one At room temperature, an N,N-dimethylformamide solution (3 ml) of the chloroacetyl compound (422 mg, 0.983 mmol) obtained in (b) was added to a 2-methylbutan-2-ol solution (12 ml) of potassium tert-butoxide (280 mg, 2.46 mmol), and stirred at room temperature for 1 hour. The reaction solution was concentrated, the residue was dissolved in ethyl acetate, and washed with water and saturated saline. The organic layer was dried with sodium sulfate, and the solvent was concentrated under reduced pressure to obtain the entitled compound as a crude product (372 mg, 96%).

(d) 4-Cyclopropyl-9-(4-hydroxyphenyl)-1-oxa-4,9-diazaspiro[5,5]undecan-3-one

The entitled compound was obtained as a pale brown oily substance according to the same method as in Example 4-(b) or according to a method similar to it but using the benzyloxy compound obtained in (c).

(e) 4-Cyclopropyl-9-(4-{3-[(3S)-3-methylpiperidin-1-yl]propoxy}phenyl)-1-oxa-4,9-diazaspiro[5,5]undecan-3-one The entitled compound was obtained as a pale brown solid according to the same method as in Example 4-(c) or according to a method similar to it but using the phenol compound obtained in (d) and (3S)-1-(3-bromopropyl)-3-methylpiperidine hydrobromide produced in Reference Example 4.

$^1$H-NMR (400 MHz, CDCl$_3$) δ: 0.64-0.68 (2H, m), 0.81-0.91 (6H, m), 1.53-1.78 (7H, m), 1.82-1.88 (1H, m), 1.93-2.00 (4H, m), 2.48 (2H, t, J=7.6 Hz), 2.73-2.79 (1H, m), 2.83-2.90 (2H, m), 2.97-3.03 (2H, m), 3.18-3.24 (2H, m), 3.19 (2H, s), 3.96 (2H, t, J=6.3 Hz), 4.15 (2H, s), 6.83 (2H, d, J=9.3 Hz), 6.91 (2H, d, J=8.8 Hz)

Example 4-15

Production of 4-cyclobutyl-9-(4-{3-[(3S)-3-methylpiperidin-1-yl]propoxy}phenyl)-1-oxa-4,9-diazaspiro[5,5]undecan-3-one (a) 1-[4-(Benzyloxy)phenyl]-4-[(cyclobutylamino)methyl]piperidin-4-ol 4-(Aminomethyl)-1-[4-(benzyloxy)phenyl]piperidin-4-ol (5 g, 16.0 mmol) obtained in Reference Example 7 and zinc chloride (654 mg, 4.8 mmol) were mixed in methanol, and cyclobutanone (1.2 ml, 16.0 mmol) and sodium cyanotrihydroborate (2.01 g, 32.0 mmol) were added thereto and stirred overnight at room temperature. Aqueous saturated sodium hydrogencarbonate solution was added to the reaction solution, then extracted with chloroform, and the organic layer was washed with water and saturated saline in that order, and dried with magnesium sulfate. The solvent was evaporated off under reduced pressure, and the resulting crude product was purified through silica gel column chromatography (eluate: methanol/chloroform=2/98 to 10/90) to obtain the entitled compound (3.59 g, 61%) as an orange solid.

(b) N-({1-[4-(benzyloxy)phenyl]-4-hydroxypiperidin-4-yl}methyl)-2-chloro-N-cyclobutylacetamide The entitled compound was obtained as a brown oily substance, according to the same method as in Example 4-14-(b) or according to a method similar to it but using the N-cyclopropylaminoalcohol compound obtained in (a).

(c) 9-[4-(Benzyloxy)phenyl]-4-cyclobutyl-1-oxa-4,9-diazaspiro[5,5]undecan-3-one

The entitled compound was obtained as a brown oily substance, according to the same method as in Example 4-14-(c) or according to a method similar to it but using the chloroacetyl compound obtained in (b).

(d) 4-Cyclobutyl-9-(4-hydroxyphenyl)-1-oxa-4,9-diazaspiro[5,5]undecan-3-one

The entitled compound was obtained as a pink solid, according to the same method as in Example 4-(b) or according to a method similar to it but using the benzyloxy compound obtained in (c).

(e) 4-Cyclobutyl-9-(4-{3-[(3S)-3-methylpiperidin-1-yl]propoxy}phenyl)-1-oxa-4,9-diazaspiro[5,5]undecan-3-one The entitled compound was obtained as a pale yellow solid, according to the same method as in Example 4-(c) or according to a method similar to it but using the phenol compound obtained in (d) and (3S)-1-(3-bromopropyl)-3-methylpiperidine hydrobromide produced in Reference Example 4.

$^1$H-NMR (400 MHz, CDCl$_3$) δ: 0.87 (3H, d, J=6.8 Hz), 1.50-1.91 (1H, m), 1.93-2.00 (4H, m), 2.03-2.16 (4H, m), 2.49 (2H, t, J=7.6 Hz), 2.81-2.95 (2H, brm), 3.02 (2H, td, J=11.7, 2.4 Hz), 3.21-3.26 (4H, m), 3.96 (2H, t, J=6.3 Hz), 4.16 (2H, s), 5.05-5.13 (1H, m), 6.83 (2H, d, J=9.3 Hz), 6.92 (2H, d, J=9.3 Hz)

Example 4-16

Production of 4-cyclobutyl-9-(4-{3-[(2R)-2-methylpyrrolidin-1-yl]propoxy}phenyl)-1-oxa-4,9-diazaspiro[5,5]undecan-3-one The entitled compound was obtained as a milky white solid, according to the same method as in Example 4-(c) or according to a method similar to it but using the phenol compound obtained in Example 4-15-(d) and (2R)-1-(3-bromopropyl)-2-methylpyrrolidine hydrobromide produced in Reference Example 4-2.

$^1$H-NMR (400 MHz, CDCl$_3$) δ: 1.10 (3H, d, J=6.3 Hz), 1.38-1.48 (1H, m), 1.59-1.81 (6H, m), 1.88-2.00 (5H, m), 2.03-2.23 (6H, m), 2.28-2.34 (1H, m), 2.94-3.06 (3H, m), 3.17-3.26 (3H, m), 3.24 (2H, s), 3.94-4.01 (2H, m), 4.16 (2H, s), 5.05-5.14 (1H, m), 6.84 (2H, d, J=9.3 Hz), 6.92 (2H, d, J=9.3 Hz)

Example 4-17

Production of 4-cyclopentyl-9-(4-{3-[(3S)-3-methylpiperidin-1-yl]propoxy}phenyl)-1-oxa-4,9-diazaspiro[5,5]undecan-3-one (a) 1-[4-Benzyloxy)phenyl]-4-[(cyclopentylamino)methyl]piperidin-4-ol The entitled compound was obtained according to the same method as in Example 4-15-(a) or according to a method similar to it but using 4-(aminomethyl)-1-[4-(benzyloxy)phenyl]piperidin-4-yl obtained in Reference Example 7, and cyclopentanone in place of cyclobutanone.

(b) N-({1-[4-(benzyloxy)phenyl]-4-hydroxypiperidin-4-yl}methyl)-2-chloro-N-cyclopentylacetamide The entitled compound was obtained as a brown oily substance, according to the same method as in Example 4-14-(b) or according to a method similar to it but using the N-cyclopropylaminoalcohol compound obtained in (a).

(c) 9-[4-(Benzyloxy)phenyl]-4-cyclopentyl-1-oxa-4,9-diazaspiro[5,5]undecan-3-one The entitled compound was obtained as a yellow solid, according to the same method as in Example 4-14-(c) or according to a method similar to it but using the chloroacetyl compound obtained in (b).

(d) 4-Cyclopentyl-9-(4-hydroxyphenyl)-1-oxa-4,9-diazaspiro[5,5]undecan-3-one

The entitled compound was obtained as a pink solid, according to the same method as in Example 4-(b) or according to a method similar to it but using the benzyloxy compound obtained in (c).

(e) 4-Cyclopentyl-9-(4-{3-[(3S)-3-methylpiperidin-1-yl]propoxy}phenyl)-1-oxa-4,9-diazaspiro[5,5]undecan-3-one The entitled compound was obtained as a colorless oily substance, according to the same method as in Example 4-(c) or according to a method similar to it but using the phenol compound obtained in (d) and (3S)-1-(3-bromopropyl)-3-methylpiperidine hydrobromide produced in Reference Example 4.

$^1$H-NMR (400 MHz, CDCl$_3$) δ: 0.81-0.91 (1H, m), 0.86 (3H, d, J=6.3 Hz), 1.38-1.47 (2H, m), 1.53-1.79 (11H, m), 1.82-1.88 (3H, m), 1.94-1.99 (4H, m), 2.48 (2H, t, J=7.6 Hz), 2.82-2.90 (2H, m), 3.02 (2H, td, J=11.7, 2.6 Hz), 3.12 (2H, s), 3.22 (2H, td, J=8.2, 4.1 Hz), 3.96 (2H, t, J=6.3 Hz), 4.18 (2H, s), 4.99-5.07 (1H, m), 6.83 (2H, d, J=8.8 Hz), 6.91 (2H, d, J=8.8 Hz)

Example 4-18

Production of 4-cyclohexyl-9-(4-{3-[(3S)-3-methylpiperidin-1-yl]propoxy}phenyl)-1-oxa-4,9-diazaspiro[5,5]undecan-3-one (a) 1-[4-(Benzyloxy)phenyl]-4-[(cyclohexylamino)methyl]piperidin-4-ol The entitled compound was obtained as a pale yellow solid, according to the same method as in Example 4-15-(a) or according to a method similar to it but using 4-(aminomethyl)-1-[4-(benzyloxy)phenyl]piperidin-4-ol obtained in Reference Example 7, and cyclohexanone in place of cyclobutanone.

(b) N-({1-[4-(benzyloxy)phenyl]-4-hydroxypiperidin-4-yl}methyl)-2-chloro-N-cyclohexylacetamide The entitled compound was obtained as a pale yellow oily substance, according to the same method as in Example 4-14-(b) or according to a method similar to it but using the N-cyclopropylaminoalcohol compound obtained in (a).

(c) 9-[4-(Benzyloxy)phenyl]-4-cyclohexyl-1-oxa-4,9-diazaspiro[5,5]undecan-3-one

The entitled compound was obtained as a pale yellow solid, according to the same method as in Example 4-14-(c) or according to a method similar to it but using the chloroacetyl compound obtained in (b).

(d) 4-Cyclohexyl-9-(4-hydroxyphenyl)-1-oxa-4,9-diazaspiro[5,5]undecan-3-one

The entitled compound was obtained as a pink solid, according to the same method as in Example 4-(b) or according to a method similar to it but using the benzyloxy compound obtained in (c).

(e) 4-Cyclohexyl-9-(4-{3-[(3S)-3-methylpiperidin-1-yl]propoxy}phenyl)-1-oxa-4,9-diazaspiro[5,5]undecan-3-one The entitled compound was obtained as a colorless oily substance, according to the same method as in Example 4-(c) or according to a method similar to it but using the phenol compound obtained in (d) and (3S)-1-(3-bromopropyl)-3-methylpiperidine hydrobromide produced in Reference Example 4.

$^1$H-NMR (CDCl$_3$) δ: 0.80-0.90 (1H, m), 0.86 (3H, d, J=6.3 Hz), 1.03-1.13 (1H, m), 1.25-1.47 (5H, m), 1.52-1.86 (12H, m), 1.92-1.99 (4H, m), 2.47 (2H, t, J=7.6 Hz), 2.82-2.89 (2H, m), 3.00-3.06 (2H, m), 3.13 (2H, s), 3.19-3.23 (2H, m), 3.96 (2H, t, J=6.3 Hz), 4.18 (2H, s), 4.46-4.52 (1H, m), 6.83 (2H, d, J=9.3 Hz), 6.91 (2H, d, J=9.3 Hz)

Example 4-19

Production of 4-benzyl-9-(4-{3-[(3S)-3-methylpiperidin-1-yl]propoxy}phenyl-1-oxa-4,9-diazaspiro[5,5]undecan-3-one (a) 4-Benzyl-9-[4-(benzyloxy)phenyl]-1-oxa-4,9-diazaspiro[5,5]undecan-3-one The entitled compound was obtained according to the same method as in Example 3-96 or according to a method similar to it but using 9-[4-(benzyloxy)phenyl]-1-oxa-4,9-diazaspiro[5,5]undecan-3-one obtained in Reference Example 9 and (bromomethyl)benzene.

(b) 4-Benzyl-9-(4-hydroxyphenyl)-1-oxa-4,9-diazaspiro[5,5]undecan-3-one

The entitled compound was obtained according to the same method as in Example 4-(b) or according to a method similar to it but using the benzyloxy compound obtained in (a).

(c) 4-Benzyl-9-(4-{3-[(3S)-3-methylpiperidin-1-yl]propoxyl}phenyl)-1-oxa-4,9-diazaspiro[5,5]undecan-3-one The entitled compound was obtained as a yellow solid, according to the same method as in Example 4-(c) or according to a method similar to it but using the phenol compound obtained in (b) and (3S)-1-(3-bromopropyl)-3-methylpiperidine hydrobromide produced in Reference Example 4.

$^1$H-NMR (400 MHz, CDCl$_3$) δ: 0.86 (3H, d, J=6.3 Hz), 1.50-1.76 (8H, m), 1.80-2.01 (5H, m), 2.43-2.53 (2H, m), 2.80-3.02 (4H, m), 3.06-3.11 (2H, m), 3.12 (2H, s), 3.94 (2H, t, J=6.6 Hz), 4.26 (2H, s), 4.62 (2H, s), 6.80 (2H, d, J=9.3 Hz), 6.85 (2H, d, J=9.3 Hz), 7.25-7.38 (5H, m)

Example 4-20

Production of 4-benzyl-9-[4-(3-pyrrolidin-1-ylpropoxy)phenyl]-1-oxa-4,9-diazaspiro[5,5]undecan-3-one The entitled compound was obtained as a yellow solid, according to the same method as in Example 4-(c) or according to a method similar to it but using 4-benzyl-9-(4-hydroxyphenyl)-1-oxa-4,9-diazaspiro[5,5]undecan-3-one produced in Example 4-19-(b) and 1-(3-bromopropyl)pyrrolidine hydrobromide produced according to a method described in a patent (U.S. Pat. No. 4,751,302).

$^1$H-NMR (400 MHz, CDCl$_3$) δ: 1.57-1.69 (4H, m), 1.81 (4H, brs), 1.89-2.04 (4H, m), 2.52-2.69 (4H, m), 2.92-3.01 (2H, m), 3.06-3.16 (4H, m), 3.97 (2H, t, J=6.3 Hz), 4.26 (2H, s), 4.62 (2H, s), 6.81 (2H, d, J=9.3 Hz), 6.86 (2H, d, J=9.3 Hz), 7.38-7.27 (8H, m)

Example 4-21

Production of 4-benzyl-9-[4-(3-piperidin-1-ylpropoxy)phenyl]-1-oxa-4,9-diazaspiro[5,5]undecan-3-one The entitled compound was obtained as a pale yellow solid, according to the same method as in Example 4-(c) or according to a method similar to it but using 4-benzyl-9-(4-hydroxyphenyl)-1-oxa-4,9-diazaspiro[5,5]undecan-3-one produced in Example 4-19-(b) and 1-(3-bromopropyl)pyrrolidine hydrobromide produced according to a method described in a patent (U.S. Pat. No. 4,751,302).

$^1$H-NMR (400 MHz, CDCl$_3$) δ: 1.39-1.48 (2H, brm), 1.56-1.68 (6H, m), 1.89-2.00 (4H, m), 2.35-2.52 (6H, m), 2.97 (2H, td, J=11.2, 2.9 Hz), 3.06-3.14 (4H, m), 3.94 (2H, t, J=6.3 Hz), 4.26 (2H, s), 4.62 (2H, s), 6.81 (2H, d, J=9.3 Hz), 6.85 (2H, d, J=9.3 Hz), 7.38-7.27 (5H, m)

Example 5

Production of 4-(3-fluorophenyl)-9-[4-(3-piperidin-1-ylpropoxy)phenyl]-1-oxa-4,9-diazaspiro[5,5]undecan-3-one (a) 4-(3-Fluorophenyl)-9-(4-methoxyphenyl)-1-oxa-4,9-diazaspiro[5,5]undecan-3-one 9-(4-Methoxyphenyl)-1-oxa-4,9-diazaspiro[5,5]undecan-3-one (200 mg, 0.723 mmol) obtained in Reference Example 9-1, 1-bromo-3-fluorobenzene (152 mg, 0.868 mmol), potassium phosphate (307 mg, 1.45 mmol), copper iodide (14 mg, 0.0723 mmol) and N,N'-dimethyldiaminoethane (13 mg, 0.145 mmol) were mixed in 1,4-dioxane, and stirred overnight with heating at 110° C. in a sealed tube. The reaction solution was diluted with ethyl acetate, washed with water and saturated saline in that order, and the organic layer was dried with sodium sulfate. The solvent was evaporated off, and the residue was purified through silica gel column chromatography (eluate: ethyl acetate/hexane=20/80 to 70/30) to obtain the entitled compound (205 mg, 76%) as a white solid.

(b) 4-(3-Fluorophenyl)-9-(4-hydroxyphenyl)-1-oxa-4,9-diazaspiro[5,5]undecan-3-one The methoxy compound (205 mg, 0.553 mmol) obtained in (a) was dissolved in chloroform, and at 0° C., 1.0 M boron tribromide/dichloromethane solution (2.2 ml, 2.2 mmol) was dropwise added thereto, and this was stirred overnight at room temperature. At 0° C., the reaction solution was neutralized by adding aqueous 2 N sodium hydroxide solution thereto, and extracted with chloroform, and the organic layer was washed with saturated saline. The organic layer was dried with sodium sulfate, and the solvent was evaporated off under reduced pressure to obtain the phenol compound as a crude product (165 mg, 84%).

(c) 4-(3-Fluorophenyl)-9-[4-(3-piperidin-1-ylpropoxy)phenyl]-1-oxa-4,9-diazaspiro[5,5]undecan-3-one The phenol compound (100 mg, 0.28 mmol) obtained in (b), 13-bromopropyl)piperidine hydrobromide (161 mg, 0.56 mmol) produced according to a method described in a patent (U.S. Pat. No. 4,751,302) and potassium carbonate (155 mg, 1.12 mmol) were mixed in N,N-dimethylformamide, and stirred overnight at 60° C. The reaction solution was diluted with chloroform, washed with water and saturated saline in that order, and the organic layer was dried with sodium sulfate. The solvent was evaporated off under reduced pressure, and the resulting residue was purified through reversed-phase preparative HPLC (liquid A: 0.1% TFA/water, liquid B: 0.1% TFA/acetonitrile, A/B=90/10 to 50/50, 8 minute linear concentration gradient elution, flow rate 40 ml/min), and a fraction containing the intended product was collected to obtain the entitled compound (34.6 mg, 32%) as a white solid.

$^1$H-NMR (400 MHz, CDCl$_3$) δ: 1.44 (2H, brs), 1.59 (4H, t, J=6.0 Hz), 1.82-1.99 (4H, m), 2.12 (2H, d, J=12.8 Hz), 2.41-2.49 (6H, m), 3.01-3.09 (2H, m), 3.25-3.29 (2H, m), 3.62 (2H, s), 3.96 (2H, t, J=6.4 Hz), 4.35 (2H, s), 6.83-6.85 (2H, m), 6.91-6.94 (2H, m), 6.98-7.02 (1H, m), 7.07-7.12 (2H, m), 7.35-7.41 (2H, m)

Example 5-1

Production of 4-(2-fluorophenyl)-9-[4-(3-piperidin-1-ylpropoxy)phenyl]-1-oxa-4,9-diazaspiro[5,5]undecan-3-one (a) 4-(2-Fluorophenyl)-9-(4-methoxyphenyl)-1-oxa-4,9-diazaspiro[5,5]undecan-3-one The entitled compound was obtained as a white solid, according to the same method as in Example 5-(a) or according to a method similar to it but using 1-bromo-2-fluorobenzene in place of 1-iodo-4-methoxybenzene.

(b) 4-(2-Fluorophenyl)-9-(4-hydroxyphenyl)-1-oxa-4,9-diazaspiro[5,5]undecan-3-one The entitled compound was obtained as a pale yellow solid, according to the same method as in Example 5-(b) or according to a method similar to it but using the methoxy compound obtained in (a).

(c) 4-(2-Fluorophenyl)-9-[4-(3-piperidin-1-ylpropoxy)phenyl]-1-oxa-4,9-diazaspiro[5,5]undecan-3-one The entitled compound was obtained as a pale yellow solid, according to the same method as in Example 5-(c) or according to a method similar to it but using the phenol compound obtained in (b).

$^1$H-NMR (400 MHz, CDCl$_3$) δ: 1.44 (2H, brs), 1.59 (4H, t, J=6.0 Hz), 1.85-1.99 (4H, m), 2.15 (2H, d, J=13.6 Hz), 2.40-2.49 (6H, m), 3.08 (2H, t, J=11.2 Hz), 3.24-3.28 (2H, m), 3.59 (2H, s), 3.96 (2H, t, J=6.4 Hz), 4.38 (2H, s), 6.84 (2H, d, J=8.8 Hz), 6.93 (2H, d, J=8.8 Hz), 7.15-7.22 (2H, m), 7.27-7.35 (2H, m)

Example 5-2

Production of 4-(2-fluoropyridin-4-yl)-9-[4-(3-piperidin-1-ylpropoxy)phenyl]-1-oxa-4,9-diazaspiro[5,5]undecan-3-one (a) 4-(2-Fluoropyridin-4-yl)-9-(4-methoxyphenyl)-1-oxa-4,9-diazaspiro[5,5]undecan-3-one The entitled compound was obtained as a white solid, according to the same method as in Example 5-(a) or according to a method similar to it but using 2-fluoro-4-iodopyridine in place of 1-iodo-4-methoxybenzene.

(b) 4-(2-Fluoropyridin-4-yl)-9-(4-hydroxyphenyl)-1-oxa-4,9-diazaspiro[5,5]undecan-3-one The entitled compound was obtained as a pale yellow solid, according to the same method as in Example 5-(b) or according to a method similar to it but using the methoxy compound obtained in (a).

(c) 4-(2-Fluoropyridin-4-yl)-9-[4-(3-piperidin-1-ylpropoxy)phenyl]-1-oxa-4,9-diazaspiro[5,5]undecan-3-one The entitled compound was obtained as a pale yellow solid, according to the same method as in Example 5-(c) or according to a method similar to it but using the phenol compound obtained in (b).
$^1$H-NMR (400 MHz, CDCl$_3$) δ: 1.44-1.45 (2H, m), 1.56-1.59 (4H, m), 1.82-1.89 (2H, m), 1.92-1.99 (2H, m), 2.10 (2H, d, J=12.8 Hz), 2.40 (4H, m), 2.47 (2H, t, J=7.2 Hz), 3.05 (2H, td, J=2.8, 11.8 Hz), 3.27-3.30 (2H, m), 3.68 (2H, s), 3.96 (2H, t, J=6.4 Hz), 4.38 (2H, s), 6.84 (2H, d, J=9.2 Hz), 6.87 (2H, d, J=9.2 Hz), 7.11 (1H, d, J=1.6 Hz), 7.34 (1H, dt, J=5.6, 1.2 Hz), 8.22 (1H, d, J=5.6 Hz)

Example 5-3

Production of 4-ethyl-9-[4-(3-piperidin-1-ylpropoxy)phenyl]-1-oxa-4,9-diazaspiro[5,5]undecan-3-one (a) 4-Ethyl-9-(4-methoxyphenyl)-1-oxa-4,9-diazaspiro[5,5]undecan-3-one 9-(4-Methoxyphenyl)-1-oxa-4,9-diazaspiro[5,5]undecan-3-one (800 mg, 2.89 mmol) obtained in Reference Example 9-1 was dissolved in N,N-dimethylformamide, and sodium hydride (140 mg, 3.47 mmol) and iodoethane (542 mg, 3.47 mmol) were added thereto at 0° C., and stirred overnight at room temperature. Water was added to it, the solvent was evaporated off under reduced pressure, and the residue was dissolved in ethyl acetate, and washed with water and saturated saline in that order. The organic layer was dried with sodium sulfate, the solvent was evaporated off under reduced pressure, and the residue was purified through silica gel column chromatography (eluate: ethyl acetate/hexane=40/60 to 100/0) to obtain the entitled compound (682 mg, 77%) as a yellow solid.

(b) 4-Ethyl-9-(4-hydroxyphenyl)-1-oxa-4,9-diazaspiro[5,5]undecan-3-one

The entitled compound was obtained as a brown solid, according to the same method as in Example 5-(b) or according to a method similar to it but using the methoxy compound obtained in (a).

(c) 4-Ethyl-9-[4-(3-piperidin-1-ylpropoxy)phenyl]-1-oxa-4,9-diazaspiro[5,5]undecan-3-one The entitled compound was obtained as a white solid, according to the same method as in Example 5-(c) or according to a method similar to it but using the phenol compound obtained in (b) and 1-(3-bromopropyl)piperidine hydrobromide produced according to a method described in a patent (U.S. Pat. No. 4,751,302).
$^1$H-NMR (400 MHz, CDCl$_3$) δ: 1.15 (3H, t, J=7.2 Hz), 1.44-1.45 (2H, m), 1.56-1.62 (4H, m), 1.78 (2H, td, J=11.2, 3.6 Hz), 1.92-2.02 (4H, m), 2.40 (4H, brs), 2.47 (2H, t, J=7.6 Hz), 3.02 (2H, td, J=11.8, 2.8 Hz), 3.20-3.25 (4H, m), 3.46 (2H, quint., J=7.2 Hz), 3.96 (2H, t, J=6.4 Hz), 4.16 (2H, s), 6.83 (2H, d, J=9.2 Hz), 6.91 (2H, d, J=9.2 Hz)

Example 5-4

Production of 4-ethyl-9-[4-(3-(3S)-methylpiperidin-1-ylpropoxy)phenyl]-1-oxa-4,9-diazaspiro[5,5]undecan-3-one The entitled compound was obtained as a pale yellow solid, according to the same method as in Example 5-(c) or according to a method similar to it but using 4-ethyl-9-(4-hydroxyphenyl)-1-oxa-4,9-diazaspiro[5,5]undecan-3-one obtained in Example 5-3-(b), and (3S)-1-(3-bromopropyl)-3-methylpiperidine hydrobromide obtained in Reference Example 4 in place of 1-(3-bromopropyl)piperidine hydrobromide.
$^1$H-NMR (400 MHz, CDCl$_3$) δ: 0.86 (3H, d, J=6.3 Hz), 1.15 (3H, t, J=7.2 Hz), 1.57-1.86 (9H, m), 1.95-2.01 (4H, m), 2.49 (2H, brs), 2.86 (2H, brs), 3.02 (2H, t, J=10.4 Hz), 3.21-3.26 (4H, m), 3.46 (2H, q, J=7.3 Hz), 3.96 (2H, t, J=6.5 Hz), 4.16 (2H, s), 6.83 (2H, d, J=9.4 Hz), 6.91 (2H, d, J=9.0 Hz)

Example 5-5

Production of 4-methyl-9-[4-(3-piperidin-1-ylpropoxy)phenyl]-1-oxa-4,9-diazaspiro[5,5]undecan-3-one (a) 4-Methyl-9-(4-methoxyphenyl)-1-oxa-4,9-diazaspiro[5,5]undecan-3-one The entitled compound was obtained as a pale yellow solid, according to the same method as in Example 5-3-(a) or according to a method similar to it but using iodomethane in place of iodoethane.

(b) 4-Methyl-9-(4-hydroxyphenyl)-1-oxa-4,9-diazaspiro[5,5]undecan-3-one

The entitled compound was obtained as a pale yellow solid, according to the same method as in Example 5-(b) or according to a method similar to it but using the methoxy compound obtained in (a).

(c) 4-Methyl-9-[4-(3-piperidin-1-ylpropoxy)phenyl]-1-oxa-4,9-diazaspiro[5,5]undecan-3-one The entitled compound was obtained as a white solid, according to the same method as in Example 5-(c) or according to a method similar to it but using the phenol compound obtained in (b).
$^1$H-NMR (400 MHz, CDCl$_3$) δ: 1.44-1.45 (2H, m), 1.56-1.62 (4H, m), 1.79 (2H, td, J=11.4, 4.4 Hz), 1.93-2.03 (4H, m), 2.40 (4H, brs), 2.47 (2H, t, J=7.2 Hz), 2.97-3.04 (5H, m), 3.22-3.26 (4H, m), 3.95 (2H, t, J=6.8 Hz), 4.17 (2H, s), 6.83 (2H, d, J=9.2 Hz), 6.91 (2H, d, J=9.2 Hz)

Example 6

Production of 8-[4-(3-(3S)-methylpiperidin-1-ylpropoxy)phenyl]-3-phenyl-1-oxa-3,8-diazaspiro[4,5]decan-2-one (a) 8-(4-Methoxyphenyl)-3-phenyl-1-oxa-3,8-diazaspiro[4,5]decan-2-one 8-(4-methoxyphenyl)-1-oxa-3,8-diazaspiro[4,5]decan-2-one (935 mg, 3.56 mmol) obtained in Reference Example 13, iodobenzene (872 mg, 4.28 mmol), potassium phosphate (1.51 g, 7.12 mmol), copper iodide (68 mg, 0.356 mmol), and N,N'-dimethyldiaminoethane (62 mg, 0.712 mmol) were mixed in 1,4-dioxane, and stirred overnight at 110° C. with heating in a sealed tube. The reaction solution was diluted with chloroform, washed with water and saturated saline in that order, and the organic layer was dried with sodium sulfate. The solvent was concentrated under reduced pressure to obtain the entitled compound, a crude product (1.15 g, 95%) as a white solid.

(b) 8-(4-Hydroxyphenyl)-3-phenyl-1-oxa-3,8-diazaspiro[4,5]decan-2-one

The methoxy compound (1.15 g, 3.39 mmol) obtained in (a) was dissolved in chloroform, and processed with 1.0 M boron tribromide/dichloromethane solution (11 ml, 11 mmol) at 0° C. according to the same method as in Example 5-(b) or according to a method similar to it, thereby obtaining the entitled compound as a crude product (308 mg, 28%).

(c) 8-[4-(3-chloropropoxy)phenyl]-3-phenyl-1-oxa-3,8-diazaspiro[4,5]decan-2-one

The phenol compound (150 mg, 0.462 mmol) obtained in (b), 1-bromo-3-chloropropane (145 mg, 0.924 mmol) and potassium carbonate (255 mg, 1.85 mmol) were mixed in N,N-dimethylformamide, and stirred overnight at 60° C. The reaction solution was diluted with chloroform, washed with water and saturated saline in that order, and the organic layer was dried with sodium sulfate. The solvent was evaporated off under reduced pressure, and the resulting residue was purified through reversed-phase preparative HPLC (liquid A: 0.1% TFA/water, liquid B: 0.1% TFA/acetonitrile, A/B=90/10 to 50/50, 8 minute linear concentration gradient elution, flow rate 40 mL/min), and fractions containing the intended product were collected to obtain the entitled compound (61 mg, 32%).

(d) 8-[4-(3-(3S)-methylpiperidin-1-ylpropoxy)phenyl]-3-phenyl-1-oxa-3,8-diazaspiro[4,5]decan-2-one The chlorine compound (61 mg, 0.152 mmol) obtained in (c), (3S)-3-methylpiperidine-(R) mandelate (80 mg, 0.304 mmol) produced from a starting material 3-methylpiperidine according to a method described in literature (Journal of Organic Chemistry (J. O. C.), 1987, Vol. 52, p. 5467) and potassium carbonate (85 mg, 0.608 mmol) were mixed in N,N-dimethylformamide, and stirred overnight at 60° C. The reaction solution was diluted with ethyl acetate, washed with water and saturated saline in that order, and the organic layer was dried with sodium sulfate. The solvent was evaporated off under reduced pressure, and the resulting residue was purified through reversed-phase preparative HPLC (liquid A, 0.1% TFA/water; liquid B, 0.1% TFA/acetonitrile; A/B=90/10 to 50/50; 8-minute linear concentration gradient elution; flow rate, 40 ml/min) to collect fractions containing the intended product, thereby obtaining the entitled compound (30 mg, 43%) as a whites solid.

$^1$H-NMR (400 MHz, CDCl$_3$) δ: 0.87 (3H, d, J=6.3 Hz), 1.58-1.73 (6H, m), 1.86-2.06 (5H, m), 2.15 (2H, d, J=12.5 Hz), 2.50 (2H, brs), 2.85-2.92 (2H, m), 3.25-3.28 (4H, m), 3.81 (2H, s), 3.97 (2H, t, J=6.5 Hz), 6.84 (2H, d, J=9.0 Hz), 6.93 (2H, d, J=9.0 Hz), 7.15 (1H, t, J=7.4 Hz), 7.39 (2H, t, J=8.0 Hz), 7.56 (2H, d, J=7.8 Hz)

Example 7

Production of 3-(4-hydroxyphenyl)-8-[4-(3-piperidin-1-ylpropoxy)phenyl]-1-oxa-3,8-diazaspiro[4,5]decan-2-one 8-[4-3-Piperidin-1-ylpropoxy)phenyl]-1-oxa-3,8-diazaspiro[4,5]decan-2-one (110 mg, 0.295 mmol) obtained in Reference Example 15, 4-(benzyloxy)-1-iodobenzene (110 mg, 0.353 mmol), potassium phosphate (125 mg, 0.59 mmol), copper iodide (6 mg, 0.029 mmol) and N,N'-dimethyldiaminoethane (6 mg, 0.058 mmol) were mixed in 1,4-dioxane, and stirred overnight at 110° C. with heating in a sealed tube. The reaction solution was diluted with chloroform, washed with water and saturated saline in that order, and the organic layer was dried with sodium sulfate. The solvent was concentrated under reduced pressure, and the residue was purified through reversed-phase preparative HPLC (liquid A, 0.1% TFA/water; liquid B, 0.1% TFA/acetonitrile; A/B=90/10 to 50/50; 8-minute linear concentration gradient elution; flow rate, 40 ml/min) to collect fractions containing the intended product, thereby obtaining a benzyloxy compound (130 mg, 79%). The resulting benzyloxy compound (130 mg, 0.23 mmol) was dissolved in methanol, then 10% palladium/carbon (30 mg, 0.028 mmol) was added thereto and stirred overnight in a nitrogen atmosphere. The reaction solution was filtered through Celite, the Celite was washed with chloroform and the mother liquid was concentrated to obtain the entitled compound (47 g, 43%) as a gray solid.

$^1$H-NMR (400 MHz, CDCl$_3$) δ: 1.88-1.92 (4H, m), 2.18-2.24 (4H, m), 2.38 (2H, brs), 2.71-2.78 (4H, m), 3.18-3.19 (2H, m), 3.39-3.41 (4H, m), 3.61 (2H, d, J=10.0 Hz), 3.81 (2H, s), 4.08 (2H, s), 6.84-7.05 (4H, m), 7.31-7.57 (4H, m)

Example 8

Production of 9-{4-[(1-cyclobutylpiperidin-4-yl)oxy]phenyl}-4-phenyl-1-oxa-4,9-diazaspiro[5,5]undecan-3-one (a) 9-(4-Methoxyphenyl)-4-phenyl-1-oxa-4,9-diazaspiro[5,5]undecan-3-one The entitled compound was obtained as a pale yellow solid, according to the same method as in Example 5-(a) or according to a method similar to it but using bromobenzene in place of 1-bromo-3-fluorobenzene.

(b) 9-(4-Hydroxyphenyl)-4-phenyl-1-oxa-4,9-diazaspiro[5,5]undecan-3-one

The entitled compound was obtained as a pale yellow solid, according to the same method as in Example 5-(b) or according to a method similar to it but using the methoxy compound obtained in (a).

(c) Tert-butyl 4-[4-(3-oxo-4-phenyl-1-oxa-4,9-diazaspiro[5,5]undecan-9-yl)phenoxy]piperidine-1-carboxylate The phenol compound (100 mg, 0.295 mmol) obtained in (b), tert-butyl 4-hydroxypiperidine-1-carboxylate (120 mg, 0.591 mmol) and triphenyl phosphine (155 mg, 0.591 mmol) were mixed in tetrahydrofuran, and at 0° C., diisopropyl azodicarboxylate (120 mg, 0.591 mmol) was dropwise added thereto, and stirred overnight and at room temperature. The solvent was concentrated, and the residue was purified through thin-layer chromatography (eluate: ethyl acetate/hexane=2/1) to obtain the entitled compound (92.3 mg, 60%) as a pale yellow solid.

(d) 9-{4-[(1-Cyclobutylpiperidin-4-yl)oxy]phenyl}-4-phenyl-1-oxa-4,9-diazaspiro[5,5]undecan-3-one The compound (92.3 mg, 0.18 mmol) obtained in (c) was mixed with trifluoroacetic acid (0.5 ml) at 0° C., and then stirred for 1 hour at room temperature. The solvent was concentrated, and the residue was dissolved in ethyl acetate and neutralized by adding aqueous 2 N sodium hydroxide solution thereto, and extracted with ethyl acetate. The organic layer was washed with saturated saline, dried with sodium sulfate, and the solvent was evaporated off under reduced pressure, thereby obtaining a piperidine compound as a crude product. The resulting piperidine compound (88.5 mg, 0.21 mmol) was dissolved in methanol, and cyclobutanone (30 mg, 0.42 mmol) and 0.5 M sodium cyanotrihydroborate/zinc chloride (1/1) solution in methanol (2.5 ml, 1.26 mmol) were added thereto and stirred overnight at room temperature. The solvent was concentrated, then aqueous 2 N sodium hydroxide solution and ethyl acetate were added to the residue, then the precipitated white solid was removed through Celite filtration, and the filtrate was diluted with ethyl acetate and washed with saturated saline. The organic layer was dried with sodium sulfate, and the solvent was evaporated off under reduced pressure. The resulting residue was purified through reversed-phase preparative HPLC (liquid A: 0.1% TFA/water, liquid B: 0.1% TFA/acetonitrile, A/B=90/10 to 50/50, 8 minute linear concentration gradient elution, flow rate 40 ml/min), and fractions containing the intended product were collected. This was purified through thin-layer chromatography (eluate: chloroform/methanol=9/1) to obtain the entitled compound (31.2 mg, 31%) as a pale yellow viscous substance.

$^1$H-NMR (400 MHz, CDCl$_3$) δ: 1.64-2.18 (17H, m), 2.67-2.77 (2H, m), 3.09 (2H, t, J=10.8 Hz), 3.29 (2H, t, J=12.0 Hz), 3.64 (2H, s), 4.25 (1H, brs), 4.36 (2H, s), 6.85 (2H, d, J=8.8 Hz), 6.92 (2H, d, J=8.8 Hz), 7.28-7.32 (3H, m), 7.41-7.45 (2H, m)

Example 8-1

Production of 9-[4-(1-cyclobutylpiperidin-4-yloxy)phenyl]-4-ethyl-1-oxa-4,9-diazaspiro[5,5]undecan-3-one (a) Tert-butyl 4-[4-(4-ethyl-3-oxo-1-oxa-4,9-diazaspiro[5,5]undecan-9-yl)phenoxy]piperidine-1-carboxylate The entitled compound was obtained as a pale yellow solid, according to the same method as in Example 8-(c) or according to a method similar to it but using 4-ethyl-9-(4-hydroxyphenyl)-1-oxa-4,9-diazaspiro[5,5]undecan-3-one obtained in Example 5-3-(b) in place of 9-(4-methoxyphenyl)-4-phenyl-1-oxa-4,9-diazaspiro[5,5]undecan-3-one.

(b) 9-[4-(1-Cyclobutylpiperidin-4-yloxy)phenyl]-4-ethyl-1-oxa-4,9-diazaspiro[5,5]undecan-3-one The entitled compound was obtained as a white solid, according to the same method as in Example 8-(d) or according to a method similar to it but using the N-Boc compound obtained in (a).

$^1$H-NMR (400 MHz, CDCl$_3$) δ: 1.15 (3H, t, J=7.2 Hz), 1.62-2.12 (15H, m), 2.62-2.72 (4H, m), 3.02 (2H, t, J=10.4 Hz), 3.24 (4H, d, J=12.9 Hz), 3.46 (2H, q, J=7.2 Hz), 4.16 (2H, s), 4.20 (1H, s), 6.84 (2H, d, J=9.0 Hz), 6.90 (2H, d, J=9.0 Hz)

Example 8-2

Production of 9-[4-(1-cyclobutylpiperidin-4-yloxy)phenyl]-4-(6-fluoropyridin-3-yl)-1-oxa-4,9-diazaspiro[5,5]undecan-3-one (a) Tert-butyl 4-{4-[4-(6-fluoropyridin-3-yl)-3-oxo-1-oxa-4,9-diazaspiro[5,5]undecan-9-yl]phenoxy}piperidine-1-carboxylate The entitled compound was obtained as a crude product, according to the same method as in Example 8-(c) or according to a method similar to it but using 4-(6-fluoropyridin-3-yl)-9-(4-hydroxyphenyl)-1-oxa-4,9-diazaspiro[5,5]undecan-3-one obtained in Example 4-3-(b) in place of 9-(4-hydroxyphenyl)-4-phenyl-1-oxa-4,9-diazaspiro[5,5]undecan-3-one.

(b) 9-[4-(1-Cyclobutylpiperidin-4-yloxy)phenyl]-4-(6-fluoropyridin-3-yl)-1-oxa-4,9-diazaspiro[5,5]undecan-3-one The entitled compound was obtained as a yellow solid, according to the same method as in Example 8-(d) or according to a method similar to it but using the crude product obtained in (a).

$^1$H-NMR (400 MHz, CDCl$_3$) δ: 1.64-2.18 (16H, m), 2.64-2.77 (3H, m), 3.04-3.11 (2H, m), 3.30 (2H, d, J=12.5 Hz), 3.65 (2H, s), 4.22 (1H, brs), 4.37 (2H, s), 6.85 (2H, d, J=9.0 Hz), 6.92 (2H, d, J=9.0 Hz), 7.00 (1H, dd, J=8.8, 3.3 Hz), 7.81-7.86 (1H, m), 8.19 (1H, brs)

Example 8-3

Production of 9-{4-[(1-cyclobutylpiperidin-4-yl)oxy]phenyl}-4-(6-methoxypyridin-3-yl)-1-oxa-4,9-diazaspiro[5,5]undecan-3-one (a) Tert-butyl 4-{4-[4-(6-methoxypyridin-3-yl)-3-oxo-1-oxa-4,9-diazaspiro[5,5]undecan-9-yl]phenoxy}piperidine-1-carboxylate The entitled compound was obtained as a crude product, according to the same method as in Example 8-(c) or according to a method similar to it but using 4-(6-methoxypyridin-3-yl)-9-(4-hydroxyphenyl)-1-oxa-4,9-diazaspiro[5,5]undecan-3-one obtained in Example 4-4-(b) in place of 9-(4-hydroxyphenyl)-4-phenyl-1-oxa-4,9-diazaspiro[5,5]undecan-3-one.

(b) 9-[4-(1-Cyclobutylpiperidin-4-yloxy)phenyl]-4-(6-methoxypyridin-3-yl)-1-oxa-4,9-diazaspiro[5,5]undecan-3-one The entitled compound was obtained as a pale orange solid, according to the same method as in Example 8-(d) or according to a method similar to it but using the crude product obtained in (a).

$^1$H-NMR (400 MHz, CDCl$_3$) δ: 1.50-2.40 (16H, m), 2.50-3.90 (3H, m), 2.95-3.15 (2H, m), 3.15-3.35 (2H, m), 3.60 (2H, s), 3.94 (3H, s), 4.23 (1H, br.s), 4.35 (2H, s), 6.79 (1H, d,

J=8.0 Hz), 6.85 (2H, d, J=12 Hz), 6.92 (1H, d, J=12 Hz), 7.55 (1H, dd, J=8.0, 4.0 Hz), 8.10 (1H, d, J=4.0 Hz)

Example 8-4

Production of 9-{4-[(1-cyclopropylpiperidin-4-yl)oxy]phenyl}-4-(6-methoxypyridin-3-yl)-1-oxa-4,9-diazaspiro[5,5]undecan-3-one (a) 4-(6-Methoxypyridin-3-yl)-9-[4-(piperidin-4-yloxy)phenyl]-1-oxa-4,9-diazaspiro[5,5]undecan-3-one A crude product of piperidine N-Boc-protected compound, 4-(6-methoxypyridin-3-yl)-9-[4-(piperidin-4-yloxy)phenyl]-1-oxa-4,9-diazaspiro[5,5]undecan-3-one was obtained according to the same method as in Example 8-(c) or according to a method similar to it but using 9-(4-hydroxyphenyl)-4-(6-methoxypyridin-3-yl)-1-oxa-4,9-diazaspiro[5,5]undecan-3-one obtained in Example 4-4-(b), and the N-Boc protected compound was processed according to the same method as in Example 8-(d) or according to a method similar to it, thereby obtaining the piperidine compound as a yellow oily substance.

(b) 9-{4-[(1-Cyclopropylpiperidin-4-yl)oxy]phenyl}-4-(6-methoxypyridin-3-yl)-1-oxa-4,9-diazaspiro[5,5]undecan-3-one The entitled compound was obtained as a pale brown solid, according to the same method as in Example 4-14-(a) or according to a method similar to it but using the piperidine compound obtained in (a), and (1-ethoxycyclopropyl)(trimethyl)silane in place of cyclobutanone.

$^1$H-NMR (400 MHz, CDCl$_3$) δ: 0.34-0.54 (4H, m), 1.53-2.04 (7H, m), 2.06-2.21 (2H, m), 2.37-2.56 (2H, m), 2.85-2.96 (2H, m), 3.02-3.13 (2H, m), 3.23-3.32 (2H, m), 3.60 (2H, s), 3.94 (3H, s), 4.16-4.27 (1H, m), 4.35 (2H, s), 6.79 (1H, d, J=8.8 Hz), 6.86 (2H, d, J=8.8 Hz), 6.92 (2H, d, J=8.8 Hz), 7.54 (1H, dd, J=8.8, 2.9 Hz), 8.10 (1H, d, J=2.9 Hz)

Example 8-5

Production of 4-cyclobutyl-9-{4-[(1-cyclobutylpiperidin-4-yl)oxy]phenyl}-1-oxa-4,9-diazaspiro[5,5]undecan-3-one (a) 4-Cyclobutyl-9-[4-(piperidin-4-yloxy)phenyl]-1-oxa-4,9-diazaspiro[5,5]undecan-3-one A crude product of piperidine N-Boc-protected compound, 4-cyclobutyl-9-[4-(piperidin-4-yloxy)phenyl]-1-oxa-4,9-diazaspiro[5,5]undecan-3-one was obtained according to the same method as in Example 8-(c) or according to a method similar to it but using 4-cyclobutyl-9-(4-hydroxyphenyl)-1-oxa-4,9-diazaspiro[5,5]undecan-3-one obtained in Example 4-15-(d), and the N-Boc protected compound was processed according to the same method as in Example 8-(d) or according to a method similar to it, thereby obtaining the piperidine compound as a white solid.

(b) 4-Cyclobutyl-9-{4-[(1-cyclobutylpiperidin-4-yl)oxy]phenyl}-1-oxa-4,9-diazaspiro[5,5]undecan-3-one The entitled compound was obtained as an orange oily substance, according to the same method as in Example 4-15-(a) or according to a method similar to it but using the piperidine compound obtained in (a) and cyclobutanone.

$^1$H-NMR (400 MHz, CDCl$_3$) δ: 1.51-2.27 (22H, m), 2.56-2.84 (3H, m), 2.98-3.08 (2H, m), 3.19-3.29 (2H, m), 3.24 (2H, s), 4.15 (2H, s), 4.22 (1H, brs), 5.01-5.17 (1H, m), 6.84 (2H, d, J=9.1 Hz), 6.90 (2H, d, J=9.1 Hz)

Example 8-6

Production of 4-cyclobutyl-9-{4-[(1-isopropylpiperidin-4-yl)oxy]phenyl}-1-oxa-4,9-diazaspiro[5,5]undecan-3-one The entitled compound was obtained as an orange oily substance, according to the same method as in Example 4-15-(a) or according to a method similar to it but using 4-cyclobutyl-9-[4-(piperidin-4-yloxy)phenyl]-1-oxa-4,9-diazaspiro[5,5]undecan-3-one obtained in Example 8-5-(a) and acetone.

$^1$H-NMR (400 MHz, CDCl$_3$) δ: 1.08 (6H, d, J=6.8 Hz), 1.61-1.90 (8H, m), 1.92-2.20 (6H, m), 2.32-2.49 (2H, m), 2.70-2.88 (3H, m), 2.96-3.10 (2H, m), 3.19-3.29 (2H, m), 3.24 (2H, s), 4.16 (2H, s), 4.17-4.24 (1H, m), 5.09 (1H, septet, J=6.8 Hz), 6.85 (2H, d, J=9.3 Hz), 6.91 (2H, d, J=8.8 Hz)

The compounds used in producing the compounds of the above-mentioned Examples are described as Reference Examples.

Reference Example 1

Production of 1-[(3-chloropropyl)oxy]-4-iodobenzene

4-Iodophenol (10 g, 45.4 mmol), 1-bromo-3-chloropropane (7 g, 50.0 mmol) and potassium carbonate (7.54 g, 54.5 mmol) were mixed in DMF, and stirred at room temperature for 15 hours. The reaction liquid was diluted with diethyl ether, washed with water and saturated saline in that order, and the organic layer was dried with sodium sulfate. The solvent was evaporated off under reduced pressure, and the residue was purified through silica gel column chromatography (eluate: ethyl acetate/hexane=5/95) to obtain the entitled compound (11.1 g, 82.3%) as a pale yellow solid.

$^1$H-NMR (400 MHz, CDCl$_3$) δ: 2.20-2.26 (2H, m), 3.73 (2H, t, J=6.3 Hz), 4.08 (2H, t, J=5.9 Hz), 6.69 (2H, dt, J=8.8, 3.4 Hz), 7.53-7.57 (2H, m)

Reference Example 2

Production of 1-[3-(4-iodophenoxy)propyl]piperidine

1-[(3-chloropropyl)oxy]-4-iodobenzene (10 g, 33.7 mmol) and piperidine (2.87 g, 67.4 mmol) were mixed, and stirred at 85° C. for 4 hours. After cooled to room temperature, this was concentrated, and the residue was dissolved in ethyl acetate, washed with aqueous saturated sodium hydrogencarbonate solution and saturated saline, and the organic layer was dried with sodium sulfate. The solvent was evaporated off, and the residue was purified through silica gel column chromatography (eluate: ethyl acetate/hexane=50/50 to chloroform/methanol=10/1) to obtain the entitled compound (8.39 g, 72%) as a brown solid.

$^1$H-NMR (400 MHz, CDCl$_3$) δ: 1.42-1.46 (2H, m), 1.56-1.62 (4H, m), 1.92-2.00 (2H, m), 2.39-2.47 (6H, m), 3.96 (2H, t, J=6.3 Hz), 6.67 (2H, td, J=6.1, 3.4 Hz), 7.53 (2H, td, J=6.1, 3.4 Hz)

Reference Example 3

Production of 3-[(2S)-2-methylpyrrolidin-1-yl]propan-1-ol (2S)-2-methylpyrrolidine hydrobromide (2.70 g, 16.3 mmol) produced from D-prolinol according to a method described in literature (Journal of Organic Chemistry (J. O. C.) 1989, Vol. 54, p. 209), 3-bromo-1-propanol (2.49 g, 17.9 mmol) and potassium carbonate (6.75 g, 48.9 mmol) were mixed in tetrahydrofuran (20 ml), and stirred at 60° C. for 18 hours. The precipitate was taken out through filtration, and the filtrate was concentrated. The residue was distilled under reduced pressure to obtain the entitled compound (1.88 g, 80%) as a colorless oil.

$^1$H-NMR (400 MHz, CDCl$_3$) δ: 1.14 (3H, d, J=5.9 Hz), 1.34-1.43 (1H, m), 1.50-1.58 (1H, m), 1.66-1.78 (2H, m), 1.85-1.97 (2H, m), 2.09 (1H, q, J=8.9 Hz), 2.25-2.34 (1H, m), 2.38-2.43 (1H, m), 2.99 (1H, td, J=12.0, 3.4 Hz), 3.31-3.37 (1H, m), 3.79-3.83 (2H, m)

Reference Example 3-1

Production of 3-[(2R)-2-methylpyrrolidin-1-yl]propan-1-ol

The entitled compound was obtained as a colorless oil, according to the same method as in Reference Example 3 or according to a method similar to it but using (2R)-2-methylpyrrolidine hydrobromide produced from L-prolinol according to a method described in literature (Journal of Organic Chemistry (J. O. C.) 1989, Vol. 54, p. 209).

$^1$H-NMR (400 MHz, CDCl$_3$) δ: 1.14 (3H, d, J=5.9 Hz), 1.33-1.43 (1H, m), 1.50-1.58 (1H, m), 1.66-1.77 (2H, m), 1.86-1.97 (2H, m), 2.09 (1H, q, J=8.9 Hz), 2.25-2.34 (1H, m), 2.38-2.43 (1H, m), 2.99 (1H, td, J=12.0, 3.4 Hz), 3.31-3.37 (1H, m), 3.81 (2H, dd, J=7.8, 2.4 Hz)

Reference Example 3-2

Production of 3-[(3S)-3-methylpiperidin-1-yl]propan-1-ol

The entitled compound was obtained as a colorless oil, according to the same method as in Reference Example 3 or according to a method similar to it but using (3S)-3-methylpiperidine (R)-mandelate produced from 3-methylpiperidine according to a method described in literature (Journal of Organic Chemistry (J. O. C.) 1987, Vol. 52, p. 5467), in place of (2S)-2-methylpyrrolidine hydrobromide.

$^1$H-NMR (CDCl$_3$) δ: 0.82-0.92 (4H, m), 1.43-1.74 (7H, m), 1.79-1.88 (1H, m), 2.55-2.58 (2H, m), 2.94 (2H, brt, J=10.7 Hz), 3.80 (2H, t, J=5.4 Hz), 5.84 (1H, brs)

Reference Example 4

Production of (3S)-1-(3-bromopropyl)-3-methylpiperidine hydrobromide 3-[(3S)-3-methylpiperidin-1-yl]propan-1-ol (10 g, 63.6 mmol) obtained in Reference Example 3-2 was mixed with 25% hydrogen bromide/acetic acid solution, and stirred overnight at 100° C. After left cooled, the solvent was concentrated, then diethyl ether was added to the residue, and the precipitated solid was taken out through suction filtration, and the resulting residue was dried overnight under reduced pressure at 50° C. to obtain the intended compound (18 g, 94%) as a white solid.

$^1$H-NMR (400 MHz, CDCl$_3$) δ: 0.98 (3H, d, J=6.3 Hz), 1.07-1.17 (1H, m), 1.88-1.98 (2H, m), 2.25-2.65 (6H, m), 3.11-3.17 (2H, m), 3.45-3.61 (4H, m)

Reference Example 4-1

Production of (2S)-1-(3-bromopropyl)-2-methylpyrrolidine hydrobromide

The entitled compound was obtained as a brown solid, according to the same method as in Reference Example 4 or according to a method similar to it but using 3-[(2S)-2-methylpyrrolidin-1-yl]propan-1-ol obtained in Reference Example 3.

$^1$H-NMR (400 MHz, CDCl$_3$) δ: 1.71 (3H, d, J=6.8 Hz), 2.01-2.44 (5H, m), 2.81-3.20 (3H, m), 3.30-3.75 (4H, m), 3.95-4.04 (1H, m)

Reference Example 4-2

Production of (2R)-1-(3-bromopropyl)-2-methylpyrrolidine hydrobromide

The entitled compound was obtained as a white solid, according to the same method as in Reference Example 4 or according to a method similar to it but using 3-[(2R)-2-methylpyrrolidin-1-yl]propan-1-ol obtained in Reference Example 3-1.

$^1$H-NMR (400 MHz, CDCl$_3$) δ: 1.71 (3H, d, J=6.8 Hz), 2.02-2.14 (2H, m), 2.24-2.36 (3H, m), 2.81-2.92 (2H, m), 2.98-3.08 (1H, m), 3.28-3.36 (1H, m), 3.41-3.53 (2H, m), 3.55-3.61 (1H, m), 3.93-4.00 (1H, m)

Reference Example 5

Production of 8-[4-(benzyloxy)phenyl]-1,4-dioxa-8-azaspiro[4,5]decane 1,4-Dioxa-8-azaspiro[4,5]decane (653 g, 4.56 mol), 1-(benzyloxy)-4-iodobenzene (1 kg, 3.8 mol), sodium tert-butoxide (511 g, 5.32 mol), Pd(OAc)$_2$ (17 g, 76 mmol) and biphenyl-2-yl(dicyclohexyl) phosphine (54 g, 152 mmol) were mixed, and 1,4-dioxane, this was stirred overnight at 80° C. in a nitrogen atmosphere. The reaction solution was cooled with ice, diluted with ethyl acetate, washed with water and saturated saline in that order, and the organic layer was dried with sodium sulfate. The solvent was evaporated off under reduced pressure, and the resulting residue was purified through silica gel column chromatography (eluate: chloroform/ethyl acetate=10/1), and the resulting crude product was suspended in a mixed solvent of chloroform/hexane and filtered under suction to obtain the entitled compound (910 g, 73%) as a brown solid.

$^1$H-NMR (400 MHz, CDCl$_3$) δ: 1.86 (4H, t, J=6.0 Hz), 3.19 (4H, t, J=6.0 Hz), 3.99 (4H, s), 5.01 (2H, s), 6.88-6.91 (4H, m), 7.31-7.43 (5H, m)

Reference Example 5-1

Production of 8-(4-methoxyphenyl)-1,4-dioxa-8-azaspiro[4,5]decane

The entitled compound was obtained as a brown solid, according to the same method as in Reference Example 5 or according to a method similar to it but using 1-iodo-4-methoxybenzene in place of 1-(benzyloxy)-4-iodobenzene.

$^1$H-NMR (400 MHz, CDCl$_3$) δ: 1.86 (4H, t, J=5.9 Hz), 3.19 (4H, t, J=5.9 Hz), 3.77 (3H, s), 3.99 (4H, s), 6.83 (2H, dt, J=9.3, 3.4 Hz), 6.93 (2H, dt, J=9.3, 3.4 Hz)

Reference Example 6

Production of 1-[4-(benzyloxy)phenyl]piperidin-4-one

8-[4-(benzyloxy)phenyl]-1,4-dioxa-8-azaspiro[4,5]decane (910 g, 2.8 mol) obtained in Reference Example 5 and aqueous 40% formic acid solution (10 L) were mixed, and stirred at 90° C. for 14 hours. At room temperature, the reaction solution was added to a mixed solution of chloroform (7 L)/water (12 L) containing sodium hydrogencarbonate (7.25 kg), and stirred for 4 hours. Next, this was extracted with chloroform, washed with saturated saline, and the organic layer was dried with sodium sulfate. The solvent was evaporated off under reduced pressure, the resulting residue was suspended in a mixed solvent of chloroform/hexane, and filtered under suction to obtain the entitled compound (671 g, 85%) as a yellow solid.

$^1$H-NMR (400 MHz, CDCl$_3$) δ: 2.57 (4H, t, J=6.0 Hz), 3.47 (4H, t, J=6.0 Hz), 5.03 (2H, s), 6.92-6.97 (4H, m), 7.30-7.44 (5H, m)

Reference Example 6-1

Production of 1-(4-methoxyphenyl)piperidin-4-one

The entitled compound was obtained as a brown solid, according to the same method as in Reference Example 6 or according to a method similar to it but using 8-(4-methoxyphenyl)-1,4-dioxa-8-azaspiro[4,5]decane obtained in Reference Example 5-1 in place of 8-[4-(benzyloxy)phenyl]-1,4-dioxa-8-azaspiro[4,5]decane.

$^1$H-NMR (400 MHz, CDCl$_3$) δ: 2.57 (4H, t, J=6.1 Hz), 3.46 (4H, t, J=5.9 Hz), 3.78 (3H, s), 6.87 (2H, dt, J=8.8, 3.4 Hz), 6.97 (2H, dt, J=8.8, 3.4 Hz)

Reference Example 7

Production of 4-(aminomethyl)-1-[4-(benzyloxy)phenyl]piperidin-4-ol

1-[4-(Benzyloxy)phenyl]piperidin-4-one (671 g, 2.38 mol) obtained in Reference Example 6 was dissolved in chloroform, and at 0° C., triethylamine (24.1 g, 0.24 mol) and trimethylsilylcyanide (260 g, 2.62 mol) were added thereto, and stirred for 20 minutes with cooling with ice. The reaction solution was added to aqueous saturated sodium hydrogencarbonate solution, stirred, and the organic layer was washed with saturated saline, and dried with sodium sulfate. The solvent was evaporated off under reduced pressure to obtain a crude product (1-[4-(benzyloxy)phenyl]-4-[(trimethylsilyl)oxy]piperidine-4-carbonitrile) (837.9 g, gross yield 92%) as a brown solid. With cooling with ice, a tetrahydrofuran solution of the resulting crude product (837 g, 2.2 mol) was dropwise added to a tetrahydrofuran solution of aluminium lithium hydride (108.5 g, 2.86 mol), and with cooling with ice, this was stirred for 1.2 hours. At 0° C., sodium sulfate 10-hydrate (450 g) was added to the reaction solution, and this was stirred overnight at room temperature. This was filtered through Celite under suction, and the solvent was evaporated off under reduced pressure to obtain a crude product (1.07 kg). With cooling with ice, 6 N hydrochloric acid (2 L) was added to a methanol solution of the resulting crude product (1.07 kg), heated up to room temperature, and stirred for 1 hour. With cooling with ice, this was neutralized by adding aqueous 5 N sodium hydroxide solution thereto, and the solvent was evaporated off under reduced pressure. The residue was dissolved in chloroform, washed with water and saturated saline in that order, and the organic layer was dried with sodium sulfate. The solvent was evaporated off under reduced pressure, then the residue was suspended in mixed solvent of chloroform/hexane added thereto, and this was filtered under suction to obtain the entitled compound (562.7 g, 75.5%) as a white solid.

$^1$H-NMR (400 MHz, CDCl$_3$) δ: 1.50 (2H, brs), 1.65-1.68 (4H, m), 2.66 (2H, s), 3.03-3.10 (2H, m), 3.27-3.30 (2H, m), 5.01 (2H, s), 6.89-6.95 (4H, m), 7.31-7.44 (5H, m)

Reference Example 7-1

Production of 4-(aminomethyl)-1-(4-methoxyphenyl)piperidin-4-ol

The entitled compound was obtained as a white solid, according to the same method as in Reference Example 7 or according to a method similar to it but using 1-(4-methoxyphenyl)piperidin-4-one obtained in Reference Example 6-1 in place of 1-[4-(benzyloxy)phenyl]piperidin-4-one.

$^1$H-NMR (400 MHz, CDCl$_3$) δ: 1.66-1.69 (4H, m), 2.66 (2H, s), 3.03-3.10 (2H, m), 3.31-3.25 (2H, m), 3.77 (3H, s), 6.83 (2H, dt, J=8.8, 3.9 Hz), 6.95 (2H, dt, J=8.8, 3.9 Hz)

Reference Example 7-2

Production of 4-(aminomethyl)-1-{4-[(1-cyclobutylpiperidin-4-yl)oxy]phenyl}piperidin-4-ol The entitled compound was obtained as a pale brown solid, according to the same method as in Reference Example 7 or according to a method similar to it but using 1-{4-[(1-cyclobutylpiperidin-4-yl)oxy]phenyl}piperidin-4-one obtained in Reference Example 21 as the starting compound, in place of 1-[4-(benzyloxy)phenyl]piperidin-4-one.

$^1$H-NMR (400 MHz, CDCl$_3$) δ: 1.33-2.26 (16H, m), 2.54-2.81 (3H, m), 2.66 (2H, s), 3.00-3.13 (2H, m), 3.23-3.34 (2H, m), 4.20 (1H, brs), 6.83 (2H, d, J=9.1 Hz), 6.91 (2H, d, J=9.1 Hz)

Reference Example 7-3

Production of 4-(aminomethyl)-1-{-4-[(1-isopropylpiperidin-4-yl)oxy]phenyl}piperidin-4-ol The entitled compound was obtained as a white solid, according to the same method as in Reference Example 7 or according to a method similar to it but using 1-{4-[(1-isopropylpiperidin-4-yl)oxy]phenyl}piperidin-4-one obtained in Reference Example 21-1 as the starting compound, in place of 1-[4-(benzyloxy)phenyl]piperidin-4-one.

$^1$H-NMR (400 MHz, CD$_3$OD) δ: 1.13 (6H, d, J=4.8 Hz), 1.72-1.84 (6H, m), 1.98-2.08 (2H, m), 2.42-2.52 (2H, m), 2.63 (2H, s), 2.74-2.82 (1H, m), 2.84-2.91 (2H, m), 3.02-3.09 (2H, m), 3.26 (2H, d, J=9.0 Hz), 4.26-4.34 (1H, m), 6.89 (2H, d, J=6.6 Hz), 7.01 (2H, d, J=6.6 Hz)

Reference Example 7-4

Production of 4-(aminomethyl)-1-{6-[(1-cyclobutylpiperidin-4-yl)oxy]pyridin-3-yl}piperidin-4-ol The entitled compound was obtained as a pale brown solid, according to the same method as in Reference Example 7 or according to a method similar to it but using 1-{6-[(1-cyclobutylpiperidin-4-yl)oxy]pyridin-3-yl}piperidin-4-one obtained in Reference Example 21-2 as the starting compound, in place of 1-[4-(benzyloxy)phenyl]piperidin-4-one.

$^1$H-NMR (400 MHz, CDCl$_3$) δ: 1.18-2.31 (16H, m), 2.56-2.85 (3H, m), 2.65 (2H, s), 3.00-3.15 (2H, m), 3.18-3.31 (2H, m), 4.97 (1H, brs), 6.64 (1H, d, J=8.8 Hz), 7.30 (1H, dd, J=8.8, 2.9 Hz), 7.81 (1H, d, J=2.9 Hz)

Reference Example 7-5

Production of 4-(aminomethyl)-1-{6-[(1-isopropylpiperidin-4-yl)oxy]pyridin-3-yl}piperidin-4-ol The entitled compound was obtained as a white solid, according to the same method as in Reference Example 7 or according to a method similar to it but using 1-{6-[(1-isopropylpiperidin-4-yl)oxy]pyridin-3-yl}piperidin-4-one obtained in Reference Example 21-3 as the starting compound, in place of 1-[4-(benzyloxy)phenyl]piperidin-4-one.

$^1$H-NMR (400 MHz, DMSO-d$_6$) δ: 0.95 (10H, d, J=5.9 Hz), 1.44-1.61 (6H, m), 1.86-1.96 (2H, m), 2.21-2.30 (2H, m), 2.63-2.74 (5H, m), 2.93 (2H, td, J=10.7, 3.4 Hz), 3.19 (2H, dt, J=12.2, 3.9 Hz), 4.84-4.75 (1H, m), 6.62 (1H, d, J=8.8 Hz), 7.38 (1H, dd, J=9.0, 3.2 Hz), 7.74 (1H, d, J=2.9 Hz)

Reference Example 7-6

Production of 4-(aminomethyl)-1-(4-{3-[(2R)-2-methylpyrrolidin-1-yl]propoxy}phenyl)piperidin-4-ol The entitled compound was obtained as a pale brown solid, according to the same method as in Reference Example 7 or according to a method similar to it but using 1-(4-{3-[(2R)-2-methylpyrrolidin-1-yl]propoxy}phenyl)piperidin-4-one obtained in Reference Example 21-4 as the starting compound, in place of 1-[4-(benzyloxy)phenyl]piperidin-4-one.

$^1$H-NMR (400 MHz, CDCl$_3$) δ: 1.09 (3H, d, J=3.0 Hz), 1.35-2.35 (14H, m), 2.66 (2H, s), 2.92-3.12 (3H, m), 3.27 (2H, d, J=9.0 Hz), 3.95-3.98 (2H, m), 6.83 (2H, d, J=9.3 Hz), 6.93 (2H, d, J=9.3 Hz)

Reference Example 8

Production of N-({1-[4-(benzyloxy)phenyl]-4-hydroxypiperidin-4-yl}methyl)-2-chloroacetamide An acetonitrile (5 L) suspension of 4-(aminomethyl)-1-[4-(benzyloxy)phenyl]piperidin-4-ol (250 g, 800 mmol) obtained in Reference Example 7 and aqueous potassium carbonate (221.2 g, 1.6 mol) solution (2.5 L) were mixed, and with stirring and cooling with ice, chloroacetyl chloride (109.7 g, 971 mmol) was dropwise added to it, and stirred for 40 minutes. With cooling with ice, methanol (2.5 L) was added to it, then diluted with chloroform, heated up to room temperature, and extracted with chloroform. The organic layer was dried with sodium sulfate, and the solvent was evaporated off under reduced pressure to obtain a crude product. The resulting crude product was suspended in mixed solvent of toluene/hexane, and filtered under suction to obtain the entitled compound (297 g, 95.5%) as a yellow solid.

$^1$H-NMR (400 MHz, DMSO-d$_6$) δ: 1.56-1.60 (4H, m), 2.91-2.99 (2H, m), 3.16-3.21 (4H, m), 4.15 (2H, s), 5.03 (2H, s), 6.89 (4H, s), 7.33-7.45 (5H, m), 8.19 (1H, brs)

Reference Example 8-1

Production of 2-chloro-N-{[4-hydroxy-1-(4-methoxyphenyl)piperidin-4-yl]methyl}acetamide The entitled compound was obtained as a pale yellow solid, according to the same method as in Reference Example 8 or according to a method similar to it but using 4-(aminomethyl)-1-4-(methoxyphenyl)piperidin-4-ol obtained in Reference Example 7-1 in place of 4-(aminomethyl)-1-[4-(benzyloxy)phenyl]piperidin-4-ol.

$^1$H-NMR (400 MHz, CDCl$_3$) δ: 1.71-1.80 (4H, m), 3.01-3.01 (2H, m), 3.23-3.27 (2H, m), 3.41 (2H, d, J=6.4 Hz), 3.77 (3H, s), 4.11 (2H, s), 6.82-6.85 (2H, m), 6.92 (2H, dd, J=8.8 Hz)

Reference Example 8-2

Production of 2-chloro-N-[(1-{4-[(1-cyclobutylpiperidin-4-yl)oxy]phenyl}-4-hydroxypiperidin-4-yl)methyl]acetamide 4-(Aminomethyl)-1-{4-[(1-cyclobutylpiperidin-4-yl)oxy]phenyl}piperidin-4-ol (5 g, 13.9 mmol) obtained in Reference Example 7-2 was suspended in dimethylformamide, and at 0° C., pyridine (4.5 ml, 55.6 mmol) and chloroacetyl chloride (1.4 ml, 18.1 mmol) were added thereto in that order and stirred for 2 hours. Water was added to it to stop the reaction, and pH of the system was adjusted to 9 by adding aqueous 4 N sodium hydroxide solution thereto. Then, this was extracted with 10% methanol/chloroform solution, washed with saturated saline, and dried with sodium sulfate. The organic solvent was evaporated off under reduced pressure, and the resulting residue was crystallized with isopropyl ether/ethyl acetate to obtain the entitled compound as a pale brown solid (2.55 g, 42%).

$^1$H-NMR (400 MHz, CDCl$_3$) δ: 1.46-2.24 (16H, m), 2.53-2.85 (3H, m), 2.99-3.11 (2H, m), 3.19-3.32 (2H, m), 3.41 (2H, d, J=6.8 Hz), 4.11 (2H, s), 4.20 (1H, brs), 6.83 (2H, d, J=9.3 Hz), 6.90 (2H, d, J=9.3 Hz), 6.99 (1H, d, J=6.8 Hz)

Reference Example 8-3

Production of 2-chloro-N-[(4-hydroxy-1-{4-[(1-isopropylpiperidin-4-yl)oxy]phenyl}piperidin-4-yl)methyl]acetamide The entitled compound was obtained as a brown oily substance, according to the same method as in Reference Example 8-2 or according to a method similar to it but using 4-(aminomethyl)-1-{4-[(1-isopropylpiperidin-4-yl)oxy]phenyl}piperidin-4-ol obtained in Reference Example 7-3 as the starting compound, in place of 4-(aminomethyl)-1-{4-[(1-cyclobutylpiperidin-4-yl)oxy]phenyl}piperidin-4-ol.

$^1$H-NMR (400 MHz, CD$_3$OD) δ: 1.11 (6H, d, J=6.0 Hz), 1.71-1.90 (6H, m), 2.05 (2H, brs), 2.48 (2H, brs), 2.89 (3H, brs), 3.02-3.08 (2H, m), 3.23-3.30 (2H, m), 3.41 (2H, d, J=6.0 Hz), 4.11 (2H, s), 4.23 (1H, brs), 6.84 (2H, d, J=6.6 Hz), 6.89 (2H, d, J=6.6 Hz), 7.00 (1H, brs)

Reference Example 8-4

Production of 2-chloro-N-[(1-{6-[(1-cyclobutylpiperidin-4-yl)oxy]pyridin-3-yl}-4-hydroxypiperidin-4-yl)methyl]acetamide The entitled compound was obtained as a brown oily substance, according to the same method as in Reference Example 8-2 or according to a method similar to it but using 4-(aminomethyl)-1-{6-[(1-cyclobutylpiperidin-4-yl)oxy]pyridin-3-yl}piperidin-4-ol obtained in Reference Example 7-4 as the starting compound, in place of 4-(aminomethyl)-1-{4-[(1-cyclobutylpiperidin-4-yl)oxy]phenyl}piperidin-4-ol.

$^1$H-NMR (400 MH, CDCl$_3$) δ: 1.46-2.43 (16H, m), 2.58-2.86 (3H, m), 3.00-3.12 (2H, m), 3.16-3.29 (2H, m), 3.41 (2H, d, J=6.0 Hz), 4.12 (2H, s), 4.97 (1H, brs), 6.64 (1H, d, J=8.8 Hz), 7.00 (1H, t, J=6.0 Hz), 7.29 (1H, dd, J=8.8, 2.9 Hz), 7.79 (1H, d, J=2.9 Hz)

Reference Example 9

Production of 9-[4-(benzyloxyphenyl]-1-oxa-4,9-diazaspiro[5,5]undecan-3-one

At room temperature, an N,N-dimethylformamide solution (1.5 L) of N-({1-[4-(benzyloxy)phenyl]-4-hydroxypiperidin-4-yl}methyl)-2-chloroacetamide (297 g, 766 mmol) obtained in Reference Example 8 was added to a 2-methylbutan-2-ol solution (6 L) of potassium tert-butoxide (233 g, 2.08 mol), and this was stirred for 2.5 hours at room temperature. Acetic acid (100 ml) was added thereto, then saturated sodium hydrogencarbonate solution was added thereto, and extracted with mixed solvent of chloroform/methanol. The organic layer was dried with sodium sulfate, and the solvent was concentrated under reduced pressure to obtain a crude product. The resulting crude product was suspended in mixed solvent of chloroform/hexane, and filtered under suction to obtain the entitled compound (229.6 g, 85.0%) as a brown solid.

$^1$H-NMR (400 MHz, CDCl$_3$) δ: 1.77-1.84 (2H, m), 2.04 (2H, d, J=12.8 Hz), 2.99-3.05 (2H, m), 3.24-3.28 (2H, m), 3.30 (2H, d, J=2.4 Hz), 4.21 (2H, s), 5.02 (2H, s), 6.02 (1H, brs), 6.89-6.94 (4H, m), 7.30-7.43 (5H, m)

Reference Example 9-1

Production of 9-(4-methoxyphenyl)-1-oxa-4,9-diazaspiro[5,5]undecan-3-one

The entitled compound was obtained as a pale yellow solid, according to the same method as in Reference Example 9 or according to a method similar to it but using 2-chloro-N-{[4-hydroxy-1-(4-methoxyphenyl)piperidin-4-yl]methyl}acetamide obtained in Reference Example 8-1 in place of N-({1-[4-(benzyloxy)phenyl]-4-hydroxypiperidin-4-yl}methyl)-2-chloroacetamide.

$^1$H-NMR (400 MHz, CDCl$_3$) δ: 1.80-1.83 (2H, m), 2.05 (2H, d, J=13.2 Hz), 2.99-3.06 (2H, m), 3.25 (2H, dt, J=12.7, 4.4 Hz), 3.30 (2H, d, J=2.4 Hz), 3.78 (3H, s), 4.20 (2H, s), 6.43 (1H, brs), 6.84 (2H, dt, J=9.3, 3.4 Hz), 6.94 (2H, d, J=8.8 Hz)

Reference Example 9-2

Production of 9-{4-[(1-cyclobutylpiperidin-4-yl)oxy]phenyl}-1-oxa-4,9-diazaspiro[5,5]undecan-3-one Potassium t-butoxide (1.6 g, 14.6 mmol) was dissolved in a mixed solvent of t-butanol (50 ml) and dimethylformamide (6 ml), and stirred at room temperature, and a dimethylformamide solution (2 ml) of 2-chloro-N-[(1-{4-[(1-cyclobutylpiperidin-4-yl)oxy]phenyl}-4-hydroxypiperidin-4-yl)methyl]acetamide (2.54 g, 5.83 mmol) obtained in Reference Example 8-2 was dropwise added to it, over 15 minutes. This was stirred for 4 hours, then water was added thereto to stop the reaction. This was extracted with ethyl acetate, washed with saturated saline, and dried with magnesium sulfate. The solvent was evaporated off, and the residue was purified through silica gel column chromatography (eluate: methanol/chloroform=2/98 to 15/85) to obtain the entitled compound as a pale yellow solid (1.6 g, 69%).

$^1$H-NMR (400 MHz, CDCl$_3$) δ: 1.56-2.29 (16H, m), 2.53-2.82 (3H, m), 2.95-3.08 (2H, m), 3.19-3.29 (2H, m), 3.29 (1H, s), 3.30 (1H, s), 4.17-4.26 (1H, m), 4.20 (2H, s), 6.31 (1H, brs), 6.84 (2H, d, J=9.3 Hz), 6.90 (2H, d, J=9.3 Hz)

Reference Example 9-3

Production of 9-{4-[(1-isopropylpiperidin-4-yl)oxy]phenyl}-1-oxa-4,9-diazaspiro[5,5]undecan-3-one The entitled compound was obtained as a pale yellow solid, according to the same method as in Reference Example 9-2 or according to a method similar to it but using 2-chloro-N-[(4-hydroxy-1-{4-[(1-isopropylpiperidin-4-yl)oxy]phenyl}piperidin-4-yl)methyl]acetamide obtained in Reference Example 8-3 as the starting compound, in place of 2-chloro-N-[(1-{4-[(1-cyclobutylpiperidin-4-yl)oxy]phenyl}-4-hydroxypiperidin-4-ylmethyl]acetamide.

$^1$H-NMR (CDCl$_3$) δ: 1.06 (6H, d, J=6.3 Hz), 1.73-1.86 (4H, m), 1.93-2.09 (4H, m), 2.30-2.44 (2H, brm), 2.69-2.84 (3H, brm), 3.02 (2H, td, J=11.2, 2.9 Hz), 3.25 (2H, dt, J=12.7, 3.9 Hz), 3.30 (2H, d, J=2.4 Hz), 4.14-4.25 (3H, m), 6.06 (1H, brs), 6.85 (2H, d, J=9.3 Hz), 6.90 (2H, d, J=9.3 Hz)

Reference Example 9-4

Production of 9-{6-[1-cyclobutylpiperidin-4-yl)oxy]pyridin-3-yl}-1 oxa-4,9-diazaspiro[5,5]undecan-3-one The entitled compound was obtained as a brown solid, according to the same method as in Reference Example 9-2 or according to a method similar to it but using 2-chloro-N-[(1-{6-[(1-cyclobutylpiperidin-4-yl)oxy]pyridin-3-yl}-4-hydroxypiperidin-4-yl)methyl]acetamide obtained in Reference Example 84 as the starting compound, in place of 2-chloro-N-[(1-{4-[(1-cyclobutylpiperidin-4-yl)oxy]phenyl}-4-hydroxypiperidin-4-ylmethyl]acetamide.

$^1$H-NMR (CDCl$_3$) δ: 2.04-3.31 (23H, m), 3.31 (2H, s), 4.20 (2H, s), 5.09 (1H, brs), 6.02 (1H, brs), 6.65 (1H, d, J=8.9 Hz), 7.30 (4H, dd, J=8.9, 2.8 Hz), 7.79 (1H, d, J=2.8 Hz)

Reference Example 10

Production of tert-Butyl 9-[4-(benzyloxy)phenyl]-3-oxo-1-oxa-4,9-diazaspiro[5,5]undecane-4-carboxylate In chloroform, 9-[4-(benzyloxy)phenyl]-1-oxa-4,9-diazaspiro[5,5]undecan-3-one (5 g, 14.2 mmol) obtained in Reference Example 9 was mixed with di-tert-butyl dicarbonate (6.2 g, 28.4 mmol), triethylamine (1.45 g, 14.2 mmol) and 4-dimethylaminopyridine (350 mg, 2.84 mmol), and this was stirred overnight at room temperature. The reaction solution was diluted with chloroform, then washed with water and saturated saline in that order, and the organic layer was dried with sodium sulfate. The solvent was evaporated off under reduced pressure, and the resulting residue was purified through silica gel column chromatography (eluate: chloroform/ethyl acetate=95/5 to 88/12), then suspended in diisopropyl ether, and filtered under suction to obtain the entitled compound (5.34 g, 83%) as a white solid.

$^1$H-NMR (400 MHz, CDCl$_3$) δ: 1.55 (9H, s), 1.77-1.84 (2H, m), 1.97 (2H, d, J=13.2 Hz), 3.02 (2H, td, J=11.2, 2.4 Hz), 3.25 (2H, dt, J=12.7, 3.9 Hz), 3.64 (2H, s), 4.22 (2H, s), 5.02 (2H, s), 6.91 (4H, s), 7.30-7.44 (5H, m)

Reference Example 11

Production of Tert-Butyl 9-[4-(hydroxyphenyl)]-3-oxo-1-oxa-4,9-diazaspiro[5,5]undecane-4-carboxylate Tert-butyl 9-[4-(benzyloxy)phenyl]-3-oxo-1-oxa-4,9-diazaspiro[5,5]undecane-4-carboxylate (5.34 g, 11.8 mmol) obtained in Reference Example 10 was dissolved in mixed solvent of methanol/ethyl acetate, and 10% palladium-carbon (1.1 g, 1.03 mmol) was added thereto, and stirred overnight in a hydrogen atmosphere. The reaction solution was filtered through Celite, the Celite was washed with mixed solvent of chloroform/methanol, and the mother liquid was concentrated to obtain the entitled compound (4.54 g, 100%) as a violet solid.

$^1$H-NMR (CDCl$_3$) δ: 1.57 (9H, s), 1.98-2.07 (4H, brm), 3.14-3.32 (4H, m), 3.73 (2H, s), 4.23 (2H, s), 6.81 (2H, d, J=8.8 Hz), 7.05 (2H, brs)

Reference Example 12

Production of 9-[4-(3-piperidin-1-ylpropoxy)phenyl]-1-oxa-4,9-diazaspiro[5,5]undecan-3-one Tert-butyl 9-[4-(hydroxyphenyl)]-3-oxo-1-oxa-4,9-diazaspiro[5,5]undecane-4-carboxylate (2 g, 5.52 mmol) obtained in Reference Example 11, 1-(3-bromopropyl)piperidine hydrobromide (2.37 g, 8.28 mmol) produced according to a method described in a patent (U.S. Pat. No. 4,751,302), and cesium carbonate (5.4 g, 16.6 mmol) were mixed in N,N-dimethylformamide, and stirred overnight at room temperature. The reaction solution was diluted with ethyl acetate, washed with water and saturated saline in that order, and the organic layer was dried with sodium sulfate. The solvent was evaporated off under reduced pressure, to obtain a crude product (tert-butyl 3-oxo-9-[4-(3-piperidin-1-ylpropoxy) phenyl]-1-oxa-4,9-diazaspiro[5,5]undecan-3-one) (2.64 g). Trifluoroacetic acid was added to the resulting crude product with cooling with ice, and stirred at room temperature for 1 hour. With cooling with ice, this was neutralized by adding aqueous 2 N sodium hydroxide solution thereto, and extracted with ethyl acetate. The organic layer was washed with saturated saline, dried with sodium sulfate, and the solvent was concentrated under reduced pressure. The resulting residue was suspended by adding hexane thereto, and filtered under suction to obtain the entitled compound (1.58 g, 74%) as a pale yellow solid.

$^1$H-NMR (400 MHz, CDCl$_3$) δ: 1.43-1.45 (2H, brm), 1.58-1.60 (4H, m), 1.77-1.84 (2H, m), 1.93-1.99 (2H, m), 2.04 (2H, d, J=13.2 Hz), 2.42 (4H, brs), 2.48 (2H, t, J=7.6 Hz), 3.01 (2H, td, J=11.7, 2.9 Hz), 3.24 (2H, dt, J=12.7, 4.4 Hz), 3.30 (2H, d, J=2.9 Hz), 3.96 (2H, t, J=6.3 Hz), 4.20 (2H, s), 6.18 (1H, brs), 6.83 (2H, dt, J=9.3, 3.9 Hz), 6.92 (2H, dt, J=9.3, 3.9 Hz)

Reference Example 12-1

Production of 9-(4-{3-[(3S)-3-methylpiperidin-1-yl]propoxy}phenyl)-1-oxa-4,9-diazaspiro[5,5]undecan-3-one The entitled compound was obtained as a pale brown solid, according to the same method as in Reference Example 12 or according to a method similar to it or according to a combination of the method with an ordinary method but using tert-butyl 9-[4-(hydroxyphenyl)]-3-oxo-1-oxa-4,9-diazaspiro[5,5]undecane-4-carboxylate obtained in Reference Example 11, and (3S)-1-(3-bromopropyl)-3-methylpiperidine hydrobromide obtained in Reference Example 4 in place of 1-(3-bromopropyl)piperidine hydrobromide.

$^1$H-NMR (400 MHz, CDCl$_3$) δ: 0.87 (3H, d, J=6.3 Hz), 1.57-1.72 (6H, m), 1.77-1.84 (3H, m), 1.93-2.00 (2H, m), 2.04 (2H, d, J=12.7 Hz), 2.50 (2H, brs), 2.85-2.92 (2H, brm), 3.01 (2H, td, J=2.8, 11.7 Hz), 3.24 (2H, dt, J=3.4, 12.2 Hz), 3.30 (2H, d, J=2.9 Hz), 3.96 (2H, t, J=6.3 Hz), 4.21 (2H, s), 6.03 (1H, s), 6.83 (2H, dt, J=9.3, 3.4 Hz), 6.91 (2H, dt, J=9.3, 3.4 Hz)

Reference Example 12-2

Production of 9-[4-(3-pyrrolidin-1-ylpropoxy)phenyl]-1-oxa-4,9-diazaspiro[5,5]undecan-3-one The entitled compound was obtained as a pale brown solid, according to the same method as in Reference Example 12 or according to a method similar to it or according to a combination of the method with an ordinary method but using tert-butyl 9-[4-(hydroxyphenyl)]-3-oxo-1-oxa-4,9-diazaspiro[5,5]undecane-4-carboxylate obtained in Reference Example 11, and 1-(3-bromopropyl)pyrrolidine hydrobromide produced according to a method described in a patent (U.S. Pat. No. 4,751,302), in place of 1-(3-bromopropyl)piperidine hydrobromide.

$^1$H-NMR (400 MHz, CDCl$_3$) δ: 1.77-1.84 (6H, m), 2.00-2.06 (4H, m), 2.62 (4H, brs), 2.70 (2H, t, J=7.3 Hz), 3.01 (2H, td, J=11.7, 2.9 Hz), 3.24 (2H, dt, J=12.7, 4.9 Hz), 3.30 (2H, d, J=2.9 Hz), 3.98 (2H, t, J=6.3 Hz), 4.21 (2H, s), 6.05 (1H, brs), 6.83 (2H, dt, J=9.3, 3.4 Hz), 6.92 (2H, dt, J=9.3, 3.4 Hz)

Reference Example 12-3

Production of 9-(4-{3-[(2S)-2-methylprrolidin-1-yl]propoxy}phenyl)-1-oxa-4,9-diazaspiro[5,5]undecan-3-one The entitled compound was obtained as a pale brown solid, according to the same method as in Reference Example 12 or according to a method similar to it but using tert-butyl 9-[4-(hydroxyphenyl)]-3-oxo-1-oxa-4,9-diazaspiro[5,5]undecane-4-carboxylate obtained in Reference Example 11, and (2S)-1-(3-bromopropyl)-2-methylpyrrolidine hydrobromide obtained in Reference Example 4-1 in place of 1-(3-bromopropyl)piperidine hydrobromide.

Reference Example 12-4

Production of 9-(4-{3-[(2R)-2-methylpyrrolidin-1-yl]propoxy}phenyl)-1-oxa-4,9-diazaspiro[5,5]undecan-3-one The entitled compound was obtained as a pale brown solid, according to the same method as in Reference Example 12 or according to a method similar to it or according to a combination of the method with an ordinary method but using tert-butyl 9-[4-(hydroxyphenyl)]-3-oxo-1-oxa-4,9-diazaspiro[5,5]undecane-4-carboxylate obtained in Reference Example 11, and (2R)-1-(3-bromopropyl)-2-methylpyrrolidine hydrobromide obtained in Reference Example 4-2 in place of 1-(3-bromopropyl)piperidine hydrobromide.

$^1$H-NMR (400 MHz, CDCl$_3$) δ: 1.09 (3H, d, J=6.3 Hz), 1.37-1.46 (1H, m), 1.56-1.84 (4H, m), 1.87-2.21 (7H, m), 2.24-2.32 (1H, m), 2.93-3.04 (3H, m), 3.15-3.29 (5H, m), 3.95-4.01 (2H, m), 4.19 (2H, s), 6.64 (1H, brs), 6.84 (2H, d, J=9.2 Hz), 6.91 (2H, d, J=9.2 Hz)

Reference Example 13

Production of 8-(4-methoxyphenyl)-1-oxa-3,8-diazaspiro[4,5]decan-2-one 4-(Aminomethyl)-1-(4-methoxyphenyl)piperidin-4-ol (1 g, 4.23 mmol) obtained in Reference Example 7-1 was mixed with triphosgene (1.26 g, 4.23 mmol) in chloroform, and stirred overnight at room temperature. The reaction solution was diluted with chloroform, then aqueous saturated sodium carbonate solution was added thereto, extracted with chloroform and washed with saturated saline. The organic layer was dried with sodium sulfate, and the solvent was evaporated off under reduced pressure to obtain the entitled compound (1.17 g, 100%) as a white solid.

$^1$H-NMR (400N Hz, CDCl$_3$) δ: 1.97-2.15 (4H, m), 3.26 (4H, brs), 3.46 (2H, s), 3.78 (3H, s), 4.99 (1H, brs), 6.86-7.01 (4H, m)

Reference Example 13-1

Production of 8-{-4-[(1-cyclobutylpiperidin-4-yl)oxy]phenyl}-1-oxa-3,8-diazaspiro[4,5]decan-2-one The entitled compound was obtained as a pale orange solid, according to the same method as in Reference Example 13 or according to a method similar to it but using 4-(aminomethyl)-1-{4-[(1-cyclobutylpiperidin-4-yl)oxy]phenyl}piperidin-4-ol obtained in Reference Example 7-2 as the starting compound, in place of 4-(aminomethyl)-1-(4-methoxyphenyl)piperidin-4-ol.

$^1$H-NMR (400 MHz, CDCl$_3$) δ: 1.59-2.17 (16H, m), 2.53-2.83 (3H, m), 3.14-3.28 (4H, m), 3.39 (2H, s), 4.21 (1H, brs), 4.95 (1H, brs), 6.84 (2H, d, J=9.3 Hz), 6.89 (2H, d, J=9.3 Hz)

Reference Example 13-2

Production of 8-{4-[(1-isopropylpiperidin-4-yl)oxy]phenyl}-1-oxa-3,8-diazaspiro[4,5]decan-2-one The entitled compound was obtained as a white solid, according to the same method as in Reference Example 13 or according to a method similar to it but using 4-(aminomethyl)-1-{4-[(1-isopropylpiperidin-4-yl)oxy]phenyl}piperidin-4-ol obtained in Reference Example 7-3 as the starting compound, in place of 4-(aminomethyl)-1-(4-methoxyphenyl)piperidin-4-ol.

$^1$H-NMR (400 MHz, CDCl$_3$) δ: 1.37 (4H, brs), 1.67 (6H, s), 1.85-2.19 (7H, m), 2.95-3.31 (6H, m), 3.35-3.47 (3H, m), 6.83 (2H, d, J=9.3 Hz), 6.92 (2H, d, J=9.3 Hz)

Reference Example 13-3

Production of 8-{6-[(1-cyclobutylpiperidin-4-yl)oxy]pyridin-3-yl}-1-oxa-3,8-diazaspiro[4,5]decan-2-one The entitled compound was obtained as a white solid, according to the same method as in Reference Example 13 or according to a method similar to it but using 4-(aminomethyl)-1-{6-[(1-cyclobutylpiperidin-4-yl)oxy]pyridin-3-yl}piperidin-4-ol obtained in Reference Example 7-4 as the starting compound, in place of 4-(aminomethyl)-1-(4-methoxyphenyl)piperidin-4-ol.

$^1$H-NMR (400 MHz, CDCl$_3$) δ: 1.27-2.13 (16H, m), 2.65-2.97 (3H, brm), 3.15-3.24 (4H, m), 3.40 (2H, s), 5.03 (1H, brs), 5.19 (1H, brs), 6.65 (1H, d, J=9.3 Hz), 7.29 (1H, dd, J=9.0, 3.2 Hz), 7.79 (1H, d, J=2.9 Hz)

Reference Example 13-4

Production of 8-{6-[(1-isopropylpiperidin-4-yl)oxy]pyridin-3-yl}-1-oxa-3,8-diazaspiro[4,5]decan-2-one The entitled compound was obtained as a white solid, according to the same method as in Reference Example 13 or according to a method similar to it but using 4-(aminomethyl)-1-{6-[(1-isopropylpiperidin-4-yl)oxy]pyridin-3-yl}piperidin-4-ol obtained in Reference Example 7-5 as the starting compound, in place of 4-(aminomethyl)-1-(4-methoxyphenyl)piperidin-4-ol.

$^1$H-NMR (CDCl$_3$) δ: 1.06 (6H, d, J=6.3 Hz), 1.72-1.84 (2H, m), 1.87-1.99 (2H, m), 2.00-2.17 (4H, m), 2.35-2.48 (2H, m), 2.75-2.85 (2H, m), 2.75 (1H, t, J=6.3 Hz), 3.14-3.26 (4H, m), 3.40 (2H, s), 4.93-4.94 (1H, m), 5.18 (1H, brs), 6.66 (1H, d, J=9.3 Hz), 7.28 (3H, dd, J=9.3, 2.9 Hz), 7.80 (1H, d, J=2.9 Hz)

Reference Example 13-5

Production of 8-(4-{3-[(2R)-2-methylpyrrolidin-1-yl]propoxy}phenyl)-1-oxa-3,8-diazaspiro[4,5]decan-2-one The entitled compound was obtained as a pale brown solid, according to the same method as in Reference Example 13 or according to a method similar to it but using 4-(aminomethyl)-1-(4-{3-[(2R)-2-methylpyrrolidin-1-yl]propoxy}phenyl)piperidin-4-ol obtained in Reference Example 7-5 as the starting compound, in place of 4-(aminomethyl)-1-(4-methoxyphenyl)piperidin-4-ol.

$^1$H-NMR (400 MHz, CDCl$_3$) δ: 1.12 (3H, d, J=5.9 Hz), 1.44-2.48 (14H, m), 2.94-3.03 (1H, m), 3.16-3.24 (4H, m), 3.39 (2H, s), 3.94-4.01 (2H, m), 5.30 (1H, brs), 6.83 (2H, d, J=9.3 Hz), 6.90 (2H, d, J=9.3 Hz)

Reference Example 14

Production of 8-(4-hydroxyphenyl)-1-oxa-3,8-diazaspiro[4,5]decan-2-one 8-(4-Methoxyphenyl)-1-oxa-3,8-diazaspiro[4,5]decan-2-one (8.43 g, 32.1 mmol) obtained in Reference Example 13 was dissolved in chloroform, and at 0° C., 1.0 M boron tribromide/dichloromethane solution (96 ml, 96.4 mmol) was dropwise added thereto, and stirred overnight at room temperature. At 0° C., the reaction solution was neutralized by adding aqueous saturated sodium carbonate solution thereto, and extracted with mixed solvent chloroform/methanol (4/1).

The organic layer was dried with sodium sulfate, and the solvent was evaporated off under reduced pressure. The resulting residue was suspended in a mixed solvent of chloroform/methanol, and filtered under suction to obtain the entitled compound (7.46 g, 93.4%) as a brown solid.

$^1$H-NMR (400 MHz, CD$_3$OD) δ: 2.35-2.38 (2H, m), 3.34 (2H, s), 3.53 (2H, brs), 3.63-3.66 (2H, brm), 3.78-3.83 (2H, brm), 6.94 (2H, d, J=8.8 Hz), 7.54 (2H, d, J=8.8 Hz)

Reference Example 15

Production of 8-[4-(3-piperidin-1-ylpropoxy)phenyl]-1-oxa-3,8-diazaspiro[4,5]decan-2-one 8-(4-Hydroxyphenyl)-1-oxa-3,8-diazaspiro[4,5]decan-2-one (1.72 g, 6.92 mmol) obtained in Reference Example 14, 1-(3-chloropropyl)piperidine hydrochloride (1.51 g, 7.62 mmol) produced according to the method described in a patent, WO03/101931 or according to a method similar to it, and potassium carbonate (2.87 g, 20.76 mmol) were mixed in DMF, and stirred overnight at 80° C. The solvent was evaporated off under reduced pressure, and the residue was dissolved in chloroform, and washed with water and saturated saline in that order. The organic layer was dried with sodium sulfate, and the solvent was evaporated off under reduced pressure. The residue was suspended in mixed solvent of ethyl acetate/diethyl ether (1/1), and filtered under suction to obtain the entitled compound (1.45 g, 56%) as a brown solid.

$^1$H-NMR (400 MHz, CDCl$_3$) δ: 1.47 (2H, s), 1.66 (4H, s), 1.89-1.96 (2H, m), 1.99-2.06 (2H, m), 2.11 (2H, d, J=13.2 Hz), 2.51-2.57 (6H, m), 3.20 (4H, dd, J=9.0, 3.7 Hz), 3.39 (2H, s), 3.97 (2H, t, J=6.1 Hz), 5.36 (1H, brs), 6.82 (2H, d, J=8.8 Hz), 6.90 (2H, d, J=8.8 Hz)

Reference Example 16

Production of 5-bromo-2-(difluoromethoxy)pyridine

5-Bromopyridin-2(1H)-one (17.4 g, 100 mmol) was mixed with sodium sulfate (1.42 g, 10 mmol) and 2-(fluorosulfonyl) difluoroacetic acid (11.4 ml, 100 mmol) in acetonitrile, and stirred overnight at room temperature. Aqueous saturated sodium hydrogencarbonate solution was added to the reaction solution, and the solvent was concentrated under reduced pressure. The residue was dissolved in diethyl ether, washed with saturated saline, the organic layer was dried with sodium sulfate, and the solvent was evaporated off under reduced pressure. The residue was purified through silica gel column chromatography (eluate: ethyl acetate/hexane=20/80 to 50/50) to obtain the entitled compound (18.75 g, 84%) as a pale yellow oily substance.

$^1$H-NMR (400 MHz, CDCl$_3$) δ: 6.83 (1H, d, J=9.3 Hz), 7.40 (1H, t, J=72.7 Hz), 7.82 (1H, dd, J=8.8, 2.4 Hz), 8.25 (1H, d, J=2.4 Hz)

Reference Example 17

Production of 5-bromo-2-isopropoxypyridine

5-Bromopyridin-2(1H)-one (5 g, 28.7 mmol) and potassium carbonate (9.93 g, 71.8 mmol) were mixed in dimethyl sulfoxide, and at room temperature, 2-iodoisopropyl (3.73 ml, 37.3 mmol) was added thereto, and stirred at room temperature for 4 hours. The reaction solution was diluted with ethyl acetate, and washed with water and saturated saline in that order. The organic layer was dried with sodium sulfate, and the solvent was evaporated off under reduced pressure.

The residue was purified through silica gel column chromatography (eluate: ethyl acetate/hexane=20/80 to 50/50) to obtain the entitled compound (4.72 g, 76%) as a colorless oily substance.

$^1$H-NMR (400 MHz, CDCl$_3$) δ: 1.33 (6H, d, J=6.3 Hz), 5.18-5.28 (1H, m), 6.59 (1H, d, J=8.8 Hz), 7.61 (1H, dd, J=8.8, 2.9 Hz), 8.17 (1H, d, J=2.0 Hz)

Reference Example 18

Production of Tert-Butyl 4-[(5-nitropyridin-2-yl)oxy]piperidine-1-carboxylate

The entitled compound was obtained as a pale yellow solid, according to the same method as that described in a patent (WO2005/077905) or according to a method similar to it but using 2-chloro-5-nitropyridine as the starting compound in place of 4-fluoro-1-nitrobenzene.

$^1$H-NMR (400 MHz, CDCl$_3$) δ: 1.48 (9H, s), 1.67-1.83 (2H, m), 1.94-2.07 (2H, m), 3.23-3.36 (2H, m), 3.70-3.86 (2H, m), 5.29-5.39 (1H, m), 6.80 (1H, d, J=9.6 Hz), 8.35 (1H, dd, J=9.6, 2.7 Hz), 9.05 (1H, d, J=2.7 Hz)

Reference Example 19

Production of 1-isopropyl-4-(4-nitrophenoxy)piperidine

The entitled compound was obtained as an orange solid, according to the same method as that described in a patent (WO2005/077905) or according to a method similar to it but using 4-(4-nitrophenoxy)piperidine as the staring compound.

$^1$H-NMR (400 MHz, CDCl$_3$) δ: 1.08 (6H, d, J=6.3 Hz), 1.81-1.92 (2H, m), 2.01-2.12 (2H, m), 2.40-2.51 (2H, m), 2.74-2.85 (3H, m), 4.40-4.48 (1H, m), 6.95 (2H, d, J=9.3 Hz), 8.19 (2H, d, J=9.3 Hz)

Reference Example 19-1

Production of 2-[(1-cyclobutylpiperidin-4-yl)oxy]-5-nitropyridine

The entitled compound was obtained as an orange solid, according to the same method as that described in a patent (WO2005/077905) or according to a method similar to it but using 5-nitro-2-(piperidin-4-yloxy)pyridine, which had been obtained through Boc removal from tert-butyl 4-[(5-nitropyridin-2-yl)oxy]piperidine-1-carboxylate obtained in Reference Example 18, as the starting compound.

$^1$H-NMR (400 MHz, CDCl$_3$) δ: 1.58-2.27 (12H, m), 2.56-2.84 (3H, m), 5.21 (1H, brs), 6.79 (1H, d, J=9.2 Hz), 8.34 (1H, dd, J=9.2, 2.8 Hz), 9.05 (1H, d, J=2.8 Hz)

Reference Example 19-2

Production of 2-[(1-isopropylpiperidin-4-yl)oxy]-5-nitropyridin 4-methylbenzenesulfonate The entitled compound was obtained as a white solid, according to the same method as that described in a patent (WO2005/077905) or according to a method similar to it but using 5-nitro-2-(piperidin-4-yloxy)pyridine, which had been obtained through Boc removal from tert-butyl 4-[(5-nitropyridin-2-yl)oxy]piperidine-1-carboxylate obtained in Reference Example 18, as the starting compound.

¹H-NMR (400 MHz, DMSO-d₆) δ: 1.28 (6H, t, J=5.1 Hz), 1.82-1.87 (1H, m), 2.19-2.20 (2H, m), 2.30 (3H, s), 2.35 (2H, d, J=9.3 Hz), 3.10-3.26 (2H, m), 3.47-3.58 (2H, m), 5.32-5.48 (1H, m), 7.06-7.09 (1H, m), 7.13 (2H, d, J=6.3 Hz), 7.49 (2H, d, J=6.3 Hz), 8.51-8.57 (1H, m), 9.16 (1H, brs), 9.09 (1H, dd, J=2.1, 7.2 Hz)

Reference Example 20

Production of 4-[(1-isopropylpiperidin-4-yl)oxy]aniline

The entitled compound was obtained as a solid, according to the same method as that described in a patent (WO2005/077905) or according to a method similar to it but using 1-isopropyl-4-(4-nitrophenoxy)piperidine obtained in Reference Example 19, as the starting compound.

¹H-NMR (400 MHz, CDCl₃) δ: 1.05 (6H, d, J=4.8 Hz), 1.73-1.81 (2H, m), 1.95-1.97 (2H, m), 2.32-2.38 (2H, m), 2.71-2.81 (3H, m), 4.07-4.11 (1H, m), 6.59 (2H, d, J=6.6 Hz), 6.74 (2H, d, J=6.6 Hz)

Reference Example 20-1

Production of 5-amino-2-[(1-cyclobutylpiperidin-4-yl)oxy]pyridine

The entitled compound was obtained as a brown liquid, according to the same method as that described in a patent (WO2005/077905) or according to a method similar to it but using 2-[(1-cyclobutylpiperidin-4-yl)oxy]-5-nitropyridine obtained in Reference Example 19-1, as the starting compound.

¹H-NMR (400 MHz, CDCl₃) δ: 1.52-2.25 (10H, m), 2.50-2.78 (3H, m), 3.15-3.51 (2H, m), 4.82-4.98 (1H, m), 6.57 (1H, d, J=8.7 Hz), 7.01 (1H, dd, J=8.7, 2.8 Hz), 7.63 (1H, d, J=2.8 Hz)

Reference Example 20-2

Production of 5-amino-2-[(1-isopropylpiperidin-4-yl)oxy]pyridine

The entitled compound was obtained as an oily substance, according to the same method as that described in a patent (WO2005/077905) or according to a method similar to it but using 2-[(1-isopropylpiperidin-4-yl)oxy]-5-nitropyridine 4-methylbenzenesulfonate obtained in Reference Example 19-2, as the starting compound.

¹H-NMR (400 MHz, CDCl₃) δ: 1.08 (6H, d, J=4.8 Hz), 1.75-1.83 (2H, m), 2.04-2.08 (2H, m), 2.39-2.46 (2H, m), 2.73-2.84 (3H, m), 3.37 (2H, brs), 4.87-4.94 (1H, m), 6.60 (1H, d, J=6.3 Hz), 7.04 (2H, dd, J=2.1, 6.6 Hz), 7.66 (1H, d, J=2.4 Hz)

Reference Example 21

Production of 1-{4-[(1-cyclobutylpiperidin-4-yl)oxy]phenyl}piperidin-4-one

4-[(1-Cyclobutylpiperidin-4-yl)oxy]aniline (41 g, 170 mmol) produced according to a method described in a patent (WO2005/077905) and potassium carbonate (33 g, 238 mmol) were suspended in ethanol (1.35 L) and water (470 ml), and with heating under reflux, an aqueous solution (about 200 ml) of 1-ethyl-1-methyl-4-oxopiperidinium (64 g, 238 mmol), which had been produced from 1-methylpiperidin-4-one according to a method described in literature (Organic Letters, Vol. 1, 1999, pp. 1261-1262), was dropwise added thereto, over 1 hour. This was further stirred for 2 hours. After this was left cooled, ethanol was evaporated off under reduced pressure, and the residue was applied to liquid-liquid separation extraction by adding water (700 ml) and chloroform (400 ml) thereto. Then, the aqueous layer was extracted three times with chloroform (400 ml), and the organic layer was dried with magnesium sulfate. The solvent was evaporated off, and the residue was purified through silica gel column chromatography (eluate: methanol\chloroform=2/98 to 4/96) and crystallized from isopropyl ether/hexane=1/9 to obtain the entitled compound as a pale brown solid (28 g, 50%).

¹H-NMR (400 MHz, CDCl₃) δ: 1.58-2.50 (12H, m), 2.56 (4H, t, J=6.1 Hz), 2.62-2.79 (2H, m), 2.88 (1H, brs), 3.47 (4H, t, J=6.1 Hz), 4.30 (1H, brs), 6.86 (2H, d, J=8.8 Hz), 6.94 (2H, d, J=8.8 Hz)

Reference Example 21-1

Production of 1-{4-[(1-isopropylpiperidin-4-yl)oxy]phenyl}piperidin-4-one

The entitled compound was obtained as a brown oily substance, according to the same method as in Reference Example 21 or according to a method similar to it but using 4-[(1-isopropylpiperidin-4-yl)oxy]aniline obtained in Reference Example 20 as the starting compound, in place of 4-[(1-cyclobutylpiperidin-4-yl)oxy]aniline.

¹H-NMR (400 MHz, CD₃OD) δ: 0.92 (6H, d, J=4.8 Hz), 1.52-1.66 (6H, m), 1.76-1.86 (2H, m), 2.44-2.50 (2H, m), 2.63 (2H, s), 2.74-2.88 (3H, m), 2.82-2.98 (2H, m), 4.03-4.12 (1H, m), 6.89 (2H, d, J=6.0 Hz), 7.01 (2H, d, J=6.0 Hz)

Reference Example 21-2

Production of 1-{6-[(1-cyclobutylpiperidin-4-yl)oxy]pyridin-3-yl}piperidin-4-one The entitled compound was obtained as an orange solid, according to the same method as in Reference Example 21 or according to a method similar to it but using 5-amino-2-[(1-cyclobutylpiperidin-4-yl)oxy]pyridine obtained in Reference Example 20-1 as the starting compound, in place of 4-[(1-cyclobutylpiperidin-4-yl)oxy]aniline.

¹H-NMR (400 MHz, CDCl₃) δ: 1.57-1.97 (6H, m), 1.98-2.25 (6H, m), 2.58 (4H, t, J=6.1 Hz), 2.60-2.81 (3H, m), 3.44 (4H, t, J=6.1 Hz), 4.89-5.04 (1H, m), 6.69 (1H, d, J=8.8 Hz), 7.33 (1H, dd, J=8.8, 2.9 Hz), 7.84 (1H, d, J=2.9 Hz)

Reference Example 21-3

Production of 1-{6-[(1-isopropylpiperidin-4-yl)oxy]pyridin-3-yl}piperidin-4-one

The entitled compound was obtained as a brown oily substance, according to the same method as in Reference Example 21 or according to a method similar to it but using 5-amino-2-[(1-isopropylpiperidin-4-yl)oxy]pyridine obtained in Reference Example 20-2 as the starting compound, in place of 4-[(1 cyclobutylpiperidin-4-yl)oxy]aniline.

¹H-NMR (400 MHz, CDCl₃) δ: 1.09 (6H, d, J=5.1 Hz), 1.78-1.87 (2H, m), 2.06-2.14 (2H, m), 2.42-2.52 (2H, m), 2.60 (4H, t, J=4.5 Hz), 2.76-2.88 (3H, m), 3.46 (4H, t, J=4.5

Hz), 4.94-5.02 (1H, m), 6.71 (1H, d, J=6.6 Hz), 7.35 (2H, dd, J=2.1, 6.6 Hz), 7.87 (1H, d, J=2.1 Hz)

Reference Example 21-4

Production of 1-(4-{3-[(2R)-2-methylpyrrolidin-1-yl]propoxy}phenyl)piperidin-4-one The entitled compound was obtained as a brown oily substance, according to the same method as in Reference Example 21 or according to a method similar to it but using 4-{3-[(2R)-2-methylpyrrolidin-1-yl]propoxy}aniline 4-methylbenzenesulfonate produced according to a method described in a patent (WO2005/077905), as the starting compound in place of 4-[(1-cyclobutylpiperidin-4-yl)oxy] aniline.

$^1$H-NMR (400 MHZ, CDCl$_3$) δ: 1.11 (3H, d, J=5.9 Hz), 1.38-1.49 (1H, m), 1.67-1.82 (2H, m), 1.89-2.02 (3H, m), 2.09-2.26 (2H, m), 2.27-2.38 (1H, m), 2.57 (4H, t, J=6.1 Hz), 2.93-3.03 (1H, m), 3.16-3.23 (1H, m), 3.46 (4H, t, J=5.9 Hz), 3.95-4.04 (2H, m), 6.86 (2H, d, J=8.8 Hz), 6.95 (2H, d, J=8.8 Hz)

Pharmacological test examples with the compounds of the invention are shown below.

Pharmacological Test Example 1

Histamine Analogue-Binding Inhibition Test

A cDNA sequence coding for a human histamine-H3 receptor (see WO00/39164) was cloned with expression vectors pCR2.1, pEF1x (by Invitrogen) and pCI-neo (by Promega). The resulting expression vector was transfected into host cells, HEK293 and CHO-K1 (American Type Culture Collection), according to a cationic lipid process [see Proceedings of the National Academy of Sciences of the United States of America, Vol., 84, p. 7413 (1987)] to obtain histamine-H3 receptor expression cells.

A membrane specimen prepared from the cells having expressed a histamine-H3 receptor was incubated in an assay buffer (50 mM Tris buffer, pH 7.4) along with a test compound and 20,000 cpm [$^3$H]N-α-methylhistamine (by NEN) therein, at 25° C. for 2 hours, and then filtered through a glass filter GF/C. After washed with 50 mM Tris buffer (pH 7.4), the radioactivity on the glass filter was determined. The nonspecific binding was determined in the presence of 10 μM thioperamide (by SIGAM), and the 50% inhibitory concentration (IC$_{50}$) of the test compound to the specific N-alpha-methylhistamine binding was calculated [Molecular Pharmacology, Vol. 55, p. 1101 (1999)]. IC$_{50}$ of test compounds is shown in Table 1.

TABLE 1

| Example | IC$_{50}$ (nM) |
| --- | --- |
| 2-6 | 3.00 |
| 3-8 | 4.20 |
| 3-15 | 0.22 |
| 3-42 | 0.94 |
| 3-79 | 0.19 |
| 3-95 | 1.20 |
| 3-96 | 0.41 |
| 3-107 | 0.18 |
| 3-138 | 1.08 |
| 3-150 | 0.66 |
| 3-168 | 0.09 |
| 4-17 | 1.20 |

As in the above, the compounds of the invention strongly inhibited the binding of N-alpha-methylhistamine (histamine analogue) to histamine-H3 receptor.

Pharmacological Test Example 2

Test for Antagonistic Effect to Water-Drinking Action Induced by Histamine-H3 Receptor Selective Agonist, R-α-Methylhistamine Under anesthesia with ketamine xylazine (74 and 11 mg/kg intraabdominal single administration), a brain stereotaxic device was set in the third ventricle of a male SD rat (7 to 10-week age, 300 to 300 g), and a chronic guide cannula (26 gauge, length 11 mm) was inserted into it and fixed with a dental resin. The position of the tip of the guide cannula is at 2.2 mm after the bregrna on the midline, and at a depth of 8 mm from the surface of the skull. After a restoration term of about 1 week, R-α-methylhistamine (0.3 μg/l μL/head, 30% propylene glycol liquid) was administered into the third ventricle. A test compound (compound of Example 3-8) suspended in an aqueous 0.5% methyl cellulose solution was orally administered to the rat before 2 hours before the R-α-methylhistamine administration; and after the R-α-methylhistamine administration, the amount of water drunk by the rat for 1 hour was measured. As a result, the test compound at a dose of 30 mg/kg significantly inhibited the increase in the water drinking induced by the administration of R-α-methylhistamine in the third ventricle or the rat.

Pharmacological Test Example 3

Test for Brain/Cerebrospinal Fluid Transition

A test compound (compound of Example 3-8) was orally or intravenously administered to an SD male rat (7 to 10-week age, 200 to 400 g), and under anesthesia with ether for a predetermined period of time, the whole blood was collected from it through the abdominal aorta thereof using a heparin-processed syringe. Next, the head skin was cut, and a dental 30 G needle was stuck into the cervical spine to run through the subarachnoid cavity. Via a tube connected to the dental 30 G needle, from 50 to 100 μl of the cerebrospinal fluid was collected in a 1-mL syringe, and then the brain was taken out. The blood sample was centrifuged (4° C., 6000 revolutions, 10 minutes), and the resulting plasma was stirred with ethanol (containing an internal standard substance) in an amount of three times thereof added to it. The brain sample was homogenized with 2 mL of water added thereto; and a part of it was taken out and stirred with ethanol (containing an internal standard substance) in an amount of three times thereof added to it. The cerebrospinal fluid was stirred with ethanol (containing an internal standard substance) in an amount of three times thereof added to it. The above samples were left at −20° C. for 20 minutes, then centrifuged (4° C., 12,000 g, 10 minutes), and the supernatant was analyzed through LC/MS/MS. According to a relative calibration curve method, the compound concentration in the plasma, in the brain and in the cerebrospinal fluid was determined. As a result, the test compound concentration in the brain was 0.99 nmol/g, that in the cerebrospinal fluid was 0.074 μM and that in the plasma was 0.6 μM, after 2 hours after the oral administration (10 mg/kg).

INDUSTRIAL APPLICABILITY

The invention provides a noble substance that acts as a histamine-H3 receptor antagonistic effect or reverse-agonistic effect, or that is, acts as a histamine-H3 receptor antagonist or inverse-agonist in living bodies, and is therefore useful as a preventive or a remedy for metabolic system diseases, for example, obesity, diabetes, hormone secretion disorder, hyperlipemia, gout and fatty liver, for circulatory system diseases, for example, stenocardia, acute/congestive cardiac insufficiency, cardiac infarction, coronary arteriosclerosis, hypertension, nephropathy and electrolyte disorder, for sleep disorder and various diseases accompanied by sleep disorder, for example, idiopathic hypersomnnia, repetitive hypersomnia, true hypersomnnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia and true insomnia, and for central and peripheral nervous system diseases, for example, bulimia, emotional disorder, depression, anxiety, delirium, dementia, schizophrenia, attention deficit/hyperactivity disorder, memory disorder, Alzheimer's disease, Parkinson's disease, sleep disorder, cognition disorder, motion disorder, paresthesia, dysosmia, epilepsy, morphine resistance, drug dependency and alcoholism.

The invention claimed is:
1. A compound of the formula (I):

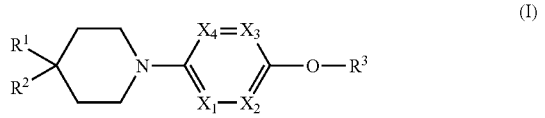

wherein:
- $R^1$ is selected from the group consisting of: an aryl group optionally having from 1 to 3 substituents selected from a substituent group α; a 5- or 6-membered heteroaryl group having from 1 to 3 hetero atoms selected from a group consisting of a nitrogen atom, a sulfur atom and an oxygen atom, and optionally having from 1 to 3 substituents selected from the substituent group α; a heteroarylalkyl group optionally having from 1 to 3 substituents selected from the substituent group α; an aralkyl group optionally having from 1 to 3 substituents selected from the substituent group α; an arylcarbonyl group optionally having from 1 to 3 substituents selected from the substituent group α; and wherein the heteroaryl group may form a condensed ring with a phenyl group or a pyridyl group;
- $R^2$ is selected from the group consisting of: an aryl group; a heteroaryl group having from 1 to 3 hetero atoms selected from a group consisting of a nitrogen atom, a sulfur atom and an oxygen atom; a cyano group; a lower alkyl group; a lower alkoxy group; or a hydroxy group; or
- $R^1$ and $R^2$, taken together, may form a 5- or 6-membered aliphatic heterocyclic group having from 1 to 3 hetero atoms selected from a group consisting of a nitrogen atom, a sulfur atom and an oxygen atom, the aliphatic heterocyclic group may further form a condensed ring with a phenyl group or a pyridyl group, the aliphatic heterocyclic group may have 1 or 2, the same or different substituents selected from a substituent group β, the phenyl group or the pyridyl group that may be condensed with the aliphatic heterocyclic group to form a condensed ring may have 1 or 2, the same or different substituents selected from a substituent group γ;
- $R^3$ is selected from the group consisting of:
  a) a group of a formula (II-1):

wherein $R^4$ and $R^5$ may be the same or different, each representing a lower alkyl group optionally substituted with a halogen atom, or a cycloalkyl group optionally substituted with a halogen atom; or $R^4$ and $R^5$, taken together with the nitrogen atom, form a 5- to 8-membered monocyclic ring, or 6- to 8-membered bicyclic ring, and the monocyclic ring may have, as a substituent, a lower alkyl group optionally substituted with a halogen atom, or a halogen atom or an oxo group; m 1 indicates an integer of from 2 to 4; the hydrogen atom in —(CH$_2$)m1— may be substituted with a lower alkyl group having from 1 to 3 carbon atoms;
  b) a group of a formula (II-2):

wherein $R^6$ represents a lower alkyl group or a cycloalkyl group; m2 indicates an integer of from 0 to 4; or
  c) a group of a formula (II-3):

wherein $R^7$ and $R^8$ may be the same or different, each representing a lower alkyl group optionally substituted with a halogen atom, or a cycloalkyl group optionally substituted with a halogen atom; or $R^7$ and $R^8$, taken together with the nitrogen atom, form a 5- to 8-membered monocyclic ring, or 6- to 8-membered bicyclic ring, and the monocyclic ring may have, as a substituent, a lower alkyl group optionally substituted with a halogen atom, or a halogen atom or an oxo group; m3 indicates an integer of from 0 to 4;
- $X_1$ to $X_4$ are all carbon atoms, wherein $X_1$ to $X_4$ are carbon atoms, then $X_1$ to $X_4$ may be substituted with a lower alkyl group optionally substituted with a halogen atom or a lower alkoxy group, a cycloalkyl group optionally substituted with a halogen atom or a lower alkoxy group, a lower alkoxy group optionally substituted with a halogen atom or a lower alkoxy group, or a cyano group or a halogen atom,
- substituent group α is selected from the group consisting of: a lower alkyl group optionally substituted with a halogen atom, a lower alkoxy group optionally substituted with a halogen atom, and a halogen atom;
- substituent group β is selected from the group consisting of: a halogen atom; an oxo group;

a lower alkyl group optionally substituted with a halogen atom or a lower alkoxy group; a lower alkoxy group optionally substituted with a halogen atom or a lower alkoxy group; a 5- or 6-membered, nitrogen-containing aliphatic hetero ring optionally substituted with an oxo group or a lower alkyl group, and optionally having 1 or 2 double bonds in the ring; an aralkyl group; a heteroarylalkyl group; a lower alkylsulfonyl group; a cycloalkylsulfonyl group; an aryl group; and a heteroaryl group;

wherein the aralkyl group, the heteroarylalkyl group, the lower alkylsulfonyl group, the cycloalkylsulfonyl group, the aryl group and the heteroaryl group may be substituted with a lower alkyl group optionally substituted with a lower alkoxy group or a halogen atom, a cycloalkyl group optionally substituted with a lower alkoxy group or a halogen atom, a lower alkoxy group optionally substituted with a halogen atom (when the group has two such lower alkoxy groups, they may form, taken together, a 5- or 6-membered ring), a halogen atom, a cyano group, a hydroxyl group, an alkylsulfonyl group, a cycloalkylsulfonyl group, an aryl group, a heteroaryl group, an alkylaminocarbonyl group, an alkanoylamino group, an alkylamino group or a dialkylamino group;

substituent group γ is selected from the group consisting of: a lower alkyl group optionally substituted with a lower alkoxy group or a halogen atom, a lower alkoxy group optionally substituted with a halogen atom, and a halogen atom;

or a pharmaceutically acceptable salt thereof.

2. The compound of claim 1 wherein $R^1$ is an aryl group optionally having from 1 to 3 substituents selected from the substituent group α, or a 5- or 6-membered heteroaryl group having from 1 to 3 hetero atoms selected from a group consisting of a nitrogen atom, a sulfur atom and an oxygen atom and optionally having from 1 to 3 substituents selected from the substituent group α.

3. The compound of claim 1 wherein $R^2$ is an aryl group, a heteroaryl group having from 1 to 3 hetero atoms selected from a group consisting of a nitrogen atom, a sulfur atom and an oxygen atom, or a cyano group, a lower alkyl group, or a hydroxy group.

4. The compound of claim 1 wherein $R^1$ and $R^2$, taken together, form a 5- or 6-membered aliphatic heterocyclic group optionally having from 1 to 3 hetero atoms selected from a group consisting of a nitrogen atom, a sulfur atom and an oxygen atom, and the aliphatic heterocyclic group may have 1 or 2, the same or different substituents selected from the substituent group β.

5. The compound of claim 1 wherein $R^1$ and $R^2$, taken together, form a 5- or 6-membered aliphatic heterocyclic group having from 1 to 3 hetero atoms selected from a group consisting of a nitrogen atom, a sulfur atom and an oxygen atom, the aliphatic heterocyclic group forms a condensed ring with a phenyl group or a pyridyl group, the aliphatic heterocyclic group may have 1 or 2, the same or different substituents selected from the substituent group β, and the phenyl group or the pyridyl group condensed with the aliphatic heterocyclic group may have 1 or 2, the same or different substituents selected from the substituent group γ.

6. The compound of claim 1 wherein the 5- or 6-membered aliphatic heterocyclic group formed by $R^1$ and $R^2$, taken together, and optionally having 1 or 2, the same or different substituents selected from the substituent group β is a group of a formula (III):

(III)

wherein $X_5$ represents an oxygen atom or a single bond; $X_6$ represents a carbon atom or an oxygen atom; $X_7$ represents a carbon atom or a nitrogen atom; $X_8$ represents a carbon atom or a nitrogen atom; when $X_8$ is a carbon atom, then the group may be condensed with a phenyl group or a pyridyl group to form a condensed ring at the site between $X_8$ and the carbon atom adjacent to $X_8$.

7. The compound of claim 6 wherein the group formed by $R^1$ and $R^2$, taken together, is a group selected from the groups of formula (III-1):

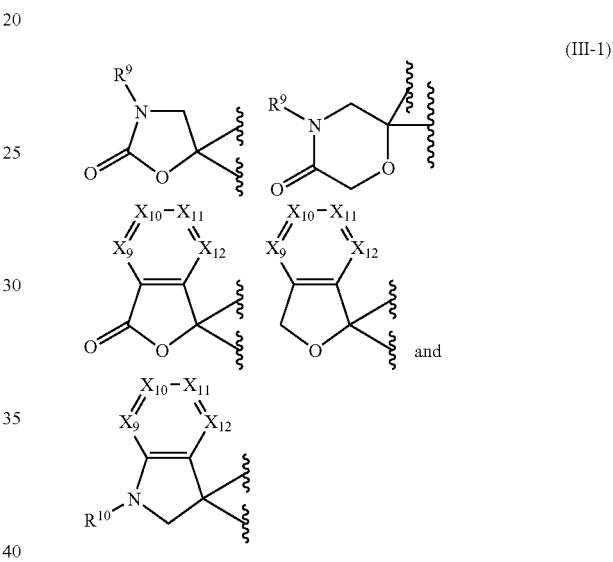

(III-1)

wherein $R^9$ is selected from the group consisting of:
1) a lower alkyl group optionally substituted with a halogen atom or a lower alkoxy group,
2) an aryl group,
3) an aralkyl group,
4) a heteroarylalkyl group, or
5) a heteroaryl group, in which the aryl, aralkyl, heteroarylalkyl and heteroaryl groups may be substituted with a halogen atom, a lower alkyl group optionally substituted with a lower alkoxy group or from 1 to 3 halogen atoms, a lower alkoxy group optionally substituted with from 1 to 3 halogen atoms, a cyano group, a hydroxy group, an alkylsulfonyl group, a cycloalkylsulfonyl group, an aryl group, a heteroaryl group, an alkylaminocarbonyl group, an alkanoylamino group, an alkylamino group or a dialkylamino group;

$R^{10}$ represents a lower alkyl group optionally substituted with from 1 to 3 halogen atoms, or a lower alkylsulfonyl group;

$X_9$ to $X_{12}$ represent a carbon atom or a nitrogen atom, in which the carbon atom may be independently substituted with a lower alkyl group optionally substituted with a halogen atom or a lower alkoxy group, a lower alkoxy group optionally substituted with a halogen atom, or a cyano group or a halogen atom.

8. The compound of claim 6 wherein the group formed by R¹ and R², taken together, is a group of the formula (III-2) or the formula (III-3):

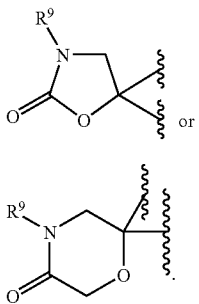

(III-2)

(III-3)

9. The compound of claim 6 wherein the group formed by R¹ and R², taken together, is a group of the formula (III-4), the formula (III-5) or the formula (III-6):

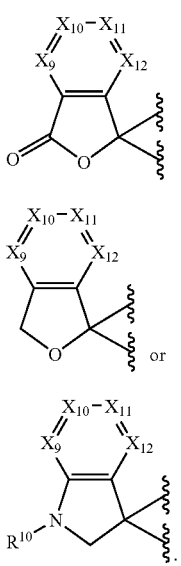

(III-4)

(III-5)

(III-6)

10. The compound of claim 1 wherein $R^3$ is the formula (II-1) and m1 is 3.

11. The compound of claim 1 wherein $R^3$ is the formula (II-2) and m2 is 1 or 2.

12. A compound which is selected from the group consisting of:
- 1'-[4-(3-piperidin-1-ylpropoxy)phenyl]-3H-spiro[2-benzofuran-1,4'-piperidine],
- 4-phenyl-1-[4-(3-piperidin-1-ylpropoxy)phenyl]piperidin-4-ol,
- 3-phenyl-8-[4-(3-piperidin-1-ylpropoxy)phenyl]-1-oxa-3,8-diazaspiro[4,5]decan-2-one,
- 1'-[4-(3-piperidin-1-ylpropoxy)phenyl]-3H-spiro[2-benzofuran-1,4'-piperidine]-3-one,
- 4-phenyl-9-[4-(3-pyrrolidin-1-ylpropoxy)phenyl]-1-oxa-4,9-diazaspiro[5,5]undecan-3-one,
- 9-[4-(3-((2S)-2-methylpyrrolidin-1-yl)propoxy)phenyl]-4-phenyl-1-oxa-4,9-diazaspiro[5,5]undecan-3-one,
- 9-[4-(3-((3S)-3-methylpiperidin-1-yl)propoxy)phenyl]-4-phenyl-1-oxa-4,9-diazaspiro[5,5]undecan-3-one,
- 4-(4-fluorophenyl)-1-[4-(3-piperidin-1-ylpropoxy)phenyl]piperidin-4-ol trifluoroacetate,
- 1-[4-(3-piperidin-1-ylpropoxy)phenyl]-4-pyridin-3-ylpiperidin-4-ol trifluoroacetate,
- 4-(4-methoxyphenyl)-1-[4-(3-piperidin-1-ylpropoxy)phenyl]piperidin-4-ol trifluoroacetate,
- 5-fluoro-1'-[4-(3-piperidin-1-ylpropoxy)phenyl]-3H-spiro[2-benzofuran-1,4'-piperidine]trifluoroacetate,
- 5-fluoro-1'-[4-(3-piperidin-1-ylpropoxy)phenyl]-3H-spiro[2-benzofuran-1,4'-piperidin]-3-one trifluoroacetate,
- 7-fluoro-1'-[4-(3-piperidin-1-ylpropoxy)phenyl]-3H-spiro[2-benzofuran-1,4'-piperidin]-3-one trifluoroacetate,
- 5-methoxy-1'-[4-(3-piperidin-1-ylpropoxy)phenyl]-3H-spiro[2-benzofuran-1,4'-piperidin]-3-one trifluoroacetate,
- 6-methoxy-1'-[4-(3-piperidin-1-ylpropoxy)phenyl]-3H-spiro[2-benzofuran-1,4'-piperidin]-3-one trifluoroacetate,
- 7-methoxy-1'-[4-(3-piperidin-1-ylpropoxy)phenyl]-3H-spiro[2-benzofuran-1,4'-piperidin]-3-one trifluoroacetate,
- 1'-[4-(3-piperidin-1-ylpropoxy)phenyl]-1H-spiro[furo[3,4-c]pyridine-3,4'-piperidin]-1-one trifluoroacetate,
- 1-(methylsulfonyl)-1'-[4-(3-piperidin-1-ylpropoxy)phenyl]-1,2-dihydrospiro[indole-3,4'-piperidine]trifluoroacetate,
- 1-(ethylsulfonyl)-7-fluoro-1'-[4-(3-piperidin-1-ylpropoxy)phenyl]-1,2-dihydrospiro[indole-3,4'-piperidine] trifluoroacetate,
- 1-(ethylsulfonyl)-5-fluoro-1'-[4-(3-piperidin-1-ylpropoxy)phenyl]-1,2-dihydrospiro[indole-3,4'-piperidine] trifluoroacetate,
- 4-tert-butoxy-1'-[4-(3-piperidin-1-ylpropoxy)phenyl]-3H-spiro[2-benzofuran-1,4'-piperidin]-3-one trifluoroacetate,
- 1-(ethylsulfonyl)-1'-[4-(3-piperidin-1-ylpropoxy)phenyl]-1,2-dihydrospiro[indole-3,4'-piperidine]trifluoroacetate,
- 3,3-dimethyl-1'-[4-(3-piperidin-1-ylpropoxy)phenyl]-3H-spiro[2-benzofuran-1,4'-piperidine]trifluoroacetate,
- 3-methyl-1'-[4-(3-piperidin-1-ylpropoxy)phenyl]-3H-spiro[2-benzofuran-1,4'-piperidine]trifluoroacetate,
- 1'-[4-(3-piperidin-1-ylpropoxy)phenyl]-3,4-dihydrospiro[chromene-2,4'-piperidine]trifluoroacetate,
- phenyl {1-[4-(3-piperidin-1-ylpropoxy)phenyl]piperidin-4-yl}methanone trifluoroacetate,
- 4-phenyl-1-[4-(3-piperidin-1-ylpropoxy)phenyl]piperidine-4-carbonitrile trifluoroacetate,
- 4-benzyl-1-[4-(3-piperidin-1-ylpropoxy)phenyl]piperidine-4-carbonitrile trifluoroacetate,
- 4-methyl-4-phenyl-1-[4-(3-piperidin-1-ylpropoxy)phenyl]piperidine trifluoroacetate,
- 4,4-diphenyl-1-[4-(3-piperidin-1-ylpropoxy)phenyl]piperidine trifluoroacetate,
- 4-(3-methoxyphenyl)-1-[4-(3-piperidin-1-ylpropoxy)phenyl]piperidin-4-ol trifluoroacetate,
- 4-(4-fluorophenyl)-9-[4-(3-[(3S)-3-methylpiperidin-1-yl]propoxy)phenyl]-1-oxa-4,9-diazaspiro[5,5]undecan-3-one,
- 4-(6-fluoropyridin-3-yl)-9-[4-{3-[(3S)-3-methylpiperidin-1-yl]propoxy}phenyl]-1-oxa-4,9-diazaspiro[5,5]undecan-3-one,
- 4-(4-methoxyphenyl)-9-[4-{3-[(3S)-3-methylpipendin-1-yl]propoxy}phenyl]-1-oxa-4,9-diazaspiro[5,5]undecan-3-one 4-(4-methylphenyl)-9-[4-{3-[(3S)-3-methylpiperidin-1-yl]propoxy}phenyl]-1-oxa-4,9-diazaspiro[5,5]undecan-3-one,
4-(6-methoxypyridin-3-yl)-9-[4-{3-[(3S)-3-methylpiperidin-1-yl]propoxy}phenyl]-1-oxa-4,9-diazaspiro[5,5]undecan-3-one,
9-[4-{3-[(3S)-3-methylpiperidin-1-yl]propoxy}phenyl]-4-(2-methylpyridin-5-yl)-1-oxa-4,9-diazaspiro[5,5]undecan-3-one,
4-(3,4-difluorophenyl)-9-[4-{3-[(3S)-3-methylpiperidin-1-yl]propoxy}phenyl]-1-oxa-4,9-diazaspiro[5,5]undecan-3-one,
4-phenyl-9-[4-(3-piperidin-1-ylpropoxy)phenyl]-1-oxa-4,9-diazaspiro[5,5]undecan-3-one,
9-[4-(3-piperidin-1-ylpropoxy)phenyl]-4-pyridin-4-yl-1-oxa-4,9-diazaspiro[5,5]undecan-3-one,
9-[4-(3-piperidin-1-ylpropoxy)phenyl]-4-pyridin-2-yl-1-oxa-4,9-diazaspiro[5,5]undecan-3-one,
4-[6-(difluoromethoxy)pyridin-3-yl]-9-(4-{3-[(3S)-3-methylpiperidin-1-yl]propoxy}phenyl]-1-oxa-4,9-diazaspiro[5,5]undecan-3-one,
4-(6-isopropoxypyridin-3-yl)-9-(4-{3-[(3S)-3-methylpiperidin-1-yl]propoxy}phenyl)-1-oxa-4,9-diazaspiro[5,5]undecan-3-one,
4-(6-isopropoxypyridin-3-yl)-9-[4-(3-piperidin-1-ylpropoxy)phenyl]-1-oxa-4,9-diazaspiro[5,5]undecan-3-one,
4-[6-(difluoromethoxy)pyridin-3-yl]-9-[4-(3-piperidin-1-ylpropoxy)phenyl]-1-oxa-4,9-diazaspiro[5,5]undecan-3-one,
4-(2-methoxypyrimidin-5-yl)-9-[4-(3-piperidin-1-ylpropoxy)phenyl]-1-oxa-4,9-diazaspiro[5,5]undecan-3-one,
4-(2-methoxypyrimidin-5-yl)-9-[4-{3-[(3S)-3-methylpipendin-1-yl]propoxy}phenyl]-1-oxa-4,9-diazospiro[5,5]undecan-3-one
4-(6-methoxypyridin-3-yl)-9-[4-(3-pyrrolidin-1-ylpropoxy)phenyl]-1-oxa-4,9-diazaspiro[5,5]undecan-3-one,
4-(2-methoxypyridin-5-yl)-9-[4-{3-[(2S)-2-methylpyrrolidin-1-yl]propoxy}phenyl]-1-oxa-4,9-diazaspiro[5,5]undecan-3-one
4-(6-methoxypyridin-3-yl)-9-(4-{3-[(2R)-2-methylpyrrolidin-1-yl]propoxy}phenyl)-1-oxa-4,9-diazaspiro[5,5]undecan-3-one,
4-(4-fluorophenyl)-9-(4-{3-[(2R)-2-methylpyrrolidin-1-yl]propoxy}phenyl)-1-oxa-4,9-diazaspiro[5,5]undecan-3-one,
4-(4-methoxyphenyl)-9-(4-{3-[(2R)-2-methylpyrrolidin-1-yl]propoxy}phenyl)-1-oxa-4,9-diazaspiro[5,5]undecan-3-one,
4-(1,3-benzodioxol-5-yl)-9-(4-{3-[(2R)-2-methylpyrrolidin-1-yl]propoxy}phenyl)-1-oxa-4,9-diazaspiro[5,5]undecan-3-one,
4-(2-methoxypyridin-4-yl)-9-(4-{3-[(3S)-3-methylpiperidin-1-yl]propoxy}phenyl)-1-oxa-4,9-diazaspiro[5,5]undecan-3-one,
4-(1-methyl-6-oxo-1,6-dihydropyridin-3-yl)-9-(4-{3-[(3S)-3-methylpiperidin-1-yl]propoxy}phenyl)-1-oxa-4,9-diazaspiro[5,5]undecan-3-one,
4-(2-methoxypyridin-4-yl)-9-[4-(3-piperidin-1-ylpropoxy)phenyl]-1-oxa-4,9-diazaspiro[5,5]undecan-3-one,
4-(1-methyl-6-oxo-1,6-dihydropyridin-3-yl)-9-[4-(3-piperidin-1-yl]propoxy)phenyl]-1-oxa-4,9-diazaspiro[5,5]undecan-3-one,
9-(4-{3-[(2R)-2-methylpyrrolidin-1-yl]propoxy}phenyl)-4-pyridin-2-yl-1-oxa-4,9-diazaspiro[5,5]undecan-3-one,
4-(5-methylpyridin-2-yl)-9-(4-{3-[(2R)-2-methylpyrrolidin-1-yl]propoxy}phenyl)-1-oxa-4,9-diazaspiro[5,5]undecan-3-one,
4-(4-methylpyridin-2-yl)-9-(4-{3-[(2R)-2-methylpyrrolidin-1-yl]propoxy}phenyl)-1-oxa-4,9-diazaspiro[5,5]undecan-3-one,
4-(3-methylpyridin-2-yl)-9-(4-{3-[(2R)-2-methylpyrrolidin-1-yl]propoxy}phenyl)-1-oxa-4,9-diazaspiro[5,5]undecan-3-one,
4-(5-methoxypyridin-2-yl)-9-(4-{3-[(2R)-2-methylpyrrolidin-1-yl]propoxy}phenyl)-1-oxa-4,9-diazaspiro[5,5]undecan-3-one,
4-(6-methoxypyridin-2-yl)-9-(4-{3-[(2R)-2-methylpyrrolidin-1-yl]propoxy}phenyl)-1-oxa-4,9-diazaspiro[5,5]undecan-3-one,
9-(4-{3-[(2R)-2-methylpyrrolidin-1-yl]propoxy}phenyl)-4-(3-thienyl)-1-oxa-4,9-diazaspiro[5,5]undecan-3-one,
9-(4-{3-[(2R)-2-methylpyrrolidin-1-yl]propoxy}phenyl)-4-(2-thienyl)-1-oxa-4,9-diazaspiro[5,5]undecan-3-one,
4-(4-methoxyphenyl)-9-[4-(3-pyrrolidin-1-ylpropoxy)phenyl]-1-oxa-4,9-diazaspiro[5,5]undecan-3-one,
4-(6-fluoropyridin-3-yl)-9-[4-(3-pyrrolidin-1-ylpropoxy)phenyl]-1-oxa-4,9-diazaspiro[5,5]undecan-3-one,
4-[6-(difluoromethoxy)pyridin-3-yl]-9-[4-(3-pyrrolidin-1-ylpropoxy)phenyl]-1-oxa-4,9-diazaspiro[5,5]undecan-3-one,
5-[9-(4-{3-[(2R)-2-methylpyrrolidin-1-yl]propoxy}phenyl)-3-oxo-1-oxa-4,9-diazaspiro[5,5]undecan-4-yl]nicotinonitrile,
9-(4-{3-[(2R)-2-methylpyrrolidin-1-yl]propoxy}phenyl)-4-(1,3-thiazol-2-yl)-1-oxa-4,9-diazaspiro[5,5]undecan-3-one,
3-(4-fluorophenyl)-8-[4-(3-piperidin-1-ylpropoxy)phenyl]-1-oxa-3,8-diazaspiro[4,5]decan-2-one,
8-[4-(3-piperidin-1-ylpropoxy)phenyl]-3-(pyridin-2-yl)-1-oxa-3,8-diazaspiro[4,5]decan-2-one,
8-[4-(3-piperidin-1-ylpropoxy)phenyl]-3-(pyridin-4-yl)-1-oxa-3,8-diazaspiro[4,5]decan-2-one,
3-(6-fluoropyridin-3-yl)-8-[4-(3-piperidin-1-ylpropoxy)phenyl]-1-oxa-3,8-diazaspiro[4,5decan-2-one,
8-[4-(3-piperidin-1-ylpropoxy)phenyl]-3-[6-(trifluoromethyl)pyridin-3-yl]-1-oxa-3,8-diazaspiro[4,5]decan-2-one,
3-(2-fluorophenyl)-8-[4-(3-piperidin-1-ylpropoxy)phenyl]-1-oxa-3,8-diazaspiro[4,5]decan-2-one,
3-(2-fluoropyridin-4-yl)-8-[4-(3-piperidin-1-ylpropoxy)phenyl]-1-oxa-3,8-diazaspiro[4,5]decan-2-one,
3-[6-(difluoromethyl)pyridin-3-yl]-8-[4-(3-piperidin-1-ylpropoxy)phenyl]-1-oxa-3,8-diazaspiro[4,5]decan-2-one,
3-(5-fluoropyridin-2-yl)-8-[4-(3-piperidin-1-ylpropoxy)phenyl]-1-oxa-3,8-diazaspiro[4,5]decan-2-one,
3-(6-fluoropyridin-2-yl)-8-[4-(3-piperidin-1-ylpropoxy)phenyl]-1-oxa-3,8-diazaspiro[4,5]decan-2-one,
3-(3-fluorophenyl)-8-[4-(3-piperidin-1-ylpropoxy)phenyl]-1-oxa-3,8-diazaspiro[4,5]decan-2-one,
3-(4-methoxyphenyl)-8-[4-(3-piperidin-1-ylpropoxy)phenyl]-1-oxa-3,8-diazaspiro[4,5]decan-2-one,
3-(3-methoxyphenyl)-8-[4-(3-piperidin-1-ylpropoxy)phenyl]-1-oxa-3,8-diazaspiro[4,5]decan-2-one,
3-(6-methoxypyridin-3-yl)-8-[4-(3-piperidin-1-ylpropoxy)phenyl]-1-oxa-3,8-diazaspiro[4,5]decan-2-one,
3-(6-methylpyridin-3-yl)-8-[4-(3-piperidin-1-ylpropoxy)phenyl]-1-oxa-3,8-diazaspiro[4,5]decan-2-one, 3-(2-methoxyphenyl)-8-[4-(3-piperidin-1-ylpropoxy)phenyl]-1-oxa-3,8-diazaspiro[4,5]decan-2-one, 8-[4-(3-piperidin-1-ylpropoxy)phenyl]-3-[4-(trifluoromethoxy)phenyl]-1-oxa-3,8-diazaspiro[4,5]decan-2-one, 4-(1-ethyl-6-oxo-1,6-dihydropyridin-3-yl)-9-(4-{3-[(3S)-3-methylpiperidin-1-yl]propoxyl}phenyl)-1-oxa-4,9-diazaspiro[5,5]undecan-3-one, 9-(4-{3-[(3S)-3-methylpiperidin-1-yl]propoxy}phenyl)-4-pyrazin-2-yl-1-oxa-4,9-diazaspiro[5,5]undecan-3-one, 9-(4-{3-[(3S)-3-methylpiperidin-1-yl]propoxy}phenyl)-4-pyridin-2-yl-1-oxa-4,9-diazaspiro[5,5]undecan-3-one, 4-(3-methoxypyridin-2-yl)-9-(4-{3-[(3S)-3-methylpiperidin-1-yl]propoxy}phenyl)-1-oxa-4,9-diazaspiro[5,5]undecan-3-one, 4-(1-ethyl-5-methyl-6-oxo-1,6-dihydropyridin-3-yl)-9-(4-{3-[(3S)-3-methylpiperidin-1-yl]propoxy}phenyl)-1-oxa-4,9-diazaspiro[5,5]undecan-3-one, 4-(1-ethyl-5-methoxy-6-oxo-1,6-dihydropyridin-3-yl)-9-(4-{3-[(3S)-3-methylpiperidin-1-yl]propoxy}phenyl)-1-oxa-4,9-diazaspiro[5,5]undecan-3-one, 4-(5-methoxypyridin-2-yl)-9-(4-{3-[(3S)-3-methylpiperidin-1-yl]propoxy}phenyl)-1-oxa-4,9-diazaspiro[5,5]undecan-3-one, 4-(5-fluoropyridin-2-yl)-9-(4-{3-[(3S)-3-methylpiperidin-1-yl]propoxy}phenyl)-1-oxa-4,9-diazaspiro[5,5]undecan-3-one, 5-[9-(4-{3-[(3S)-3-methylpiperidin-1-yl]propoxy}phenyl)-3-oxo-1-oxa-4,9-diazaspiro[5,5]undecan-4-yl]nicotinonitrile, 9-(4-{3-[(3S)-3-methylpiperidin-1-yl]propoxy}phenyl)-4-(3-methylpyridin-2-yl)-1-oxa-4,9-diazaspiro[5,5]undecan-3-one, 4-[1-(difluoromethyl)-6-oxo-1,6-dihydropyridin-3-yl]-9-(4-{3-[(3S)-3-methylpiperidin-1-yl]propoxy}phenyl)-1-oxa-4,9-diazaspiro[5,5]undecan-3-one, 4-(1-isopropyl-6-oxo-1,6-dihydropyridin-3-yl)-9-(4-{3-[(3S)-3-methylpiperidin-1-yl]propoxy}phenyl)-1-oxa-4,9-diazaspiro[5,5]undecan-3-one, 9-[4-(3-piperidin-1-ylpropoxy)phenyl]-4-pyrazin-2-yl-1-oxa-4,9-diazaspiro[5,5]undecan-3-one, 4-(3,4-difluorophenyl)-9-[4-(3-pyrrolidin-1-ylpropoxy)phenyl]-1-oxa-4,9-diazaspiro[5,5]undecan-3-one, 4-(2,4-difluorophenyl)-9-[4-(3-pyrrolidin-1-ylpropoxy)phenyl]-1-oxa-4,9-diazaspiro[5,5]undecan-3-one, 9-[4-(3-pyrrolidin-1-ylpropoxy)phenyl]-4-[6-(trifluoromethyl)pyridin-3-yl]-1-oxa-4,9-diazaspiro[5,5]undecan-3-one, 4-(6-isopropoxypyridin-3-yl)-9-[4-(3-pyrrolidin-1-ylpropoxy)phenyl]-1-oxa-4,9-diazaspiro[5,5]undecan-3-one, 4-(2-ethoxypyrimidin-5-yl)-9[4-{3-[(2R)-2-methylpyrrolidin-1-yl]propoxy}phenyl]-1-oxa-4,9-diazaspiro[5,5]undecan-3-one, 4-(5-methoxypyrazin-2-yl)-9-[4-{3-[(2R)-2-methylpyrrolidin-1-yl]propoxy}phenyl]-1-oxa-4,9-diazaspiro[5,5]undecan-3-one, 4-(4-chlorophenyl)-9-[4-{3-[(2R)-2-methylpyrrolidin-1-yl]propoxy}phenyl]-1-oxa-4,9-diazaspiro[5,5]undecan-3-one, 9-[4-{3-[(2R)-2-methylpyrrolidin-1-yl]propoxy}phenyl]-4-[4-(trifluoromethyl)phenyl]-1-oxa-4,9-diazaspiro[5,5]undecan-3-one 4-[9-(4-{3-[(2R)-2-methylpyrrolidin-1-yl]propoxy}phenyl)-3-oxo-1-oxa-4,9-diazaspiro[5,5]undecan-4-yl]benzonitrile, 9-(4-{3-[(2R)-2-methylpyrrolidin-1-yl]propoxy}phenyl)-4-[4-(methylsulfonyl)phenyl]-1-oxa-4,9-diazaspiro[5,5]undecan-3-one, 9-(4-{3-[(2R)-2-methylpyrrolidin-1-yl]propoxy}phenyl)-4-pyrazin-2-yl-1-oxa-4,9-diazaspiro[5,5]undecan-3-one, 4-(2-methoxypyrimidin-5-yl)-9-(4-{3-[(2R)-2-methylpyrrolidin-1-yl]propoxy}phenyl)-1-oxa-4,9-diazaspiro[5,5]undecan-3-one, 4-(3-methylpyridin-2-yl)-9-(4-{3-[(2R)-2-methylpyrrolidin-1-yl]propoxy}phenyl)-1-oxa-4,9-diazaspiro[5,5]undecan-3-one, 4-(3-methoxypyridin-2-yl)-9-(4-{3-[(2R)-2-methylpyrrolidin-1-yl]propoxy}phenyl)-1-oxa-4,9-diazaspiro[5,5]undecan-3-one, 9-(4-{3-[(2R)-2-methylpyrrolidin-1-yl]propoxy}phenyl)-4-pyridin-3-yl-1-oxa-4,9-diazaspiro[5,5]undecan-3-one, 9-(4-{3-[(2R)-2-methylpyrrolidin-1-yl]propoxy}phenyl)-4-[5-(trifluoromethyl)pyridin-3-yl]-1-oxa-4,9-diazaspiro[5,5]undecan-3-one, 4-(1-methyl-1H-pyrazol-3-yl)-9-(4-{3-[(2R)-2-methylpyrrolidin-1-yl]propoxy}phenyl)-1-oxa-4,9-diazaspiro[5,5]undecan-3-one, 4-(1-methyl-1H-pyrazol-4-yl)-9-(4-{3-[(2R)-2-methylpyrrolidin-1-yl]propoxy}phenyl)-1-oxa-4,9-diazaspiro[5,5]undecan-3-one, 4-(5-methoxypyridin-3-yl)-9-(4-{3-[(2R)-2-methylpyrrolidin-1-yl]propoxy}phenyl)-1-oxa-4,9-diazaspiro[5,5]undecan-3-one, 5-[9-(4-{3-[(2R)-2-methylpyrrolidin-1-yl]propoxyl}phenyl)-3-oxo-1-oxa-4,9-diazaspiro[5,5]undecan-4-yl]nicotinonitrile, 9-(4-{3-[(2S)-2-methylpyrrolidin-1-yl]propoxy}phenyl)-4-pyridin-3-yl-1-oxa-4,9-diazaspiro[5,5]undecan-3-one, 4-(2-methoxypyrimidin-5-yl)-9-(4-{3-[(2S)-2-methylpyrrolidin-1-yl]propoxy}phenyl)-1-oxa-4,9-diazaspiro[5,5]undecan-3-one, 5-[9-(4-{3-[(2S)-2-methylpyrrolidin-1-yl]propoxy}phenyl)-3-oxo-1-oxa-4,9-diazaspiro[5,5]undecan-4-yl]nicotinonitrile, 4-(5-methoxypyridin-3-yl)-9-(4-{3-[(2S)-2-methylpyrrolidin-1-yl]propoxy}phenyl)-1-oxa-4,9-diazaspiro[5,5]undecan-3-one, 4-(5-methoxypyrazin-2-yl)-9-(4-{3-[(2S)-2-methylpyrrolidin-1-yl]propoxy}phenyl)-1-oxa-4,9-diazaspiro[5,5]undecan-3-one, 4-(1-methyl-1H-pyrazol-4-yl)-9-(4-{3-[(2S)-2-methylpyrrolidin-1-yl]propoxy}phenyl)-1-oxa-4,9-diazaspiro[5,5]undecan-3-one, 3-ethyl-8-(4-{3-[(2R)-2-methylpyrrolidin-1-yl]propoxy}phenyl)-1-oxa-3,8-diazaspiro[4,5]decan-2-one, 8-(4-{3-[(2R)-2-methylpyrrolidin-1-yl]propoxy}phenyl)-3-[4-(methylsulfonyl)phenyl]-1-oxa-3,8-diazaspiro[4,5]decan-2-one, 3-(2-ethoxypyrimidin-5-yl)-8-(4-{3-[(2R)-2-methylpyrrolidin-1-yl]propoxy}phenyl)-1-oxa-3,8-diazaspiro[4,5]decan-2-one, 3-(1-methyl-1H-pyrazol-4-yl)-8-(4-{3-[(2R)-2-methylpyrrolidin-1-yl]propoxy}phenyl)-1-oxa-3,8-diazaspiro[4,5]decan-2-one, 3-(1-methyl-1H-pyrazol-3-yl)-8-(4-{3-[(2R)-2-methylpyrrolidin-1-yl]propoxy}phenyl)-1-oxa-3,8-diazaspiro[4,5]decan-2-one, 5-[8-(4-{3-[(2R)-2-methylpyrrolidin-1-yl]
propoxy}phenyl)-2-oxo-1-oxa-3,8-diazaspiro[4,5]decan-3-yl]nicotinonitrile, 8-(4-{3-[(2R)-2-methylpyrrolidin-1-yl]propoxy}phenyl)-3-pyrazin-2-yl-1-oxa-3,8-diazaspiro[4,5]decan-2-one, 3-(6-methoxypyridin-3-yl)-8-(4-{3-[(2R)-2-methylpyrrolidin-1-yl]propoxy}phenyl)-1-oxa-3,8-diazaspiro[4,5]decan-2-one, 3-(2-methoxypyrimidin-5-yl)-8-(4-{3-[(2R)-2-methylpyrrolidin-1-yl]propoxy}phenyl)-1-oxa-3,8-diazaspiro[4,5]decan-2-one, 3-(5-methoxypyridin-3-yl)-8-(4-{3-[(2R)-2-methylpyrrolidin-1-yl]propoxy}phenyl)-1-oxa-3,8-diazaspiro[4,5]decan-2-one, 3-(2-methoxypyrimidin-5-yl)-8-[4-(3-piperidin-1-ylpropoxy)phenyl]-1-oxa-3,8-diazaspiro[4,5]decan-2-one, 9-{4-[(1-cyclobutylpiperidin-4-yl)oxy]phenyl}-4-(4-methoxyphenyl)-1-oxa-4,9-diazaspiro[5,5]undecan-3-one, 9-{4-[(1-cyclobutylpiperidin-4-yl)oxy]phenyl}-4-(6-methylpyridin-3-yl)-1-oxa-4,9-diazaspiro[5,5]undecan-3-one, 9-{4-[(1-cyclobutylpiperidin-4-yl)oxy]phenyl}-4-[6-(difluoromethoxy)pyridin-3-yl]-1-oxa-4,9-diazaspiro[5,5]undecan-3-one, 9-{4-[(1-cyclobutylpiperidin-4-yl)oxy]phenyl}-4-isopropyl-1-oxa-4,9-diazaspiro[5,5]undecan-3-one, 9-{4-[(1-cyclobutylpiperidin-4-yl)oxy]phenyl}-4-(6-isopropoxypyridin-3-yl)-1-oxa-4,9-diazaspiro[5,5]undecan-3-one, 9-{4-[(1-cyclobutylpiperidin-4-yl)oxy]phenyl}-4-(2-isopropoxypyrimidin-5-yl)-1-oxa-4,9-diazaspiro[5,5]undecan-3-one, 9-{4-[(1-cyclobutylpiperidin-4-yl)oxy]phenyl}-4-(1-methyl-1H-pyrazol-3-yl)-1-oxa-4,9-diazaspiro[5,5]undecan-3-one, 9-{4-[(1-cyclobutylpiperidin-4-yl)oxy]phenyl}-4-(5-methoxypyridin-3-yl)-1-oxa-4,9-diazaspiro[5,5]undecan-3-one, 9-{4-[(1-cyclobutylpiperidin-4-yl)oxy]phenyl}-4-[5-(trifluoromethyl)pyridin-3-yl]-1-oxa-4,9-diazaspiro[5,5]undecan-3-one, 9-{4-[(1-cyclobutylpiperidin-4-yl)oxy]phenyl}-4-[3-(trifluoromethyl)pyridin-2-yl]-1-oxa-4,9-diazaspiro[5,5]undecan-3-one, 9-{4-[(1-cyclobutylpiperidin-4-yl)oxy]phenyl}-4-(6-methoxypyridin-2-yl)-1-oxa-4,9-diazaspiro[5,5]undecan-3-one, 9-{4-[(1-cyclobutylpiperidin-4-yl)oxy]phenyl}-4-imidazo[1,2-a]pyridin-3-yl-1-oxa-4,9-diazaspiro[5,5]undecan-3-one, 9-{4-[(1-cyclobutylpiperidin-4-yl)oxy]phenyl}-4-[4-(methylsulfonyl)phenyl]-1-oxa-4,9-diazaspiro[5,5]undecan-3-one, 9-{4-[(1-cyclobutylpiperidin-4-yl)oxy]phenyl}-4-pyrazin-2-yl-1-oxa-4,9-diazaspiro[5,5]undecan-3-one, 9-{4-[(1-cyclobutylpiperidin-4-yl)oxy]phenyl}-4-(3-methylpyridin-2-yl)-1-oxa-4,9-diazaspiro[5,5]undecan-3-one, 9-{4-[(1-cyclobutylpiperidin-4-yl)oxy]phenyl}-4-(5-methoxypyridin-2-yl)-1-oxa-4,9-diazaspiro[5,5]undecan-3-one, 9-{4-[(1-cyclobutylpiperidin-4-yl)oxy]phenyl}-4-(4-fluorophenyl)-1-oxa-4,9-diazaspiro[5,5]undecan-3-one, 9-{4-[(1-cyclobutylpiperidin-4-yl)oxy]phenyl}-4-(1-methyl-1H-pyrazol-4-yl)-1-oxa-4,9-diazaspiro[5,5]undecan-3-one, 9-{-4-[(1-cyclobutylpiperidin-4-yl)oxy]phenyl}-4-(2-methoxypyrimidin-5-yl)-1-oxa-4,9-diazaspiro[5,5]undecan-3-one, 9-{4-[(1-cyclobutylpiperidin-4-yl)oxy]phenyl}-4-(1-methyl-6-oxo-1,6-dihydropyridin-3-yl)-1-oxa-4,9-diazaspiro[5,5]undecan-3-one, 9-{4-[(1-cyclobutylpiperidin-4-yl)oxy]phenyl}-4-(2-fluoropyridin-4-yl)-1-oxa-4,9-diazaspiro[5,5]undecan-3-one, 9-{4-[(1-cyclobutylpiperidin-4-yl)oxy]phenyl}-4-(1-ethyl-6-oxo-1,6-dihydropyridin-3-yl)-1-oxa-4,9-diazaspiro[5,5]undecan-3-one, 9-{4-[(1-cyclobutylpiperidin-4-yl)oxy]phenyl}-4-(1-isopropyl-6-oxo-1,6-dihydropyridin-3-yl)-1-oxa-4,9-diazaspiro[5,5]undecan-3-one, 9-{4-[(1-cyclobutylpiperidin-4-yl)oxy]phenyl}-4-pyridin-3-yl-1-oxa-4,9-diazaspiro[5,5]undecan-3-one, 5-(9-{4-[(1-cyclobutylpiperidin-4-yl)oxy]phenyl}-3-oxo-1-oxa-4,9-diazaspiro[5,5]undecan-4-yl)nicotinonitrile, 9-{4-[(1-cyclobutylpiperidin-4-yl)oxy]phenyl}-4-(5-methoxypyrazin-2-yl)-1-oxa-4,9-diazaspiro[5,5]undecan-3-one, 4-ethyl-9-{4-[(1-isopropylpiperidin-4-yl)oxy]phenyl}-1-oxa-4,9-diazaspiro[5,5]undecan-3-one, 9-{4-[(1-isopropylpiperidin-4-yl)oxy]phenyl}-4-(2,2,2-trifluoroethyl)-1-oxa-4,9-diazaspiro[5,5]undecan-3-one, 9-{4-[(1-isopropylpiperidin-4-yl)oxy]phenyl}-4-[4-(methylsulfonyl)phenyl]-1-oxa-4,9-diazaspiro[5,5]undecan-3-one, 9-{4-[(1-isopropylpiperidin-4-yl)oxy]phenyl}-4-[5-(trifluoromethyl)pyridin-3-yl]-1-oxa-4,9-diazaspiro[5,5]undecan-3-one, 9-{4-[(1-isopropylpiperidin-4-yl)oxy]phenyl}-4-(5-methoxypyridin-3-yl)-1-oxa-4,9-diazaspiro[5,5]undecan-3-one, 9-{4-[(1-isopropylpiperidin-4-yl)oxy]phenyl}-4-pyrazin-2-yl-1-oxa-4,9-diazaspiro[5,5]undecan-3-one, 9-{4-[(1-isopropylpiperidin-4-yl)oxy]phenyl}-4-(3-methoxypyridin-2-yl)-1-oxa-4,9-diazaspiro[5,5]undecan-3-one, 9-{4-[(1-isopropylpiperidin-4-yl)oxy]phenyl}-4-(2-methoxypyrimidin-5-yl)-1-oxa-4,9-diazaspiro[5,5]undecan-3-one, 9-{4-[(1-isopropylpiperidin-4-yl)oxy]phenyl}-4-(1-methyl-1H-pyrazol-4-yl)-1-oxa-4,9-diazaspiro[5,5]undecan-3-one, 9-{4-[(1-isopropylpiperidin-4-yl)oxy]phenyl}-4-(1-methyl-1H-pyrazol-3-yl)-1-oxa-4,9-diazaspiro[5,5]undecan-3-one, 5-{9-4-[(1-isopropylpiperidin-4-yl)oxy]phenyl}-3-oxo-1-oxa-4,9-diazaspiro[5,5]undecan-4-yl)nicotinonitrile, 4-(2-ethoxypyrimidin-5-yl)-9-{4-[(1-isopropylpiperidin-4-yl)oxy]phenyl}-1-oxa-4,9-diazaspiro[5,5]undecan-3-one, 9-{4-[(1-isopropylpiperidin-4-yl)oxy]phenyl}-4-(5-methoxypyrazin-2-yl)-1-oxa-4,9-diazaspiro[5,5]undecan-3-one, 9-{4-[(1-isopropylpiperidin-4-yl)oxy]phenyl}-4-(6-methoxypyridin-3-yl)-1-oxa-4,9-diazaspiro[5,5]undecan-3-one, 8-{4-[(1-cyclobutylpiperidin-4-yl)oxy]phenyl}-3-(6-methylpyridin-3-yl)-1-oxa-3,8-diazaspiro[4,5]decan-2-one, 5-(8-{4-[(1-cyclobutylpiperidin-4-yl)oxy]phenyl}-2-oxo-1-oxa-3,8-diazaspiro[4,5]decan-3-yl)nicotinonitrile,
8-{4-[(1-cyclobutylpiperidin-4-yl)oxy]phenyl}-3-pyridin-3-yl-1-oxa-3,8-diazaspiro[4,5]decan-2-one,
8-{4-[(1-cyclobutylpiperidin-4-yl)oxy]phenyl}-3-(1-methyl-1H-pyrazol-4-yl)-1-oxa-3,8-diazaspiro[4,5]decan-2-one,
8-{4-[(1-cyclobutylpiperidin-4-yl)oxy]phenyl}-3-(1-methyl-1H-pyrazol-3-yl)-1-oxa-3,8-diazaspiro[4,5]decan-2-one,
8-{4-[(1-cyclobutylpiperidin-4-yl)oxy]phenyl}-3-(6-methoxypyridin-3-yl)-1-oxa-3,8-diazaspiro[4,5]decan-2-one,
8-{4-[(1-cyclobutylpiperidin-4-yl)oxy]phenyl}-3-imidazo[1,2-a]pyridin-3-yl-1-oxa-3,8-diazaspiro[4,5]decan-2-one,
8-{4-[(1-cyclobutylpiperidin-4-yl)oxy]phenyl}-3-(3-methylpyridin-2-yl)-1-oxa-3,8-diazaspiro[4,5]decan-2-one,
8-{4-[(1-cyclobutylpiperidin-4-yl)oxy]phenyl}-3-(6-fluoropyridin-3-yl)-1-oxa-3,8-diazaspiro[4,5]decan-2-one,
8-{4-[(1-cyclobutylpiperidin-4-yl)oxy]phenyl}-3-[4-(methylsulfonyl)phenyl]-1-oxa-3,8-diazaspiro[4,5]decan-2-one,
8-{4-[(1-cyclobutylpiperidin-4-yl)oxy]phenyl}-3-(2-fluoropyridin-4-yl)-1-oxa-3,8-diazaspiro[4,5]decan-2-one,
8-{4-[(1-cyclobutylpiperidin-4-yl)oxy]phenyl}-3-(1-methyl-6-oxo-1,6-dihydropyridin-3-yl)-1-oxa-3,8-diazaspiro[4,5]decan-2-one,
8-{4-[(1-cyclobutylpiperidin-4-yl)oxy]phenyl}-3-(2-methoxypyrimidin-5-yl)-1-oxa-3,8-diazaspiro[4,5]decan-2-one,
3-ethyl-{8-4-[(1-isopropylpiperidin-4-yl)oxy]phenyl}-1-oxa-3,8-diazaspiro[4,5]decan-2-one,
8-{4-[(1-isopropylpiperidin-4-yl)oxy]phenyl}-3-(1-methyl-1H-pyrazol-4-yl)-1-oxa-3,8-diazaspiro[4,5]decan-2-one,
8-{4-[(1-isopropylpiperidin-4-yl)oxy]phenyl}-3-(1-methyl-1H-pyrazol-3-yl)-1-oxa-3,8-diazaspiro[4,5]decan-2-one,
5-(8-{4-[(1-isopropylpiperidin-4-yl)oxy]phenyl}-2-oxo-1-oxa-3,8-diazaspiro[4,5]decan-3-yl)nicotinonitrile,
8-{4-[(1-isopropylpiperidin-4-yl)oxy]phenyl}-3-pyrazin-2-yl-1-oxa-3,8-diazaspiro[4,5]decan-2-one,
8-{4-[(1-isopropylpiperidin-4-yl)oxy]phenyl}-3-(5-methoxypyridin-2-yl)-1-oxa-3,8-diazaspiro[4,5]decan-2-one,
8-{4-[(1-isopropylpiperidin-4-yl)oxy]phenyl}-3-(2-methoxypyrimidin-5-yl)-1-oxa-3,8-diazaspiro[4,5]decan-2-one,
8-{4-[(1-isopropylpiperidin-4-yl)oxy]phenyl}-3-(3-methoxypyridin-2-yl)-1-oxa-3,8-diazaspiro[4,5]decan-2-one,
8-{4-[(1-isopropylpiperidin-4-yl)oxy]phenyl}-3-(6-methoxypyridin-3-yl)-1-oxa-3,8-diazaspiro[4,5]decan-2-one,
8-{4-[(1-isopropylpiperidin-4-yl)oxy]phenyl}-3-(5-methoxypyridin-3-yl)-1-oxa-3,8-diazaspiro[4,5]decan-2-one,
4-(4-methoxyphenyl)-9-[4-(3-piperidin-1-ylpropoxy)phenyl]-1-oxa-4,9-diazaspiro[5,5]undecan-3-one,
4-(3-methoxyphenyl)-9-[4-(3-piperidin-1-ylpropoxy)phenyl]-1-oxa-4,9-diazaspiro[5,5]undecan-3-one,
4-(4-fluorophenyl)-9-[4-(3-piperidin-1-ylpropoxy)phenyl]-1-oxa-4,9-diazaspiro[5,5]undecan-3-one,
4-(6-fluoropyridin-3-yl)-9-[4-(3-piperidin-1-ylpropoxy)phenyl]-1-oxa-4,9-diazaspiro[5,5]undecan-3-one,
4-(6-methoxypyridin-3-yl)-9-[4-(3-piperidin-1-ylpropoxy)phenyl]-1-oxa-4,9-diazaspiro[5,5]undecan-3-one,
4-(6-methoxypyridin-2-yl)-9-[4-(3-piperidin-1-ylpropoxy)phenyl]-1-oxa-4,9-diazaspiro[5,5]undecan-3-one,
4-methyl-9-(4-{3-[(2R)-2-methylpyrrolidin-1-yl]propoxy}phenyl)-1-oxa-4,9-diazaspiro[5,5]undecan-3-one,
4-methyl-9-(4-{3-[(2S)-2-methylpyrrolidin-1-yl]propoxy}phenyl)-1-oxa-4,9-diazaspiro[5,5]undecan-3-one,
4-ethyl-9-(4-{3-[(2R)-2-methylpyrrolidin-1-yl]propoxyl}phenyl)-1-oxa-4,9-diazaspiro[5,5]undecan-3-one,
9-(4-{3-[(3S)-3-methylpiperidin-1-yl]propoxy}phenyl)-4-propyl-1-oxa-4,9-diazaspiro[5,5]undecan-3-one,
4-isopropyl-9-(4-{3-[(3S)-3-methylpiperidin-1-yl]propoxy}phenyl)-1-oxa-4,9-diazaspiro[5,5]undecan-3-one,
4-isopropyl-9-(4-{3-[(2R)-2-methylpyrrolidin-1-yl]propoxy}phenyl)-1-oxa-4,9-diazaspiro[5,5]undecan-3-one,
4-(1-ethylpropyl)-9-(4-{3-[(3S)-3-methylpiperidin-1-yl]propoxy}phenyl)-1-oxa-4,9-diazaspiro[5,5]undecan-3-one,
9-(4-{3-[(2R)-2-methylpyrrolidin-1-yl]propoxy}phenyl)-4-(2,2,2-trifluoroethyl)-1-oxa-4,9-diazaspiro[5,5]undecan-3-one,
4-cyclopropyl-9-(4-{3-[(3S)-3-methylpiperidin-1-yl]propoxy}phenyl)-1-oxa-4,9-diazaspiro[5,5]undecan-3-one,
4-cyclobutyl-9-(4-{3-[(3S)-3-methylpiperidin-1-yl]propoxy}phenyl)-1-oxa-4,9-diazaspiro[5,5]undecan-3-one,
4-cyclobutyl-9-(4-{3-[(2R)-2-methylpyrrolidin-1-yl]propoxy}phenyl)-1-oxa-4,9-diazaspiro[5,5]undecan-3-one,
4-cyclopentyl-9-(4-{3-[(3S)-3-methylpiperidin-1-yl]propoxy}phenyl)-1-oxa-4,9-diazaspiro[5,5]undecan-3-one,
4-cyclohexyl-9-(4-{3-[(3S)-3-methylpiperidin-1-yl]propoxy}phenyl)-1-oxa-4,9-diazaspiro[5,5]undecan-3-one,
4-benzyl-9-(4-{3-[(3S)-3-methylpiperidin-1-yl]propoxy}phenyl)-1-oxa-4,9-diazaspiro[5,5]undecan-3-one,
4-benzyl-9-[4-(3-pyrrolidin-1-ylpropoxy)phenyl]-1-oxa-4,9-diazaspiro[5,5]undecan-3-one,
4-benzyl-9-[4-(3-piperidin-1-ylpropoxy)phenyl]-1-oxa-4,9-diazaspiro[5,5]undecan-3-one,
4-(3-fluorophenyl)-9-[4-(3-piperidin-1-ylpropoxy)phenyl]-1-oxa-4,9-diazaspiro[5,5]undecan-3-one,
4-(2-fluorophenyl)-9-[4-(3-piperidin-1-ylpropoxy)phenyl]-1-oxa-4,9-diazaspiro[5,5]undecan-3-one,
4-(2-fluoropyridin-4-yl)-9-[4-(3-piperidin-1-ylpropoxy)phenyl]-1-oxa-4,9-diazaspiro[5,5]undecan-3-one,
4-ethyl-9-[4-(3-piperidin-1-ylpropoxy)phenyl]-1-oxa-4,9-diazaspiro[5,5]undecan-3-one,
4-ethyl-9-[4-(3-(3S)-methylpiperidin-1-ylpropoxy)phenyl]-1-oxa-4,9-diazaspiro[5,5]undecan-3-one,
4-methyl-9-[4-(3-piperidin-1-ylpropoxy)phenyl]-1-oxa-4,9-diazaspiro[5,5]undecan-3-one,
8-[4-(3-(3S)-methylpiperidin-1-ylpropoxy)phenyl]-3-phenyl-1-oxa-3,8-diazaspiro[4,5]decan-2-one, 3-(4-hydroxyphenyl)-8-[4-(3-piperidin-1-ylpropoxy)phenyl]-1-oxa-3,8-diazaspiro[4,5]decan-2-one, 9-{4-[(1-cyclobutylpiperidin-4-yl)oxy]phenyl}-4-phenyl-1-oxa-4,9-diazaspiro[5,5]undecan-3-one, 9-[4-(1-cyclobutylpiperidin-4-yloxy)phenyl]-4-ethyl-1-oxa-4,9-diazaspiro[5,5]undecan-3-one, 9-[4-(1-cyclobutylpiperidin-4-yloxy)phenyl]-4-(6-fluoropyridin-3-yl)-1-oxa-4,9-diazaspiro[5,5]undecan-3-one, 9-{4-[(1-cyclobutylpiperidin-4-yl)oxy]phenyl}-4-(6-methoxypyridin-3-yl)-1-oxa-4,9-diazaspiro[5,5]undecan-3-one, 9-{4-[(1-cyclopropylpiperidin-4-yl)oxy]phenyl}-4-(6-methoxypyridin-3-yl)-1-oxa-4,9-diazaspiro[5,5]undecan-3-one, 4-cyclobutyl-9-{4-[(1-cyclobutylpiperidin-4-yl)oxy]phenyl}-1-oxa-4,9-diazaspiro[5,5]undecan-3-one, and 4-cyclobutyl-9-{4-[(1-isopropylpiperidin-4-yl)oxy]phenyl}-1-oxa-4,9-diazaspiro[5,5]undecan-3-one, or a pharmaceutically acceptable salt thereof.

13. The compound of claim 12 which is selected from the group consisting of:

4-(2-methoxypyrimidin-5-yl)-9-(4-{3-[(2R)-2-methylpyrrolidin-1-yl]propoxy}phenyl)-1-oxa-4,9-diazaspiro[5,5]undecan-3-one;

4-methyl-9-(4-{3-[(2R)-2-methylpyrrolidin-1-yl]propoxy}phenyl)-1-oxa-4,9-diazaspiro[5,5]undecan-3-one;

5-[9-(4-{3-[(2R)-2-methylpyrrolidin-1-yl]propoxy}phenyl)-3-oxo-1-oxa-4,9-diazaspiro[5,5]undecan-4-yl]nicotinonitrile;

9-{4-[(1-cyclobutylpiperidin-4-yl)oxy]phenyl}-4-pyridin-3-yl-1-oxa-4,9-diazaspiro[5,5]undecan-3-one;

9-{4-[(1-cyclobutylpiperidin-4-yl)oxy]phenyl}-4-ethyl-1-oxa-4,9-diazaspiro[5,5]undecan-3-one;

9-{4-[(1-cyclobutylpiperidin-4-yl)oxy]phenyl}-4-(1-methyl-1H-pyrazol-4-yl)-1-oxa-4,9-diazaspiro[5,5]undecan-3-one;

8-{4-[(1-cyclobutylpiperidin-4-yl)oxy]phenyl}-3-(1-methyl-1H-pyrazol-4-yl)-1-oxa-3,8-diazaspiro[4,5]decan-2-one;

9-{4-[(1-isopropylpiperidin-4-yl)oxy]phenyl}-4-(2-methoxypyrimidin-5-yl)-1-oxa-4,9-diazaspiro[5,5]undecan-3-one;

5-[9-{4-[(1-isopropylpiperidin-4-yl)oxy]phenyl}-3-oxo-1-oxa-4,9-diazaspiro[5,5]undecan-4-yl)nicotinonitrile; and 8-{4-[(1-isopropylpiperidin-4-yl)oxy]phenyl}-3-(1-methyl-1H-pyrazol-4-yl)-1-oxa-3,8-diazaspiro[4,5]decan-2-one;

or a pharmaceutically acceptable salt thereof.

14. A pharmaceutical composition which comprises a pharmaceutically-acceptable additive and the compound of claim 1 or a pharmaceutically acceptable salt thereof.

15. A compound which is 4-(2-methoxypyrimidin-5-yl)-9-(4-{3-[(2R)-2- methylpyrrolidin-l-yl]propoxy} phenyl)-1-oxa-4,9-diazaspiro[5,5]undecan-3-one or a pharmaceutically acceptable salt thereof 16. A compound which is 4-(2-methoxypyrimidin-5-yl)-9-(4-{3-[(2R)-2- methylpyrrolidin-1-yl]propoxy} phenyl)-1-oxa-4,9-diazaspiro[5,5]undecan-3 -one.

17. A compound which is 4-(2-methoxypyrimidin-5-yl)-9-(4-{3-[(2R)-2- methylpyrrolidin-1-yl]propoxy} phenyl)-1 -oxa-4,9-diazaspiro[5,5]undecan-3-one in the form of a pharmaceutically acceptable salt thereof.

18. A pharmaceutical composition which comprises a pharmaceutically- acceptable additive and the compound of claim 15 or a pharmaceutically acceptable salt thereof.

19. A pharmaceutical composition which comprises a pharmaceutically- acceptable additive and the compound of claim 16.

20. A pharmaceutical composition which comprises a pharmaceutically- acceptable additive and the compound of claim 17 in the form of a pharmaceutically acceptable salt thereof.

* * * * *